United States Patent
Gotschall

(10) Patent No.: US 11,357,834 B2
(45) Date of Patent: Jun. 14, 2022

(54) RECOMBINANT α-GALACTOSIDASE A FOR TREATMENT OF FABRY DISEASE

(71) Applicant: Amicus Therapeutics, Inc., Cranbury, NJ (US)

(72) Inventor: Russell Gotschall, Doylestown, PA (US)

(73) Assignee: Amicus Therapeutics, Inc., Philadelphia, PA (US)

( * ) Notice: Subject to any disclaimer, the term of this patent is extended or adjusted under 35 U.S.C. 154(b) by 0 days.

(21) Appl. No.: 16/476,751

(22) PCT Filed: Jan. 10, 2018

(86) PCT No.: PCT/US2018/013165
§ 371 (c)(1),
(2) Date: Jul. 9, 2019

(87) PCT Pub. No.: WO2018/132471
PCT Pub. Date: Jul. 19, 2018

(65) Prior Publication Data
US 2019/0358302 A1 Nov. 28, 2019

Related U.S. Application Data

(60) Provisional application No. 62/444,578, filed on Jan. 10, 2017, provisional application No. 62/524,692, filed on Jun. 26, 2017.

(51) Int. Cl.
*C12N 9/40* (2006.01)
*A61K 38/47* (2006.01)
*A61K 31/445* (2006.01)
*C12P 21/00* (2006.01)

(52) U.S. Cl.
CPC ............ *A61K 38/47* (2013.01); *A61K 31/445* (2013.01); *C12N 9/2465* (2013.01); *C12P 21/005* (2013.01); *C12Y 302/01022* (2013.01)

(58) Field of Classification Search
None
See application file for complete search history.

(56) References Cited

U.S. PATENT DOCUMENTS

| | | | |
|---|---|---|---|
| 5,356,804 A | 10/1994 | Desnick et al. | |
| 6,083,725 A | 7/2000 | Selden et al. | |
| 8,841,427 B2 | 9/2014 | Zhu | |
| 2002/0025550 A1* | 2/2002 | Canfield | C07K 16/40 435/68.1 |
| 2005/0058634 A1* | 3/2005 | Zhu | A61K 38/1709 424/94.61 |
| 2015/0210992 A1* | 7/2015 | Asano | C12N 9/2465 435/208 |
| 2017/0335301 A1* | 11/2017 | Do | C12Y 302/0102 |

FOREIGN PATENT DOCUMENTS

| | | |
|---|---|---|
| EP | 2287319 A1 | 2/2011 |
| WO | 03090695 A2 | 11/2003 |
| WO | 2014014938 A1 | 1/2014 |
| WO | 2015061464 A2 | 4/2015 |
| WO | 2016054231 A1 | 4/2016 |
| WO | 2017173059 A1 | 10/2017 |

OTHER PUBLICATIONS

Sakuraba et al., J. Hum. Genet. 51:180-188, 2006 (Year: 2006).*
Bohnsack et al., J. Biol. Chem. 284:35215-35226, 2009 (Year: 2009).*
PCT International Search Report and Written Opinion in PCT/US2018/013165 dated Jun. 22, 2018, 20 pages.
Bohnsack, Richard N., et al., "Cation-independent Mannose 6-Phosphate Receptor A Composite of Distinct Phosphomannosyl Binding Sites", The Journal of Biological Chemistry, vol. 284, No. 50, p. 35215-35226, Dec. 11, 2009.
Morimoto, Hideto, et al., "Non-clinical evaluation of JR-051 as a biosimilar to agalsidase beta for the treatment of Fabry disease", Molecular Genetics and Metabolism 125 (2018) 153-160.
Sakuraba, Hitoshi, et al., "Comparison of the effects of agalsidase alfa and agalsidase beta on cultured human Fabry fibroblasts and Fabry mice", J Hum Genet (2006) 51:180-188.
Sohn, Youngsoo, et al., "Enhanced sialylation and in vivo efficacy of recombinant human α-galactosidase through in vitro glycosylation", BMB Reports, (2012), pp. 157-162.

* cited by examiner

*Primary Examiner* — David Steadman
(74) *Attorney, Agent, or Firm* — Servilla Whitney LLC

(57) ABSTRACT

Described are compositions comprising α-galactosidase A enzymes with unique carbohydrate profiles, as well as methods for manufacturing and purifying such enzymes. Also described methods of treating, preventing, and/or ameliorating Fabry Disease by administering such enzymes to a subject in need thereof. Also described are compositions comprising migalastat in combination with such α-galactosidase A enzymes.

24 Claims, 65 Drawing Sheets
Specification includes a Sequence Listing.

Structure and Receptor Affinity for High Mannose and Phosphorylated Oligosaccharides Non-phosporylated High Mannose N-glycan:

Mono-M6P N-glycan: Lower Affinity for CI-MPR ($K_n \sim 7000$ nM)

Bis-M6P N-glycan: High Affinity for CI-MPR ($K_n = 2$ nM)

Chemical Structure of Mannose 6-phosphate

Mannose 6-phosphate (M6P)

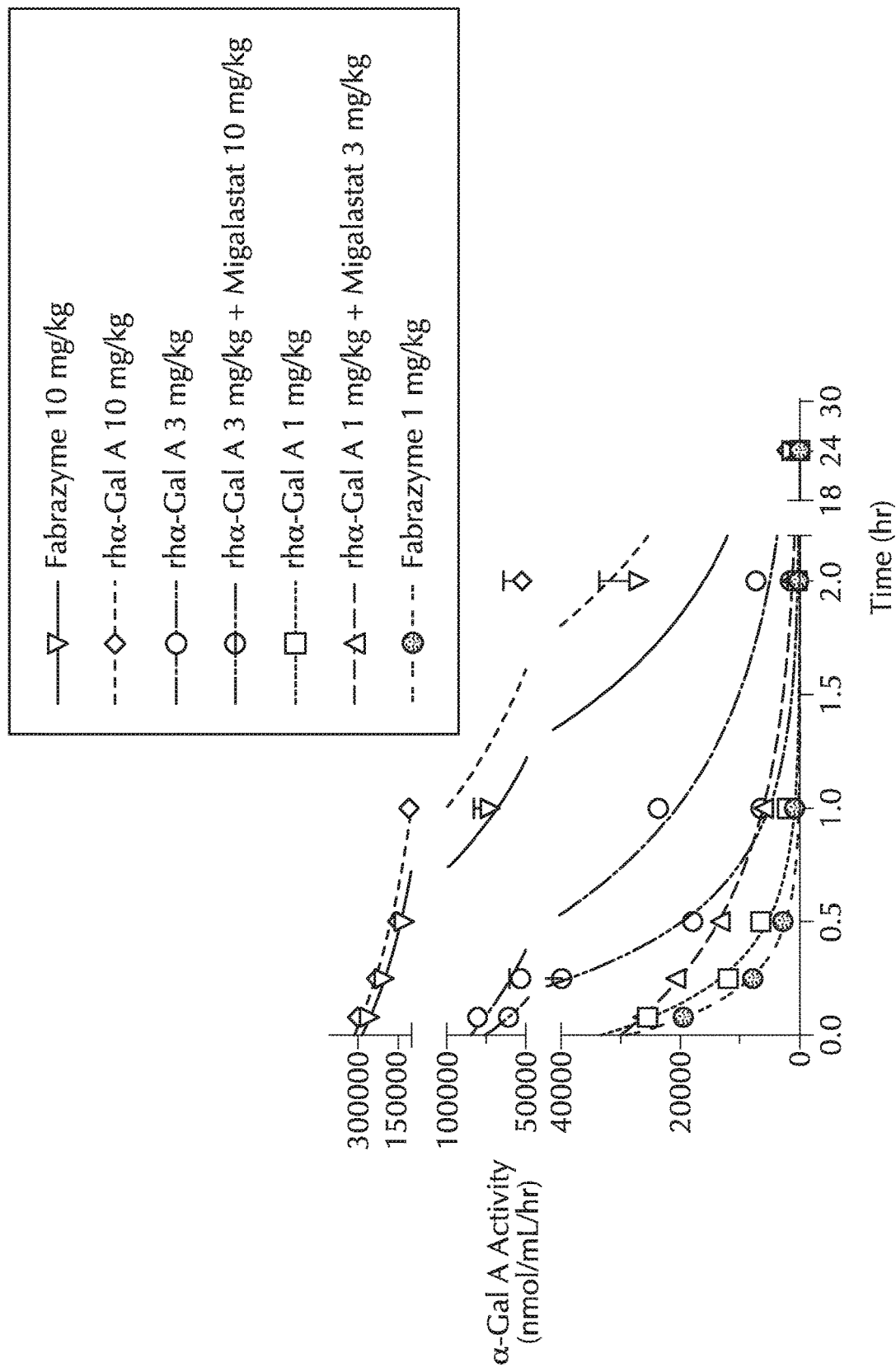

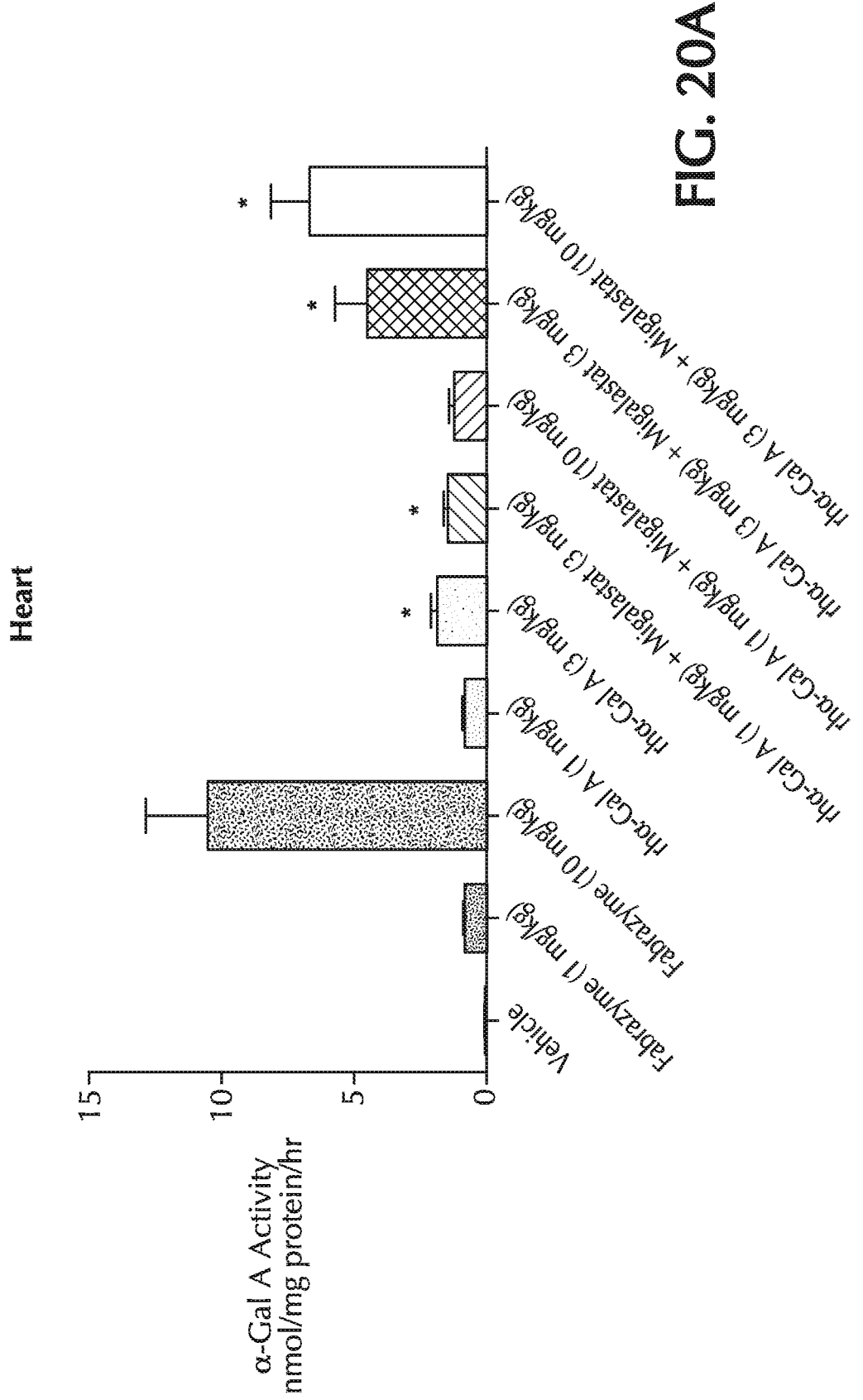

RECOMBINANT α-GALACTOSIDASE A FOR TREATMENT OF FABRY DISEASE

CROSS-REFERENCE TO RELATED APPLICATIONS

This application is the National Stage entry of PCT/US18/13165, filed on Jan. 10, 2018, which claims priority to United States Application Nos. 62/444,578, filed on Jan. 10, 2017 and 62/524,692, filed on Jun. 26, 2017, which are hereby incorporated by reference in their entireties.

TECHNICAL FIELD

Principles and embodiments of the present invention relate generally to lysosomal storage disorders, particularly recombinant α-galactosidase A for the treatment of Fabry disease.

REFERENCE TO THE SEQUENCE LISTING

The Sequence Listing text file submitted herewith, identified as "00712837.TXT" (9 Kb, created Jan. 10, 2018), is hereby incorporated by reference.

BACKGROUND

Fabry disease is a progressive, X-linked inborn error of glycosphingolipid metabolism caused by a deficiency in the lysosomal enzyme α-galactosidase A (α-Gal A) as a result of mutations in the α-Gal A gene (Gla). Despite being an X-linked disorder, females can express varying degrees of clinical manifestations. Fabry is a rare disease with incidence estimated between 1 in 40,000 males to 1 in 117,000 in the general population. Moreover, there are variants of later onset phenotype of Fabry disease that can be under-diagnosed, as they do not present with classical signs and symptoms. This, and newborn screening for Fabry disease, suggests that the actual incidence of Fabry disease can be higher than currently estimated.

Untreated, life expectancy in Fabry patients is reduced and death usually occurs in the fourth or fifth decade because of vascular disease affecting the kidneys, heart and/or central nervous system. The enzyme deficiency leads to intracellular accumulation of the substrate globotriaosylceramide (GL-3) in the vascular endothelium and visceral tissues throughout the body. Gradual deterioration of renal function and the development of azotemia, due to glycosphingolipid deposition, usually occur in the third to fifth decades of life, but can occur as early as in the second decade. Renal lesions are found in both hemizygous (male) and heterozygous (female) patients.

Cardiac disease as a result of Fabry disease occurs in most males and many females. Early cardiac findings include left ventricular enlargement, valvular involvement and conduction abnormalities. Mitral insufficiency is the most frequent valvular lesion typically present in childhood or adolescence. Cerebrovascular manifestations result primarily from multifocal small-vessel involvement and can include thromboses, transient ischemic attacks, basilar artery ischemia and aneurysm, seizures, hemiplegia, hemianesthesia, aphasia, labyrinthine disorders, or cerebral hemorrhages. Average age of onset of cerebrovascular manifestations is 33.8 years. Personality change and psychotic behavior can manifest with increasing age.

Fabry disease commonly presents with dermatological symptoms, most commonly angiokeratoma (small papules that can reside on any region of the body). Angiokeratomas appear as dark red or purple skin lesions ranging in size up to several millimeters in diameter. Lesions usually appear in adolescence or young adulthood and may increase with age. Other dermatological and soft-tissue related symptoms include acroparesthesia, abnormal sweating (hypohidrosis and hyperhidrosis) and lymphedema. The presence and extent of cutaneous vascular lesions may correlate with the severity of systemic disease.

In addition to dermatological symptoms, patients frequently experience neuropathy such as burning pain in the extremities (acroparesthesia—often hands and feet). Patients may also experience a pain crisis beginning with pain in the extremities and radiating inward which can persist for several days. Neuropathic pain is pain caused by damage to the somatosensory nervous system. Many types of sensory receptors are affected including those in skin, epithelial tissues, skeletal muscles, bones and joints, internal organs, and the cardiovascular system.

The current approved treatment for Fabry disease is enzyme replacement therapy ("ERT"). Two α-Gal A products are currently available for the treatment of Fabry disease: agalsidase alfa (Replagal®, Shire Human Genetic Therapies) and agalsidase beta (Fabrazyme®; Sanofi Genzyme Corporation). These two forms of ERT are intended to compensate for a patient's inadequate α-Gal A activity with a recombinant form of the enzyme, administered intravenously. While ERT is effective in many settings, the treatment also has limitations. For example, these two α-Gal A products have not been demonstrated to decrease sufficient risk of stroke, cardiac muscle responds to treatment slowly, and GL-3 elimination from some of the cell types of the kidneys is limited.

Accordingly, there remains a need for further improvements for treating Fabry disease. Among others, the present invention includes an improved recombinant human alpha-galactosidase A (rhα-Gal A) over the existing ERTs and a method of treating a patient in need using the improved enzyme with a pharmacological chaperone.

SUMMARY

One aspect of the present invention relates to a human recombinant α-galactosidase A (rhα-Gal A).

In various embodiments of this aspect, the rhα-Gal A comprises a protein having at least 98% sequence identity to SEQ ID NO: 1 or SEQ ID NO: 2, wherein the rhα-Gal A has at least 25% of total N-linked oligosaccharides that are mono-mannose-6-phosphate (mono-M6P) and at least 12% of total N-linked oligosaccharides that are bis-mannose-6-phosphate (bis-M6P). In one or more embodiments, the rhα-Gal A has at least 25% of total N-linked oligosaccharides that contain sialic acid. In one or more embodiments, the rhα-Gal A has less than 20% of total N-linked oligosaccharides that are neutral.

In various embodiments of this aspect, the rhα-Gal A comprises a protein having at least 98% sequence identity to SEQ ID NO: 1 or SEQ ID NO: 2, wherein the rhα-Gal A has less than 10% of total N-linked oligosaccharides that are neutral. In one or more embodiments, the rhα-Gal A has at least 50% of total N-linked oligosaccharides that contain sialic acid. In one or more embodiments, the rhα-Gal A has at least 25% of total N-linked oligosaccharides that are mono-M6P and at least 6% of total N-linked oligosaccharides that are bis-M6P.

In one or more embodiments, the rhα-Gal A has one or more of:
a. at least 17% of total N-linked oligosaccharides that contain a single sialic acid residue;
b. at least 20% of total N-linked oligosaccharides that contain two sialic acid residues;
c. at least 40% of total N-linked oligosaccharides that contain one or two sialic acid residues; or
d. at least 6 moles of sialic acid residues per mole of rhα-Gal A homodimer.

In one or more embodiments, the rhα-Gal A has two, three, or four of:
a. at least 17% of total N-linked oligosaccharides that contain a single sialic acid residue;
b. at least 20% of total N-linked oligosaccharides that contain two sialic acid residues;
c. at least 40% of total N-linked oligosaccharides that contain one or two sialic acid residues; or
d. at least 6 moles of sialic acid residues per mole of rhα-Gal A homodimer.

In one or more embodiments, the rhα-Gal A has at least 7 moles of sialic acid residues per mole of rhα-Gal A homodimer.

In one or more embodiments, the rhα-Gal A has at least 22% of total N-linked oligosaccharides that contain two sialic acid residues.

In one or more embodiments, the rhα-Gal A has at least 14% of total N-linked oligosaccharides that are bis-mannose-6-phosphate.

Another aspect of the present invention relates to a method of producing a recombinant protein product comprising rhα-Gal A. In various embodiments of this aspect, the method comprises culturing Chinese hamster ovary (CHO) host cells in a bioreactor that secrete rhα-Gal A, wherein the rhα-Gal A comprises a protein having at least 98% sequence identity to SEQ ID NO: 1 or SEQ ID NO: 2; removing media from the bioreactor; filtering the media to provide a filtrate; loading the filtrate onto an anion exchange chromatography (AEX) column to capture the rhα-Gal A; and eluting a first protein product comprising the rhα-Gal A from the AEX column. In one or more embodiments, the first protein product is an intermediate protein product that is subjected to further processing and/or purification before becoming a finalized protein product (e.g. suitable to use as an ERT). In other embodiments, the first protein product is a finalized protein product.

Another aspect of the present invention relates to recombinant protein product made by the processes described herein.

Another aspect of the present invention relates to a method of treating Fabry disease, wherein a patient in need thereof is administered the rhα-Gal A as described herein or a recombinant protein product comprising rhα-Gal A as described herein.

Another aspect of the present invention relates to a pharmaceutical composition comprising a pharmaceutically acceptable carrier and the rhα-Gal A as described herein or a recombinant protein product comprising rhα-Gal A as described herein. In one or more embodiments, the pharmaceutical composition comprises about 0.5 to about 20 µM rhα-Gal A and about 50 to about 20,000 µM migalastat or salt thereof. In one or more embodiments, the pharmaceutical composition comprises about 1 to about 10 µM rhα-Gal A and about 100 to about 10,000 µM migalastat or salt thereof. In one or more embodiments, the migalastat and rhα-Gal A are present in a molar ratio of migalastat to α-galactosidase A of between about 13,000:1 and about 50:1.

Another aspect of the present invention relates to a method of treating Fabry disease, the method comprising administering a pharmaceutical composition as described herein. In one or more embodiments, the rhα-Gal A is administered at a dose of about 0.5 mg/kg to about 10 mg/kg.

In one or more embodiments, the patient is co-administered a pharmacological chaperone for α-Gal A within 4 hours of the administration of the rhα-Gal A or the pharmaceutical composition comprising the recombinant protein product. In one or more embodiments, the pharmacological chaperone comprises migalastat or salt thereof.

In one or more embodiments, the pharmacological chaperone is administered orally and pharmaceutical composition comprising rhα-Gal A is administered intravenously.

In one or more embodiments, the pharmacological chaperone is co-formulated with the rhα-Gal A. In one or more embodiments, the migalastat or salt thereof is administered at a dose of about 1 mg/kg to about 100 mg/kg.

In one or more embodiments, the pharmaceutical composition comprising rhα-Gal A (and optionally a pharmacological chaperone such as migalastat) is administered once a month to once a week. In one or more embodiments, the pharmaceutical composition is administered every other week.

Another aspect of the present invention relates to a method for treating Fabry disease, the method comprising administering a pharmaceutical composition comprising rhα-Gal A as described herein and optionally a pharmacological chaperone such as migalastat to a patient in need thereof.

In one or more embodiments, the patient is co-administered a pharmacological chaperone for α-Gal A within 4 hours of the administration of the pharmaceutical composition comprising rhα-Gal A.

In one or more embodiments, the pharmacological chaperone is administered orally and pharmaceutical composition comprising rhα-Gal A is administered intravenously.

In one or more embodiments, the migalastat or salt thereof is administered at a dose of about 1 mg/kg to about 100 mg/kg.

In one or more embodiments, the pharmaceutical composition is administered once a month to once a week.

In one or more embodiments, the pharmaceutical composition is administered every other week.

In one or more embodiments, the administering is contacting a cell with the rhα-Gal A bound to the pharmacological chaperone.

In one or more embodiments, the cell is located in the patient's heart.

In one or more embodiments, the cell is located in the patient's kidney.

In one or more embodiments, the cell is located in the patient's skin

In one or more embodiments, the pharmacological chaperone is migalastat hydrochloride.

Another aspect of the present invention relates to a method of enhancing the activity level of α-galactosidase-A protein in a lysosome in a mammalian cell, the method comprising contacting the mammalian cell with rhα-Gal A as described herein, wherein the rhα-Gal A is optionally bound to a pharmacological chaperone.

In one or more embodiments, the rhα-Gal A is administered at a dose of about 0.5 mg/kg to about 10 mg/kg.

In one or more embodiments, the pharmacological chaperone is co-formulated with the rhα-Gal A.

In one or more embodiments, the patient is co-administered a pharmacological chaperone for α-Gal A within 4 hours of the administration of the pharmaceutical composition comprising rhα-Gal A.

In one or more embodiments, the pharmacological chaperone is administered orally and pharmaceutical composition comprising rhα-Gal A is administered intravenously.

In one or more embodiments, the migalastat or salt thereof is administered at a dose of about 1 mg/kg to about 100 mg/kg.

In one or more embodiments, the pharmaceutical composition is administered once a month to once a week.

In one or more embodiments, the pharmaceutical composition is administered every other week.

In one or more embodiments, the cell is a heart cell.

In one or more embodiments, the cell is a kidney cell.

In one or more embodiments, the cell is a skin cell.

In one or more embodiments, the contacting is performed by administration of the rhα-Gal A and the pharmacological chaperone.

In one or more embodiments, the administering is systemic administration of both the pharmacological chaperone and the rhα-Gal A.

In one or more embodiments, both the pharmacological chaperone and the rhα-Gal A are co-administered.

In one or more embodiments, the pharmacological chaperone and the rhα-Gal A are present in a composition formulated for intravenous, intraarterial, intramuscular, intradermal, subcutaneous, or intraperitoneal administration.

In one or more embodiments, the composition is formulated for intravenous administration.

In one or more embodiments, the pharmacological chaperone is migalastat or salt thereof.

In one or more embodiments, the pharmaceutical composition comprises:
 about 0.5 to about 20 µM rhα-Gal A; and
 about 50 to about 20,000 µM migalastat or salt thereof.

In one or more embodiments, the pharmaceutical composition comprises:
 about 1 to about 10 µM rhα-Gal A; and
 about 100 to about 10,000 µM migalastat or salt thereof.

In one or more embodiments, the ratio of migalastat or salt thereof to α-galactosidase A of between about 13,000:1 and about 50:1.

In one or more embodiments, the cell is in vitro.

In one or more embodiments, the cell is a human cell.

In one or more embodiments, the cell is in a subject.

In one or more embodiments, the subject is a patient in need.

In one or more embodiments, the cell is located in the subject's heart, kidney or skin.

In one or more embodiments, the cell is located in the subject's heart.

In one or more embodiments, the cell is located in the subject's kidney.

In one or more embodiments, the cell is located in the subject's skin.

In one or more embodiments, the patient has been diagnosed as having Fabry disease.

Another aspect of the present invention relates to a method of reducing the level of GL-3 in an organ of a patient in need, the method comprising administering to the patient a composition comprising a therapeutically effective amount of (i) a pharmacological chaperone and (ii) rhα-Gal A as described herein.

In one or more embodiments, the administering is performed by co-administration.

In one or more embodiments, the administering is systemic administration of both the pharmacological chaperone and the rhα-Gal A.

In one or more embodiments, the composition is formulated for intravenous, intraarterial, intramuscular, intradermal, subcutaneous, or intraperitoneal administration.

In one or more embodiments, the composition is formulated for intravenous administration.

In one or more embodiments, the pharmacological chaperone is migalastat or salt thereof.

In one or more embodiments, the pharmaceutical composition comprises:
 about 0.5 to about 20 µM rhα-Gal A; and
 about 50 to about 20,000 µM migalastat or salt thereof.

In one or more embodiments, the pharmaceutical composition comprises:
 about 1 to about 10 µM rhα-Gal A; and
 about 100 to about 10,000 µM migalastat or salt thereof.

In one or more embodiments, the ratio of migalastat or salt thereof to α-galactosidase A of between about 13,000:1 and about 50:1.

In one or more embodiments, the organ is heart, kidney or skin.

In one or more embodiments, the organ is heart.

In one or more embodiments, the organ is kidney.

In one or more embodiments, the organ is skin.

In one or more embodiments, the subject has been diagnosed as having Fabry disease.

Another aspect of the present invention relates to a method of treating Fabry disease, the method comprising contacting a mammalian cell with an effective amount of rhα-Gal A, wherein contacting the cell with the rhα-Gal A provides a greater reduction in GL-3 than contacting with Fabrazyme (agalsidase beta).

In one or more embodiments, the contacting is administering to a subject an effective amount of the rhα-Gal A.

In one or more embodiments, the cell is in a subject.

In one or more embodiments, the subject is a patient in need.

In one or more embodiments, the reduction in GL-3 is measured in heart tissue.

In one or more embodiments, the reduction in GL-3 is measured in kidney tissue.

In one or more embodiments, the reduction in GL-3 is measured in skin tissue.

In one or more embodiments, the rhα-Gal A is bound to a pharmacological chaperone.

In one or more embodiments, the pharmacological chaperone is migalastat or a salt thereof.

In one or more embodiments, the migalastat or salt thereof is administered at a dose of 3 mg/kg.

In one or more embodiments, the migalastat or salt thereof is administered at a dose of 10 mg/kg.

In one or more embodiments, the migalastat or salt thereof is administered at a dose of 30 mg/kg.

In one or more embodiments, the migalastat or salt thereof is administered at a dose of 300 mg/kg.

In one or more embodiments, the rhα-Gal A and the pharmacological chaperone is co-administered.

In one or more embodiments, the rhα-Gal A and the pharmacological chaperone is co-formulated.

In one or more embodiments, a dose of 1 mg/kg rhα-Gal A provides a greater reduction in GL-3 than administration of Fabrazyme (agalsidase beta) to Gla knockout mice at a dose of 1 mg/kg.

In one or more embodiments, a dose of 10 mg/kg rhα-Gal A provides a greater reduction in GL-3 than administration of Fabrazyme (agalsidase beta) to Gla knockout mice at a dose of 10 mg/kg.

In one or more embodiments, the reduction in GL-3 after administration of the pharmaceutical composition to Gla knockout mice is at least 10% greater than the reduction in GL-3 after administration of Fabrazyme (agalsidase beta).

In one or more embodiments, the reduction in GL-3 after administration of the pharmaceutical composition to Gla knockout mice is at least 20% greater than the reduction in GL-3 after administration of Fabrazyme (agalsidase beta).

Another aspect of the present invention relates to a method of treating Fabry disease, the method comprising contacting a mammalian cell with an effective amount of rhα-Gal A, wherein contacting the cell with the rhα-Gal A provides a greater reduction in plasma lyso-Gb3 than contacting with Fabrazyme (agalsidase beta).

In one or more embodiments, the contacting is administering an effective to a subject an effective amount of the rhα-Gal A.

In one or more embodiments, the cell is in a subject.

In one or more embodiments, the subject is a patient in need.

In one or more embodiments, the reduction in plasma lyso-Gb3 is measured in heart tissue.

In one or more embodiments, the reduction in plasma lyso-Gb3 is measured in kidney tissue.

In one or more embodiments, the reduction in plasma lyso-Gb3 is measured in skin tissue.

In one or more embodiments, the rhα-Gal A is bound to a pharmacological chaperone.

In one or more embodiments, the pharmacological chaperone is migalastat or a salt thereof.

In one or more embodiments, the migalastat or salt thereof is administered at a dose of 3 mg/kg.

In one or more embodiments, the migalastat or salt thereof is administered at a dose of 10 mg/kg.

In one or more embodiments, the migalastat or salt thereof is administered at a dose of 30 mg/kg.

In one or more embodiments, the migalastat or salt thereof is administered at a dose of 300 mg/kg.

In one or more embodiments, the rhα-Gal A and the pharmacological chaperone is co-administered.

In one or more embodiments, the rhα-Gal A and the pharmacological chaperone is co-formulated.

In one or more embodiments, a dose of 1 mg/kg rhα-Gal A provides a greater reduction in plasma lyso-Gb3 than administration of Fabrazyme (agalsidase beta) to Gla knockout mice at a dose of 1 mg/kg.

In one or more embodiments, a dose of 10 mg/kg rhα-Gal A provides a greater reduction in plasma lyso-Gb3 than administration of Fabrazyme (agalsidase beta) to Gla knockout mice at a dose of In one or more embodiments, the reduction in plasma lyso-Gb3 after administration of the pharmaceutical composition to Gla knockout mice is at least 10% greater than the reduction in plasma lyso-Gb3 after administration of Fabrazyme (agalsidase beta).

In one or more embodiments, the reduction in plasma lyso-Gb3 after administration of the pharmaceutical composition to Gla knockout mice is at least 20% greater than the reduction in plasma lyso-Gb3 after administration of Fabrazyme (agalsidase beta).

Another aspect of the present invention relates to a method of treating Fabry disease, the method comprising contacting a mammalian cell with an effective amount rhα-Gal A), wherein contacting the cell with the rhα-Gal A provides a greater reduction in one or more substrates than contacting with Fabrazyme (agalsidase beta).

In one or more embodiments, the one or more substrates comprises GL-3 or plasma lyso-Gb3.

In one or more embodiments, the one or more substrates is GL-3.

In one or more embodiments, the one or more substrates is plasma lyso-Gb3.

In one or more embodiments, the rhα-Gal A is bound to a pharmacological chaperone.

In one or more embodiments, the pharmacological chaperone is migalastat or a salt thereof.

In one or more embodiments, the migalastat or salt thereof is administered at a dose of 3 mg/kg.

In one or more embodiments, the migalastat or salt thereof is administered at a dose of 10 mg/kg.

In one or more embodiments, the migalastat or salt thereof is administered at a dose of 30 mg/kg.

In one or more embodiments, the migalastat or salt thereof is administered at a dose of 300 mg/kg

BRIEF DESCRIPTION OF THE DRAWINGS

Further features of the present invention will become apparent from the following written description and the accompanying figures, in which:

FIGS. 18A-18F show the pharmacokinetics of Fabrazyme and rhα-Gal A at various doses with and without migalastat;

FIGS. 20A-20C show α-Gal A activity in Gla KO mice heart (20A), kidney (20B) and skin (20C) after repeat administrations of various ERTs with and without migalastat;

DETAILED DESCRIPTION

Figure 1A:
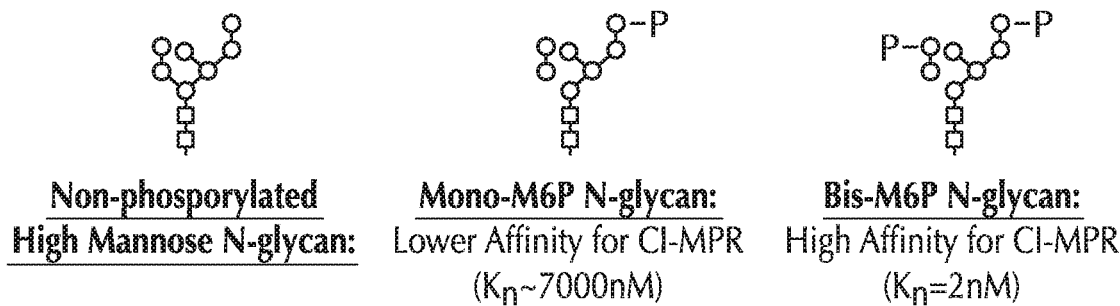
FIG. 1A shows non-phosphorylated high mannose glycan, a mono-M6P glycan, and a bis-M6P glycan.

Before describing several exemplary embodiments of the invention, it is to be understood that the invention is not limited to the details of construction or process steps set forth in the following description. The invention is capable of other embodiments and of being practiced or being carried out in various ways.

Various aspects of the invention pertain to novel recombinant human α-galactosidase A (rhα-Gal A). Other aspects of the invention pertain to recombinant proteins produced by the processes described herein, as well as pharmaceutical compositions, methods of treatment, and uses of such recombinant proteins.

Definitions

The terms used in this specification generally have their ordinary meanings in the art, within the context of this invention and in the specific context where each term is used. Certain terms are discussed below, or elsewhere in the specification, to provide additional guidance to the practitioner.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

As used herein, the term "Fabry disease," (also referred to as alpha-galactosidase A deficiency; Anderson-Fabry disease; angiokeratoma corporis diffusum; angiokeratoma diffuse; ceramide trihexosidase deficiency; GLA deficiency, and hereditary dystopic lipidosis) is intended to refer to a genetic lysosomal storage disorder characterized by mutations in the Gla gene which codes for human alpha-galactosidase A. The term includes all stages and forms of the disease experienced by infantile, juvenile, and adult patients.

As used here the term "alpha-galactosidase A" (also known as α-Gal A; E.C. 3.2.1.22 family of alpha-galactosidases) is intended to refer to a lysosomal enzyme which breaks down alpha-galactosides in the lysosome. Human α-galactosidase is a homodimeric glycoprotein that hydrolyses the terminal alpha-galactosyl moieties from glycolipids and glycoproteins. The enzyme predominantly hydrolyzes globotriaosylceramide ("GL-3", also known as Gb3 or ceramide trihexoside), and can catalyze the hydrolysis of melibiose into galactose and glucose. Another substrate of the enzyme is plasma globotriaosylsphingosine ("plasma lyso-Gb3"). A variety of mutations in the gene affect the synthesis, processing, and stability of the enzyme which cause Fabry disease as a result of a failure to catabolize alpha-D-galactosyl glycolipid moieties. Alpha-galactosidase A catalyzes the removal of terminal α-galactose residues from polysaccharides, glycolipids, and glycopeptides. The Gla gene (National Center for Biotechnology Information (NCBI) Gene ID 2717) encodes for human alpha-galactosidase A and has been mapped to the long arm of the X chromosome at position 22. As used herein the abbreviation "α-Gal A" is intended to refer to the alpha-galactosidase A enzyme. The italicized "Gla" is intended to refer to the human gene coding for human α-Gal A. The abbreviation rhα-Gal A is intended to refer to recombinant human α-Gal A. There are currently more than 400 mutations identified in Fabry patients. The most common form of mutation leads to a single amino acid change in the enzyme. Other types of mutations include deletions, insertions, premature stop codons, frame-shift mutations, and splice site mutations.

The term "agalsidase beta" is intended to refer to a homodimeric recombinant human α-Gal A marketed by Genzyme under the name Fabrazyme®. Fabrazyme (agalsidase beta) has a molecular weight of approximately 100 kDa with a recommended dosage of 1.0 mg/kg body weight infused every two weeks as an IV infusion. The initial infusion rate is recommended to be no more than 0.25 mg/min (15 mg/hr). Infusion reactions to Fabrazyme (agalsidase beta), some of which are severe, have occurred in Fabry patients. Infusion reactions include fever, rigors, chest tightness, hypertension, hypotension, pruritis, myalgia, dyspnea, urticarial, abdominal pain, and headache. It is suggested that patients be given antipyretic prior to infusion.

The term "agalsidase alfa" is intended to refer to a homodimeric recombinant human α-Gal A marketed by Shire Human Genetic Therapies Inc. under the name Replagal®. Replagal (agalsidase alfa) is a homodimer of approximately 100 kDa with each subunit containing 398 amino acid residues with an identical amino acid sequence to wild-type human α-Gal A. The recommended dose of Replagal is 0.2 mg/kg every other week by intravenous infusion.

The term "rhα-Gal A" is intended to refer to a recombinant human alpha-galactosidase A as described herein and as exemplified in the Examples below.

As used herein, the term "glycan" or "oligosaccharide" is intended to refer to a polysaccharide chain covalently bound to an amino acid residue on a protein or polypeptide. As used herein, the term "N-glycan", "N-oligosaccharide" "N-linked glycan" or "N-linked oligosaccharide" is intended to refer to a polysaccharide chain attached to an amino acid residue on a protein or polypeptide through covalent binding to a nitrogen atom of the amino acid residue. For example, an N-glycan can be covalently bound to the side chain nitrogen atom of an asparagine residue. Glycans can contain one or several monosaccharide units, and the monosaccharide units can be covalently linked to form a straight chain or a branched chain. In at least one embodiment, N-glycan units attached to rhα-Gal A can comprise one or more monosaccharide units each independently selected from N-acetylglucosamine, mannose, galactose or sialic acid. The N-glycan units on the protein can be determined by any appropriate analytical technique, such as mass spectrometry. In some embodiments, the N-glycan units can be determined by liquid chromatography-tandem mass spectrometry (LC-MS/MS) utilizing an instrument such as the Thermo Scientific Orbitrap Velos Pro™ Mass Spectrometer, Thermo Scientific Orbitrap Fusion Lumos Tribid™ Mass Spectrometer or Waters Xevo® G2-XS QT of Mass Spectrometer.

As used herein, the term "high-mannose N-glycan" is intended to refer to an N-glycan having one to six or more mannose units. In at least one embodiment, a high mannose N-glycan unit can contain a bis(N-acetylglucosamine) chain bonded to an asparagine residue and further bonded to a branched polymannose chain. As used herein interchangeably, the term "M6P" or "mannose-6-phosphate" is intended to refer to a mannose unit phosphorylated at the 6 position; i.e. having a phosphate group bonded to the hydroxyl group at the 6 position. In at least one embodiment, one or more mannose units of one or more N-glycan units are phosphorylated at the 6 position to form mannose-6-phosphate units. In at least one embodiment, the term "M6P" or "mannose-6-phosphate" refers to both a mannose phosphodiester having N-acetylglucosamine (GlcNAc) as a "cap" on the phosphate group, as well as a mannose unit having an exposed phosphate group lacking the GlcNAc cap. In at least one embodiment, the N-glycans of a protein can have multiple M6P groups, with at least one M6P group having a GlcNAc cap and at least one other M6P group lacking a GlcNAc cap.

As used herein, the term "complex N-glycan" is intended to refer to an N-glycan containing one or more N-acetylglucosamine, N-acetylgalactosamine, galactose, fucose and/or sialic acid units. In at least one embodiment, a complex N-glycan can be a high-mannose N-glycan in which one or mannose units are further bonded to one or more monosaccharide units each independently selected from N-acetylglucosamine, N-acetylgalactosamine, galactose, fucose and sialic acid.

As used herein, the compound migalastat, also known as 1-deoxygalactonojirimycin (1-DGJ), (2R, 3S, 4R, 5S0-2-(hydroxymethyl)piperidine-3,4,5-triol and is a compound having the following chemical formula:

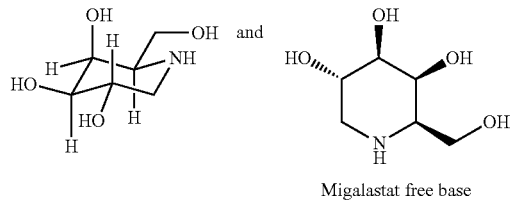 [SMILES: OCC1NCC(O)C(O)C1O ; OC[C@H]1NC[C@H](O)[C@@H](O)[C@H]1O]

Migalastat free base

As discussed below, pharmaceutically acceptable salts of migalastat may also be used in the present invention. When a salt of migalastat is used, the dosage of the salt will be adjusted so that the dose of migalastat received by the patient is equivalent to the amount which would have been received had the migalastat free base been used. One example of a pharmaceutically acceptable salt of migalastat is migalastat HCl:

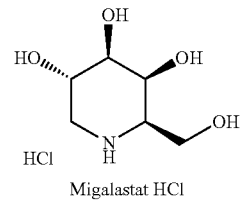 [SMILES: OC[C@H]1NC[C@H](O)[C@@H](O)[C@H]1O ; Cl]

Migalastat HCl

The term "migalastat" encompasses migalastat free base or a pharmaceutically acceptable salt thereof (e.g., migalastat HCl as shown above), unless specifically indicated to the contrary.

As used herein, the term "pharmacological chaperone" or sometimes simply the term "chaperone" is intended to refer to a molecule that specifically binds to α-Gal A and has one or more of the following effects: enhances the formation of a stable molecular conformation of the protein; enhances proper trafficking of the protein from the endoplasmic reticulum to another cellular location, preferably a native cellular location, so as to prevent endoplasmic reticulum-associated degradation of the protein; prevents aggregation of conformationally unstable or misfolded proteins; restores and/or enhances at least partial wild-type function, stability, and/or activity of the protein; and/or improves the phenotype or function of the cell harboring α-Gal A. Thus, a pharmacological chaperone for α-Gal A is a molecule that binds to α-Gal A, resulting in proper folding, trafficking, non-aggregation, and activity of α-Gal A. As used herein, this term includes but is not limited to active site-specific chaperones (ASSCs) which bind in the active site of the enzyme, inhibitors or antagonists, and agonists. In at least one embodiment, the pharmacological chaperone can be an inhibitor or antagonist of α-Gal A. As used herein, the term "antagonist" is intended to refer to any molecule that binds to α-Gal A and either partially or completely blocks, inhibits, reduces, or neutralizes an activity of α-Gal A. In at least one embodiment, the pharmacological chaperone is migalastat. Another non-limiting example of a pharmacological chaperone for α-Gal A is N-butyldeoxygalactonojirimycin (NB-DGJ) or a salt thereof.

As used herein, the term "active site" is intended to refer to a region of a protein that is associated with and necessary for a specific biological activity of the protein. In at least one embodiment, the active site can be a site that binds a substrate or other binding partner and contributes the amino acid residues that directly participate in the making and breaking of chemical bonds. Active sites in this invention can encompass catalytic sites of enzymes, antigen binding sites of antibodies, ligand binding domains of receptors, binding domains of regulators, or receptor binding domains of secreted proteins. The active sites can also encompass transactivation, protein-protein interaction, or DNA binding domains of transcription factors and regulators.

As used herein, the term "AUC" is intended to refer to a mathematical calculation to evaluate the body's total exposure over time to a given drug. In a graph plotting how concentration in the blood of a drug administered to a subject changes with time after dosing, the drug concentration variable lies on the y-axis and time lies on the x-axis. The area between the drug concentration curve and the x-axis for a designated time interval is the AUC ("area under the curve"). AUCs are used as a guide for dosing schedules and to compare the bioavailability of different drugs' availability in the body.

As used herein, the term "$C_{max}$" is intended to refer to the maximum plasma concentration of a drug achieved after administration to a subject.

As used herein, the term "$t_{max}$" is intended to refer to the time of the maximum plasma concentration of a drug achieved after administration to a subject.

As used herein, the term "t½" is intended to refer to the terminal elimination half-life.

As used herein, the term "volume of distribution" or "V" is intended to refer to the theoretical volume that would be necessary to contain the total amount of an administered drug at the same concentration that it is observed in the blood plasma, and represents the degree to which a drug is distributed in body tissue rather than the plasma. Higher values of V indicate a greater degree of tissue distribution. "Central volume of distribution" or "$V_c$" is intended to refer to the volume of distribution within the blood and tissues highly perfused by blood. "Peripheral volume of distribution" or "V2" is intended to refer to the volume of distribution within the peripheral tissue.

As used interchangeably herein, the terms "clearance", "systemic clearance" or "CL" are intended to refer to the volume of plasma that is completely cleared of an administered drug per unit time. "Peripheral clearance" is intended to refer to the volume of peripheral tissue that is cleared of an administered drug per unit time.

As used herein, the "therapeutically effective dose" and "effective amount" are intended to refer to an amount of α-galactosidase A and/or of a pharmacological chaperone (e.g., migalastat or a salt thereof) and/or of a combination thereof, which is sufficient to result in a therapeutic response in a subject. A therapeutic response may be any response that a user (for example, a clinician) will recognize as an effective response to the therapy, including any surrogate clinical markers or symptoms described herein and known in the art. Thus, in at least one embodiment, a therapeutic response can be an amelioration or inhibition of one or more symptoms or markers of Fabry disease such as those known in the art. Symptoms or markers of Fabry disease include but are not limited to decreased α-galactosidase A tissue activity; cloudiness of the cornea, burning sensations in hands and feet, skin blemishes (reddish-purple raised lesions), gastrointestinal problems, frequent bowel movements shortly after eating, telangiectasia, pain attacks, autonomic dysfunction, angina, EKG changes, paresthesia, lymphedema, skin lesions, angiokeratomas, corneal opacities, hypertension, renal failure, acroparesthesia, hypohidrosis, transient ischemic attacks, stroke, muscle weakness, hemiparesis, vertigo, hearing loss, tinnitus, nystagmus, head pain, hemiataxia, ataxia, leg swelling, cataracts, chronic airflow obstructions, dyspnea, coronary heart disease, myocardial infarction, arrhythmias, episodic diarrhea, nausea, vomiting, protein urea. It should be noted that a concentration of migalastat that has an inhibitory effect on α-galactosidase A may constitute an "effective amount" for purposes of this invention because of dilution (and consequent shift in binding due to the change in equilibrium), bioavailability and metabolism of migalastat upon administration in vivo.

As used herein, the term "enzyme replacement therapy" or "ERT" is intended to refer to the introduction of a non-native, purified enzyme into an individual having a deficiency in such enzyme. The administered protein can be obtained from natural sources or by recombinant expression. The term also refers to the introduction of a purified enzyme in an individual otherwise requiring or benefiting from administration of a purified enzyme. In at least one embodiment, such an individual suffers from enzyme insufficiency. The introduced enzyme may be a purified, recombinant enzyme produced in vitro, or a protein purified from isolated tissue or fluid, such as, for example, placenta or animal milk, or from plants.

As used herein, the term "combination therapy" is intended to refer to any therapy wherein two or more individual therapies are administered concurrently or consecutively. In at least one embodiment, the results of the combination therapy are enhanced as compared to the effect of each therapy when it is performed individually. Enhancement may include any improvement of the effect of the various therapies that may result in an advantageous result as compared to the results achieved by the therapies when performed alone. Enhanced effect or results can include a synergistic enhancement, wherein the enhanced effect is more than the additive effects of each therapy when performed by itself; an additive enhancement, wherein the enhanced effect is substantially equal to the additive effect of each therapy when performed by itself; or less than a synergistic effect, wherein the enhanced effect is lower than the additive effect of each therapy when performed by itself, but still better than the effect of each therapy when performed by itself. Enhanced effect may be measured by any means known in the art by which treatment efficacy or outcome can be measured. An enhanced effect can include a lessening in the frequency or severity of side-effects or off target activity of the therapeutic.

As used herein, the term "pharmaceutically acceptable" is intended to refer to molecular entities and compositions that are physiologically tolerable and do not typically produce untoward reactions when administered to a human. Preferably, as used herein, the term "pharmaceutically acceptable" means approved by a regulatory agency of the federal or a state government or listed in the U.S. Pharmacopeia or other generally recognized pharmacopeia for use in animals, and more particularly in humans.

As used herein, the term "carrier" is intended to refer to a diluent, adjuvant, excipient, or vehicle with which a compound is administered. Suitable pharmaceutical carriers are known in the art and, in at least one embodiment, are described in "Remington's Pharmaceutical Sciences" by E. W. Martin, 18th Edition, or other editions.

As used herein, the terms "subject" or "patient" are intended to refer to a human or non-human animal. In at least one embodiment, the subject is a mammal. In at least one embodiment, the subject is a human.

As used herein, the term "anti-drug antibody" is intended to refer to an antibody specifically binding to a drug administered to a subject and generated by the subject as at least part of a humoral immune response to administration of the drug to the subject. In at least one embodiment the drug is a therapeutic protein drug product. The presence of the anti-drug antibody in the subject can cause immune responses ranging from mild to severe, including but not limited to life-threatening immune responses which include but are not limited to anaphylaxis, cytokine release syndrome and cross-reactive neutralization of endogenous proteins mediating critical functions. In addition or alternatively, the presence of the anti-drug antibody in the subject can decrease the efficacy of the drug.

As used herein, the terms "about" and "approximately" are intended to refer to an acceptable degree of error for the quantity measured given the nature or precision of the measurements. For example, the degree of error can be indicated by the number of significant figures provided for the measurement, as is understood in the art, and includes but is not limited to a variation of ±1 in the most precise significant figure reported for the measurement.

Typical exemplary degrees of error are within 20 percent (%), preferably within 10%, and more preferably within 5% of a given value or range of values. Alternatively, and particularly in biological systems, the terms "about" and "approximately" can mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The term "concurrently" as used herein is intended to mean at the same time as or within a reasonably short period of time before or after, as will be understood by those skilled in the art. For example, if two treatments are administered concurrently with each other, one treatment can be administered before or after the other treatment, to allow for time needed to prepare for the later of the two treatments. Therefore "concurrent administration" of two treatments includes but is not limited to one treatment following the other by 20 minutes or less, about 20 minutes, about 15 minutes, about 10 minutes, about 5 minutes, about 2 minutes, about 1 minute or less than 1 minute.

Recombinant Human α-galactosidase A

Various embodiments of the present invention relate to recombinant human α-galactosidase A (rhα-Gal A) having unique carbohydrate profiles. Lysosomal enzyme replacement therapies generally rely on the binding of the enzyme to the cation independent mannose-6-phosphate receptor (CIMPR). Specifically, specific carbohydrates have affinity for the CIMPR, most notably M6P and particularly bis-M6P. Upon binding the CIMPR on the surface of a cell the enzyme is internalized and trafficked to the lysosome. The lysosome is the primary site of substrate accumulation and ultimately the site where enzyme is required to degrade the substrate.

Figure 1B:
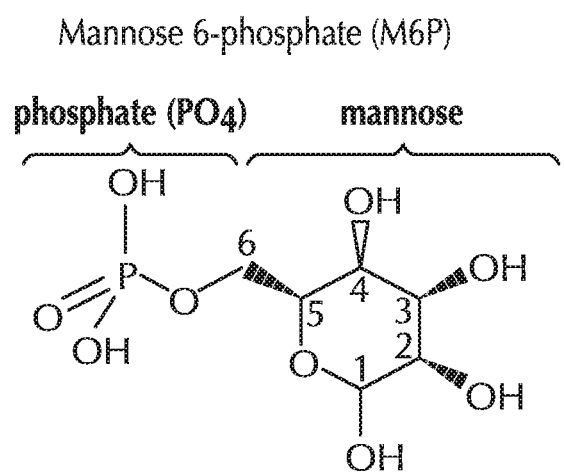
FIG. 1B shows the chemical structure of the M6P group.
Figures 2A, 2B:
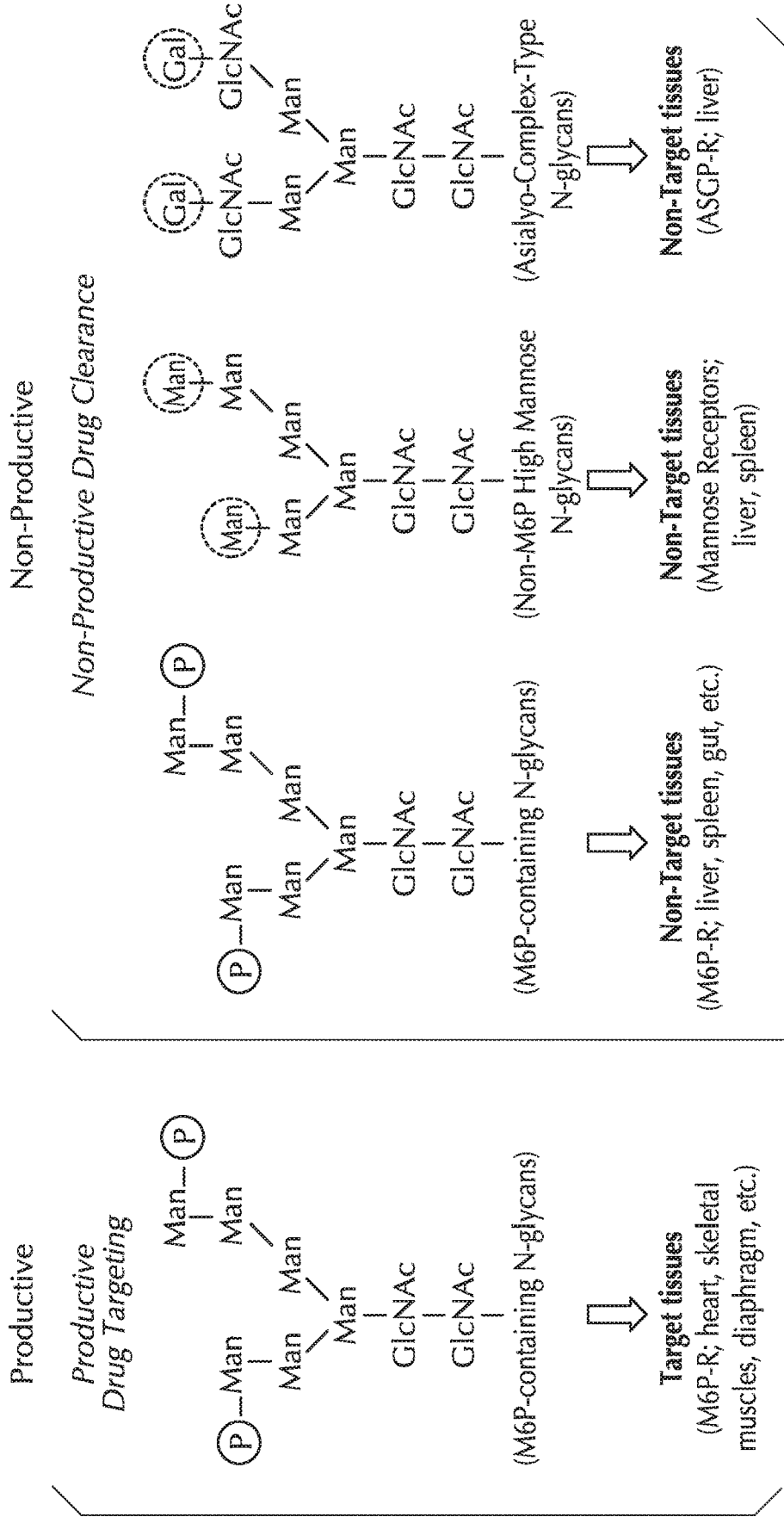
FIG. 2A shows productive targeting of rhα-Gal A via glycans bearing M6P to target tissues.
FIG. 2B shows non-productive drug clearance to non-target tissues (e.g. liver and spleen) or by binding of non-M6P glycans to non-target tissues.

There are four potential N-linked glycosylation sites on each chain of the rhα-Gal A homodimer, three of which are typically glycosylated. Since each glycosylation site is heterogeneous in the type of N-linked oligosaccharides (N-glycans) present, rhα-Gal A consists of a complex mixture of proteins with N-glycans having varying binding affinities for carbohydrate receptors. The rhα-Gal A that contains high mannose N-glycans having one M6P group (mono-M6P) binds to CIMPR with low (~7,000 nM) affinity while rhα-Gal A that contains two M6P groups on the same N-glycan (bis-M6P) bind with high (~2 nM) affinity. Representative structures for non-phosphorylated, mono-M6P, and bis-M6P glycans are shown by FIG. 1A. The M6P group is shown by FIG. 1B. Productive drug targeting is shown in FIG. 2A.

Recombinant proteins that do not have phosphorylated N-glycans lack affinity for the CIMPR. Non-phosphorylated high mannose glycans can also be cleared by the mannose receptor which results in nonproductive clearance of the ERT (FIG. 2B).

The other type of N-glycans, complex carbohydrates, which contain galactose and sialic acids, are also present on rhα-Gal A. Since complex N-glycans are not phosphorylated they have no affinity for CIMPR. Complex-type N-glycans with exposed galactose residues have moderate to high affinity for the asialoglycoprotein receptor on liver hepatocytes which leads to rapid non-productive clearance of rhα-Gal A (FIG. 2B). Asialoglycoprotein receptors and mannose receptors are highly expressed in liver cells and remove proteins from circulation that have exposed galactose and mannose (among others). One way to avoid this non-productive pathway of enzyme absorption through the asialoglycoprotein receptor is to block terminal sites with sialic acid. Proteins with terminal sialic acid are not subject to this non-productive pathway of removal and are thus available for targeting to the CIMPR.

Due to the inefficiency of delivering conventional enzyme replacement therapies to lysosomes, such therapies are often associated with problems, including generation of immune responses to rhα-Gal A. The most serious and most common adverse reactions reported with administration of existing ERT are infusion reactions. Infusion reactions can include: tachycardia, hypertension, throat tightness, chest pain/tightness, dyspnea, fever, chills/rigors, abdominal pain, pruritus, urticaria, nausea, vomiting, lip or ear edema, and rash.

Most patients receiving Fabrazyme (agalsidase beta) develop IgG antibodies, some developing IgE or skin test reactivity specific to the recombinant enzyme. To ameliorate infusion reactions some patients are pretreated with acetaminophen and/or an antihistamine or steroids. Another strategy to control infusion reactions is to increase the infusion time.

While different N-linked carbohydrates impart desirable characteristics to the ERT, there are a limited number of glycosylation sites. Thus, design of ERT is not simply a case of adding desirable carbohydrates because choosing one characteristic or one type of carbohydrate may be at the expense of another characteristic. Accordingly, the development of a novel ERT presents many difficulties. The rhα-Gal A enzymes described herein are the result of careful monitoring of the glycan map during ERT selection, expression, and purification to ensure minimized off-target clearance via the mannose and asialoglycoprotein receptors and maximal productive high affinity targeting to the lysosome via the CIMPR.

Through diligent study and extensive experimentation the inventors have balanced many protein characteristics to minimize non-productive clearance of rhα-Gal A and efficiently target the rhα-Gal A to lysosomes. Among the characteristics that have been applied to the rhα-Gal A described herein are: high production of protein, phosphorylation, terminal sialic acid capping of complex-type glycans, low content of neutral glycans, high enzyme activity, and stability in the blood.

In at least one embodiment, the rhα-Gal A is expressed in Chinese hamster ovary (CHO) cells and comprises an increased content of N-glycan units bearing one or more M6P residues when compared to a content of N-glycan units bearing one or more M6P residues of Replagal (agalsidase alfa) or Fabrazyme (agalsidase beta). The rhα-Gal A as described herein has been shown to bind CIMPR with high affinity ($K_D$~3 nM). The rhα-Gal A as described herein was characterized in vivo and shown to have a longer apparent plasma half-life ($t^{1/2}$~13.2 min) than Fabrazyme (agalsidase beta) ($t^{1/2}$~7.8 min).

In at least one embodiment, the rhα-Gal A has both low levels of neutral glycans (e.g. 1.5-6%) and high levels of bis-phosphorylated oligosaccharides (e.g. 7%-14%). In at least one other embodiment, the rhα-Gal A has very high levels of mono-phosphorylated oligosaccharides (e.g. greater than 25%) and very high levels of bis-phosphorylated oligosaccharides (e.g. greater than 12%). The rhα-Gal A may also have very high levels of oligosaccharides containing sialic acid (e.g. greater than 50%). In these and other embodiments, the ERT has minimal non-productive off-target clearance via the mannose and asialoglycoprotein receptors while maximizing productive high affinity targeting to the lysosome via the CIMPR.

In at least one embodiment, the rhα-Gal A is a homodimer. In at least one embodiment, the rhα-Gal A is initially expressed as having the full-length 429 amino acid sequence of wild-type α-Gal A as set forth in SEQ ID NO: 1 and is associated with GenBank accession number NP_00160.1. The full-length rhα-Gal A undergoes intracellular processing that removes a portion of the amino acids, e.g. the first 31 amino acids. Accordingly, the rhα-Gal A that is produced and secreted by the host cell can have a shorter amino acid sequence than the rhα-Gal A that is initially expressed within the cell. In at least one embodiment, the shorter protein can have the amino acid sequence set forth in SEQ ID NO: 2, which only differs from SEQ ID NO: 1 in that the first 31 amino acids comprising the signal peptide have been removed, thus resulting in a protein having 398 amino acids. In another embodiment each chain is approximately 49 kDa before removal of the signal peptide and approximately 45 kDa after removal of the signal peptide, not accounting for the additional weight of glycans. Other variations in the number of amino acids is also possible, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2. In some embodiments, the rhα-Gal A product includes a mixture of rhα-Gal A molecules having different amino acid lengths.

In at least one embodiment, the homodimer has 796 amino acids with a molecular weight of approximately 91 kDa, not accounting for the additional weight of glycans.

```
                                                        SEQ ID NO: 1
        Met Gln Leu Arg Asn Pro Glu Leu His Leu Gly Cys Ala Leu Ala Leu

Arg Phe Leu Ala Leu Val Ser Trp Asp Ile Pro Gly Ala Arg Ala Leu

Asp Asn Gly Leu Ala Arg Thr Pro Thr Met Gly Trp Leu His Trp Glu

Arg Phe Met Cys Asn Leu Asp Cys Gln Glu Glu Pro Asp Ser Cys Ile

Ser Glu Lys Leu Phe Met Glu Met Ala Glu Leu Met Val Ser Glu Gly

Trp Lys Asp Ala Gly Tyr Glu Tyr Leu Cys Ile Asp Asp Cys Trp Met

Ala Pro Gln Arg Asp Ser Glu Gly Arg Leu Gln Ala Asp Pro Gln Arg

Phe Pro His Gly Ile Arg Gln Leu Ala Asn Tyr Val His Ser Lys Gly

Leu Lys Leu Gly Ile Tyr Ala Asp Val Gly Asn Lys Thr Cys Ala Gly

Phe Pro Gly Ser Phe Gly Tyr Tyr Asp Ile Asp Ala Gln Thr Phe Ala

Asp Trp Gly Val Asp Leu Leu Lys Phe Asp Gly Cys Tyr Cys Asp Ser

Leu Glu Asn Leu Ala Asp Gly Tyr Lys His Met Ser Leu Ala Leu Asn

Arg Thr Gly Arg Ser Ile Val Tyr Ser Cys Glu Trp Pro Leu Tyr Met

Trp Pro Phe Gln Lys Pro Asn Tyr Thr Glu Ile Arg Gln Tyr Cys Asn

His Trp Arg Asn Phe Ala Asp Ile Asp Asp Ser Trp Lys Ser Ile Lys

Ser Ile Leu Asp Trp Thr Ser Phe Asn Gln Glu Arg Ile Val Asp Val

Ala Gly Pro Gly Gly Trp Asn Asp Pro Asp Met Leu Val Ile Gly Asn

Phe Gly Leu Ser Trp Asn Gln Gln Val Thr Gln Met Ala Leu Trp Ala

Ile Met Ala Ala Pro Leu Phe Met Ser Asn Asp Leu Arg His Ile Ser

Pro Gln Ala Lys Ala Leu Leu Gln Asp Lys Asp Val Ile Ala Ile Asn

Gln Asp Pro Leu Gly Lys Gln Gly Tyr Gln Leu Arg Gln Gly Asp Asn

Phe Glu Val Trp Glu Arg Pro Leu Ser Gly Leu Ala Trp Ala Val Ala

Met Ile Asn Arg Gln Glu Ile Gly Gly Pro Arg Ser Tyr Thr Ile Ala

Val Ala Ser Leu Gly Lys Gly Val Ala Cys Asn Pro Ala Cys Phe Ile

Thr Gln Leu Leu Pro Val Lys Arg Lys Leu Gly Phe Tyr Glu Trp Thr

Ser Arg Leu Arg Ser His Ile Asn Pro Thr Gly Thr Val Leu Leu Gln

Leu Glu Asn Thr Met Gln Met Ser Leu Lys Asp Leu Leu

SEQ ID NO: 2
        Leu Asp Asn Gly Leu Ala Arg Thr Pro Thr Met Gly Trp Leu His Trp

Glu Arg Phe Met Cys Asn Leu Asp Cys Gln Glu Glu Pro Asp Ser Cys
```

-continued

Ile Ser Glu Lys Leu Phe Met Glu Met Ala Glu Leu Met Val Ser Glu
Gly Trp Lys Asp Ala Gly Tyr Glu Tyr Leu Cys Ile Asp Asp Cys Trp
Met Ala Pro Gln Arg Asp Ser Glu Gly Arg Leu Gln Ala Asp Pro Gln
Arg Phe Pro His Gly Ile Arg Gln Leu Ala Asn Tyr Val His Ser Lys
Gly Leu Lys Leu Gly Ile Tyr Ala Asp Val Gly Asn Lys Thr Cys Ala
Gly Phe Pro Gly Ser Phe Gly Tyr Tyr Asp Ile Asp Ala Gln Thr Phe
Ala Asp Trp Gly Val Asp Leu Leu Lys Phe Asp Gly Cys Tyr Cys Asp
Ser Leu Glu Asn Leu Ala Asp Gly Tyr Lys His Met Ser Leu Ala Leu
Asn Arg Thr Gly Arg Ser Ile Val Tyr Ser Cys Glu Trp Pro Leu Tyr
Met Trp Pro Phe Gln Lys Pro Asn Tyr Thr Glu Ile Arg Gln Tyr Cys
Asn His Trp Arg Asn Phe Ala Asp Ile Asp Asp Ser Trp Lys Ser Ile
Lys Ser Ile Leu Asp Trp Thr Ser Phe Asn Gln Glu Arg Ile Val Asp
Val Ala Gly Pro Gly Gly Trp Asn Asp Pro Asp Met Leu Val Ile Gly
Asn Phe Gly Leu Ser Trp Asn Gln Gln Val Thr Gln Met Ala Leu Trp
Ala Ile Met Ala Ala Pro Leu Phe Met Ser Asn Asp Leu Arg His Ile
Ser Pro Gln Ala Lys Ala Leu Leu Gln Asp Lys Asp Val Ile Ala Ile
Asn Gln Asp Pro Leu Gly Lys Gln Gly Tyr Gln Leu Arg Gln Gly Asp
Asn Phe Glu Val Trp Glu Arg Pro Leu Ser Gly Leu Ala Trp Ala Val
Ala Met Ile Asn Arg Gln Glu Ile Gly Gly Pro Arg Ser Tyr Thr Ile
Ala Val Ala Ser Leu Gly Lys Gly Val Ala Cys Asn Pro Ala Cys Phe
Ile Thr Gln Leu Leu Pro Val Lys Arg Lys Leu Gly Phe Tyr Glu Trp
Thr Ser Arg Leu Arg Ser His Ile Asn Pro Thr Gly Thr Val Leu Leu
Gln Leu Glu Asn Thr Met Gln Met Ser Leu Lys Asp Leu Leu

SEQ ID NO: 3
ATGCAGCTGAGGAATCCCGAGCTCCACCTGGGCTGTGCTCTGGCTCTGCGGTTCCTGGCCCT
CGTGTCCTGGGACATCCCTGGCGCTAGGGCCCTCGATAACGGACTGGCCCGGACCCCCACAA
TGGGATGGCTCCACTGGGAAAGGTTCATGTGCAATCTGGACTGTCAGGAGGAACCCGACTCC
TGCATCAGCGAAAAGCTCTTCATGGAGATGGCCGAGCTGATGGTGAGCGAGGGCTGGAAGGA
CGCCGGCTACGAGTATCTGTGCATCGATGACTGCTGGATGGCCCCTCAAAGGGACTCCGAAG
GCAGGCTGCAGGCTGATCCCCAAAGGTTTCCCCACGGAATCCGGCAGCTCGCCAACTACGTG
CATTCCAAGGGCCTCAAGCTCGGCATCTACGCCGACGTGGGCAACAAAACATGCGCCGGATT
CCCCGGCAGCTTCGGCTACTACGACATCGACGCCCAGACATTCGCTGATTGGGGAGTGGACC
TGCTGAAGTTCGACGGCTGTTACTGCGATTCCCTGGAAAACCTGGCCGACGGCTACAAACAC
ATGTCCCTCGCCCTGAACCGGACAGGCAGGTCCATCGTGTACAGCTGCGAGTGGCCCCTGTA
CATGTGGCCTTTCCAGAAGCCCAACTACACAGAGATCAGGCAGTACTGCAACCACTGGAGGA
ACTTCGCTGACATCGACGACTCCTGGAAGAGCATCAAGAGCATCCTGGACTGGACCAGCTTC
AACCAGGAGAGGATCGTGGACGTGGCTGGACCCGGAGGCTGGAACGACCCCGATATGCTGGT
GATTGGCAACTTCGGACTGAGCTGGAACCAGCAGGTGACCCAGATGGCCCTGTGGGCCATTA
TGGCCGCTCCCCTGTTCATGTCCAACGACCTGAGGCACATCAGCCCCCAGGCCAAGGCTCTG
CTGCAGGACAAGGATGTGATCGCCATCAACCAGGACCCCCTGGGCAAGCAGGGCTACCAGCT
GAGGCAAGGAGATAACTTCGAGGTGTGGGAGAGGCCCCTGTCCGGACTGGCTTGGGCCGTGG

-continued

```
CCATGATCAATCGGCAGGAGATCGGCGGACCCCGGTCCTACACCATTGCTGTGGCCAGCCTG

GGAAAAGGAGTCGCCTGCAACCCCGCCTGCTTCATTACCCAGCTGCTCCCCGTGAAGCGGAA

GCTGGGCTTCTATGAGTGGACCAGCAGGCTGAGGTCCCATATCAATCCTACCGGCACCGTCC

TCCTCCAGCTCGAGAATACCATGCAGATGAGCCTCAAGGATCTGCTGTGA
```

In at least one embodiment, the rhα-Gal A undergoes post-translational and/or chemical modifications at one or more amino acid residues in the protein. For example, methionine and tryptophan residues can undergo oxidation. As another example, the N-terminal glutamine can form pyro-glutamate. As another example, asparagine residues can undergo deamidation to aspartic acid. As yet another example, aspartic acid residues can undergo isomerization to iso-aspartic acid. As yet another example, unpaired cysteine residues in the protein can form disulfide bonds with free glutathione and/or cysteine. Accordingly, in some embodiments the enzyme is initially expressed as having an amino acid sequence as set forth in SEQ ID NO: 1, SEQ ID NO: 2 or as encoded by SEQ ID NO: 3, and the enzyme undergoes one or more of these post-translational and/or chemical modifications. Such modifications are also within the scope of the present disclosure.

In various embodiments, the rhα-Gal A is a variant that is at least 90%, 95%, 98%, 99% or 99.5% identical to SEQ ID NO: 1 or SEQ ID NO: 2. These variant α-galactosidase A amino acid sequences may contain deletions, substitutions and/or insertions relative to SEQ ID NO: 1 or SEQ ID NO: 2, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2.

Polynucleotide sequences encoding Gla and such variant human Glas are also contemplated and may be used to recombinantly express rhα-Gal A according to the invention.

The rhα-Gal A is preferably produced by CHO cells. DNA constructs which may express allelic variants of α-galactosidase A or other variant α-galactosidase amino acid sequences such as those that are at least 90%, 95%, 98%, 99% or 99.5% identical to SEQ ID NO: 1 or SEQ ID NO: 2, may be constructed and expressed in CHO cells. These variant α-galactosidase A amino acid sequences may contain deletions, substitutions and/or insertions relative to SEQ ID NO: 1 or SEQ ID NO: 2, such as having 1, 2, 3, 4, 5, 6, 7, 8, 9, 10, 11, 12, 13, 14, 15 or more deletions, substitutions and/or insertions relative to the amino acid sequence described by SEQ ID NO: 1 or SEQ ID NO: 2. The DNA constructs can be at least 80%, 85%, 90%, 95%, 98%, 99% or 99.5% identical to SEQ ID NO: 3. Those of skill in the art can select alternative vectors suitable for transforming CHO cells for production of such variant α-galactosidase amino acid sequences.

Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 90%, 95%, 98% or 99% identity to specific polypeptides described herein and preferably exhibiting substantially the same functions, as well as polynucleotide encoding such polypeptides, are contemplated. Unless otherwise indicated a similarity score will be based on use of BLOSUM62. When BLASTP is used, the percent similarity is based on the BLASTP positives score and the percent sequence identity is based on the BLASTP identities score. BLASTP "Identities" shows the number and fraction of total residues in the high scoring sequence pairs which are identical; and BLASTP "Positives" shows the number and fraction of residues for which the alignment scores have positive values and which are similar to each other. Amino acid sequences having these degrees of identity or similarity or any intermediate degree of identity of similarity to the amino acid sequences disclosed herein are contemplated and encompassed by this disclosure. The polynucleotide sequences of similar polypeptides are deduced using the genetic code and may be obtained by conventional means, in particular by reverse translating its amino acid sequence using the genetic code.

Preferably, no more than 70, 65, 60, 55, 45, 40, 35, 30, 25, 20, 15, 10, or 5% of the total rhα-Gal A molecules lack an N-glycan unit bearing one or more M6P residues or lacks a capacity to bind to the CIMPR. Alternatively, 30, 35, 40, 45, 50, 55, 60, 65, 70, 75, 80, 85, 90, 95, 99%, <100% or more of the rhα-Gal A molecules comprise at least one N-glycan unit bearing one or more M6P residues or has the capacity to bind to CIMPR.

The rhα-Gal A molecules may have 1, 2, 3 4, 5 or 6 M6P groups on their glycans per subunit or 1, 2, 3, 4, 5, 6, 7, 8, 9, 10, 11 or 12 M6P groups per homodimer. For example, only one N-glycan on a rhα-Gal A molecule may bear M6P (mono-phosphorylated), a single N-glycan may bear two M6P groups (bis-phosphorylated), or two different N-glycans on the same rhα-Gal A molecule may each bear single M6P groups. The rhα-Gal A molecules may also have N-glycans bearing no M6P groups. In another embodiment, on average the N-glycans contain greater than 2 mol/mol of M6P and greater than 4 mol/mol sialic acid, such that the rhα-Gal A comprises on average at least 2 moles of M6P residues per mole of rhα-Gal A and at least 4 moles of sialic acid per mole of rhα-Gal A homodimer. On average at least about 3, 4, 5, 6, 7, 8, 9, 10, 11, 12, 13, 14, 15, 20, 25, 30 or 35% of the total glycans on the rhα-Gal A may be in the form of a mono-M6P glycan, and on average, at least about 0.5, 1, 1.5, 2.0, 2.5, 3.0, 4, 5, 6, 7, 8, 9, 10, 11, 12, 13, 14, 15, 16, 17, 18, 19 or 20% of the total glycans on the rhα-Gal A are in the form of a bis-M6P glycan and on average less than about 75, 70, 65, 60, 55, 50, 45, 40, 35, 30 or 25% of the total glycans on the rhα-Gal A contains no phosphorylated glycan binding to CIMPR.

The rhα-Gal A may have an average content of N glycans carrying M6P ranging from 0.5 to 6.0 mol/mol rhα-Gal A homodimer or any intermediate value of subrange including 0.5, 1.0, 1.5, 2.0, 2.5, 3.0, 3.5, 4.0, 4.5, 5.0, 5.5, or 6.0 mol/mol rhα-Gal A homodimer. The rhα-Gal A can be fractionated to provide rhα-Gal A preparations with different average numbers of mono-M6P-bearing or bis-M6P-bearing glycans thus permitting further customization of rhα-Gal A targeting to the lysosomes in target tissues by selecting a particular fraction or by selectively combining different fractions.

Up to 60% of the N-glycans on the rhα-Gal A may be fully sialylated, for example, up to 10%, 20%, 30%, 40%, 50% or 60% of the N-glycans may be fully sialylated. In some embodiments from 4 to 20% of the total N-glycans are fully sialylated. In other embodiments no more than 5%, 10%, 15%, 20%, 25% or 30% of N-glycans on the rhα-Gal A carry sialic acid and a terminal galactose residue (Gal). This range includes all intermediate values and subranges, for example, 7 to 30% of the total N-glycans on the rhα-Gal A can carry sialic acid and terminal galactose. In yet other embodiments, no more than 5, 10, 15, 16, 17, 18, 19 or 20% of the N-glycans on the rhα-Gal A have a terminal galactose only and do not contain sialic acid. This range includes all intermediate values and subranges, for example, from 8 to 19% of the total N-glycans on the rhα-Gal A in the composition may have terminal galactose only and do not contain sialic acid.

In other embodiments of the invention, 40, 45, 50, 55 or 60% of the total N glycans on the rhα-Gal A are complex-type N-glycans; or no more than 1, 2, 3, 4, 5, 6, 7% of total N-glycans on the rhα-Gal A are hybrid-type N-glycans; no more than 5, 10, or 15% of the high mannose-type N-glycans on the rhα-Gal A are non-phosphorylated; at least 5, 10, 15, 20, 25, 30 or 35% of the high mannose-type N-glycans on the rhα-Gal A are mono-M6P phosphorylated; and/or at least 1, 2, 3, 4, 5, 6 or 7% of the high mannose-type N-glycans on the rhα-Gal A are bis-M6P phosphorylated. These values include all intermediate values and subranges. The rhα-Gal A may meet one or more of the content ranges described above.

In one or more embodiments, the rhα-Gal A will bear, on average, 2.0 to 9.0 moles of sialic acid residues per mole of rhα-Gal A. This range includes all intermediate values and subranges including 2.0, 2.5, 3.0, 3.5, 4.0, 4.5, 5.0, 5.5, 6.0, 6.5, 7.0, 7.5, 8.0, 8.5 and 9.0 mol residues/mol rhα-Gal A homodimer. Without being bound by theory, it is believed that the presence of N-glycan units bearing sialic acid residues may prevent non-productive clearance of the rhα-Gal A by asialoglycoprotein receptors.

In one or more embodiments, at least 10, 11, 12, 13, 14, 15, 16, 17, 18, 19, 20, 21, 22, 23, 24 or 25% of the total N-glycans on the rhα-Gal A contain a single sialic acid residue.

In one or more embodiments, at least 10, 11, 12, 13, 14, 15, 16, 17, 18, 19, 20, 21, 22, 23, 24, 25, 26, 27, 28, 29 or 30% of the total N-glycans on the rhα-Gal A contain two sialic acid residues. These values include all intermediate values and subranges.

In one or more embodiments, at least 30, 31, 32, 33, 34, 35, 36, 37, 38, 39, 40, 41, 42, 43, 44, 45, 46, 47, 48, 49 or 50% of the total N-glycans on the rhα-Gal A contain one or two sialic acid residues. These values include all intermediate values and subranges.

In one or more embodiments, at least 5, 6, 7, 8, 9, 10, 11, 12, 13, 14, 15, 16, 17, 18, 19 or 20% of the total N-glycans on the rhα-Gal A contain three sialic acid residues. In one or more embodiments, less than 30, 25, 20, 19, 18, 17, 16, 15, 14, 13, 12, 11 or 10% of the total N-glycans on the rhα-Gal A contain three sialic acid residues. These values include all intermediate values and subranges.

In one or more embodiments, at least 0.5, 1, 1.5, 2, 2.5, 3, 3.5, 4, 4.5 or 5% of the total N-glycans on the rhα-Gal A contain four sialic acid residues. In one or more embodiments, less than 10, 9, 8, 7, 6, 5, 4.5, 4, 3.5, 3, 2.5, 2, 1.5, 1 or 0.5% the total N-glycans on the rhα-Gal A contain four sialic acid residues. These values include all intermediate values and subranges.

In one or more embodiments, less than 2.0, 2.5, 3.0, 3.5, 4.0, 4.5, 5.0, 5.5, 6.0, 6.5, 7.0, 7.5, 8, 9, 10, 11, 12, 13, 14, 15, 20 or 25% of the total N-glycans on the rhα-Gal A are neutral glycans.

In one or more embodiments, the rhα-Gal A has M6P and/or sialic acid units at certain N-glycosylation sites of the recombinant human lysosomal protein. For example, there are three N-linked glycosylation sites on each of the two identical subunits of rhα-Gal A. There are four potential glycosylation sites corresponding to the positions of SEQ ID NO: 1: Asn-139, Asn-192, Asn-215 and Asn-408. Similarly, for mature peptide of SEQ ID NO: 2, these potential glycosylation sites are at positions: Asn-108, Asn-161, Asn-184 and Asn-377. Typically, only the first three sites are glycosylated. Other variants of rhα-Gal A can have similar glycosylation sites, depending on the location of asparagine residues. Generally, sequences of ASN-X-SER or ASN-X-THR in the protein amino acid sequence indicate potential glycosylation sites, with the exception that X cannot be HIS or PRO.

The inventors have found that rhα-Gal A having superior ability to target CIMPR and cellular lysosomes as well as glycosylation patterns that reduce its non-productive clearance in vivo can be produced CHO cells. These cells can express rhα-Gal A with significantly higher levels of N-glycan units bearing one or more M6P residues than conventional recombinant human α-galactosidase A products such as Replagal (agalsidase alfa) or Fabrazyme (agalsidase beta). The rhα-Gal A produced by these cells, for example, as exemplified in the Examples below, has significantly more M6P and bis-M6P N-glycan residues and/or significantly more sialic acid N-glycan residues and/or significantly less neutral N-glycans than conventional α-galactosidase A, such as Replagal (agalsidase alfa) or Fabrazyme (agalsidase beta). Without being bound by theory, it is believed that this unique glycosylation allows the rhα-Gal A enzyme to be taken up more effectively into target cells, and therefore to be cleared from the circulation more efficiently than other recombinant human α-galactosidase A molecules, such as for example, Replagal (agalsidase alfa) or Fabrazyme (agalsidase beta), which has a much lower M6P and bis-M6P content and/or higher content of neutral glycans. The rhα-Gal A as described herein has been shown to efficiently bind to CIMPR and be efficiently taken up by kidney and cardiac muscle and to have a glycosylation pattern that provides a favorable pharmacokinetic profile and reduces non-productive clearance in vivo.

It is also contemplated that the unique glycosylation of the rhα-Gal A as described herein can contribute to a reduction of the immunogenicity of the rhα-Gal A compared to, for example, Replagal (agalsidase alfa) or Fabrazyme (agalsidase beta). As will be appreciated by those skilled in the art, glycosylation of proteins with conserved mammalian sugars generally enhances product solubility and diminishes product aggregation and immunogenicity. Glycosylation indirectly alters protein immunogenicity by minimizing protein aggregation as well as by shielding immunogenic protein epitopes from the immune system (Guidance for Industry—Immunogenicity Assessment for Therapeutic Protein Products, US Department of Health and Human Services, Food and Drug Administration, Center for Drug Evaluation and Research, Center for Biologics Evaluation and Research, August 2014). Therefore, in at least one embodiment, administration of the rhα-Gal A does not induce anti-drug antibodies. In at least one embodiment, administration of the rhα-Gal A induces a lower incidence of anti-drug antibodies in a subject than the level of anti-drug antibodies induced by administration of Replagal (agalsidase alfa) or Fabrazyme (agalsidase beta).

Methods of Generating Cell Lines for Producing the rhα-Gal A

The rhα-Gal A having high content of mono-M6P, high content of bis-M6P, high content of sialic acid and/or low content neutral glycans can be produced by transforming host cells with a DNA construct that encodes Gla. Suitable host cells include mammalian cells, for example CHO cells such as CHO-DG44 cells, CHO-K1 cells, and CHO-DXB11 cells. While CHO cells have been previously used to make recombinant human α-galactosidase A, it was not appreciated that transformed CHO cells could be created and cultured in a way that would produce recombinant enzyme having a high content of mono-M6P, bis-M6P and sialic acid-containing glycans and/or have a low content of neutral glycans.

Suitable vectors for transfecting host cells can include DNA constructs that are at least 80%, 85%, 90%, 95%, 98%, 99%. 99.5% or 100% identical to SEQ ID NO: 3. Alternative DNA constructs may also be used to produce amino acid sequences that are at least 90%, 95%, 98%, 99%, 99.5% or 100% identical to SEQ ID NO: 1 or SEQ ID NO: 2. Exemplary vectors include, but are not limited to, plasmids. The vector(s) can include other sequences such as promoter sequences and/or sequences encoding selection genes. Promoter sequences include, but are not limited to, simian virus 40 (SV40) and human cytomegalovirus (CMV) promoter genes. Selection genes include, but are not limited to, Zeocin resistance genes, ampicillin resistance genes, blasticidin S-resistance genes and dihydrofolate reductase genes. Other promoter sequences and selection genes are known in the art. Multiple vectors may also be used in a transfection, e.g. dual vector transfections.

Multiple transfections may be performed in host cells to provide separate pools for evaluation. These pools may be evaluated for specific properties, such as cell culture viability, rhα-Gal A expression and/or glycan content such as mono-M6P, bis-M6P, sialic acid and/or neutral glycan content. These properties can be evaluated throughout culturing such as 1, 2, 3, 4, 5, 6, 7, 8, 9, 10, 15, 20, etc. days after transfection.

Pools having desirable characteristics can be selected for generating clones, and these clones can be further evaluated according to similar criteria (e.g. cell culture viability, rhα-Gal A expression and/or glycan content). Selected clones can also be evaluated in other conditions, on different scales (e.g. spin tube or bioreactor scales), or at different time points during culturing.

Methods of generating expression vectors, generating cell lines, and producing recombinant cell lines are commonly used, but others may be used according to the knowledge of the skilled artisan. For example, such methods are described in: U.S. Patent App. Pub. No. US2016/0264953; International Publication No. WO 2014/137903; Brown et al., *Trends in Biotechnology*, vol. 25, Issue 9, September 2007, pp. 425-432; Tong et al., *J. Biol. Chem.*, 264(14), 7970-7975 (1989); Matsuura et al, *Glycobiology*, 8(4): 329-339 (1998); and Dittermer et al., *Biochem. J.*, 340:729-736 (1999), which are herein incorporated by reference in their entireties.

Expression Vectors

Also provided herein are expression vectors containing a sequence (e.g., cDNA) encoding recombinant human α-galactosidase-A proteins of the present invention. For example, the expression vector can include a sequence (e.g., a cDNA) encoding recombinant human α-galactosidase-A protein that is at least 90% identical (e.g., at least 90%, 92%, 94%, 96%, 98%, 99% or 100% identical) to SEQ ID NO: 1 or SEQ ID NO: 2. In addition to that sequence, the expression vectors can include a promoter (and optionally one or more enhancer sequences) operably linked to the 5' end of the sequence (e.g., cDNA) encoding the recombinant human α-galactosidase-A protein. The expression vectors can include a sequence encoding a peptide of human CD52 protein with a TTG start codon operably linked to the 5' end of the sequence (e.g., cDNA) encoding the recombinant protein and a sequence encoding a poly(A) recognition site operably linked to the 3' end of the sequence (e.g., cDNA) encoding the recombinant protein. The expression vectors can include a sequence (e.g., cDNA) encoding a mammalian selection marker (e.g., a human or dog synthetase protein) and a promoter sequence operably linked to the 5' end of the sequence (e.g., cDNA) encoding the mammalian selection marker, and optionally, a SV40 early intron sequence and poly(A) signal sequence that are both operably linked to the 3' end of the sequence (e.g., cDNA) encoding the mammalian selection gene. Expression vectors can include one or more (e.g., two or three) of: a prokaryotic promoter sequence that is operably linked to the 5' end of the sequence encoding a prokaryotic selection gene (e.g., an ampicillin resistance gene), a prokaryotic origin of replication sequence, and a eukaryotic origin of replication sequence.

Non-limiting examples of promoter sequences (and optionally one or more enhancer sequence(s)) that can be operably linked to the sequence (e.g., cDNA) encoding recombinant human α-galactosidase-A protein include: Simian Virus 40 (SV 40) early promoter, ribosomal protein 21 (rpS21) promoter, hamster β-actin promoter, cytomegalovirus (CMV) promoter (e.g., CMV immediate early promoter (see, e.g., Teschendorf et al., Anticancer Res. 22:3325-3330, 2002), ubiquitin C (UBC) promoter, elongation factor 1-a (EF1A) promoter, phosphoenolpyruvate carboxykinase (PCK) promoter, 1E2 promoter/enhancer region from mouse CMV (see, e.g., Chatellard et al., Biotechnol. Bioeng. 96: 106-117, 2007), and chicken β-actin promoter. Additional non-limiting examples of human gene promoters that can be used in any of the expression vectors described herein are described in the Mammalian Promoter Database (Wistar Institute website at mrpombdb.wister.upenn.edu). Additional examples of mammalian promoter sequences that can be used in the expression vectors are known in the art. One non-limiting example of a promoter and an enhancer that can be used in an expression plasmid is a chicken β-actin promoter with a CMV enhancer (known in the art as a CAGG promoter). The expression vectors provided herein can include a rpS21 promoter, a hamster β-actin promoter, or a SV 40 early promoter sequence operably linked to the 5' end of the sequence (e.g., cDNA) encoding human recombinant α-galactosidase-A protein, a sequence encoding a peptide of human CD52 protein with a TTG start codon operably linked to the 5' end of the nucleic acid (e.g., cDNA) encoding human recombinant α-galactosidase-A protein (e.g., any of the nucleic acids encoding human recombinant α-galactosidase-A protein described herein), and a sequence containing a poly(A) recognition site operably linked to a 3' end of the nucleic acid sequence encoding recombinant human α-galactosidase-A protein.

Non-limiting examples of poly(A) recognition site sequences are bovine growth hormone poly(A) recognition site. The structural features of a human poly(A) recognition site are described in Nunes et al., EMBO J 29:1523-1536, 2010. Additional poly(A) recognitions sites are well-known in the art.

In some examples, the expression vector includes a hamster β-actin promoter and sequence encoding a peptide of human CD52 protein with a TTG start codon both operably linked to the 5' end of the sequence (e.g., cDNA) encoding the recombinant human α-galactosidase-A protein, and a SV 40 early intron and poly(A) recognition sequence operably linked to the 3' end of the sequence (e.g., cDNA) encoding the recombinant human α-galactosidase-A protein.

Some expression vectors can include a sequence encoding a mammalian selection gene. Non-limiting examples of mammalian selection genes include: dihydrofolate reductase gene, hydromycin resistance genes, neomycin resistance genes, blasticidin resistance genes, zeocin resistance genes, glutamine synthetase genes, dihydrofolate resistance genes, and hypoxanthine-guanine phosphoribosyltransferase genes. Examples of sequences encoding these mammalian selection genes are known in the art. The 5' end of the sequence encoding the mammalian selection gene can be operably linked to a promoter (e.g., any of the exemplary promoters described herein or known in the art).

Some expression vectors (e.g., any of the expression vector described herein) can include a mammalian origin of replication sequence and/or a prokaryotic origin of replication sequence. Mammalian origin of replication sequences are known in the art (e.g., Todorovic et al., Front. Biosci. 4:D859-D568, 1999; Aladjem, Front. Biosci. 9:2540-2547, 2004; Hamlin, Bioessays 14:651-659, 1992). Prokaryotic origin of replication sequences are also known in the art (e.g., Marczynski et al., Curr. Opin. Genet. Dev. 3:775-782, 1993).

Figure 3:
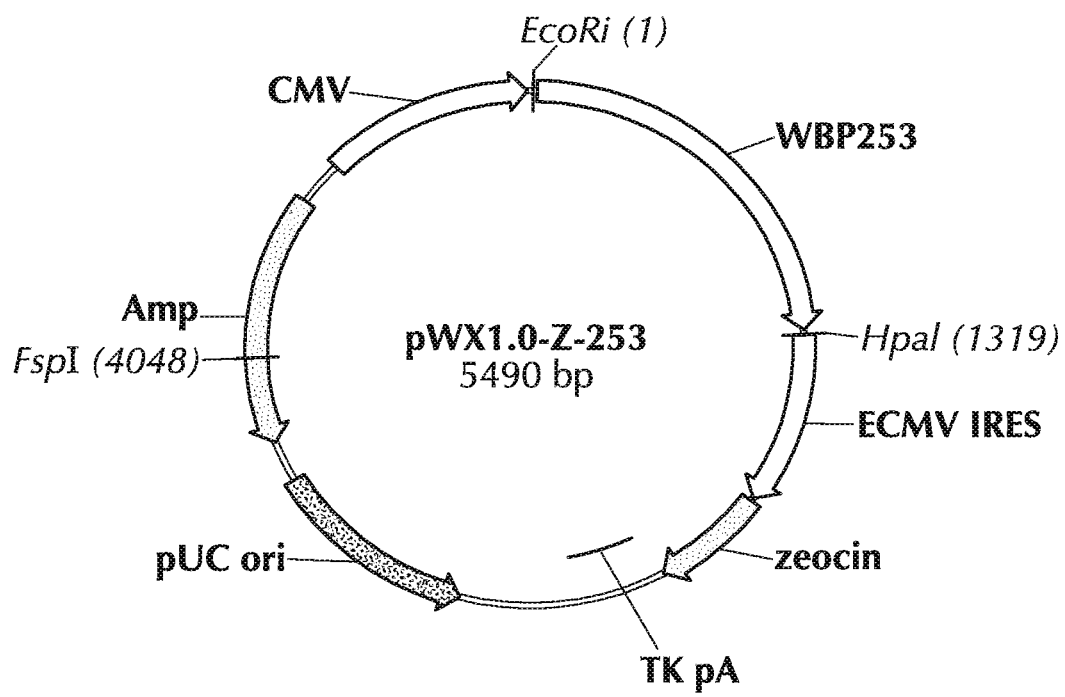
FIG. 3 shows the dual expression vectors used to transfect a suspension CHO-K1 culture.
Figure 3:
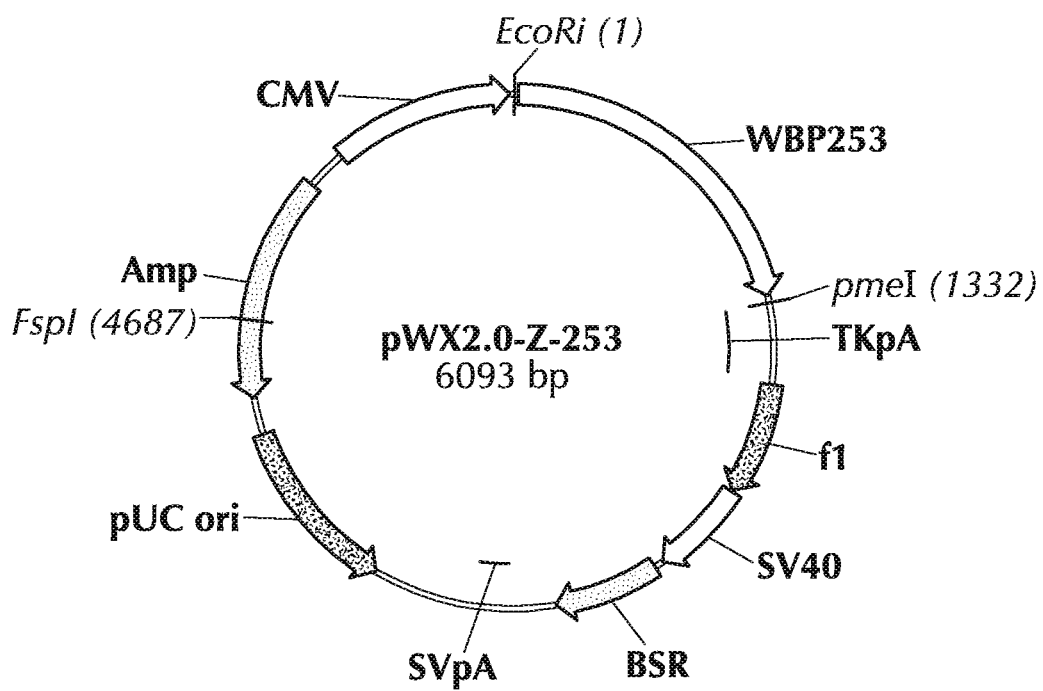

A non-limiting example of a vector is a plasmid. Non-limiting examples of plasmids provided herein are shown in FIG. 3.

An expression vector can be a viral vector. Non-limiting examples of viral vectors include adenovirus vectors, herpes virus vectors, baculovirus vectors, and retroviral vectors. An expression vector can also be a plasmid or a cosmid.

Host Cells

Also provided herein are host cells that include a sequence encoding recombinant human α-galactosidase-A protein described herein. The sequence can be operably linked to a promoter sequence (e.g., any of the exemplary promoter sequences described herein or any of the viral or mammalian promoter sequences known in the art). For example, the sequence encoding recombinant human α-galactosidase-A protein and the sequence of the promoter sequence operably linked to the 5' end of the sequence encoding recombinant human α-galactosidase-A protein can be integrated within a chromosome in the host cell. In other examples, the sequence encoding recombinant human α-galactosidase-A protein and the promoter sequence that is operably linked to the 5' end of the sequence encoding recombinant human α-galactosidase-A protein are present in an expression vector (e.g., any of the expression vectors described herein) within the host cell.

Methods for introducing nucleic acids (e.g., any of the nucleic acids or expression vectors described herein) into a cell (e.g., a mammalian host cell) are known in the art. For example, nucleic acid can be introduced into a cell using lipofection, electroporation, calcium phosphate-mediated transfection, virus (e.g., retroviral) transduction, DEAE-dextran-medicated cell transfection, dendrimer-mediated transfection, sonoporation, optical transfection, impalefection, hydrodynamic delivery, magnetofection, or ballistic transfection.

A host cell can be any type of mammalian cell. For example, a host cell can be a cell line, e.g., Chinese hamster ovary (CHO) cells (e.g., CHO DG44 cells, CHO-K1s cells, C02.31 clonal cells, A14.13 clonal cells, C02.57 clonal cells, and F05.43 clonal cells), Sp2.0, myeloma cells (e.g., NS/0), B-cells, hybridoma cells, T-cells, human embryonic kidney (HEK) cells (e.g., HEK 293E and HEK 293F), African green monkey kidney epithelial cells (Vero) cells, or Madin-Darby Canine (Cocker Spaniel) kidney epithelial cells (MDCK) cells. Additional mammalian cells that can be cultured using the methods described herein are known in the art. A host cell can be, e.g., an epithelial cell, an endothelial cell, a lymphocyte, a kidney cell, a lung cell, a T-cell, a myeloma cell, or a B-cell. Some host cells can be grown in a suspension cell culture or in an adherent cell culture.

Methods of Generating a Mammalian Cell Line

Also provided herein are methods for generating a mammalian cell line useful for recombinant expression of a glycoprotein.

Also provided are methods of generating a mammalian cell line useful for recombinant expression of a glycoprotein (e.g., any of the recombinant proteins described herein or known in the art) that include: (a) generating single-cell subclone cultures from the culture after the sequential culturing, and selecting a subclone culture that has acceptable transfection efficiency, cell growth in serum-free culture medium, and recombinant protein expression (e.g., selecting a subclone culture that has the best transfection efficiency, cell growth, and recombinant protein expression as compared to the other tested subclone cultures); (c) generating single-cell subclone cultures from the selected subclone culture in (a); and (d) selecting a single-cell subclone culture generated in (b) that has acceptable transfection efficiency, peak cell density (e.g., peak cell density in serum-free medium), growth properties (e.g., growth in serum-free medium), volumetric productivity rate (VPR), and recombinant protein expression, where the selected subclone of (c) is useful for recombinant expression of a glycoprotein (e.g., a subclone culture that has the best transfection efficiency, peak cell density, growth properties, VPR, and recombinant protein expression) as compared to the other tested subclone cultures).

Also provided herein are mammalian cells or mammalian cell lines produced by any of the methods described herein. Non-limiting examples of serum-dependent immortalized cell lines that can be used in any of the methods described herein include Chinese Hamster Ovary (CHO) cells, myeloma cells, B-cells, hybridoma cells, T-cells, human embryonic kidney (HEK) cells, African green monkey kidney epithelial cells (Vero) cells, and Madin-Darby Canine (Cocker Spaniel) kidney epithelial cells (MDCK) cells. Other serum-dependent immortalized cell lines that can be used in any of the methods described herein are known in the art. For example, the serum-dependent immortalized cell line can be an epithelial cell line, an endothelial cell line, a lymphocyte cell line, a kidney cell line, a lung cell line, a T-cell line, a myeloma cell line, or a B-cell line. In some examples, the serum-dependent immortalized cell line grows in suspension. In other examples, the serum-dependent immortalized cell line grows in adherent cell culture.

In some examples, the serum-dependent immortalized cell line does not endogenously express dihydrofolate reductase. The selected subclone (either the first or the second subclone selected in the methods) can be grown in suspension.

Methods for culturing an immortalized mammalian cell line are known in the art. Methods for determining the transfection efficiency, cell growth in a serum-free culture medium, recombinant protein expression, peak cell density (e.g., peak viable cell density), cell growth properties, volumetric productivity rate, and the glycosylation profile of a produced recombinant protein are well-known in the art. For example, transfection efficiency can be determined by detecting the level of expression of a reporter gene in an expression plasmid transfected into the cell (e.g., the expression of such a reporter gene can be detected using fluorescence-assisted cell sorting). Recombinant protein expression can, for example, be determined by detecting the levels of the recombinant protein present in a tissue culture medium or within the cell using an antibody that specifically binds to the recombinant protein. Peak cell density and cell growth can be assessed, e.g., by measuring the cell density (e.g., viable cell density) over time in a cell culture (e.g., using a hemocytometer or other commercially available automated cell counters). The volumetric productivity rate of a cell can be determined using methods known in the art by assessing the levels of recombinant protein present in a cell culture medium or within the cell over time. The glycosylation profile of a recombinant glycoprotein produced by a cell can be determined, for example, using any of the methods described in the Examples section of the present specification (e.g., 2-anthilic acid (AA)-derivatization and HPLC with fluorescent detection).

As is well-known in the art, a mammalian cell line produced by the methods described herein can be stored at low temperature (e.g., below −20° C., below −30° C., below −40° C., below −50° C., below −60° C., below −70° C., or below −80° C.) for future use. Methods for preparing stocks of a mammalian cell line for storage at low temperatures is described, for example, in Hewitt, Methods Mal. Biol. 640:83-105, 2010, and Phelan, Curr. Protoc. Hum. Genet. Appendix 3: 3G, 2006). In some examples, the mammalian cell lines produced by the methods described herein are not exposed to serum-containing and/or serum-containing culture medium (e.g., prior to storage and/or after storage). In some examples, the mammalian cell lines produced by the methods described herein are cultured only in animal-derived component (ADC)-free culture medium. In some examples, the mammalian cell lines produced by the methods described herein are only cultured in serum-free, protein-free, chemically defined growth medium Methods of Producing a Recombinant Glycoprotein Also provided herein are methods of producing a recombinant glycoprotein (e.g., recombinant human α-galactosidase-A protein, or any recombinant glycoprotein known in the art). These methods include providing a mammalian cell produced by any of the methods described herein, introducing into the cell a nucleic acid (e.g., an expression vector) that includes a sequence encoding a glycoprotein (e.g., recombinant human α-galactosidase-A protein and any other glycoprotein known in the art), culturing the cell in a serum-free culture medium under conditions sufficient to produce the glycoprotein, and harvesting the glycoprotein from the cell or the growth culture medium. Also provided are recombinant glycoproteins (e.g., recombinant human α-galactosidase-A protein) produced by any of the methods described herein.

In some instances, the nucleic acid that includes a sequence encoding a glycoprotein is an expression vector (e.g., any of the expression vectors described herein). In other examples, the nucleic acid that includes a sequence encoding a glycoprotein is integrated into a chromosome of the mammalian cell.

In some examples, the culturing is performed using a bioreactor. The bioreactor can have a volume of, e.g., between about 1 L to about 10,000 L (e.g., between about 1 L to about 50 L, between about 50 L to about 500 L, between about 500 L to about 1000 L, between 500 L to about 5000 L, between about 500 L to about 10,000 L, between about 5000 L to about 10,000 L, between about 1 L and about 10,000 L, between about IL and about 8,000 L, between about 1 L and about 6,000 L, between about 1 L and about 5,000 L, between about 100 L and about 5,000 L, between about 10 L and about 100 L, between about 10 L and about 4,000 L, between about 10 L and about 3,000 L, between about 10 L and about 2,000 L, or between about 10 L and about 1,000 L). The amount of liquid culture medium present in a bioreactor can be, e.g., between about between about 0.5 L to about 5,000 L (e.g., between about 0.5 L to about 25 L, between about 25 L to about 250 L, between about 250 L to about 500 L, between 250 L to about 2500 L, between about 250 L to about 5,000 L, between about 2500 L to about 5,000 L, between about 0.5 L and about 5,000 L, between about 0.5 L and about 4,000 L, between about 0.5 L and about 3,000 L, between about 0.5 L and about 2,500 L, between about 50 L and about 2,500 L, between about 5 L and about 50 L, between about 5 L and about 2,000 L, between about 5 L and about 1,500 L, between about 5 L and about 1,000 L, or between about 5 L and about 500 L). Culturing cells can be performed, e.g., using a fed-batch bioreactor or a perfusion bioreactor. Culturing can be performed by fed-batch culturing or perfusion culturing (e.g., in a bioreactor).

The interior surface of any of the bioreactors described herein as is known in the art, one or more ports for the sparging of $O_2$, $CO_2$, and $N_2$ into the liquid culture medium, and a stir mechanism for agitating the liquid culture medium. The bioreactor can incubate the cell culture in a controlled humidified atmosphere (e.g., at a humidity of greater than 20%, 30%, 40%, 50%, 60%, 70%, 75%, 80%, 85%, 90%, or 95%, or a humidity of 100%). The bioreactor can also be equipped with a mechanical device that is capable of removing a volume of liquid culture medium from the bioreactor and optionally, a filter within the mechanical device that removes the cells from the liquid culture medium during the process of transfer of the liquid culture medium out of the bioreactor (e.g., an alternating tangential flow (ATF) or tangential flow filtration (TFF) system). Culturing can include exposing the liquid culture medium in the bioreactor to an atmosphere that includes at most or about 15% CO2 (e.g., at most or about 14% CO2, 12% CO2, 10% CO2, 8% CO2, 6% CO2, 5% CO2, 4% CO2, 3% CO2, 2% CO2, or at most or about 1% CO2).

Culturing can be performed at a temperature of about 31° C. to about 40° C. Skilled practitioners will appreciate that the temperature can be changed at specific time point(s) during the culturing, e.g., on an hourly or daily basis. For example, the temperature can be changed or shifted (e.g., increased or decreased) at about one day, two days, three days, four days, five days, six days, seven days, eight days, nine days, ten days, eleven days, twelve days, fourteen days, fifteen days, sixteen days, seventeen days, eighteen days, nineteen days, or about twenty days or more after the initial seeding of the bioreactor with the mammalian cell). For example, the temperature can be shifted upwards (e.g., a change of up to or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). For example, the temperature can be shifted downwards (e.g., a change of greater than 0.05° C. or about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or up to or about 20° C.). The culturing can be performed using protein-free, serum-free, chemically-defined medium. Non-limiting examples of such media are known in the art and are commercially available. Non-limiting examples of useful culture medium include, e.g., CD CHO, Opti CHO, and Forti CHO (all available from Life Technologies; Grand Island, N.Y.), Hycell CHO medium (Thermo Fisher Scientific, Inc.; Waltham, Mass.), Ex-cell CD CHO Fusion medium (Sigma-Aldrich Co.; St. Louis, Mo.), and Power-CHO medium (Lonza Group, Ltd.; Basel, Switzerland).

The mammalian cell can be any of the mammalian cells described herein. For example, the mammalian cell can be a CHO cell. The mammalian cell can be a cell that does not endogenously express dihydrofolate reductase (e.g., a CHO cell that does not endogenously express dihydrofolate reductase).

The recombinant glycoprotein can be an enzyme (e.g., human α-galactosidase-A protein or any other glycoprotein known in the art). In some examples, the nucleic acid (e.g., expression vector) includes a sequence that is at least 90% (e.g., at least 91%, 92%, 93%, 94%, 95%, 96%, 97%, 98%, 99%, or 100%) identical to SEQ ID NO: 1. The nucleic acid (e.g., expression vector) can comprise a promoter sequence operably linked to the 5' end of the nucleic acid encoding the glycoprotein, a sequence encoding a peptide of human CD52 protein with a TTG start codon operably linked to the 5' end of the nucleic acid encoding the glycoprotein, and a sequence encoding a poly(A) recognition site operably linked to the 3' end of the nucleic acid encoding a glycoprotein. For example, the promoter sequence can be selected from the group consisting of: hamster rpS21 promoter, hamster β-actin promoter, and SV 40 early promoter. The sequence encoding the poly(A) recognition site can be a SV 40 early poly(A) recognition sequence. In some examples, the promoter sequence can be hamster β-actin promoter and the poly(A) recognition sequence is a SV 40 early poly(A) recognition sequence. In some examples, the nucleic acid further includes a sequence encoding a human or dog glutamine synthetase (e.g., where the 5' end of the nucleic acid encoding the human or dog glutamine synthetase is operably linked to a SV 40 early promoter and the 3' end of the nucleic acid encoding the human or dog glutamine synthetase is operably linked to a SV 40 early intron and poly(A) signal sequence). In some examples, the nucleic acid further includes a sequence encoding a dihydrofolate reductase (DHFR) (e.g., human or mouse DHFR) (e.g., where the 5' end of the nucleic acid encoding the dihydrofolate reductase is operably linked to a SV 40 early promoter and the 3' end of the nucleic acid encoding the dihydrofolate reductase is operably linked to a SV 40 early intron and poly(A) signal sequence).

The culturing can be performed using a perfusion bioreactor. Perfusion culturing is well-known in the art and includes removing from a bioreactor a first volume of a first liquid culture medium (e.g., that includes any concentration of mammalian cells, e.g., a first volume of a first liquid culture medium that is substantially free of cells), and adding to the first liquid culture medium a second volume of a second liquid culture medium. Removal and adding can be performed simultaneously or sequentially, or a combination of the two. Further, removal and adding can be performed continuously (e.g., at a rate that removes and replaces a volume of between 0.1% to 800% (e.g., between 1% and 700%, between 1% and 600%, between 1% and 500%, between 1% and 400%, between 1% and 350%, between 1% and 300%, between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is removed or replaced (e.g., within about a 24-hour period, within an incremental time period of about 1 hour to about 24 hours, or within an incremental time period of greater than 24 hours) can be, e.g., between 0.1% to 800% (e.g., between 1% and 700%, between 1% and 600%, between 1% and 500%, between 1% and 400%, between 1% and 300%, between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The first volume of the first liquid culture medium removed and the second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the first volume of the first liquid culture medium is removed (volume/unit of time) and the rate at which the second volume of the second liquid culture medium is added (volume/unit of time) can be varied. The rate at which the first volume of the first liquid culture medium is removed (volume/unit of time) and the rate at which the second volume of the second liquid culture medium is added (volume/unit of time) can be about the same or can be different.

Alternatively, the volume removed and added can change (e.g., gradually increase) over each 24-hour period (or alternatively, an incremental time period of between 1 hour and about 24 hours or an incremental time period of greater than 24 hours) during the culturing period. For example the volume of the first liquid culture medium removed and the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume.

Skilled practitioners will appreciate that the first liquid culture medium and the second liquid culture medium can be the same type of media (e.g., serum-free or serum-free, protein-free chemically-defined medium). In other instances, the first liquid culture medium and the second liquid culture medium can be different.

The first volume of the first liquid culture medium can be removed, e.g., using a mechanical system and/or by seeping or gravity flow of the volume through a sterile membrane with a molecular weight cut-off that excludes mammalian cells present in the volume. The second volume of the second liquid culture medium can be added to the first liquid culture medium in an automated fashion, e.g., by perfusion pump. In some instances, removing the first volume of the first liquid culture medium (e.g., a first volume of the first liquid culture medium that is substantially free of mammalian cells) and adding to the first liquid culture medium a second volume of the second liquid culture medium does not occur within at least 1 hour (e.g., within 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours) of the seeding of the bioreactor with a mammalian cell.

Alternatively or in addition, culturing can be performed using a fed-batch bioreactor. Such culturing is known in the art and includes, over the majority of the culturing period, addition (e.g., periodic or continuous addition) to the first liquid culture medium of a second volume of a second liquid culture medium. Adding of the second liquid culture medium can be performed continuously (e.g., at a rate that adds a volume of between 0.1% to 300% (e.g., between 1% and 250%, between 1% and 100%, between 100% and 200%, between 5% and 150%, between 10% and 50%, between 15% and 40%, between 8% and 80%, and between 4% and 30%) of the volume of the bioreactor or the first liquid culture medium volume over any given time period (e.g., over a 24-hour period, over an incremental time period of about 1 hour to about 24 hours, or over an incremental time period of greater than 24 hours)) or periodically (e.g., once every third day, once every other day, once a day, twice a day, three times a day, four times a day, or five times a day), or any combination thereof. Where performed periodically, the volume that is added (e.g., within about a 24-hour period, within an incremental time period of about 1 hour to about 24 hours, or within an incremental time period of greater than 24 hours) can be, e.g., between 0.1% to 300% (e.g., between 1% and 200%, between 1% and 100%, between 100% and 200%, between 5% and 150%, between 10% and 50%, between 15% and 40%, between 8% and 80%, and between 4% and 30%) of the volume of the bioreactor or the first liquid culture medium volume. The second volume of the second liquid culture medium added can in some instances be held approximately the same over each 24-hour period (or, alternatively, an incremental time period of about 1 hour to about 24 hours or an incremental time period of greater than 24 hours) over the entire or part of the culturing period. As is known in the art, the rate at which the second volume of the second liquid culture medium is added (volume/unit of time) can be varied over the entire or part of the culturing period. For example, the volume of the second liquid culture medium added can change (e.g., gradually increase) over each 24-hour period (or alternatively, an incremental time period of between 1 hour and about 24 hours or an incremental time period of greater than 24 hours) during the culturing period. For example the volume of the second liquid culture medium added within each 24-hour period (or alternatively, an incremental time period of between about 1 hour and above 24 hours or an incremental time period of greater than 24 hours) over the culturing period can be increased (e.g., gradually or through staggered increments) over the culturing period from a volume that is between 0.5% to about 20% of the bioreactor volume or the first liquid culture medium volume to about 25% to about 150% of the bioreactor volume or the first liquid culture medium volume. The rate at which the second volume of the second liquid culture medium is added (volume/unit of time) can be about the same over the entire or part of the culturing period.

Skilled practitioners will appreciate that the first liquid culture medium and the second liquid culture medium can be the same type of media (e.g., a protein-free culture medium or a serum-free, protein-free chemically-defined medium). In other instances, the first liquid culture medium can be of a type that is different from the second liquid culture medium. The volume of the second liquid culture medium can be added to the first liquid culture medium in an automated fashion, e.g., by perfusion pump.

In some instances, adding to the first liquid culture medium a second volume of the second liquid culture medium does not occur until at least 1 hour after but no more than 7 days after the seeding of the bioreactor with a mammalian cell (e.g., until at least 2 hours, within 3 hours, within 4 hours, within 5 hours, within 6 hours, within 7 hours, within 8 hours, within 9 hours, within 10 hours, within 12 hours, within 14 hours, within 16 hours, within 18 hours, within 24 hours, within 36 hours, within 48 hours, within 72 hours, within 96 hours, or after 96 hours after, but not more than 7 da7s after the seeding of the bioreactor with a mammalian cell). The cell culture medium in fed-batch cultures is typically harvested at the end of culture period, however, the cell culture medium in fed-batch cultures can also be harvested at one or more time points during the culturing period.

Skilled practitioners will appreciate that any of the various parameters for culturing (e.g., bioreactor, volumes, rates or frequencies of replacing culture volumes, agitation, temperatures, culture media, and/or CO2 concentrations) recited herein can be used in any combination in performing these methods.

An additional step of isolating the recombinant glycoprotein can be performed. As is well-known in the art, such methods differ according to the physical properties and activities of the glycoprotein. For example, parameters such as the binding specificity of the glycoprotein (e.g., substrate or antigen-binding activity), net charge, and/or size should be considered when designing the steps for isolating a recombinant glycoprotein (e.g., from culture medium or from a cell). One or more of any of the following methods can be used to isolate a recombinant glycoprotein (e.g., a recombinant glycoprotein produced using any of the methods described herein): affinity column chromatography, ionic (e.g., cationic or anionic) exchange column chromatography, size exclusion column chromatography, reverse-phase column chromatography, filtration, and precipitation. Non-limiting methods for isolating recombinant human α-galactosidase-A protein are described in the Examples.

The methods described herein can further include formulating the isolated recombinant glycoprotein into a pharmaceutically acceptable excipient or buffer (e.g., for administration to a subject). These methods can further include sterile filtering, viral inactivation, UV irradiation, and/or lyophilization, or any combination thereof.

Production, Capturing and Purification of rhα-Gal A

A typical cell manufacturing process begins with the revival of cryopreserved cells from a master cell bank. Cells are thawed in small volume vials and progressively introduced to larger volume culture vessels to achieve inoculation of a seed bioreactor. The expanded cell population in the seed bioreactor is then introduced into the production bioreactor where the therapeutic protein will be expressed.

There are many types of reactor with the choice of reactor determined empirically based on factors such as optimal cell growth, viability, protein yield, and maintenance of critical quality attributes of the therapeutic protein. Batch, fed-batch, batch refeed or intermittent harvest, and perfusion are currently the most frequently used bioreactors.

Batch culture is a closed system where culture media and cells are added at the start of production and then cultured without any other additions until the production run is terminated. The growth of cells progresses in four stages: lag phase, exponential growth phase, stationary phase, and death phase.

During a fed-batch cell culture a feed solution is added when cell culture components have been depleted. The feed solution contains amino acids, vitamins, and trace elements in a concentrated form. Thus, with the fed-batch culture the culture volume increases with each sequential addition of a feed solution.

A batch refeed or intermittent harvest culture removes a portion of the cell culture (including the cells) when culture nutrients have been depleted and the cells are entering stationary phase. This method of harvest is useful for labile proteins because the harvest can be performed frequently such as every 2-4 days.

Cells in culture have a high energy need during exponential phase and rapidly convert glucose to lactate. High lactate levels are detrimental to cell growth and productivity. Thus, lactate must be closely controlled to ensure product quality. Substitution of galactose or mannose for glucose may alleviate lactate build up because these sugars are more slowly metabolized. Other culture parameters that affect growth kinetics, cell viability, and protein production are pH, temperature, and dissolved oxygen.

After the initial cell expansion, in perfusion cell culture the cells are kept at a steady state by the addition of fresh culture media and a concomitant removal of spent culture media that contains the protein product. Higher cell densities are possible with perfusion culture than with batch culture because culture media is continuously replenished. Cells are retained in the culture while spent media containing product is removed. Periodically some media containing cells is removed to keep cell density within a productive range. Perfusion culture is also compatible with continuous processing.

Biologic drug production generates not one uniform protein but an array of different isoforms that reflect the complexity of biological processes. Protein variation can arise including glycosylation, phosphorylation, sulfation, amidation, oxidation, adduct formation, pyroglutamate formation and isomerization. Amino acid variation can arise from genetic mutations, amino acid misincorporation, clipping and N- and C-terminal heterogeneity. Structural variation can include misfolding, aggregation, and disulfide scrambling.

Impurities introduced during manufacturing can also affect protein stability, toxicity, and efficacy. Impurities of this type include host cell proteins, DNA, media elements and viral components.

Proteins designed to be secreted from the cell have their signal sequences cleaved by signal peptidase upon translocation through the endoplasmic reticulum. Protein variants can be generated by discrepancies in the cleavage of the signal sequence. N-terminal glutamic acid or glutamine can cyclize to form pyroglutamate. This leads to blocked proteins that may or may not have an effect on their biological function.

The two main types of glycosylation displayed on proteins is N-linked and O-linked glycosylation. As mentioned above, α-galactosidase A has four potential N-linked glycosylation sites on the monomer subunit, three of which are typically glycosylated. Glycosylation occurs at the consensus sequence ASN-X-SER/THR where X is any amino acid other than histidine or proline. The cell line has a large influence of the type of sugars incorporated at the glycosylation site as well as the culture conditions and downstream processing of the protein.

Cysteine is a relatively reactive amino acid and an unpaired cysteine can problematically react with other sulfhydryl groups with in cell, culture media, or cause intra- or inter-subunit bond formation.

Proteins may also be degraded or have poor product characteristics as a result of the uncontrolled action of proteases, glycosidases, and phosphatases.

In various embodiments, a protein capturing system including one or more anion exchange (AEX) columns is used for the direct product capture of rhα-Gal A, particularly rhα-Gal A having a high M6P content, a high sialic acid content, and a low content of neutral glycans. While not wishing to be bound by any particular theory, it is believed that using AEX chromatography to capture the rhα-Gal A from the filtered media ensures that the captured recombinant protein product has a higher M6P content and a higher sialic acid content, due to the more negative charge of the recombinant protein having one or more M6P groups and/or sialic acid groups. As a result, non-phosphorylated recombinant protein and host cell impurities do not bind the column resin as well as the highly phosphorylated recombinant protein, and the non-phosphorylated recombinant protein and host cell impurities passes through the column. Accordingly, the AEX chromatography can be used to enrich the M6P content of the protein product (i.e. select for protein molecules having more M6P) due to the high affinity of the M6P-containing proteins for the AEX resin. Similarly, the AEX chromatography can be used to enrich the sialic acid content of the protein product (i.e. select for protein molecules having more sialic acid) due to the affinity of the sialic acid-containing proteins for the AEX resin.

Furthermore, while not wishing to be bound by any particular theory, it is also believed that having a direct product capture of recombinant protein using AEX chromatography ensures that the recombinant proteins having high M6P content are removed from the media containing proteases and other enzymes that can degrade the protein and/or dephosphorylate the protein. As a result, the high quality product is preserved.

Strong binding to an AEX column confirms three product characteristics that are desirable: phosphorylated enzyme, adequately sialylated enzyme and enzymes with low content of neutral glycans. At physiological pH, phosphorylation and sialylation impart a negative charge and contribute to binding to AEX columns. Enzyme that possesses mono-M6P and/or bis-M6P will bind the CIMPR which in turn targets the enzyme to the lysosome (site of enzyme action). Recombinant enzyme that has been adequately sialylated also exhibits a greater half-life in the blood. This is because asialoglycoprotein receptors (located largely on liver cells) bind exposed galactose residues on proteins and remove the protein from circulation. Sialic acid on the terminal sugar residue blocks this mechanism of removal based on galactose.

Purification on AEX columns selects for phosphorylated/sialylated enzyme with low content of neutral glycans, if molecules with such characteristics are present in the cell culture supernatant. The binding to the CIMPR can be assessed by binding the enzyme preparation to immobilized CIMPR followed by elution with increasing concentrations of M6P.

Thus, one or more embodiments of the present invention relate to a recombinant α-Gal A with specific level of surface mono-M6P and/or bis-M6P and/or sialic acid and/or low content of neutral glycans, such as rhα-Gal A produced by the methods described herein. The rhα-Gal A produced by such methods can have any of the characteristics described herein.

Also, the chromatography techniques described herein can be utilized to enrich the mono-M6P and/or bis-M6P and/or sialic acid content of the enzyme molecules, relative to the enzyme molecules that are initially present in the cell supernatant. As described above, the AEX column can be used to select for enzyme molecules that have high content of phosphorylation, high content of sialic acid, and low content of neutral glycans. Other columns such as CIMPR columns can be used to selectively bind enzyme with high content of mono-M6P and bis-M6P. Thus, even if the host cells initially express enzyme molecules with glycan content similar to conventional recombinant human α-galactosidase A products such as Replagal (agalsidase alfa) or Fabrazyme (agalsidase beta), using AEX and CIMPR columns during product capture and purification can be used to enrich the mono-M6P and/or bis-M6P and/or sialic acid content and/or to lower the neutral glycan content of the enzyme molecules in the final recombinant protein product relative to the enzyme molecules that are initially present in the cell supernatant.

Pharmacological Chaperones

Migalastat hydrochloride (HCl) is a low molecular weight iminosugar that acts as a pharmacological chaperone for α-Gal A. It is an analog of the terminal galactose group that is cleaved from the substrate globotriaosylceramide (GL-3). Pharmacological chaperones are designed to bind and stabilize the intended protein target to help restore proper intracellular trafficking before dissociating from the protein, thereby allowing it to function as intended in the lysosome. As such, migalastat HCl is a potent, reversible, and competitive inhibitor of α-Gal A. It binds to mutant and wild-type forms of α-Gal A, stabilizes the enzyme, thus enabling the correctly folded protein to pass through the endoplasmic reticulum for proper trafficking to the lysosomes.

The relatively neutral pH of blood presents a hostile environment for lysosomally adapted enzymes used in enzyme replacement therapies because the ERTs are more stable in the acidic environment of the lysosome. Consequently, a proportion of the administered ERT denatures which becomes an antigen priming immune responses directed against the protein. At the very least, the denatured enzyme is cleared from the bloodstream via a non-efficacious pathway. Migalastat binds to wild-type α-Gal A ERT in the bloodstream, resulting in a stabilized enzyme with greater activity and greater uptake into the lysosome via the CIMPR. The low pH and high concentration of accumulated substrate in the lysosomes favor dissociation of migalastat HCl, allowing α-Gal A to bind and breakdown GL-3.

In one or more embodiments, the rhα-Gal A is co-formulated with the pharmacological chaperone such as migalastat.

In one or more embodiments, the co-formulation composition comprises α-Gal A at a concentration of between about 0.05 and about 100 μM, or between about 0.1 and about 75 μM, or between about 0.2 and about 50 μM, or between about 0.3 and about 40 μM, or between about 0.4 and about 30 μM, or between about 0.5 and about 20 μM, or between about 0.6 and about 15 μM, or between about 0.7 and about 10 μM, or between about 0.8 and about 9 μM, or between about 0.9 and about 8 μM, or between about 1 and about 7 μM, or between about 2 and about 6 μM, or between about 3 and about 5 μM. Concentrations and ranges intermediate to the above recited concentrations are also intended to be part of this application.

In one or more embodiments, the co-formulation composition comprises α-Gal A at a concentration of about 0.1, 0.2, 0.3, 0.4, 0.5, 0.6, 0.7, 0.8, 0.9, 1, 1.1, 1.2, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or 15 μM.

In one or more embodiments, the co-formulation composition comprises α-Gal A at a concentration of between about 0.0025 and about 5 mg/ml, or between about 0.005 and about 4.5 mg/ml, or between about 0.025 and about 4 mg/ml, or between about 0.05 and about 3.5 mg/ml, or between about 0.25 and about 3 mg/ml, or between about 0.5 and about 2.5 mg/ml, or between about 0.75 and about 2 mg/ml, or between about 1 and about 1.5 mg/ml. Concentrations and ranges intermediate to the above recited concentrations are also intended to be part of this application.

In one or more embodiments, the co-formulation composition comprises migalastat or salt thereof at a concentration of between about 10 and about 25,000 μM, or between about 50 and about 20,000 μM, or between about 100 and about 15,000 μM, or between about 150 and about 10,000 μM, or between about 200 and about 5,000 μM, or between about 250 and about 1,500 μM, or between about 300 and about 1,000 μM, or between about 350 and about 550 μM, or between about 400 and about 500 μM. Concentrations and ranges intermediate to the above recited concentrations are also intended to be part of this application.

In one or more embodiments, the co-formulation composition comprises migalastat or salt thereof at a concentration of between about 0.002 and about 5 mg/ml, or between about 0.005 and about 4.5 mg/ml, or between about 0.02 and about 4 mg/ml, or between about 0.05 and about 3.5 mg/ml, or between about 0.2 and about 3 mg/ml, or between about 0.5, and about 2.5 mg/ml, or between about 1 and about 2 mg/ml. Concentrations and ranges intermediate to the above recited concentrations are also intended to be part of this application.

In one or more embodiments, the co-formulation composition comprises migalastat or salt thereof at a concentration of about 50; 100; 150; 200; 250; 300; 350; 400; 450; 500; 550; 600; 650; 700; 750; 800; 850; 900; 950; 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000 or 20,000 μM.

In one or more embodiments, the α-Gal A enzyme and migalastat (or salt thereof) are combined to create a co-formulation with a molar ratio of migalastat to α-Gal A enzyme of between about 10:1 and about 20,000:1; or between about 20:1 and about 15,000:1; or between about 50:1 and about 10,000:1; or between about 100:1 and about 5,000:1; or between about 150:1 and about 1,000:1; or between about 200:1 and about 500:1; or between about 250:1 and about 450:1; or between about 300:1 and about 400:1. Molar ratios and ranges intermediate to the above recited molar ratios are also intended to be part of this application.

Methods of Treatment

The present invention provides a method of treating Fabry disease in a patient in need thereof, the method including administering rhα-Gal A as described herein to a patient or contacting cells with rhα-Gal A as described herein. In one or more embodiments, the rhα-Gal A is expressed in CHO cells and comprises an increased content of N-glycan units bearing one or two M6P residues when compared to a content of N-glycan units bearing one or two M6P residues of Replagal (agalsidase alfa) or Fabrazyme (agalsidase beta) and/or a substantially lower amount of neutral glycans. The cell line producing the rhα-Gal A, the conditions to express and the methods to purify have all been carefully picked, evaluated and scrutinized to maximize the potential benefits of having a glycosylated protein that minimizes non-productive targeting and maximizes productive uptake into target cells.

The present invention also provides a method of treating Fabry disease in a patient in need thereof, the method including administering a pharmacological chaperone (e.g. migalastat or salt thereof), or a pharmaceutically acceptable salt thereof, to the patient in combination with rhα-Gal A as described herein. In one or more embodiments, the rhα-Gal A is expressed in CHO cells and comprises an increased content of N-glycan units bearing one or two M6P residues when compared to a content of N-glycan units bearing one or two M6P residues of Replagal (agalsidase alfa) or Fabrazyme (agalsidase beta) and a substantially lower amount of neutral glycans. In another aspect, the present invention provides the use of a pharmacological chaperone (e.g. migalastat or salt thereof) and the rhα-Gal A in combination for the treatment of Fabry disease in a patient in need thereof.

The present invention also provides a method of reducing the level of GL-3 in an organ of a patient in need, the method comprising administering to the patient a composition comprising a therapeutically effective amount of rhα-Gal A, optionally in combination with a pharmacological chaperone. In one or more embodiments, the organ is heart, kidney or skin.

The present invention also provides a method of treating Fabry disease, the method comprising contacting a mammalian cell with an effective amount of rhα-Gal A, optionally in combination with a pharmacological chaperone, wherein contacting the cell with the rhα-Gal A provides a greater reduction in GL-3 than contacting with Fabrazyme (agalsidase beta). In one or more embodiments, the contacting is administering an effective to a subject an effective amount of the rhα-Gal A.

The present invention also provides a method of treating Fabry disease, the method comprising contacting a mammalian cell with an effective amount of rhα-Gal A, optionally in combination with a pharmacological chaperone, wherein contacting the cell with the rhα-Gal A provides a greater reduction in plasma lyso-Gb3 than contacting with Fabrazyme (agalsidase beta). In one or more embodiments, the contacting is administering an effective to a subject an effective amount of the rhα-Gal A.

The present invention also provides a method of treating Fabry disease, the method comprising administering a patient in an effective amount of rhα-Gal A, optionally in combination with a pharmacological chaperone, wherein contacting the cell with the rhα-Gal A provides a greater reduction in one or more substrates than contacting with Fabrazyme (agalsidase beta). In one or more embodiments, the contacting is administering an effective to a subject an effective amount of the rhα-Gal A. In one or more embodiments, the substrate comprises GL-3 and/or plasma lyso-Gb3

The present invention also provides a method of enhancing the activity level of α-galactosidase-A protein in a lysosome in a mammalian cell, the method comprising contacting the mammalian cell with rhα-Gal A, optionally in combination with a pharmacological chaperone. In one or more embodiments, the contacting is performed by administration of the rhα-Gal A and optionally a pharmacological chaperone. In one or more embodiments, the cell is in vitro.

In any of the above methods, the cell can be in a subject. In one or more embodiments, the cell is located in the subject's heart. In one or more embodiments, the cell is located in the subject's kidney. In one or more embodiments, the cell is located in the subject's skin. In at least one embodiment, the pharmacological chaperone (e.g. migalastat or salt thereof) is administered orally. In at least one embodiment, the migalastat or salt thereof is administered at an oral dose of about 100 mg to about 400 mg, or at an oral dose of about 100 mg, about 150 mg, about 200 mg, about 250 mg or about 300 mg. In at least one embodiment, the migalastat or salt thereof is administered at an oral dose of about 233 mg to about 400 mg. In at least one embodiment, the migalastat or salt thereof is administered at an oral dose of about 250 to about 270 mg, or at an oral dose of about 250 mg, about 255 mg, about 260 mg, about 265 mg or about 270 mg. In at least one embodiment, the migalastat or salt thereof is administered as an oral dose of about 260 mg.

In at least one embodiment, the pharmacological chaperone (e.g. migalastat or salt thereof) is administered systemically, such as intravenously. In at least one embodiment, the migalastat or salt thereof is administered at an intravenous dose of about 100 mg to about 400 mg, or at an intravenous dose of about 100 mg, about 123 mg, about 150 mg, about 200 mg, about 250 mg, about 300 mg, about 350 mg or about 400 mg. In at least one embodiment, the migalastat or salt thereof is administered at an intravenous dose of about 233 mg to about 400 mg. In at least one embodiment, the migalastat or salt thereof is administered at an intravenous dose of about 250 to about 270 mg, or at an intravenous dose of about 250 mg, about 255 mg, about 260 mg, about 265 mg or about 270 mg. In at least one embodiment, the migalastat or salt thereof is administered as an intravenous dose of about 260 mg. In at least one embodiment, the migalastat or salt thereof is administered at an intravenous dose of about 0.3 mg/kg to about 300 mg/kg, or at an intravenous dose of about 1 mg/kg to about 100 mg/kg. In at least one embodiment, the migalastat or salt thereof is administered at an intravenous dose of about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg, about 10 mg/kg, about 15 mg/kg, about 20 mg/kg, about 25 mg/kg, about 30 mg/kg, about 35 mg/kg, about 40 mg/kg, about 50 mg/kg, about 60 mg/kg, about 70 mg/kg, about 80 mg/kg, about 90 mg/kg or about 100 mg/kg.

In at least one embodiment, the pharmacological chaperone (e.g. migalastat or salt thereof) is administered subcutaneously. In at least one embodiment, the migalastat or salt thereof is administered at a subcutaneous dose of about 100 mg to about 400 mg, or at a subcutaneous dose of about 100 mg, about 123 mg, about 150 mg, about 200 mg, about 250 mg, about 300 mg, about 350 mg or about 400 mg. In at least one embodiment, the migalastat or salt thereof is administered at a subcutaneous dose of about 233 mg to about 400 mg. In at least one embodiment, the migalastat or salt thereof is administered at a subcutaneous dose of about 250 to about 270 mg, or at a subcutaneous dose of about 250 mg, about 255 mg, about 260 mg, about 265 mg or about 270 mg. In at least one embodiment, the migalastat or salt thereof is administered as a subcutaneous dose of about 260 mg.

It will be understood by those skilled in the art that an oral dose of migalastat in the range of about 100 mg to 400 mg or any smaller range therewithin can be suitable for an adult patient with an average body weight of about 70 kg. For patients having a significantly lower body weight than about 70 kg, including but not limited to infants, children or underweight adults, a smaller dose may be considered suitable by a physician. Therefore, in at least one embodiment, the migalastat or salt thereof is administered as an oral dose of from about 25 mg to about 200 mg, or as an oral dose of about 50 mg, about 75 mg, about 100 mg, 125 mg, about 150 mg, about 175 mg or about 200 mg. In at least one embodiment, the migalastat or salt thereof is administered as an oral dose of from about 65 mg to about 195 mg, or as an oral dose of about 65 mg, about 130 mg or about 195 mg.

The rhα-Gal A can be formulated in accordance with the routine procedures as a pharmaceutical composition adapted for administration to human beings. For example, in a preferred embodiment, a composition for intravenous administration is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration The rhα-Gal A (or a composition or medicament containing rhα-Gal A) is administered by an appropriate route. In one or more embodiments, the rhα-Gal A is administered systemically. In one embodiment, the rhα-Gal A is administered intravenously. In other embodiments, rhα-Gal A is administered by direct administration to a target tissue, such as to heart or skeletal muscle (e.g., intramuscular), or nervous system (e.g., direct injection into the brain; intraventricularly; intrathecally). More than one route can be used concurrently, if desired.

The rhα-Gal A (or a composition or medicament containing rhα-Gal A) is administered in a therapeutically effective amount (e.g., a dosage amount that, when administered at regular intervals, is sufficient to treat the disease, such as by ameliorating symptoms associated with the disease, preventing or delaying the onset of the disease, and/or lessening the severity or frequency of symptoms of the disease). The amount which will be therapeutically effective in the treatment of the disease will depend on the nature and extent of the disease's effects, and can be determined by standard clinical techniques. In addition, in vitro or in vivo assays may optionally be employed to help identify optimal dosage ranges. The precise dose to be employed will also depend on the route of administration, and the seriousness of the disease, and should be decided according to the judgment of a practitioner and each patient's circumstances. Effective doses may be extrapolated from dose-response curves derived from in vitro or animal model test systems. In at least one embodiment, the rhα-Gal A is administered by intravenous infusion at a dose of about 0.1 mg/kg to about 30 mg/kg, typically about 0.5 mg/kg to about 10 mg/kg. In at least one embodiment, the rhα-Gal A is administered by intravenous infusion at a dose of about 0.5 mg/kg, about 1.0 mg/kg, about 1.5 mg/kg, about 2.0 mg/kg, about 2.5 mg/kg, about 3 mg/kg, about 3.5 mg/kg, about 4 mg/kg, about 4.5 mg/kg, about 5 mg/kg, about 6 mg/kg, about 7 mg/kg, about 8 mg/kg, about 9 mg/kg or about 10 mg/kg. The effective dose for a particular individual can be varied (e.g., increased or decreased) over time, depending on the needs of the individual. For example, in times of physical illness or stress, or if anti-α-galactosidase A antibodies become present or increase, or if disease symptoms worsen, the amount can be increased to counter the reduced effect or decrease to lessen complications caused by infusion reactions.

The therapeutically effective amount of rhα-Gal A (or composition or medicament containing rhα-Gal A) is administered at regular intervals, depending on the nature and extent of the disease's effects, and on an ongoing basis. Administration at a "regular interval," as used herein, indicates that the therapeutically effective amount is administered periodically (as distinguished from a one-time dose). The interval can be determined by standard clinical techniques. In preferred embodiments, rhα-Gal A is administered monthly, bimonthly; weekly; twice weekly; or daily. Alternatively, rhα-Gal A is administered with the aid of a medical device that provides near continuous or continuous administration through any compatible route. The administration interval for a single individual need not be a fixed interval, but can be varied over time, depending on the needs of the individual. For example, in times of physical illness or stress, if anti-recombinant human galactosidase A antibodies become present or increase, or if disease symptoms worsen, the interval between doses can be decreased or decrease to improve efficacy or reduce infusion reactions. In some embodiments, a therapeutically effective amount of 0.1, 0.2, 0.3, 0.4, 0.5, 1.0, 1.5, 2.0, 2.5, 3.0, 3.5, 4.0, 4.5, 5, 10, 15, 20 or 30 mg enzyme/kg body weight is administered twice a week, weekly or every other week with or without a pharmacological chaperone.

The rhα-Gal A may be prepared for later use, such as in a unit dose vial or syringe, or in a bottle or bag or medical device for intravenous administration. Kits containing the rhα-Gal A, as well as optional excipients or other active ingredients, such as chaperones or other drugs, may be enclosed in packaging material and accompanied by instructions for reconstitution, dilution or dosing for treating a subject in need of treatment, such as a patient having Fabry disease.

In at least one embodiment, the migalastat (or salt thereof) and rhα-Gal A are administered simultaneously. In at least one embodiment, the migalastat (or salt thereof) and the rhα-Gal A are administered sequentially. In at least one embodiment, the migalastat (or salt thereof) is administered prior to administration of the rhα-Gal A. In at least one embodiment, the migalastat (or salt thereof) is administered less than three hours prior to administration of the rhα-Gal A. In at least one embodiment, the migalastat (or salt thereof) is administered about two hours prior to administration of the rhα-Gal A. In at least one embodiment, the migalastat (or salt thereof) is administered less than two hours prior to administration of the rhα-Gal A. In at least one embodiment, the migalastat (or salt thereof) is administered about 1.5 hours prior to administration of the rhα-Gal A. In at least one embodiment, the migalastat (or salt thereof) is administered about one hour prior to administration of the rhα-Gal A. In at least one embodiment, the migalastat (or salt thereof) is administered from about 50 minutes to about 70 minutes prior to administration of the rhα-Gal A. In at least one embodiment, the migalastat (or salt thereof) is administered from about 55 minutes to about 65 minutes prior to administration of the rhα-Gal A. In at least one embodiment, the migalastat (or salt thereof) is administered about 30 minutes prior to administration of the rhα-Gal A. In at least one embodiment, the migalastat (or salt thereof) is administered from about 25 minutes to about 35 minutes prior to administration of the rhα-Gal A. In at least one embodiment, the migalastat (or salt thereof) is administered from about 27 minutes to about 33 minutes prior to administration of the rhα-Gal A.

In at least one embodiment, the migalastat (or salt thereof) is administered concurrently with administration of the rhα-Gal A. In at least one embodiment, the migalastat (or salt thereof) is administered within 20 minutes before or after administration of rhα-Gal A. In at least one embodiment, the migalastat (or salt thereof) is administered within 15 minutes before or after administration of the rhα-Gal A. In at least one embodiment, the migalastat (or salt thereof) is administered within 10 minutes before or after administration of the rhα-Gal A. In at least one embodiment, the migalastat (or salt thereof) is administered within 5 minutes before or after administration of the rhα-Gal A. In at least one embodiment, the migalastat (or salt thereof) and rhα-Gal A are co-formulated.

In at least one embodiment, the migalastat (or salt thereof) is administered after administration of the rhα-Gal A. In at least one embodiment, the migalastat (or salt thereof) is administered up to 2 hours after administration of the rhα-Gal A. In at least one embodiment, the migalastat (or salt thereof) is administered about 30 minutes after administration of the rhα-Gal A. In at least one embodiment, the migalastat (or salt thereof) is administered about one hour after administration of the rhα-Gal A. In at least one embodiment, the migalastat (or salt thereof) is administered about 1.5 hours after administration of the rhα-Gal A. In at least one embodiment, the migalastat (or salt thereof) is administered about 2 hours after administration of the rhα-Gal A.

Another aspect of the invention provides a kit for combination therapy of Fabry disease in a patient in need thereof. The kit includes a pharmaceutically acceptable dosage form comprising migalastat, a pharmaceutically acceptable dosage form comprising rhα-Gal A, and instructions for administering the pharmaceutically acceptable dosage form comprising migalastat and the pharmaceutically acceptable dosage form comprising the rhα-Gal A to a patient in need thereof. In at least one embodiment, the pharmaceutically acceptable dosage form comprising migalastat is an oral dosage form as described herein, including but not limited to a tablet or a capsule. In at least one embodiment, the pharmaceutically acceptable dosage form comprising rhα-Gal A is a sterile solution suitable for injection as described herein. In at least one embodiment, the instructions for administering the dosage forms include instructions to administer the pharmaceutically acceptable dosage form comprising migalastat orally prior to administering the pharmaceutically acceptable dosage form comprising the rhα-Gal A by intravenous infusion, as described herein.

Without being bound by theory, it is believed that migalastat acts as a pharmacological chaperone for the rhα-Gal A and binds to its active site. Migalastat has been found to decrease the unfolding of rhα-Gal A and stabilize the active conformation of the rhα-Gal A, preventing denaturation and irreversible inactivation at the neutral pH, potentially allowing it to survive conditions in the circulation long enough to reach and be taken up by tissues. However, the binding of migalastat to the active site of rhα-Gal A also can result in inhibition of the enzymatic activity of rhα-Gal A by preventing the natural substrate, GL-3, from accessing the active site. It is believed that when migalastat and the rhα-Gal A are administered to a patient under the conditions described herein, the concentrations of migalastat and rhα-Gal A within the plasma and tissues are such that the rhα-Gal A is stabilized until it can be taken up into the tissues and targeted to lysosomes, but, because of the rapid clearance of migalastat, hydrolysis of GL-3 by rhα-Gal A within lysosomes is not overly inhibited by the presence of migalastat, and the enzyme retains sufficient activity to be therapeutically useful.

All the embodiments described above may be combined. This includes in particular embodiments relating to:

the nature of the pharmacological chaperone, for example migalastat; and the active site for which it is specific;

the dosage, route of administration of the pharmacological chaperone (e.g. migalastat) and the type of pharmaceutical composition including the nature of the carrier and the use of commercially available compositions;

the nature of the drug, e.g. therapeutic protein drug product, which may be a counterpart of an endogenous protein for which activity is reduced or absent in the subject, suitably rhα-Gal A, for example the rhα-Gal A expressed in CHO cells and comprising an increased content of N-glycan units bearing one or more M6P residues when compared to a content of N-glycan units bearing one or more M6P residues of Replagal (agalsidase alfa) and/or Fabrazyme (agalsidase beta) and/or containing less neutral glycans compared to Replagal (agalsidase alfa) and/or Fabrazyme (agalsidase beta); and suitably having an amino acid sequence as set forth in SEQ ID NO: 1, SEQ ID NO: 2 or as encoded by SEQ ID NO: 3.

the number and type of N-glycan units on the rhα-Gal A, e.g. N-acetylglucosamine, N-acetylgalactosamine, galactose, fucose, sialic acid or complex N-glycans formed from combinations of these) attached to the rhα-Gal A;

the degree of phosphorylation of mannose units on the rhα-Gal A to form mono-M6P and/or bis-M6P; the dosage and route of administration (e.g. intravenous administration, especially intravenous infusion, or direct administration to the target tissue) of the replacement enzyme (rhα-Gal A) and the type of formulation including carriers and therapeutically effective amount;

the dosage interval of the pharmacological chaperone (e.g. migalastat) and the rhα-Gal A;

the nature of the therapeutic response and the results of the combination therapy (e.g. enhanced results as compared to the effect of each therapy performed individually);

the timing of the administration of the combination therapy, e.g. simultaneous administration of migalastat and the rhα-Gal A or sequential administration, for example wherein the migalastat (or salt thereof) is administered prior to the rhα-Gal A or after the rhα-Gal A or within a certain time before or after administration of the rhα-Gal A; and the nature of the patient treated (e.g. mammal such as human) and the condition suffered by the individual (e.g. enzyme insufficiency).

Any of the embodiments in the list above may be combined with one or more of the other embodiments in the list.

EXAMPLES

The compositions and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the processes, formulations and/or methods of the invention may be made without departing from the spirit of the invention and the scope of the appended claims.

Example 1: Preparation of CHO Cell Clones Producing rhα-Gal A with a High Content of Mono-M6P, Bis-M6P, and/or Sialic Acid-Bearing N-Glycans DNA coding for wild-type human alpha-galactosidase A (α-Gal A) was cloned into a dual vector expression system for transfection into suspension CHO-K1 cells. The two vectors used for transforming CHO cells with DNA encoding rhα-Gal A (e.g. SEQ ID NO: 3) are shown in FIG. 3.

For transfections, each vector was linearized with FspI, which cuts within the Amp resistance gene. The digested DNA was purified with phenol chloroform extraction and quantified on a NanoDrop (Thermo Scientific, ND2000). The linearized DNA was sent for coding sequence confirmation and transfections.

CHO K1 host cells were passaged at $7\times10^5$ cells/ml in medium M1 (CD CHO+4 mM Glutamine+1% HT Supplement) 24 hours before transfection. On the day of transfection, the host cell cultures were sampled and counted.

During transfection, the host cell cultures were diluted to $10\times10^5$ cells/ml with medium M1 pre-warmed in water bath (36.5° C.) about 30 min and 5 ml of the diluted cells were added to a 50 ml spin tube and kept in a Kuhner incubator (36.5° C., 85% humidity, 6% $CO_2$ at 225 RPM).

12 μg of each vector (FIG. 3) was added into 776 μl of OptiPro™ SFM (serum-free media available from ThermoFisher Scientific) in a 50 ml spin tube. 24 μl of FreeStyle™ MAX Reagent (transfection reagent available from ThermoFisher Scientific) was added into 776 μl of OptiPro™ SFM in a second 50 ml spin tube. The DNA-OptiPro SFM mixture was added into FreeStyle MAX-OptiPro SFM mixture with gentle mixing, and incubated at room temperature for 10 minutes.

The diluted host cell cultures were removed from the Kuhner incubator, and 667 μl of DNA-Freestyle Max mixture was added into the host cell cultures. The transfected cell cultures were incubated in a Kuhner incubator (36.5° C., 85% humidity, 6% $CO_2$ at 225 RPM) for 6 hours. 5 ml of fresh M1 medium was added into the transfected cell cultures.

In total six independent transfections were performed using the above procedure.

Forty-eight hours after transfection, cells from each transfection were plated in three 96-well plates at cell densities of $1-1.6\times10^6$ cells/ml and plating densities of 3000-4000 cells/ 100 μL/well in the selective medium M2 (Medium M1+9 μg/ml Blasticidin+400 μg/ml Zeocin). The 96-well plates were incubated in a $CO_2$ incubator (36.5° C., 6% $CO_2$).

Three or four days after plating, 120 μl of fresh selective medium M2 was added to each well of the 96-well plates. Over the following 2-3 weeks, 150 μl of cell supernatant was replaced with equal volume of fresh selective medium every 3 or 4 days.

To determine which of the six stable CHO pools would provide the best product attributes, the pools were compared for cell culture viability, expression of rhα-Gal A and binding to the CIMPR. Approximately 16-18 days after plating, when most of the wells reached >70% confluency, 150 μl of cell supernatant was replaced with equal volume of fresh selective medium M2 24 hours prior to the expression analysis.

The cell pools were expanded in a pilot culture to investigate the viability over an extended period of time. The top 9 minipools with highest enzyme activity from each transfection were selected and expanded from 96- to 24-, to 6-well plates and into spin tubes for batch refeeding screening with selective medium M2. Vials were frozen down (Cryopreservation Medium: 90% M1+10% DMSO) during minipool expansion. Frozen vials were placed in cryobox freezing containers in −80° C. freezer overnight and stored in liquid nitrogen tanks.

Figure 4:
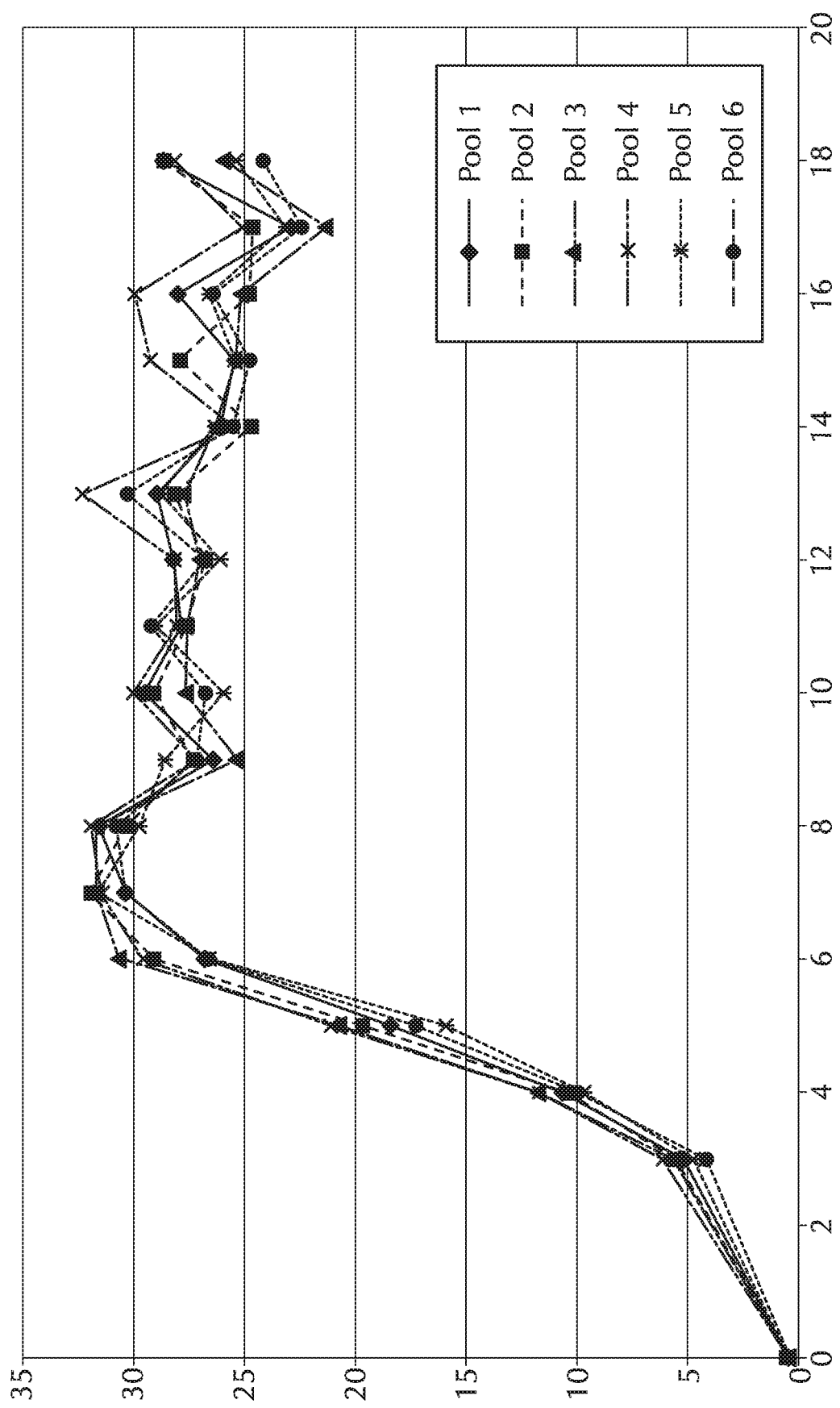
FIG. 4 shows density of viable cells from CHO cell pools transformed with plasmid expressing rhα-Gal A.

When the T9 pools were recovered, N−1 cell cultures were inoculated for batch refeeding cultures by 1:5 dilution into fresh production medium M3 (CDM4+4 mM Glutamine+1% HT Supplement) to obtain a seeding density of $3.8-5.7\times10^5$ cells/ml in spin tubes (day 0). The pool batch refeeding cultures (20 ml) were incubated in a Kuhner shaker (35° C., 85% humidity, 6% $CO_2$, and 225 RPM). Starting from day 3, cells were spun down (300 RPM, 5 min, 25° C.) and 80% supernatant was exchanged with fresh medium. When viable cell density was above $20\times10^6$ cells/ml, certain amount of cells was discarded according to their growth to target viable cells density between $25\times10^6$ and $30\times10^6$ cells/ml on the next day. Pool batch refeeding cultures were harvested on day 20 by centrifugation (3000 RPM, 10 min, 4° C.). During 18 days of culture, the viability of each cell pool was greater than 90% and the density of viable cells was about $20-30\times10^6$ cells/ml. (FIG. 4).

Figure 5:
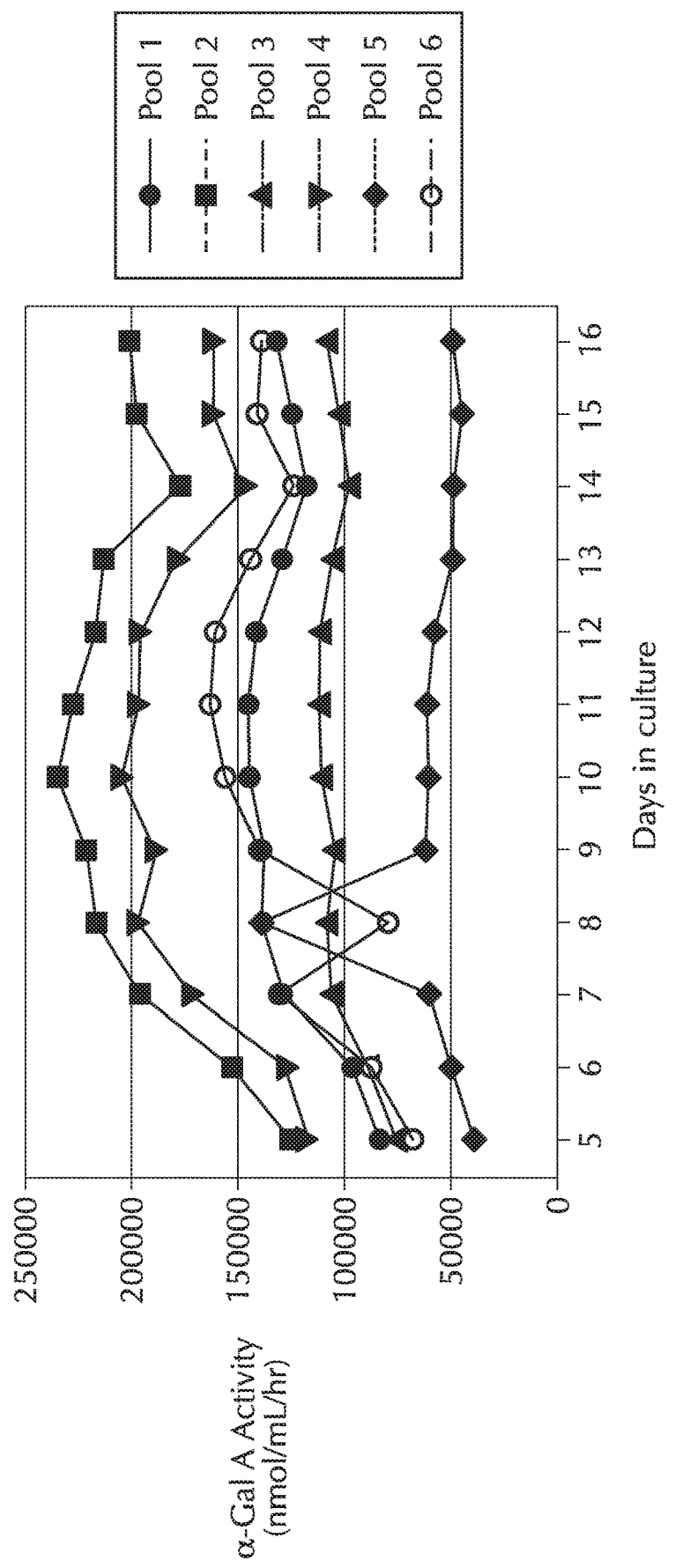
FIG. 5 shows the degree of enzyme activity produced by each cell pool over time.
Figure 6A:
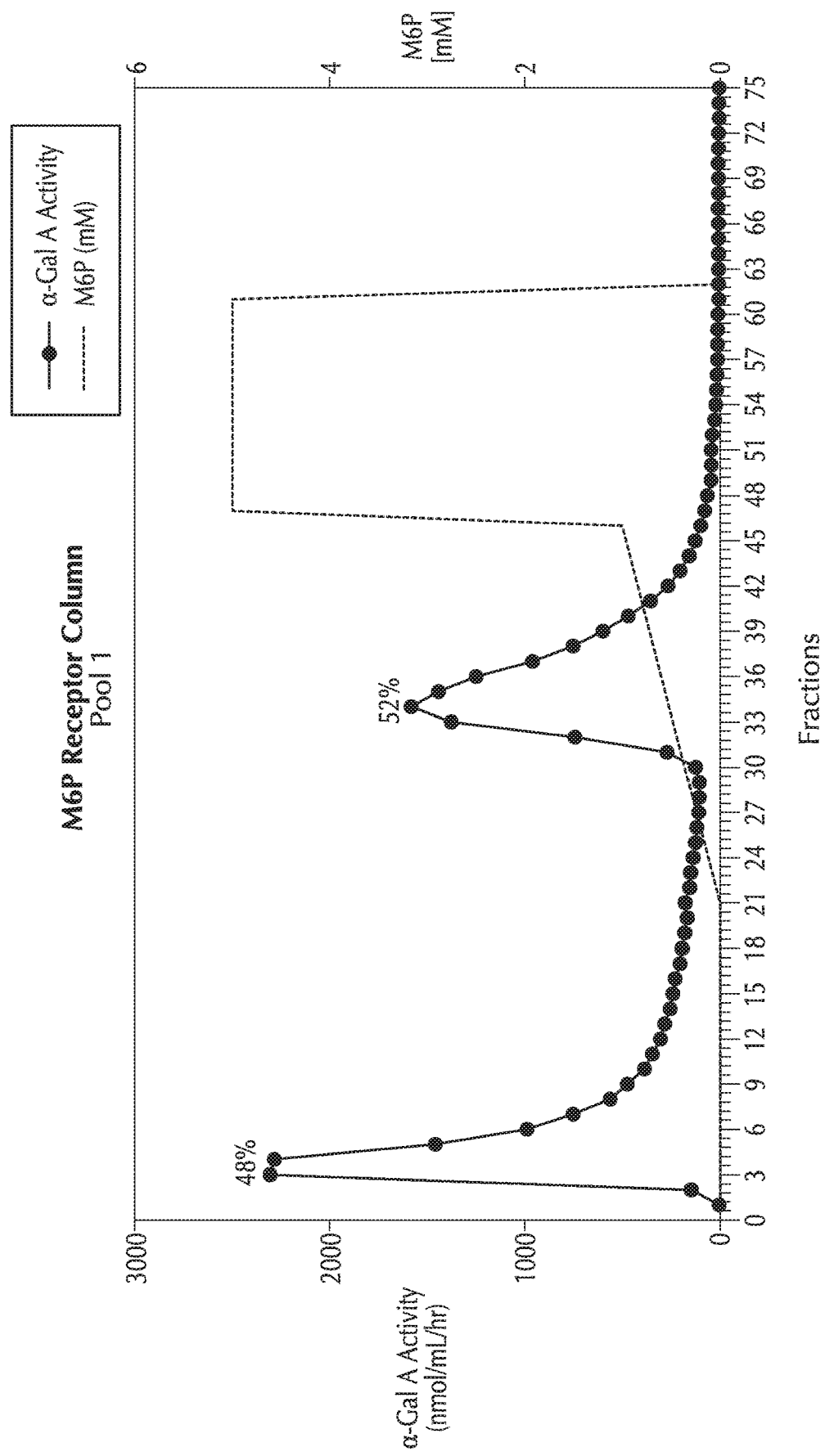
FIGS. 6A-6F show the degree of CIMPR bound rhα-Gal A in each cell-pool culture supernatant at day 15-17.
Figure 6B:
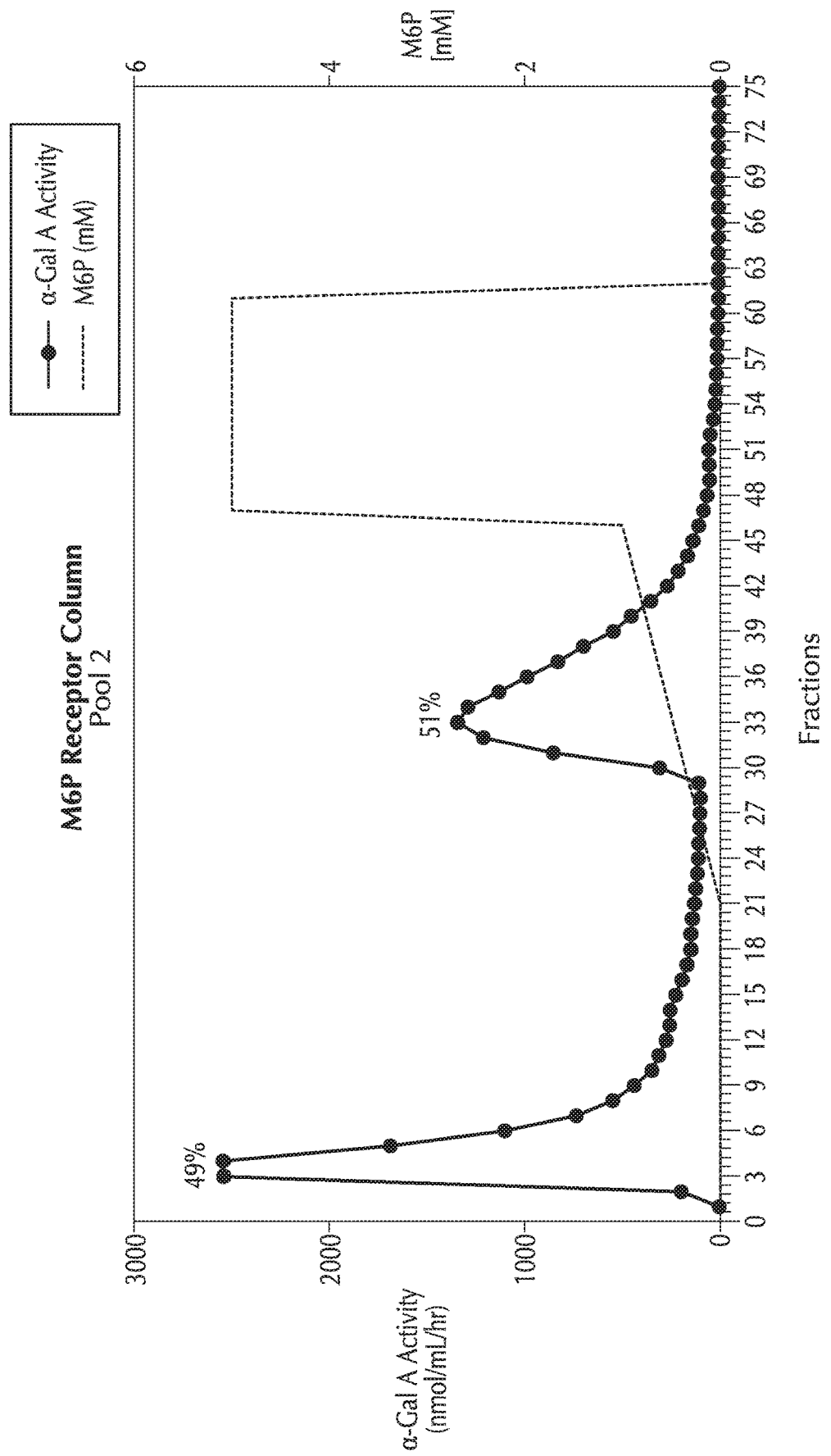
Figure 6C:
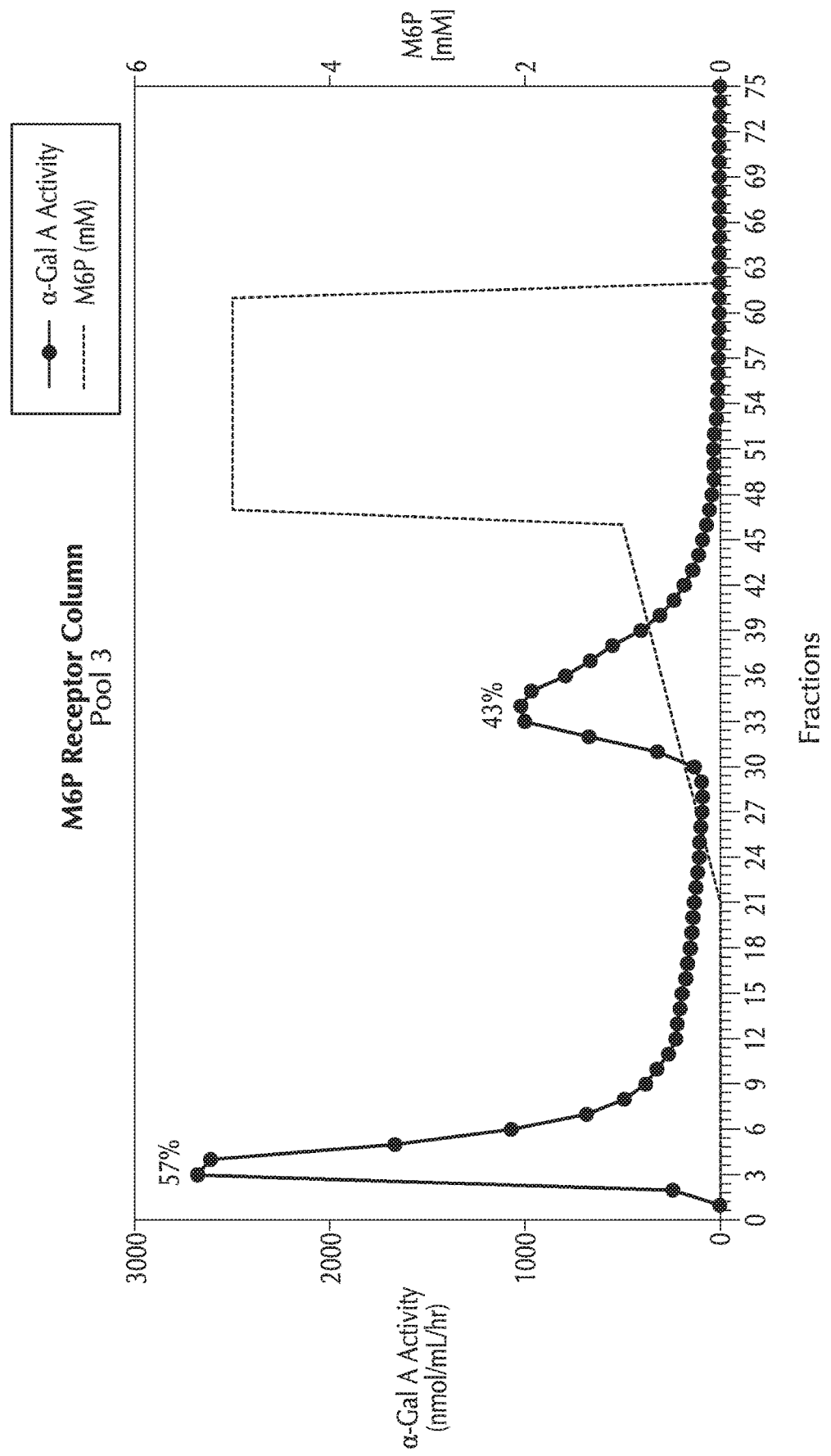
Figure 6D:
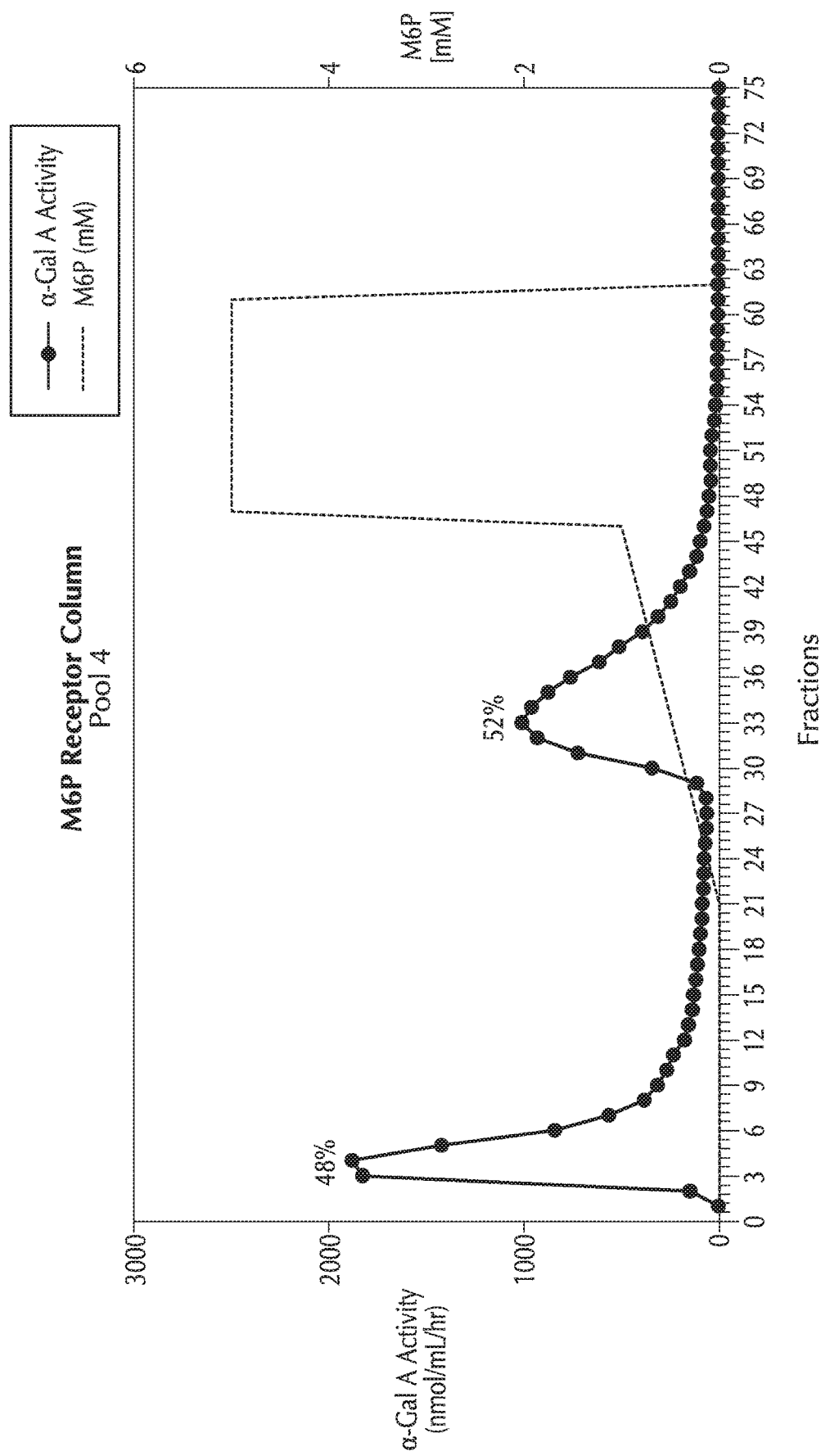
Figure 6E:
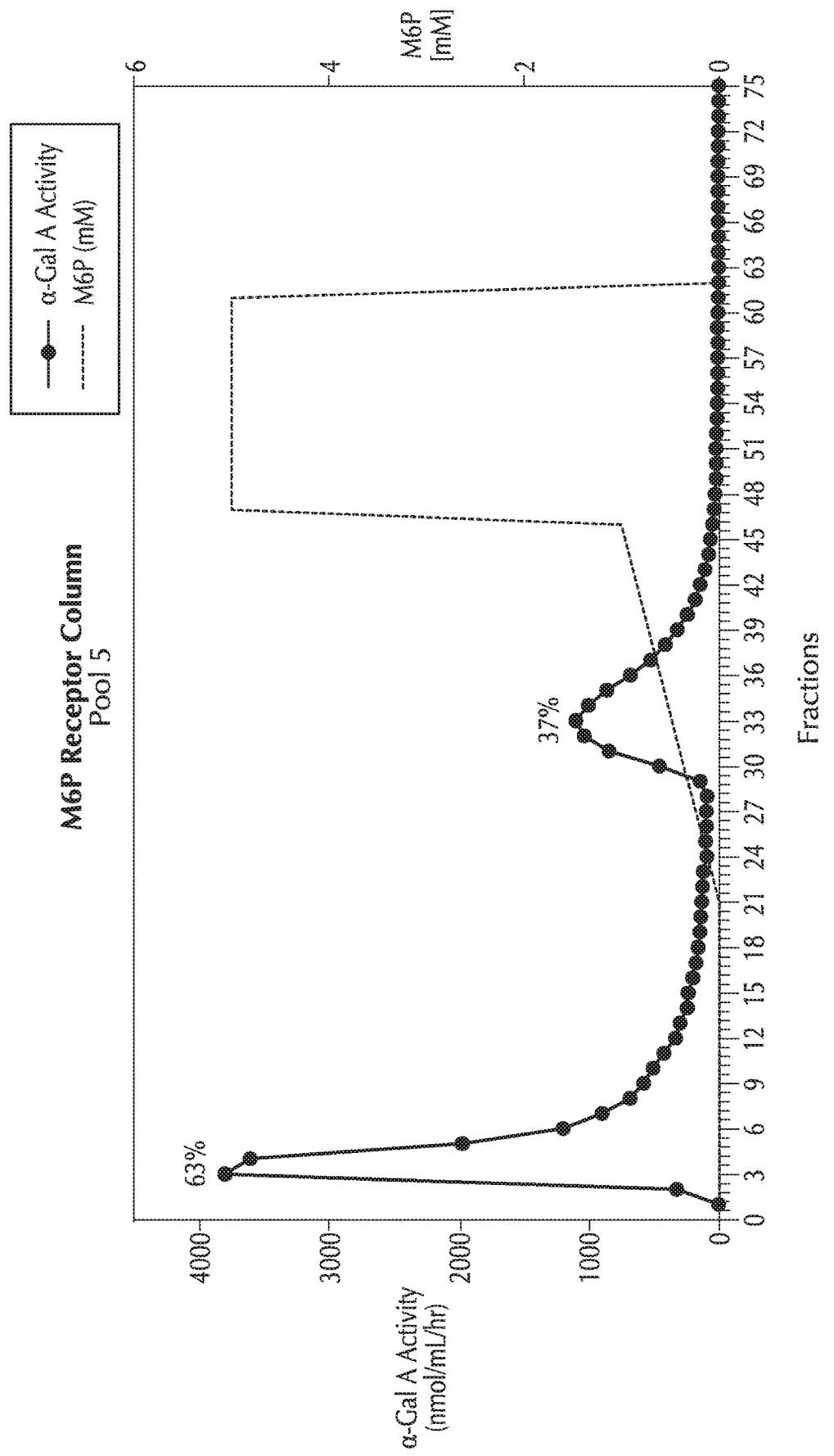
Figure 6F:
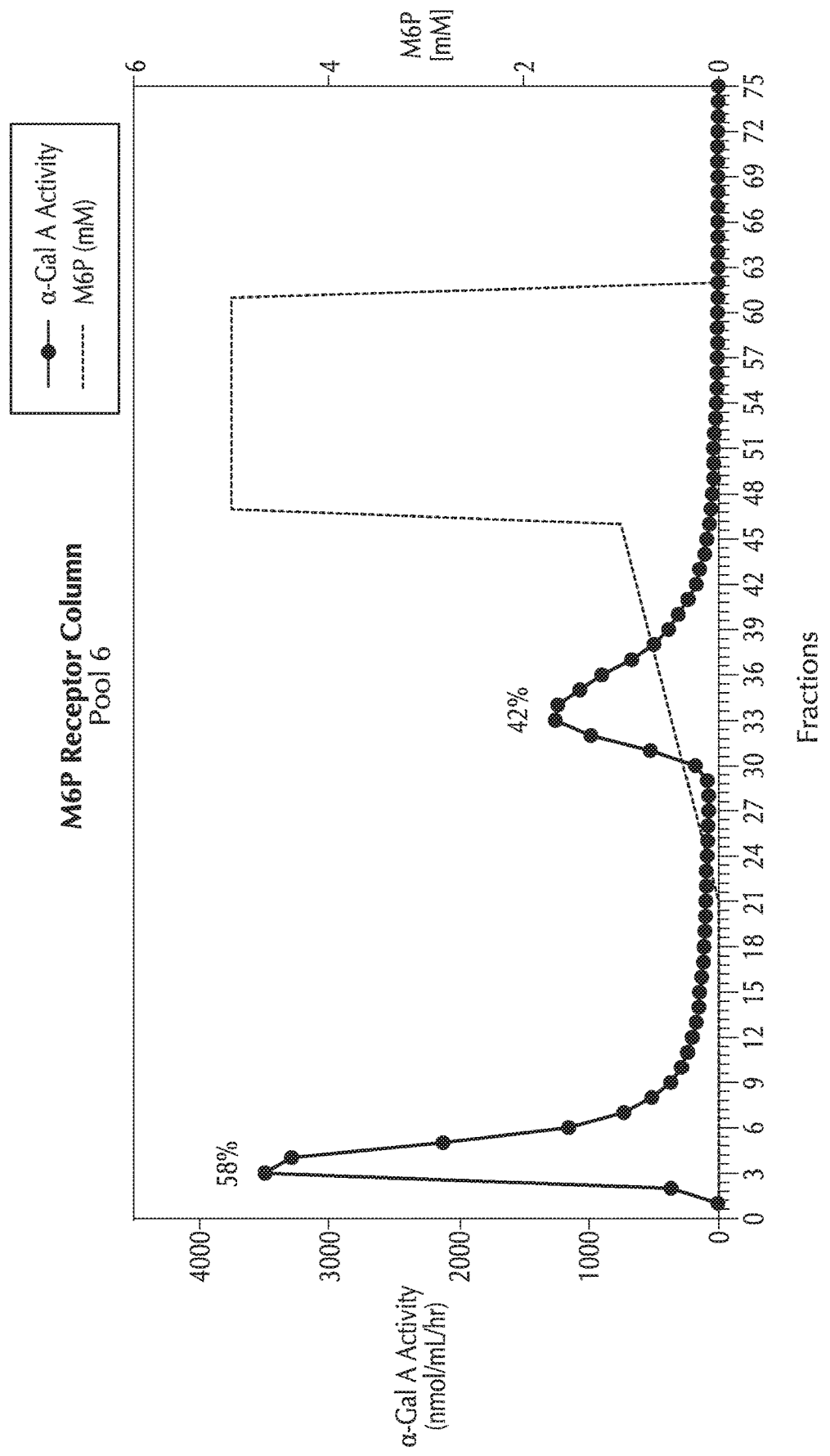

The expression of rhα-Gal A and binding to the CIMPR were assessed by 4-methylumbelliferyl-α-D-galactoside enzyme assay (4MU) and binding to a column with immobilized cation independent mannose-6-phosphate receptor (CIMPR), respectively. FIG. 5 shows that pool number 2 maintained the highest level of rhα-Gal A expression (as measured by enzyme activity) out to at least 16 days of cell culture.

A desirable product attribute is high binding to the CIMPR. Binding to CIMPR presents a pathway for enzyme uptake into the lysosome which represents a major reservoir of accumulated substrate. The ability of the enzyme candidates to bind in vivo to the correct receptor for internalization was estimated by applying the cell supernatant from each pool to a CIMPR column (FIGS. 6A-6F). Pooled culture supernatant from days 15 to 17 was loaded onto an immobilized CIMPR affinity column. Increasing concentrations of free M6P from 0 to 1 mM, followed by a step to 5 mM, were passed over the column to elute the bound enzyme. The degree of CIMPR binding for the cell pools ranged from 37% to 52% (as measured by activity). Pools 1 and 4 had the highest CIMPR binding with 52% with pool 2 slightly less at 51%. Thus, these pools had more favorable CIMPR binding characteristics than the other pools at the same time point during culturing.

The supernatants were further evaluated for binding in a 96-well plate based CIMPR binding assay. In summary, the supernatants from various time points were diluted 1; 100, 1:1,000, and 1:10,000 in CIMPR binding buffer and then added to wells coated with CIMPR receptor. After 1 hour incubation at 37° C., the unbound enzyme was washed away and the bound enzyme was measured in the 4MU enzyme activity assay. The activity was converted to nanograms of enzyme bound and the calculated values were plotted against the dilution. Pools 1 and 4 showed the best (compared to Fabrazyme (agalsidase beta)) and most consistent binding of the 6 pools.

Based on the enzyme activity data and the CIMPR binding results, Pools 1 and 4 were chosen as the top pools for further clone screening.

Pools 1 and 4 were thawed and passaged for a week. On the day of plating, plating medium was prepared freshly, and both of pools were plated into 384-well plates with cell density of 0.6 cell/30 microliter/well. The pictures of all plates were captured on the day of plating (D0), one day (D1) and two days (D2) after plating for the future clonality verification. A week after plating, 15 microliter M2 medium was supplemented into each well of all 384-well plates.

Ten days after plating, all the plates were scanned again to observe clone recovery. The recovered cells were transferred from 384-well plates to 96-well plates based on their confluency. Approximately 15 days after plating, when most of the wells reached >70% confluency, 150 μl of cell supernatant was replaced with equal volume of fresh selective medium M4 (CD CHO+4 mM Glutamine+1% HT Supplement+4 μg/mL of Blasticidin+200 μg/mL of Zeocin) 24 hours prior to the expression analysis. As for the wells with high expression level, the pictures of D0, D1 and D2 were pulled out and evaluated for clonality. A clone with 1-2-4 cell stages from D0-D2 is considered to be derived from one single cell. 22 clones from Pool 1 and 37 clones from Pool 4 with the highest expression levels and good clonality were expanded for further evaluation. At this stage in the cell line development, the expression levels ranged from 7 to 23 μg/mL.

Considering the overall higher expression of clones from Pool 4 and better product quality of Pool 4 during pool screening stage, the top 10 clones with the highest expression level from Pool 1 and top 26 clones from Pool 4 were screened with the CIMPR binding assay. The 36 clones were first analyzed for enzyme activity. After titration, two concentrations of enzyme (50 and 100 nanomoles of 4MU released per milliliter per hour) were tested in the CIMPR binding assay.

Clones having high productivity and/or high CIMPR binding were chosen for further evaluation. Four clones from Pool 1 and eight clones from Pool 4 were selected for batch refeeding evaluation in spin tubes.

Clones were expanded from 96- to 24- to 6-well plates and into spin tubes for batch refeeding screening with medium M4 containing selection pressure. Vials were frozen down (Cryopreservation Medium: 90% M1+10% DMSO) during clone expansion. Frozen vials were placed in cryobox freezing containers in −80° C. freezer overnight and stored in liquid nitrogen tanks.

When clones expanded from well-plates to spin tubes were recovered, N−1 cell cultures were inoculated for batch refeeding cultures by 1:4-1:5 dilution into fresh production medium M3 to obtain a seeding density of $4.0-5.3\times10^5$ cells/ml in spin tubes (day 0). The clone batch refeeding cultures (20 ml) were incubated in a Kuhner shaker (35° C., 85% humidity, 6% $CO_2$ and 225 RPM). Starting from day 3, cells were spun down (300 RPM, 5 min, 25° C.) and 80% supernatant was exchanged with fresh M3 medium. When viable cell density was above $20\times10^6$ cells/ml, a certain amount of cells was discarded according to their growth rate to target viable cells density between $25\times10^6$ and $30\times10^6$ cells/ml on the next clay. Pool batch refeeding cultures were harvested when viability dropped below 20% or on day 14 by centrifugation (3000 RPM, 10 min, 4° C.).

Supernatants from harvested cultures were measured for enzyme production on each day beginning day 6 (D6). The CIMPR binding assay was performed with D6 and D9 samples after titration to 50 and 100 nanomoles of 4-MU released per milliliter per hour. Based upon the growth characteristics, enzyme productivity, and CIMPR binding in the spin tube study, several clones were chosen for further evaluation.

The top 4 clones, 01-003, 04-002, 04-018 and 04-023, were selected from the top 10 clones based upon cell growth performance, enzyme production, and CIMPR binding capacity. Bioreactor studies and additional spin tube studies were used to further evaluate clones, and clones 01-003 and 04-023 were selected as the top clones from Pools 1 and 4 for further development.

Example 2: Characterization of CIMPR Affinity of rhα-Gal A

Figure 7A:
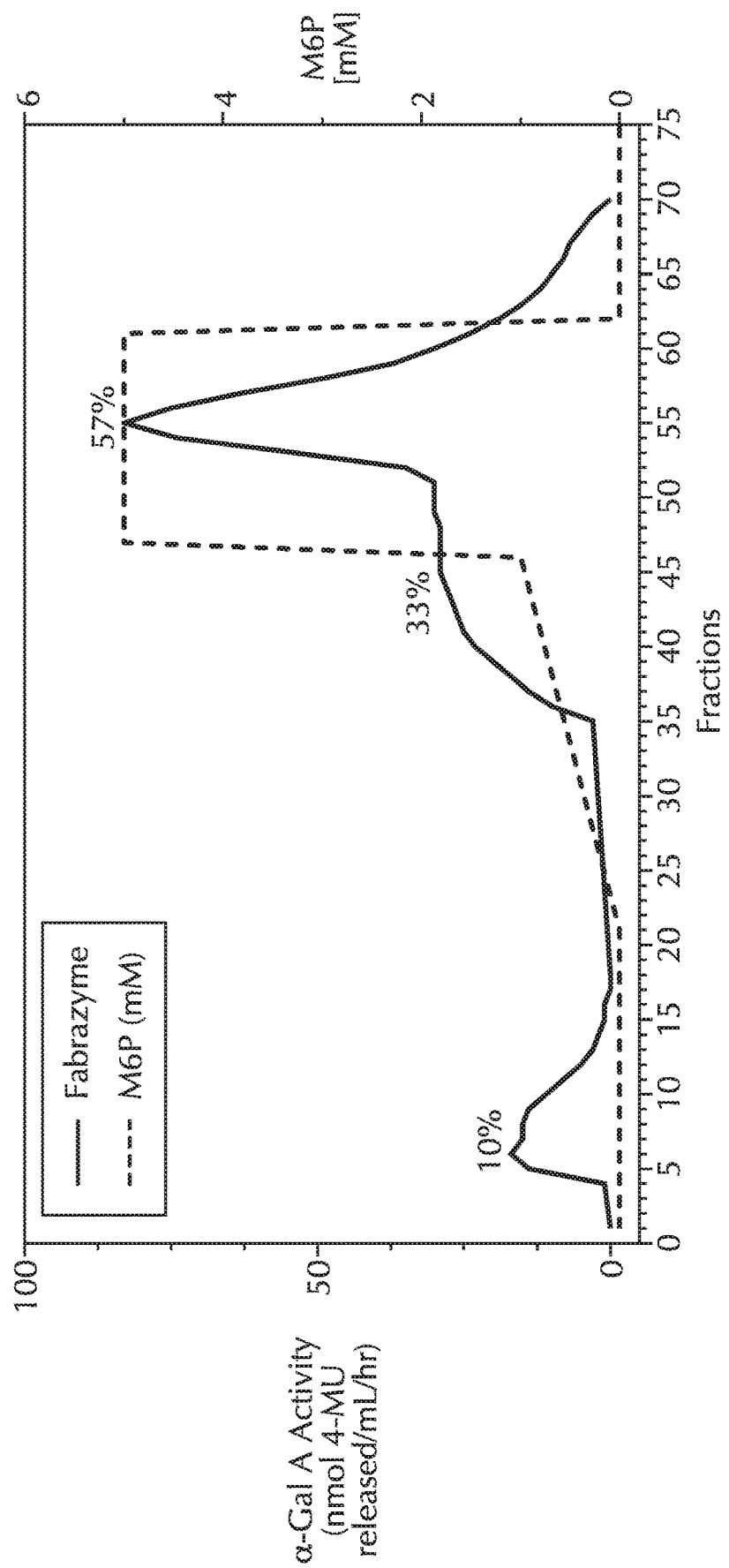
FIG. 7 shows CIMPR profiles of Fabrazyme and rhα-Gal A of different cell line and different growth conditions.
Figure 7B:
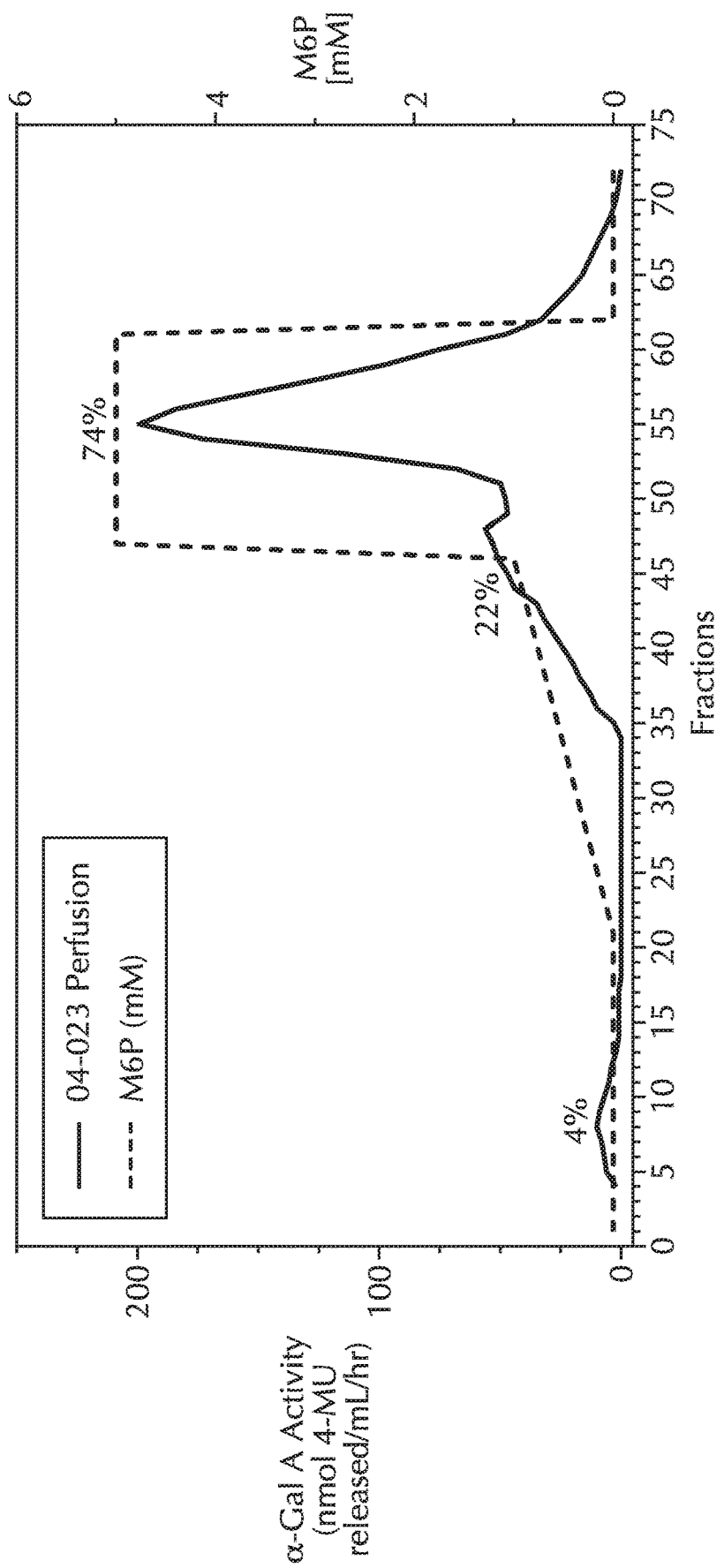
Figure 7C:
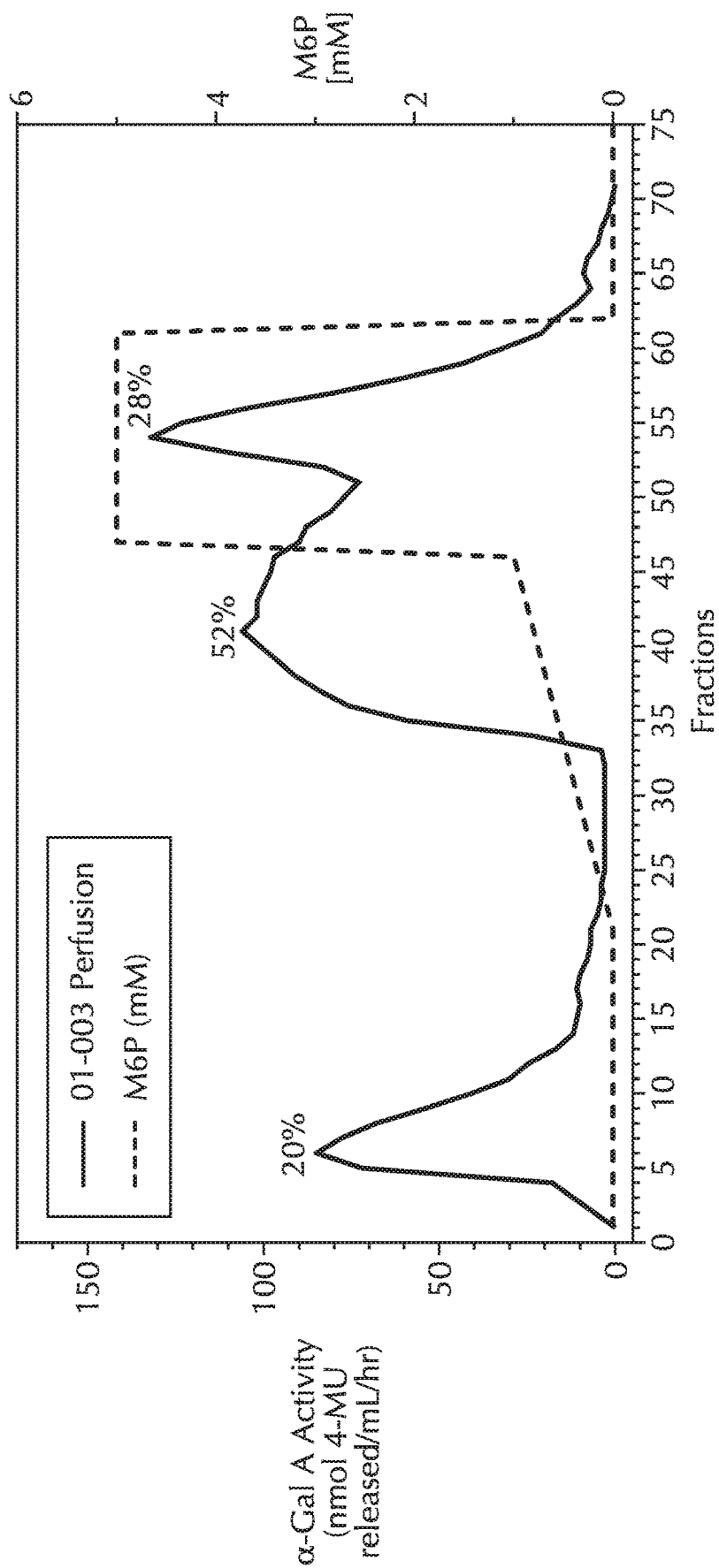
Figure 7D:
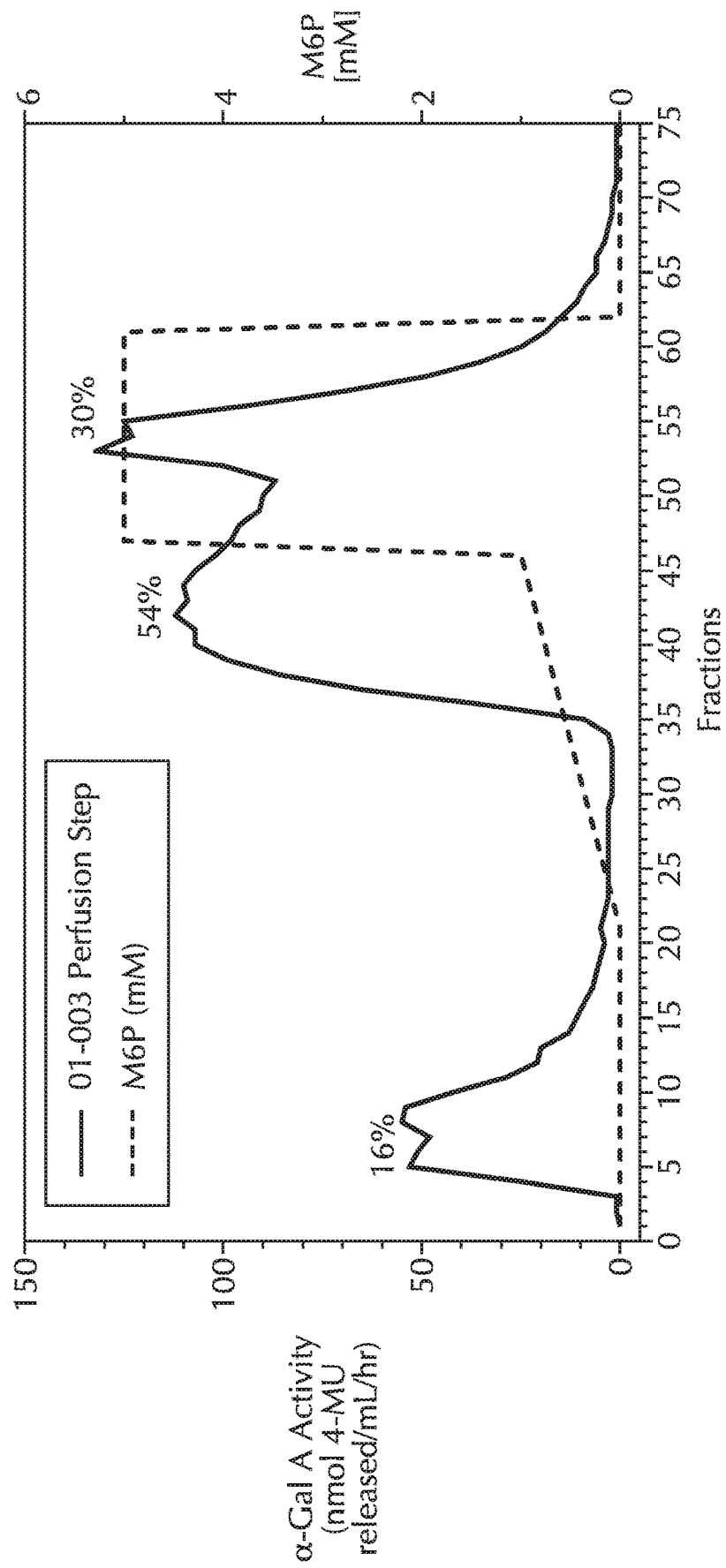
Figure 7E:
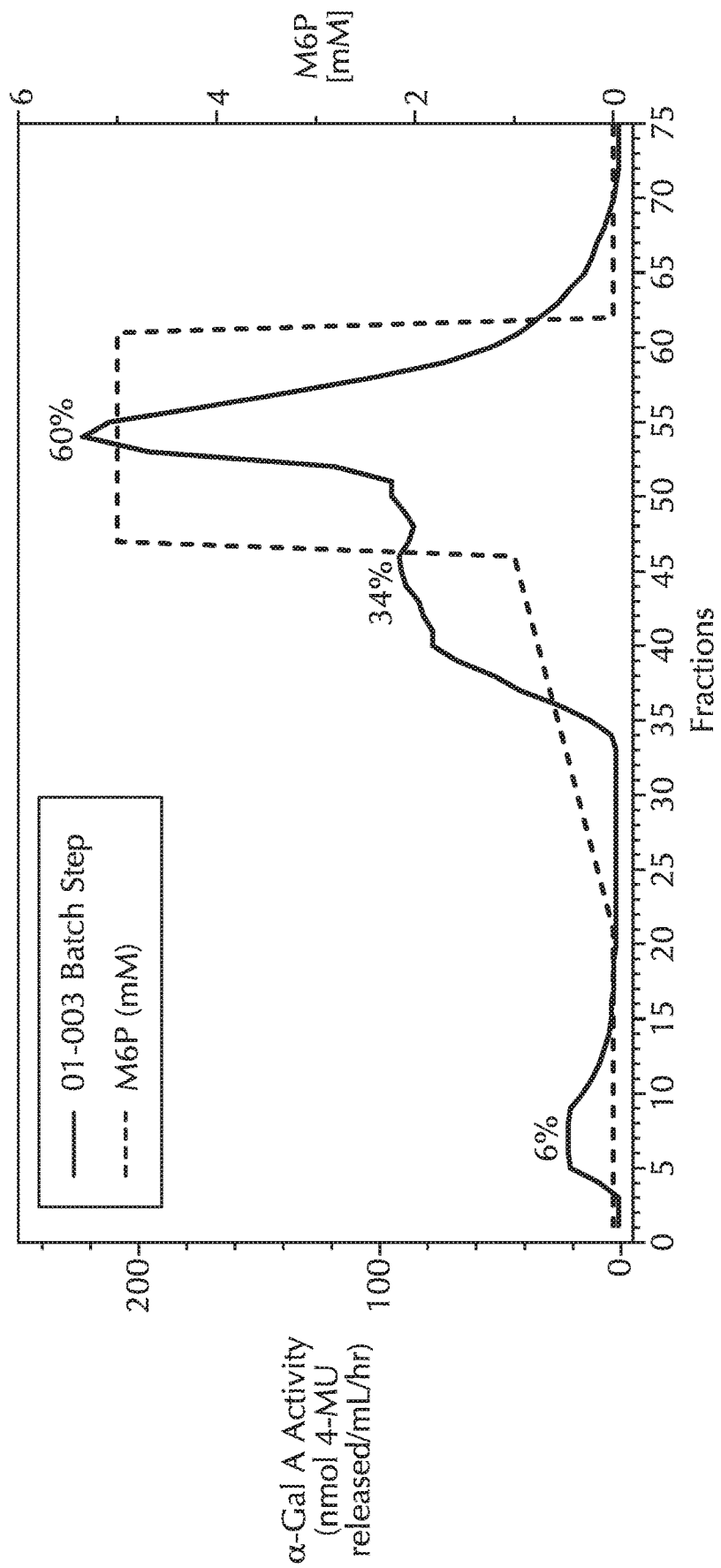
Figure 7F:
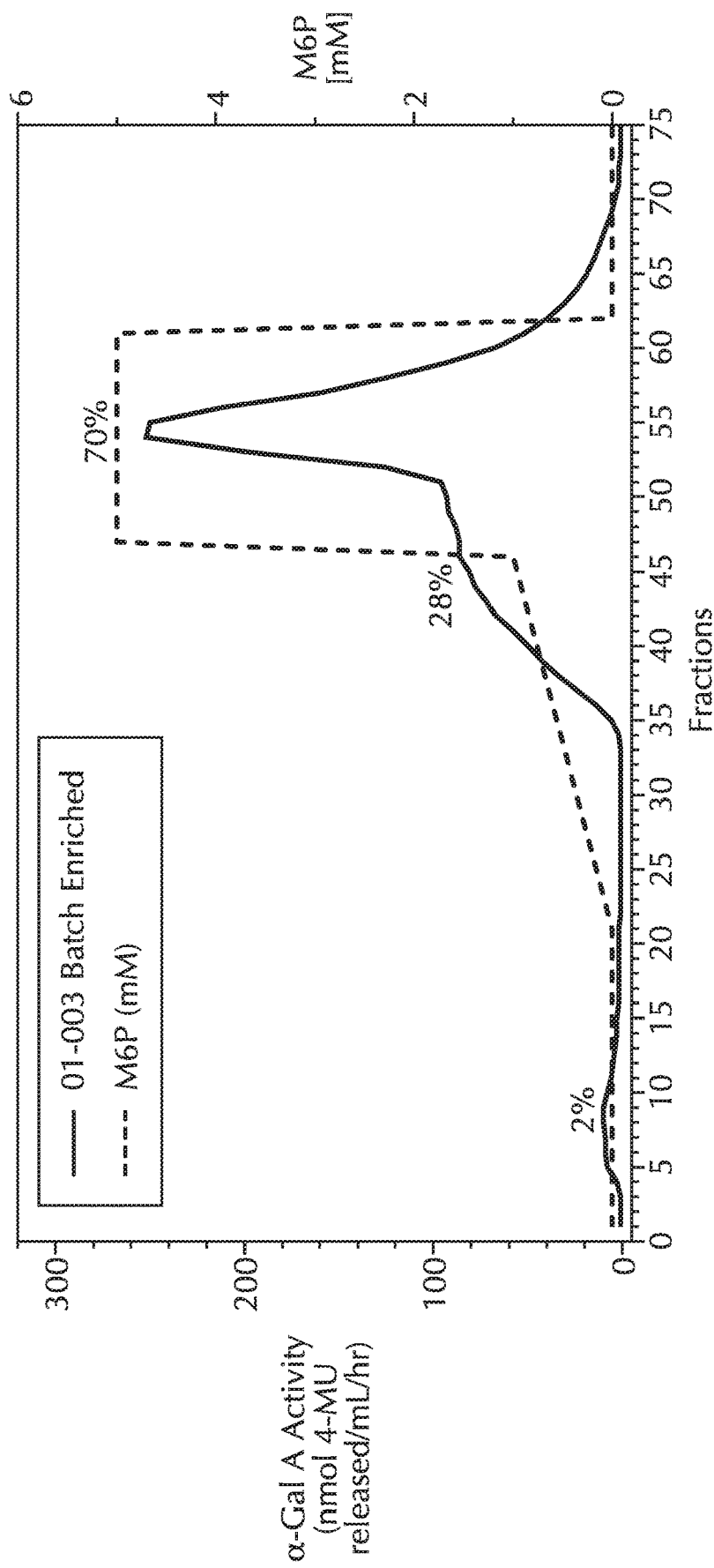

The ability of recombinant α-galactosidase A to bind to a CIMPR column in vitro is an indicator of that recombinant enzyme's ability to bind to the receptor in vivo and target the lysosomes. Two clones of rhα-Gal A (clone 01-003 and clone 04-023) were produced by perfusion culture and the binding was determined by passing each enzyme over an immobilized CIMPR affinity column (FIG. 7), as described above. FIGS. 7A-7C illustrate that 90% of Fabrazyme (agalsidase beta) bound to the CIMPR column, 80% of rhα-Gal A (01-003), and 96% of rhα-Gal A (04-023) bound the CIMPR column. FIGS. 7D-7F illustrate how the expression and purification can be varied to generate molecules that have higher binding affinity for the CIMPR column.

Example 3: Stabilization of rhα-Gal A with Migalastat

Figure 8A:
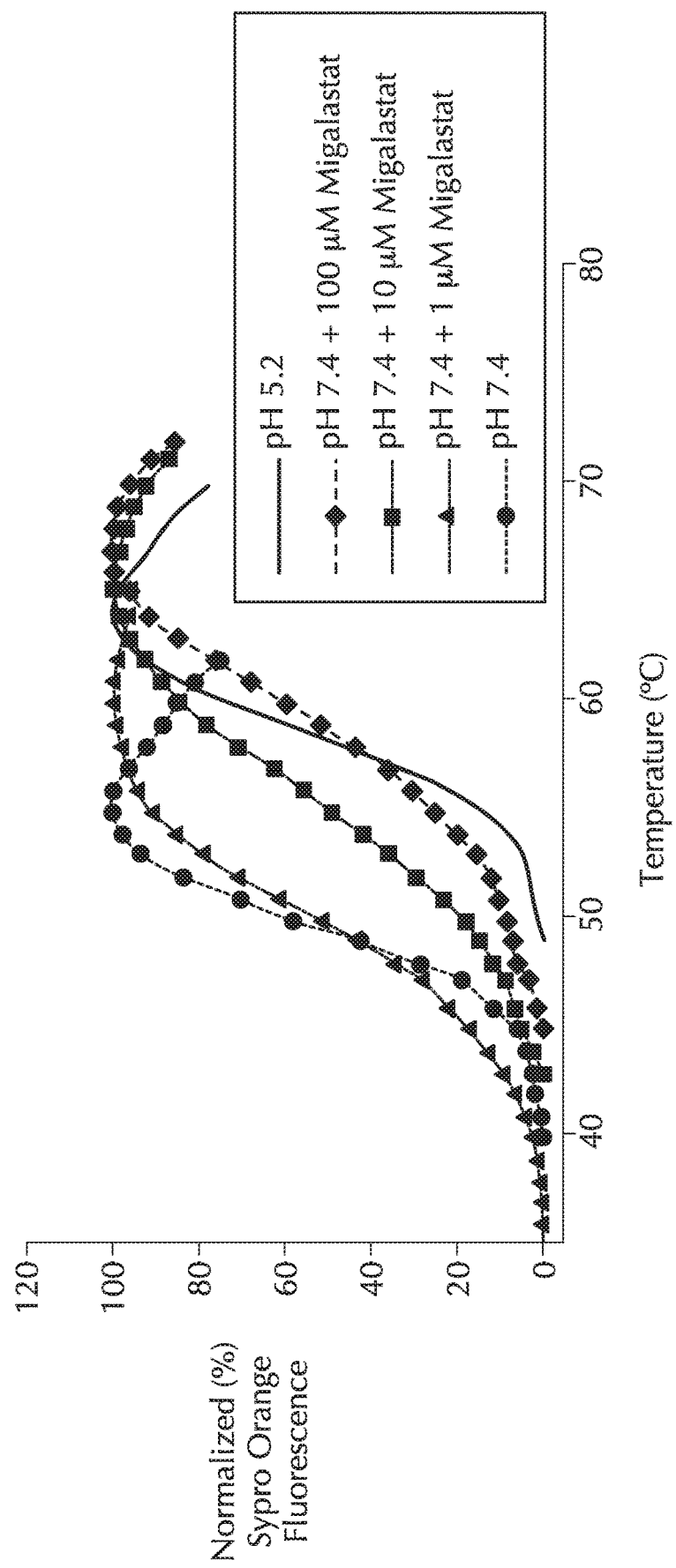
FIG. 8 shows increased thermostability of rhα-Gal A in the presence of migalastat.
Figure 8B:
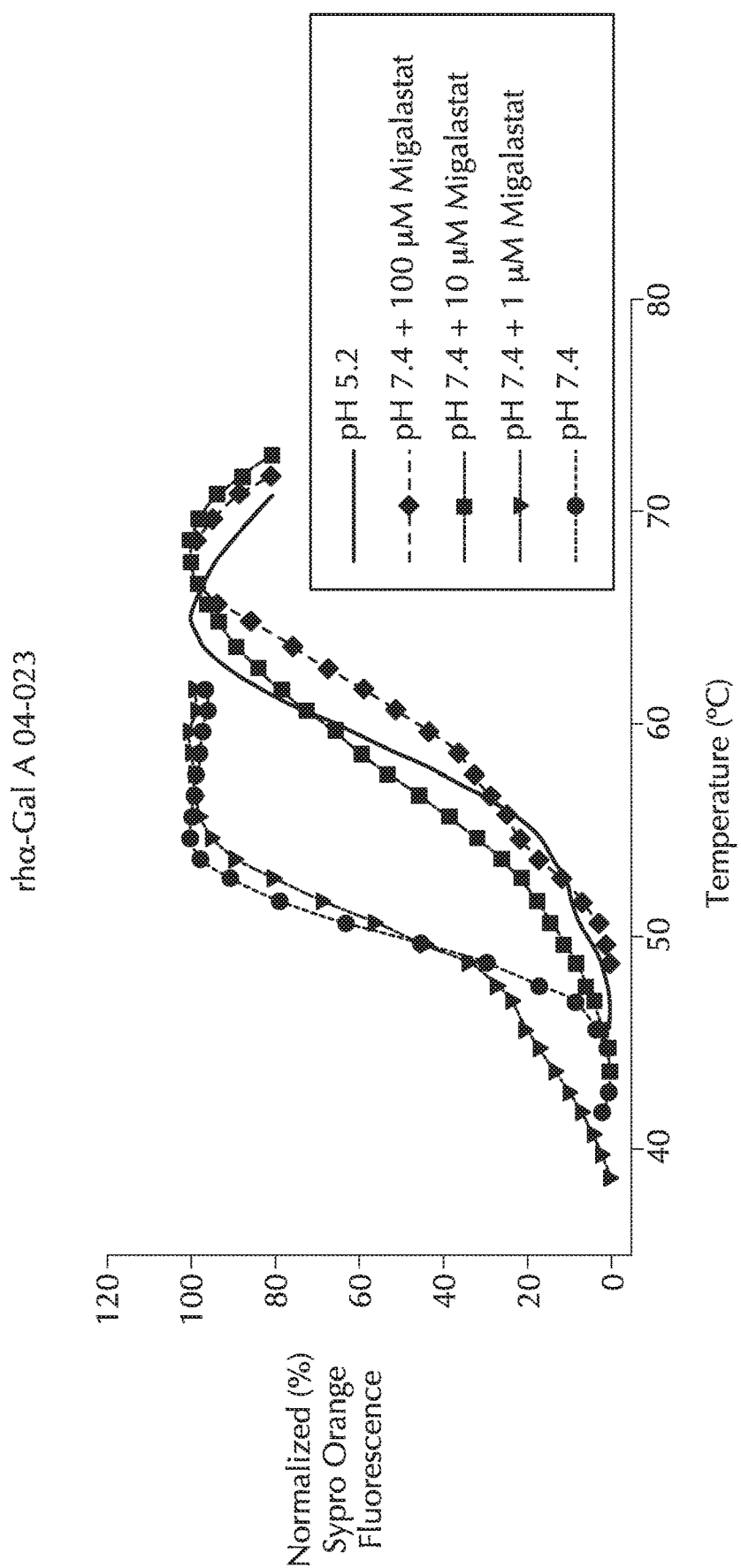

The ability of migalastat to stabilize rhα-Gal A was investigated. As seen in FIG. 8 and Table 1, migalastat has been found to decrease the unfolding of rhα-Gal A and stabilize the active conformation of rhα-Gal A, preventing denaturation and irreversible inactivation at the neutral pH, potentially allowing it to survive conditions in the circulation long enough to reach and be taken up by tissues.

TABLE 1

| | Sypro Orange Thermostability | | | | |
|---|---|---|---|---|---|
| | Tm ° C. pH 7.4 | Tm ° C. pH 7.4 + 1 μM Migalastat | Tm ° C. pH 7.4 + 10 μM Migalastat | Tm ° C. pH 7.4 + 100 μM Migalastat | Tm ° C. pH 5.2 |
| rhα-Gal A (01-003) | 48.9 | 49.4 | 54.6 | 58.4 | 57.7 |
| rhα-Gal A (04-023) | 49.9 | 50.3 | 57.0 | 60.0 | 58.3 |

Example 4: Oligosaccharide Characterization of rhα-Gal A Clones by Liquid Chromatography The glycosylation profile of α-Gal A is very important for serum half-life and lysosomal targeting which in turn has a large influence on the efficacy of the ERT. Each monomer of Replagal (agalsidase alfa) and Fabrazyme (agalsidase beta) typically has three sites glycosylated. Each glycosylation site on each α-Gal A molecule can have various types of glycans which can lead to a very heterogeneous mixture of α-Gal A molecules. FIG. 10 provides oligosaccharide profiles of the total glycans found on different rhα-Gal A ERT therapies.

Figure 9:
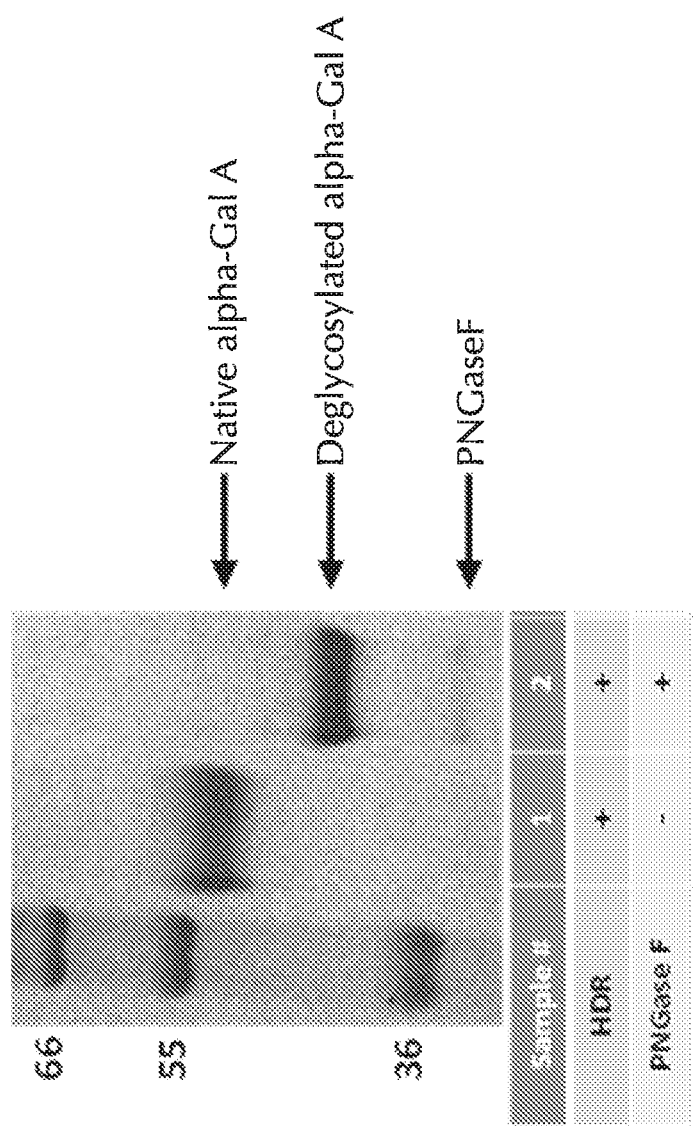
FIG. 9 shows the extent of glycosylation removal by PNGase as analyzed by SDS-PAGE.

The glycan profiles of enzymes produced by both clones were analyzed in order to elaborate on in vitro and in vivo characteristics that could affect clinical efficacy. Glycans from protein samples of each α-Gal A were removed by peptide N-glycosidase F (PNGase) under standard denaturing and reducing conditions. The extent of deglycosylation was assessed on SDS-PAGE with the protein displaying a shift to lower apparent molecular weight upon deglycosylation (FIG. 9). Following release of the glycans from the protein backbone, the glycans are reacted with anthranilic acid to form 2-anthranilic acid derivatives, which are then separated by normal-phase chromatography on an amino column.

Normal phase liquid chromatography on amino columns is a valuable technique to compare the relative abundance of all glycan forms. The retention time is influenced by charge density and overall oligosaccharide size. Glycans eluting between 15-30 minutes are neutral glycan consisting of high-mannose and asialyo-complex oligosaccharides.

FIG. 10 is representative of the analysis of two types of rhα-Gal A proteins designated 01-003 and 04-023. Purified glycans from different ERTs were compared in FIG. 10A-F to determine the glycan structures found on each ERT.

Proteins containing neutral glycan consisting of high-mannose and asialyo-complex oligosaccharides are quickly cleared from circulation by either the mannose receptor or the asialoglycoprotein receptor. Therefore it is beneficial to have the minimal high-mannose and asialyo-complex oligosaccharides on a recombinant human α-Gal A.

Another potential glycan type is phosphorylated oligosaccharides. These glycans are critical for delivery of the ERT to the lysosome via the CIMPR. A phosphorylated oligosaccharide can contain either one M6P residue (mono-M6P) or two M6P residues (bis-M6P). The bis-phosphorylated glycan is preferred since its affinity is ~3,000× greater for the CIMPR than a mono-phosphorylated. Mono-phosphorylated glycans are indicated by blue stars while bis-phosphorylated glycans elute between 110 and 120 minutes. Mono-phosphorylated glycans can be formed by either incomplete phosphorylation or dephosphorylation by acid phosphatases released into the conditioned media from cell death during manufacturing.

Figure 10A:
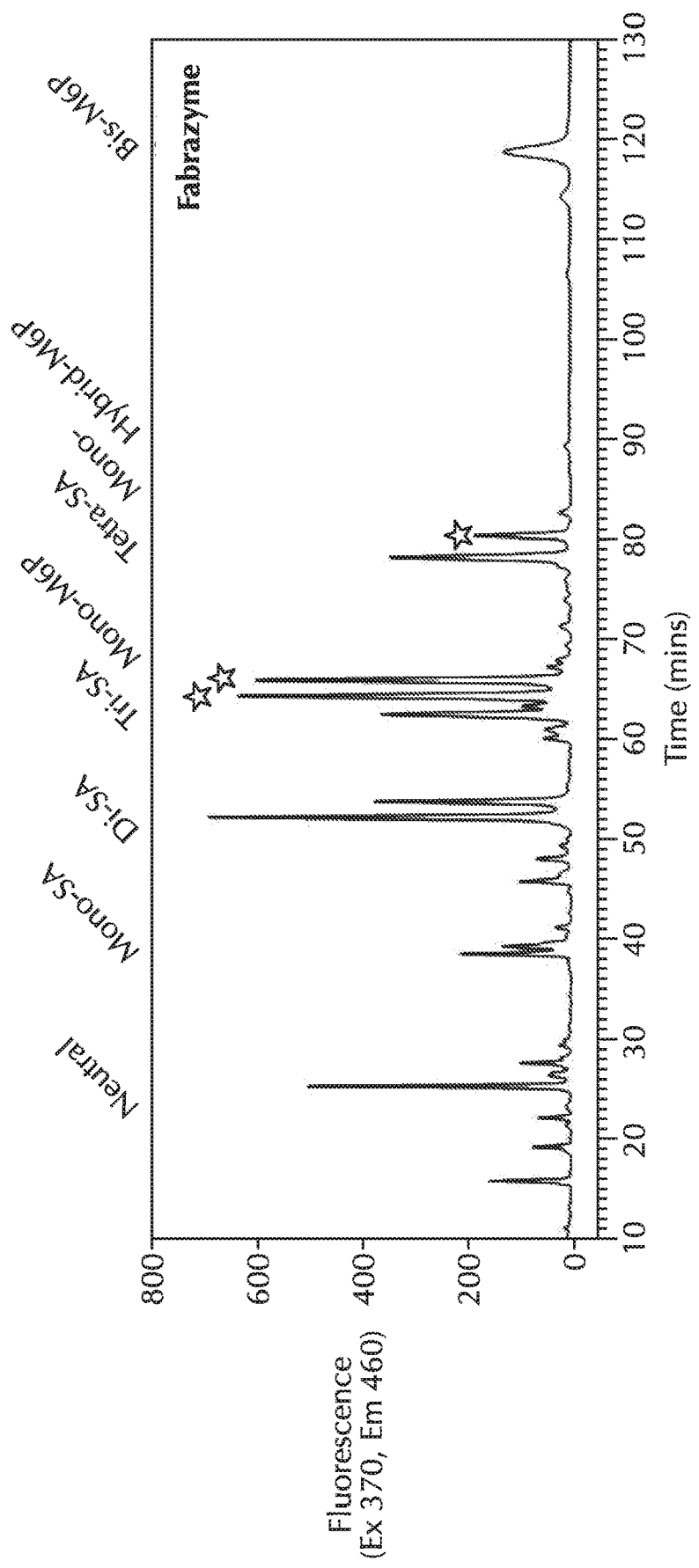
FIGS. 10A-10F show the glycan analysis of Fabrazyme and rhα-Gal A of different cell lines and different growth conditions.

FIG. 10A shows glycans from Fabrazyme (agalsidase beta). Neutral glycans (elution 15-30 mins) account for ~13% of the total glycans and bis-phosphorylated glycan (elution 110-120 mins) account for ~9% of the total glycans. There are significant amounts of mono-phosphorylated glycans present indicating partial phosphorylation or significant phosphatase degradation.

Figure 10B:
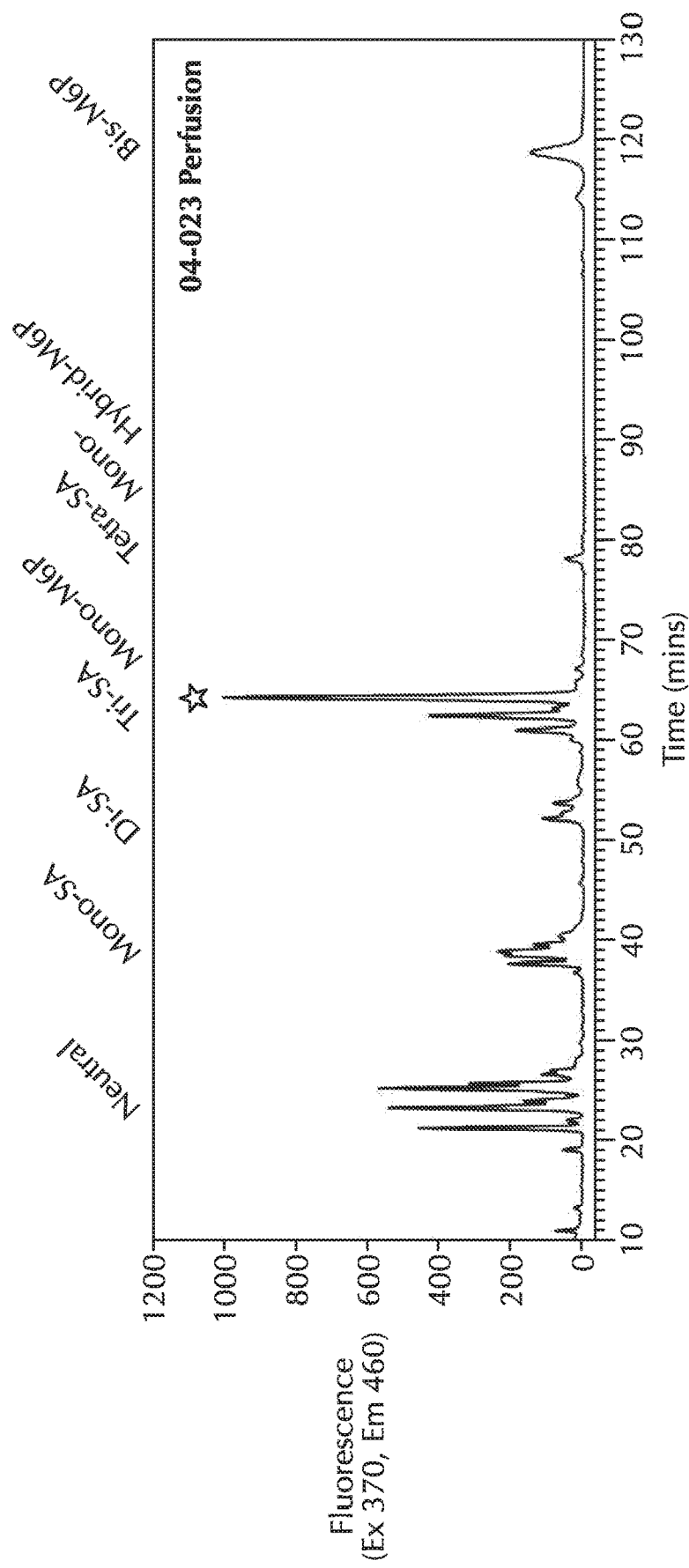

FIG. 10B shows glycans from Fabry ERT rhα-Gal A 04-023 (produced by cell line 04-023). Neutral glycans account for ~33% of the total glycans and bis-phosphorylated glycan is higher (11%) than Fabrazyme (agalsidase beta).

Figure 10C:
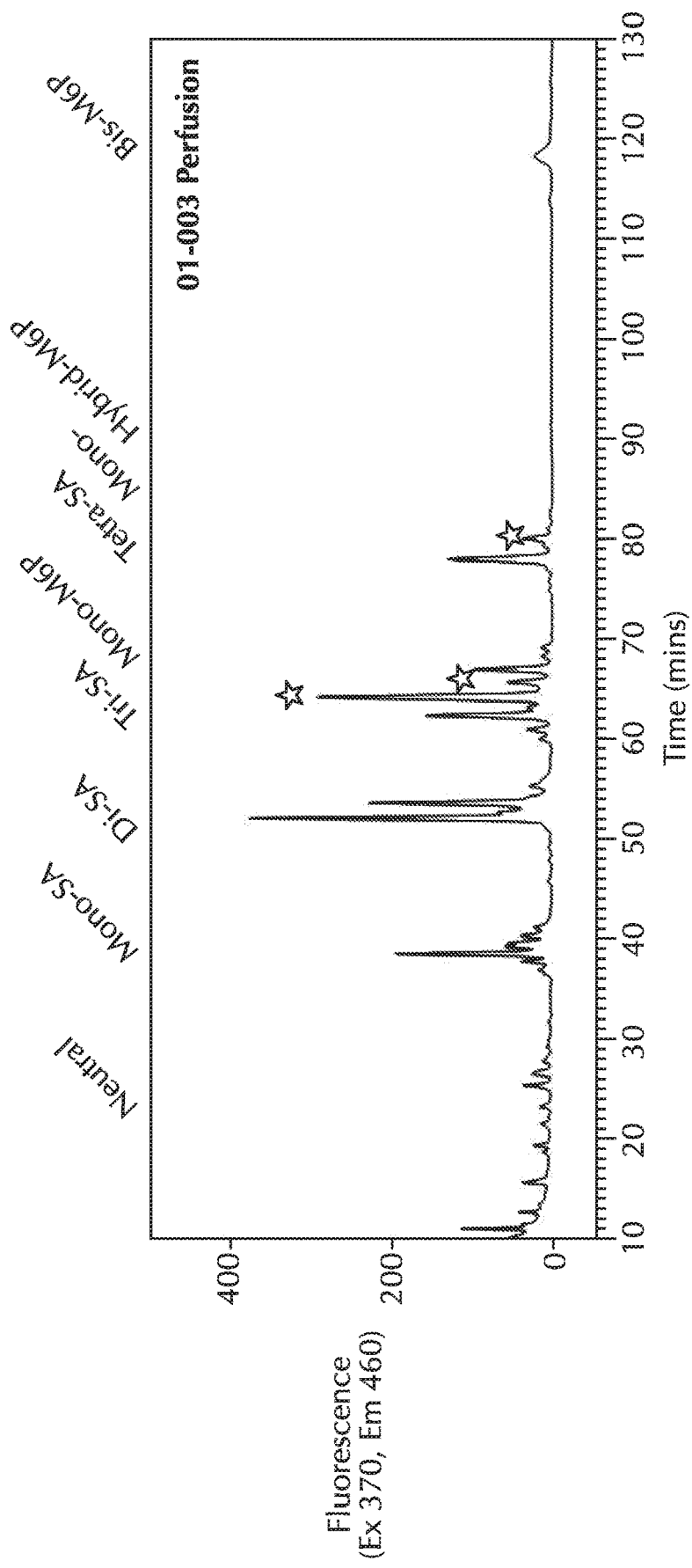

FIG. 10C shows glycans from Fabry ERT rhα-Gal A 01-003 (produced by cell line 01-003). A very low amount of neutral glycans are present (6%) which suggests that there should be reduced clearance via mannose and asialoglycoprotein receptors. However this prep contained very low amounts of bis-phosphorylated glycans (6%) which can potentially have a negative impact on lysosomal delivery via the bloodstream.

Figure 10D:
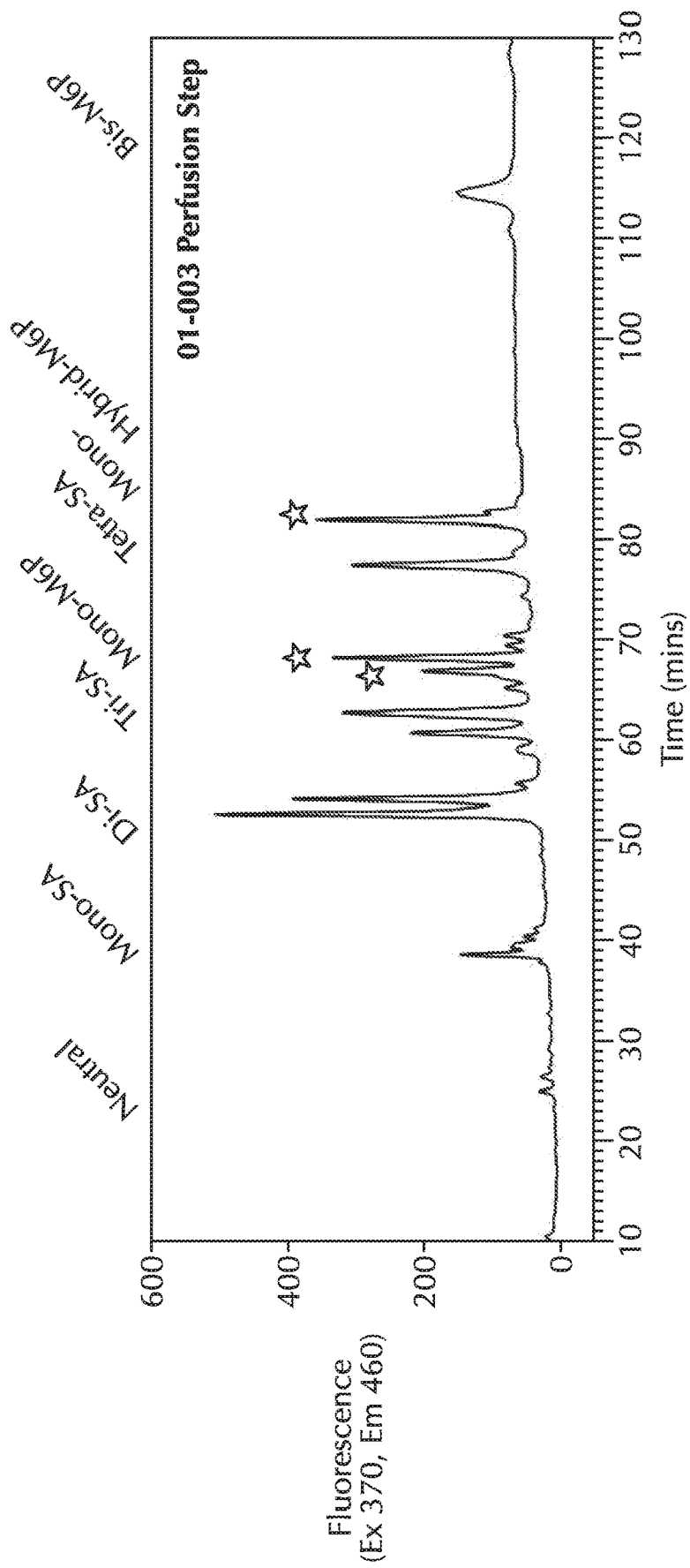
Figure 10E:
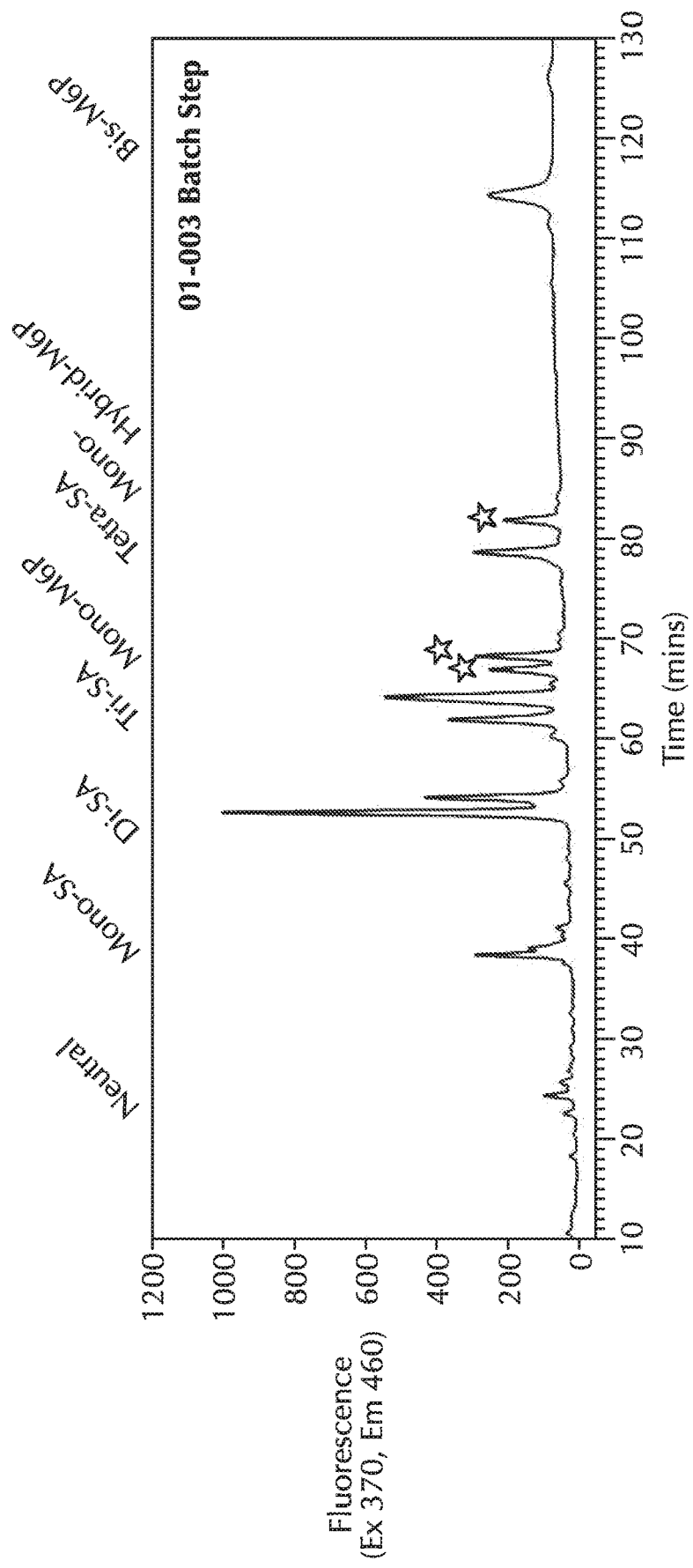
Figure 10F:
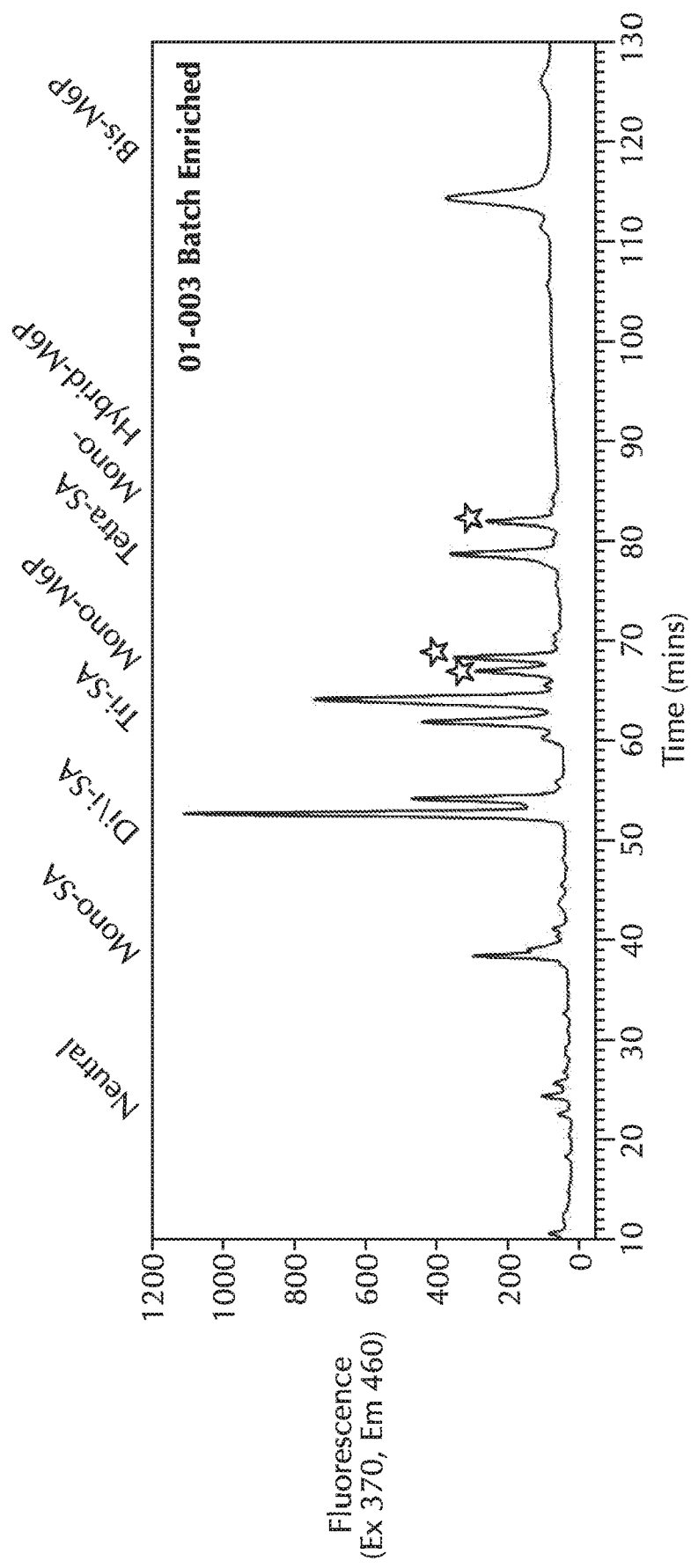

FIGS. 10D-10F illustrate how the expression and purification can be varied to generate molecules that have both low levels of neutral glycans (1.5-5%) and high levels of bis-phosphorylated oligosaccharides (9%-14%). By carefully monitoring the glycan map during ERT selection, expression and purification, rhα-Gal A product characteristics can be varied to minimize off-target clearance via the mannose and asialoglycoprotein receptors while maximizing productive high affinity targeting to the lysosome via the CIMPR.

Figure 11:
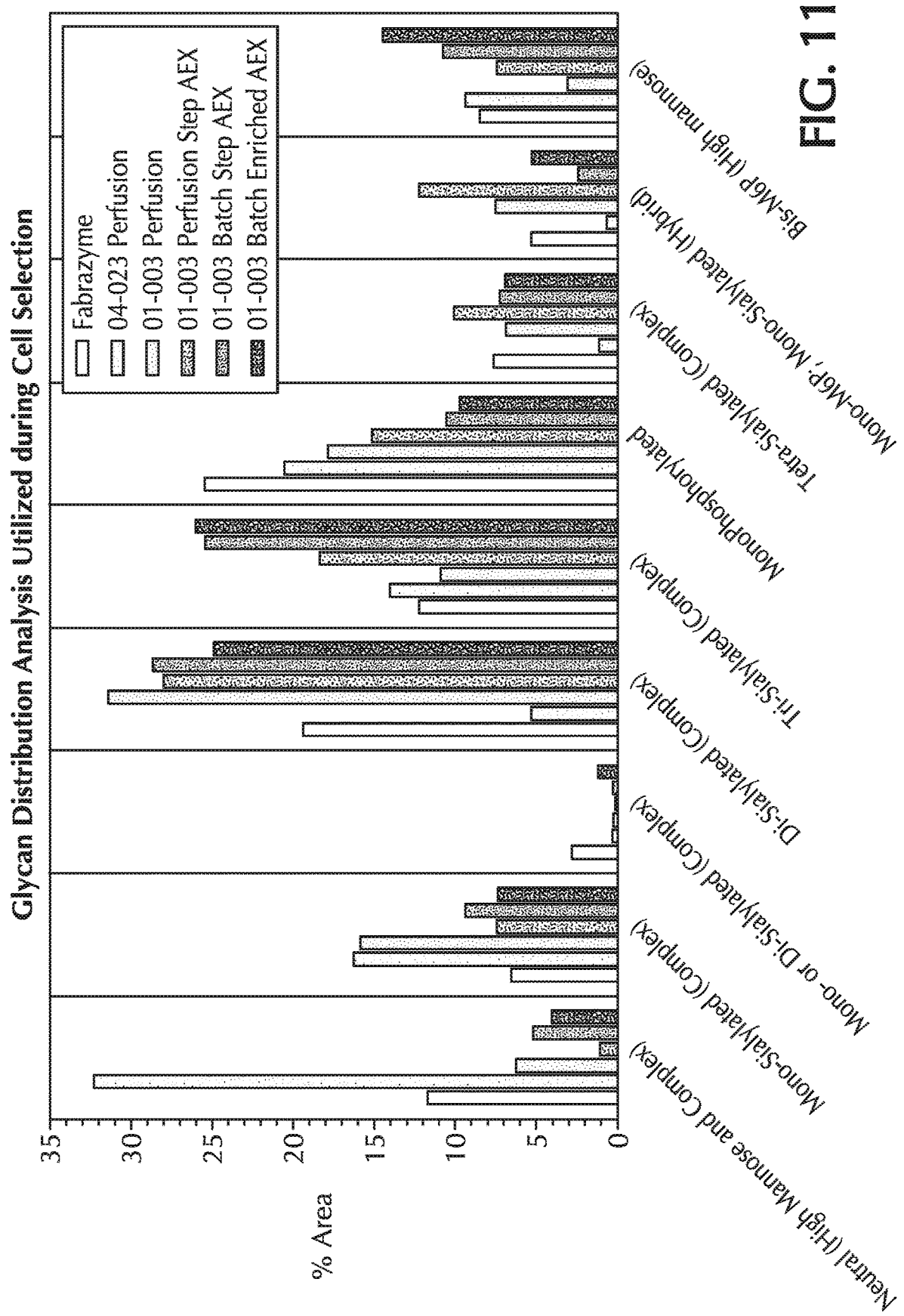
FIG. 11 shows a glycan comparison of Fabrazyme and rhα-Gal A of different cell lines and different growth conditions.

A summary of the glycan distribution for the ERTs from 10A-10F is provided in FIG. 11.

A detailed comparison of the glycans for Replagal (agalsidase alfa), Fabrazyme (agalsidase beta), rhα-Gal A 04-023 and rhα-Gal A 01-003 is provided in Tables 2-4 below. Table 2 provides a summary of a monosaccharide analysis, Table 3 provide a summary of the glycan "families", and Table 4 provides a summary of the glycan structures.

TABLE 2

| Alpha-Gal A | Mannose 6-Phosphate (mol M6P/mol protein) | Sialic Acid (mol SA/mol protein) |
|---|---|---|
| Replagal (agalsidase alfa) | 1.8 | 4.9 |
| Fabrazyme (agalsidase beta) | 3.4 | 4.8 |
| rhα-Gal A (04-023) | 3.7 | 4.5 |
| rhα-Gal A (01-003) | 3.8 | 5.6 |

TABLE 3

| | [1]Replagal (Agalsidase alfa) % Area | [2]Fabrazyme (Agalsidase beta) % Area | [1]04-023 rhα-Gal A % Area | [2]01-003 rhα-Gal A % Area |
|---|---|---|---|---|
| Neutral | | | | |
| Complex and High Mannose | 24.5 | 12.9 | 17.8 | 6.5 |
| Sialylated | | | | |
| Complex | 45.2 | 42.0 | 35.8 | 48.2 |
| Hybrid | 1.5 | 10.6 | 0.2 | 6.4 |

TABLE 3-continued

|  | [1]Replagal (Agalsidase alfa) % Area | [2]Fabrazyme (Agalsidase beta) % Area | [1]04-023 rhα-Gal A % Area | [2]01-003 rhα-Gal A % Area |
|---|---|---|---|---|
| Phosphorylated | | | | |
| Mono-M6P (Hybrid) | 1.5 | 10.6 | 0.2 | 6.4 |
| Bis-M6P (Hybrid) | Not determined | 1.2 | Not determined | 3.0 |
| Mono-M6P (High Mannose) | 25.7 | 20.7 | 31.9 | 20.8 |
| Bis-M6P (High Mannose) | 3.1 | 6.8 | 14.5 | 11.1 |
| Covered Mono-M6P (High Mannose) | Not determined | 3.4 | Not determined | 1.8 |
| Covered Bis-M6P (High Mannose) | Not determined | 0.1 | Not determined | 0.0 |

[1]Glycan values derived from HPLC analysis of 2AA labeled glycans
[2]Glycan values derived from LC/MS/MS method

TABLE 4

|  | [1]Replagal (Agalsidase alfa) % Area | [2]Fabrazyme (Agalsidase beta) % Area | [1]04-023 rhα-Gal A % Area | [2]01-003 rhα-Gal A % Area |
|---|---|---|---|---|
| Neutral (High Mannose and Complex) | 24.5 | 12.9 | 17.8 | 6.5 |
| Mono-Sialylated (Complex) | 20.7 | 5.7 | 11.6 | 10.1 |
| Mono- or Di-Sialylated (Complex) | 2.4 | 0 | 3.4 | 0 |
| Di-Sialylated (Complex) | 13.0 | 19.3 | 6.9 | 22.7 |
| Tri-Sialylated (Complex) | 8.5 | 13.1 | 11.8 | 10.6 |
| Tetra-Sialylated (Complex) | 0.7 | 3.9 | 1.6 | 4.8 |
| Mono-M6P; Mono-Sialylated (Hybrid) | 1.5 | 10.6 | 0.2 | 6.4 |
| Mono-M6P (High Mannose) | 25.7 | 20.7 | 31.9 | 20.8 |
| Bis-M6P (High Mannose) | 3.1 | 6.8 | 14.5 | 11.1 |
| Bis-M6P (Hybrid) | Not determined | 1.2 | Not determined | 3.1 |
| Covered Bis-M6P | Not determined | 0.1 | Not determined | 0.0 |
| Covered Mono-M6P | Not determined | 3.3 | Not determined | 1.8 |

[1]Glycan values derived from HPLC analysis of 2AA labeled glycans
[2]Glycan values derived from LC/MS/MS method As can be seen from Tables 2-4, rhα-Gal A 01-003 and rhα-Gal A 04-023 have certain distinguishing characteristics that are structurally distinct from Replagal (agalsidase alfa) and Fabrazyme (agalsidase beta). For example, rhα-Gal A 04-023 has very high bis-M6P content, with over 14% of glycans bearing bis-M6P. rhα-Gal A 04-023 also has high levels of mono-M6P, with over 30% of glycans being mono-M6P (high mannose). rhα-Gal A 04-023 also has over 35% of its glycans bearing sialic acid.

Table 5 provides the relative abundancies of individual glycans of rhα-Gal A 01-003 derived from LC/MS/MS method, and Table 6 provides a summary of the glycan structures. In Table 5 below, "MX" represents X number of mannose units, "AX" represents X number of N-acetylglucosamine antennae in a complex or hybrid glycan, "GX" represents X number of galactose units, "SX" represents X number of terminal sialic acid units, "F" represents a fucose unit, "P" represents a mono-M6P unit, "2(P)" represents a bis-M6P unit, "Ac" represents an acetyl unit, "X(Ac)" represents X number of acetyl caps, "KX" represents X number of deaminoneuraminic acid units and "SgX" represents an X number of N-glycolylneuraminic acid units.

TABLE 5

| Glycan Name | Glycan % of FLD Total |
|---|---|
| A1G1 | 0.19 |
| A1G1S1 | 0.37 |
| A2G1S1 | 0.29 |
| A2G2 | 0.37 |
| A2G2S1 | 1.67 |
| A2G2S1Sg1 | 0.26 |
| A2G2S2 | 5.09 |
| A2G2Sg1 | 0.06 |
| A3G3S2 | 0.16 |
| A3G3S3 | 0.30 |
| A4G4S3 | 0.04 |
| FA1 | 0.20 |
| FA1G1 | 0.23 |
| FA1G1S1 | 0.55 |
| FA2G1 | 0.52 |
| FA2G1S1 | 0.87 |
| FA2G2 | 0.66 |
| FA2G2 2(Ac)S2 | 0.06 |
| FA2G2AcS1 | 0.04 |
| FA2G2AcS2 | 0.13 |
| FA2G2S1 | 4.31 |
| FA2G2S1Sg1 | 0.70 |

TABLE 5-continued

| Glycan Name | Glycan % of FLD Total |
|---|---|
| FA2G2S2 | 14.99 |
| FA2G2Sg1 | 0.19 |
| FA3G1S1 | 0.08 |
| FA3G2 | 0.04 |
| FA3G2S1 | 0.16 |
| FA3G2S1K1 | 0.00 |
| FA3G2S2 | 0.35 |
| FA3G3 | 0.11 |
| FA3G3S1 | 0.47 |
| FA3G3S1Sg1 | 0.04 |
| FA3G3S2 | 1.59 |
| FA3G3S3 | 8.35 |
| FA4G3S2 | 0.04 |
| FA4G3S3 | 0.14 |
| FA4G4S2 | 0.19 |
| FA4G4S2Sg1 | 0.00 |
| FA4G4S3 | 1.16 |
| FA4G4S3Sg1 | 0.43 |
| FA4G4S4 | 4.70 |
| FA5G5S3 | 0.14 |
| FA5G5S4 | 0.04 |
| A1 2(P)M5 | 3.01 |
| A1G1M5 | 0.21 |
| A2G1K1/A1G1S1M4 | 0.77 |
| A1G1S1M5 | 0.72 |
| A1G1S1PM6 | 4.67 |
| A1G1Sg1M4 | 0.03 |
| A1G1Sg1M5 | 0.02 |
| A1PM6 | 0.00 |
| A1PM7 | 1.72 |
| FA1G1S1M4 | 0.05 |
| FA1G1S1M5 | 0.06 |
| FA1G1S1PM6 | 0.00 |
| FA2G2S2M4 | 0.10 |
| 2(P)M7 | 10.17 |
| 2(P)M8 | 0.98 |
| CPM6 | 1.48 |
| CPM7 | 0.35 |
| M4 | 0.29 |
| M5 | 2.19 |
| M6 | 0.63 |
| M7 | 0.27 |
| M8 | 0.21 |
| M9 | 0.33 |
| PM5 | 1.60 |
| PM6 | 9.22 |
| PM7 | 9.91 |
| PM8 | 0.07 |

TABLE 6

| | |
|---|---|
| Total Mono-M6P (% of total glycans) | 29.0 |
| Total Bis-M6P (% of total glycans) | 14.2 |
| Total M6P (% of total glycans) | 43.2 |
| Total M6P (mol/mol protein) | 3.4 |
| Total Sialic (% of total glycans) | 57.7 |
| Total Sialic Acid (mol/mol protein) | 7.0 |
| Total Neutral (% of total glycans) | 6.5 |

The rhα-Gal A 01-003 tested and shown in Tables 2-6 above has high bis-M6P (>14%), high mono-M6P (>25%), and high sialic acid (>50%) and low neutral glycans (<7%). The rhα-Gal A 01-003 tested also has high amounts of M6P (>3 mol/mol) and sialic acid residues (>5 mol/mol) per rhα-Gal A protein.

These combinations of specific glycosylation features provide unique rhα-Gal A enzymes that balance phosphorylation, sialylation and neutral glycan content, thus providing novel enzymes that can have enhanced targeting and less non-productive clearance than commercially available enzymes.

Example 5: Pharmacokinetics of rhα-Gal A and Migalastat Combination

Figure 12:
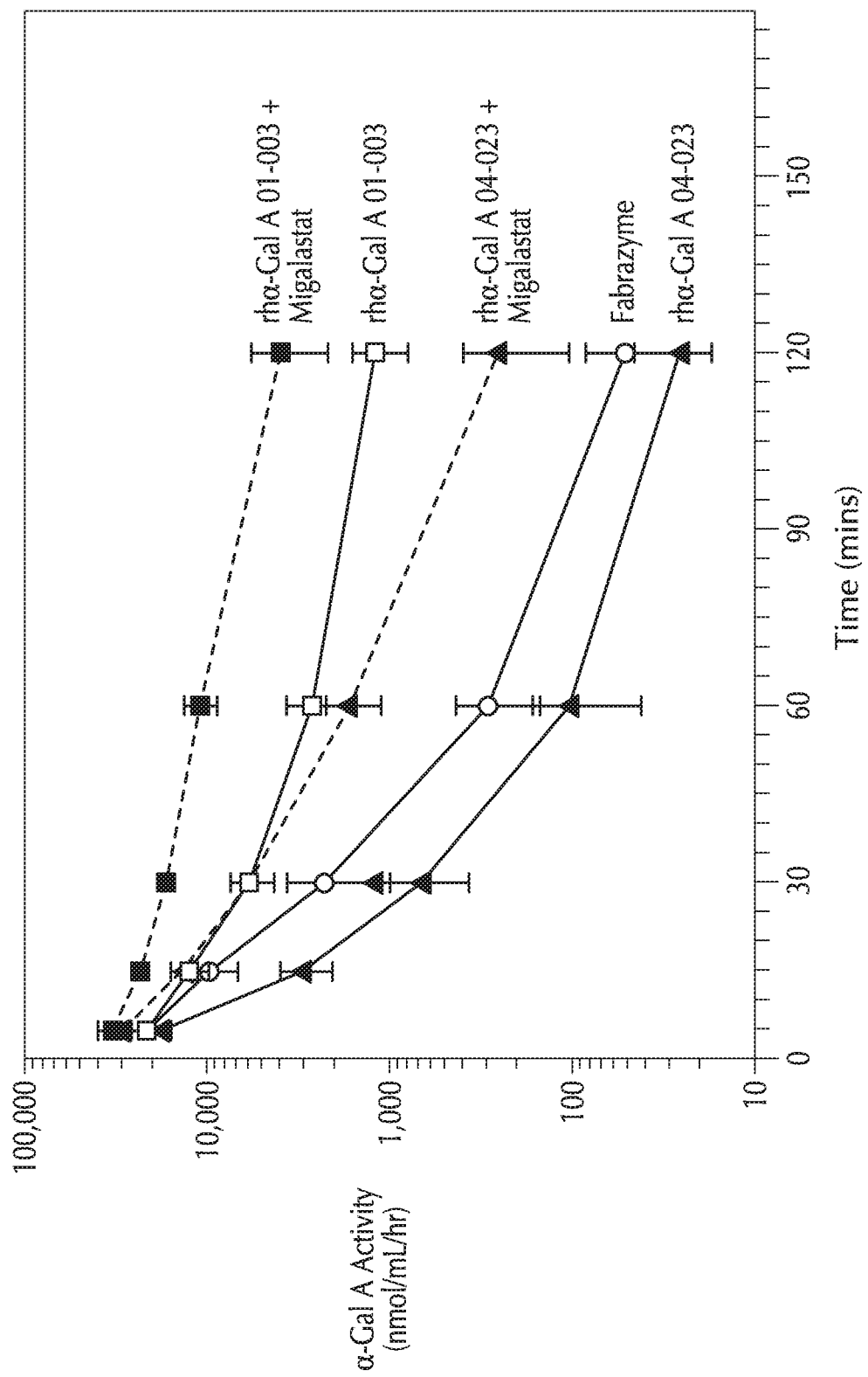
FIG. 12 shows the pharmacokinetics of Fabrazyme and two clones of rhα-Gal A in the presence and absence of migalastat.

The pharmacokinetic profiles of rhα-Gal A 01-003 and rhα-Gal A 04-023 were compared, as well as the effect of combination with migalastat (FIG. 12.) Enzyme (1 mg/kg) was administered via an intravenous bolus injection into Gla KO mice with or without co-formulation with 3 mg/kg migalastat. The Gla knockout (KO) mouse model of Fabry disease shows a high level of analogy to the pathophysiological processes of the disease in Fabry patients. Plasma enzyme activity was assessed at 5, 15, and 30 minutes post infusion as well as 1, 2, and 24 hours post infusion. The treatment groups are shown in Table 7.

TABLE 7

| Group | Treatment | Dose (mg/kg) |
|---|---|---|
| 1 | Untreated | — |
| 2 | Fabrazyme (agalsidase beta) | 1 |
| 3 | Clone 01-003 | 1 |
| 4 | Clone 04-023 | 1 |
| 5 | Clone 01-003 + Migalastat | 1 + 3 |
| 6 | Clone 04-023 + Migalastat | 1 + 3 |

FIG. 12 shows the pharmacokinetics of rhα-Gal A 01-003 and rhα-Gal A 04-023. rhα-Gal A 04-023 has a lower pharmacokinetic profile compared to Fabrazyme (agalsidase beta),while rhα-Gal A 01-003 showed a higher AUC over 2 hours, indicating a greater overall exposure to this enzyme compared to the other enzymes. FIG. 12 also shows the activity of rhα-Gal A 01-003 in plasma is enhanced by co-formulation with migalastat. Similarly, the activity of rhα-Gal A 04-023 in plasma is increased by the presence of migalastat.

Table 8 shows the respective half-life and area under the curve (AUC) for Fabrazyme (agalsidase beta), rhα-Gal A 01-003 and rhα-Gal A 04-023 in Gla KO mice. The level of tissue uptake of the recombinant enzymes was assessed at 24 hours using the enzyme activity assay.

TABLE 8

| | Fabrazyme (agalsidase beta) | rhα-Gal A 01-003 | | rhα-Gal A 04-023 | |
|---|---|---|---|---|---|
| | | ERT alone | +migalastat | ERT alone | +migalastat |
| Half-life (hr) | 0.14 | 0.24 | 0.54 | 0.07 | 0.17 |
| $AUC_{0\text{-}2\ hr}$ (nmol 4 MU/mL/hr * hr) | 4985 | 9301 | 24431 | 2545 | 8994 |

Figure 13A:
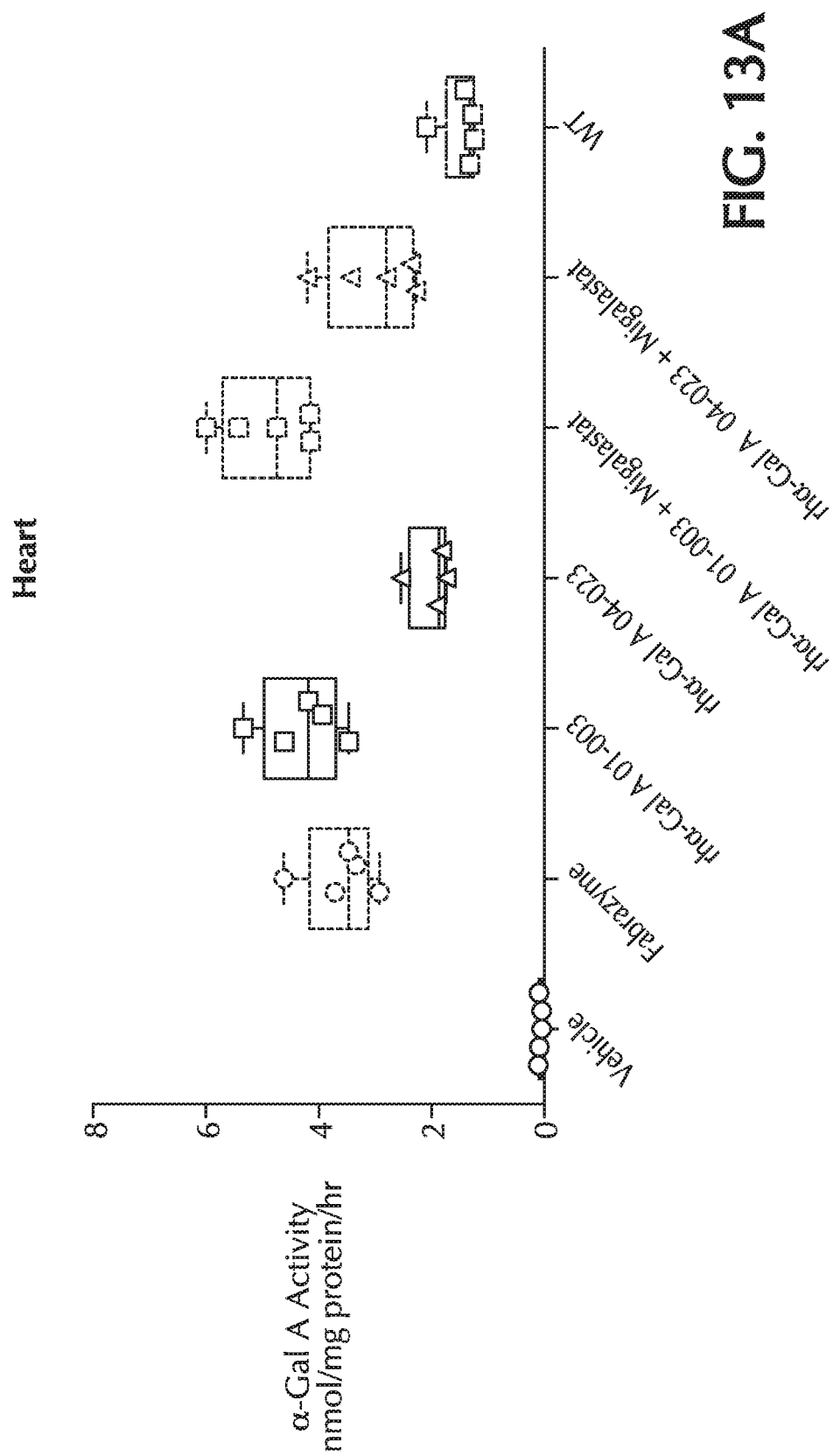
FIGS. 13A-13C show α-Gal A activity in Gla KO mice heart (13A), kidney (13B) and skin (13C) one day after a single administration of various ERTs with and without migalastat.
Figure 13B:
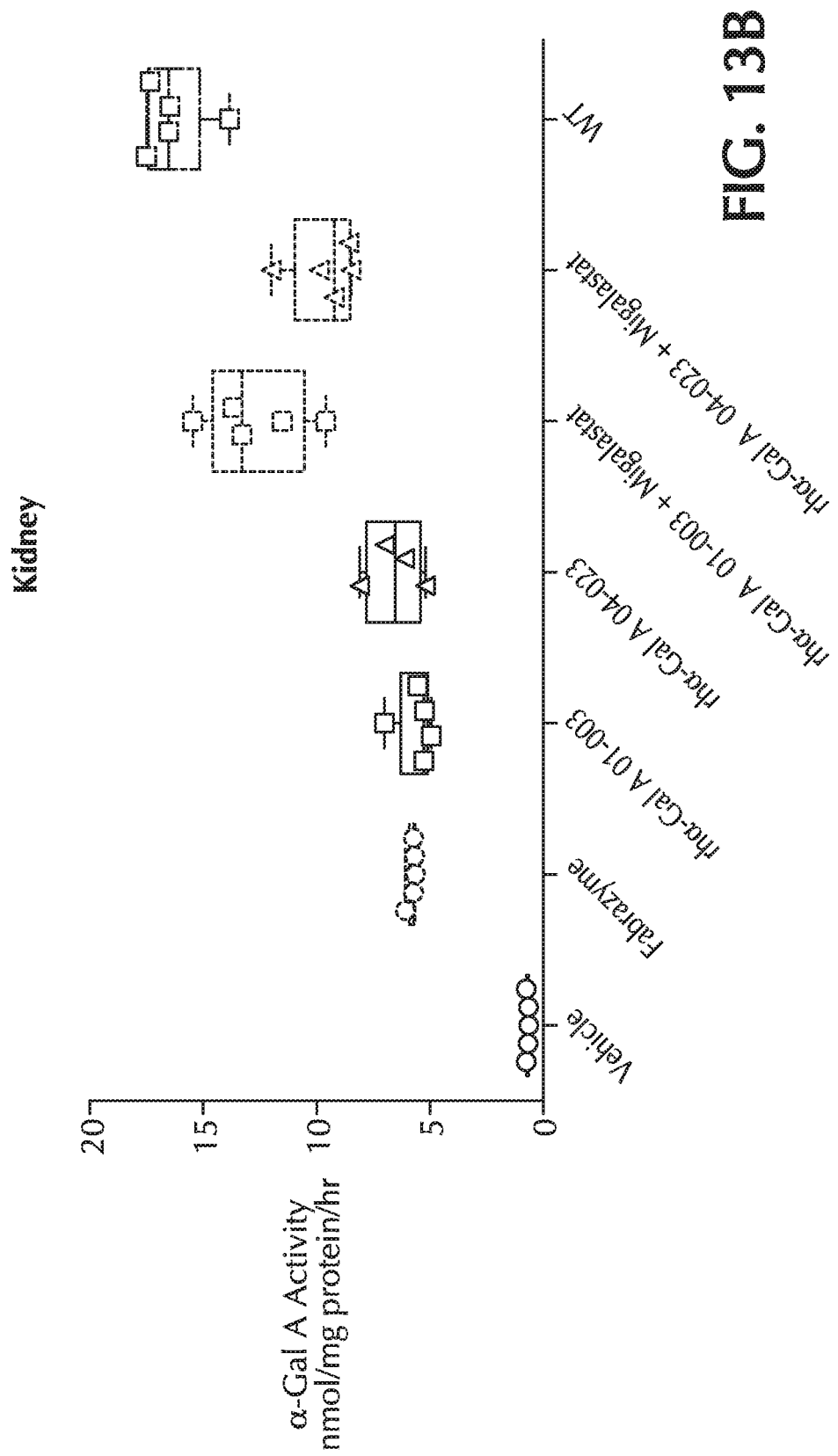
Figure 13C:
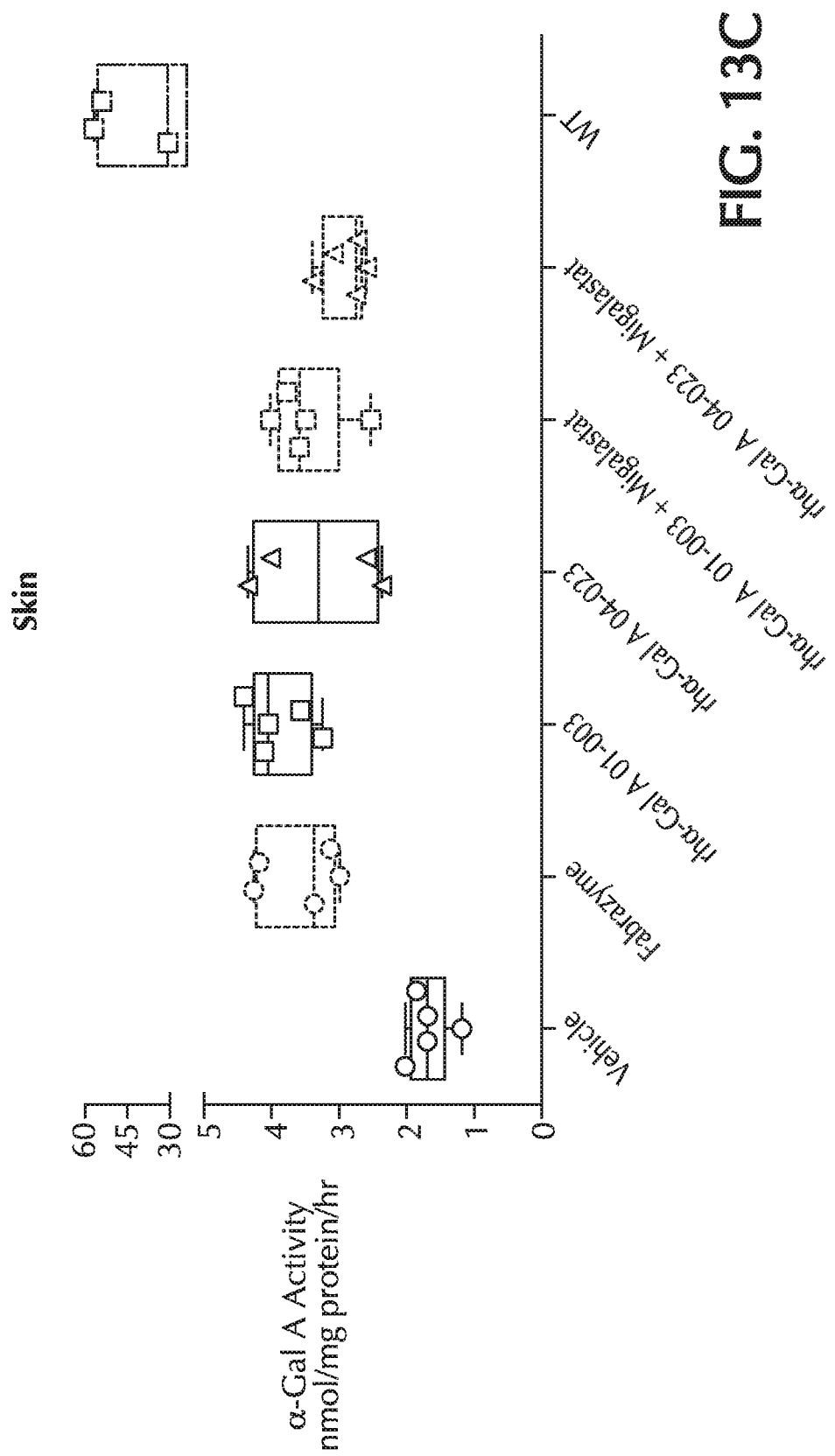

FIG. 13 A shows that enzyme activity in heart tissue after 24 hours for 01-003 was similar to that of Fabrazyme (agalsidase beta) whereas the activity of rhα-Gal A 04-023 was slightly less. The activity in heart after 24 hours for both rhα-Gal A 01-003 and rhα-Gal A 04-023 was increased by the presence of migalastat. The level of enzyme activity found in strain-matched wild type mice are included as a comparator. Interestingly, after bolus infusion of recombinant enzyme the activity levels after 24 hours are higher than those seen in wild-type heart tissue. FIG. 13B shows that the enzyme activity after 24 hour in kidney was similar for all three enzymes and both rhα-Gal A 01-003 and rhα-Gal A 04-023 were increased by the presence of migalastat with rhα-Gal A 01-003 approaching wild-type levels. FIG. 13C shows that the activity in skin tissue after 24 hours was similar across all three enzymes tested and did not appear to be affected by the presence of migalastat.

Example 6: Single Administration Efficacy Comparison of rhα-Gal A Variants

The ability of rhα-Gal A 01-003 and rhα-Gal A 04-023 to reduce plasma lyso-Gb3 and tissue GL-3 was assessed in Gla KO mice. The effect on substrate reduction when combining these enzymes in a co-formulation with migalastat was also assessed. Mice were given a dose of 1 mg/kg enzyme with or without migalastat and plasma lyso-Gb3 and tissue GL-3 (heart, kidney, and skin) was assessed seven days after enzyme administration (Table 9).

TABLE 9

| Group | Treatment | Dose (mg/kg) |
|---|---|---|
| 1 | Untreated | — |
| 2 | Fabrazyme (agalsidase beta) | 1 |
| 3 | rhα-Gal A 01-003 | 1 |
| 4 | rhα-Gal A 01-003 + Migalastat | 1 + 3 |
| 5 | rhα-Gal A 04-023 | 1 |
| 6 | rhα-Gal A 04-023 | 3 |
| 7 | rhα-Gal A 04-023 + Migalastat | 1 + 3 |

Figure 14A:
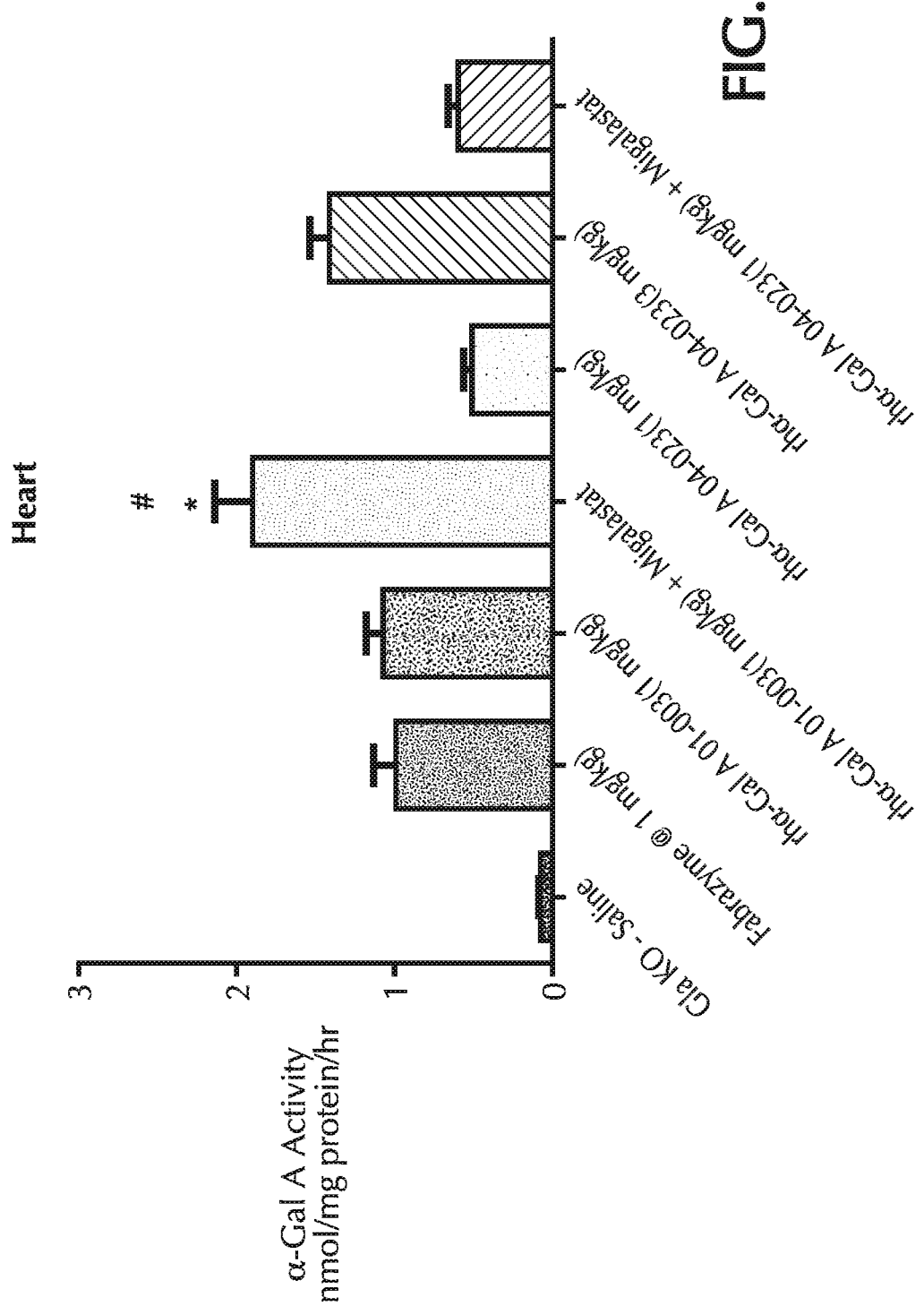
FIGS. 14A-14D show α-Gal A activity in Gla KO mice heart (14A), kidney (14B), skin (14C) and liver (14D) seven days after a single administration of various ERTs with and without migalastat.
Figure 14B:
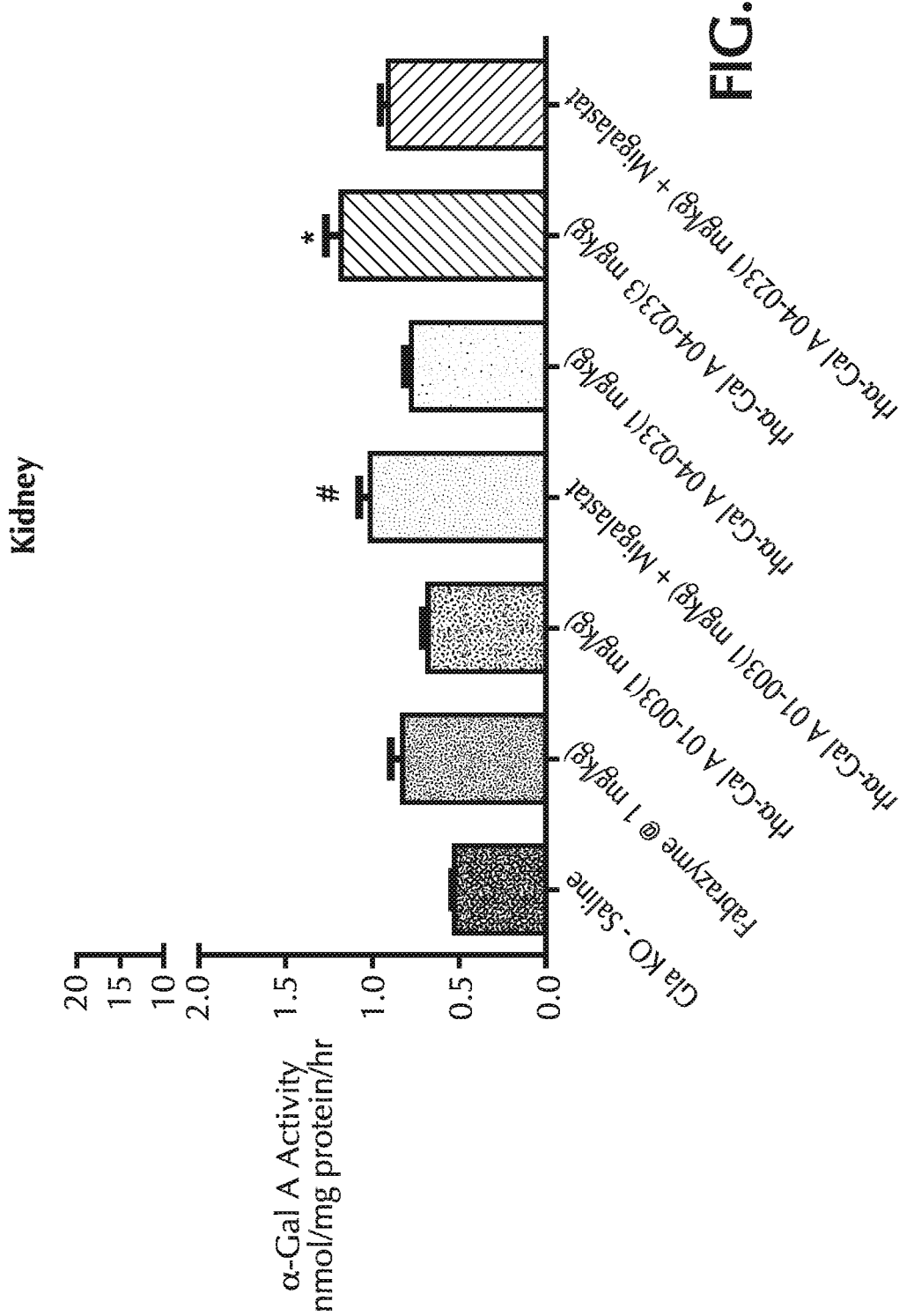
Figure 14C:
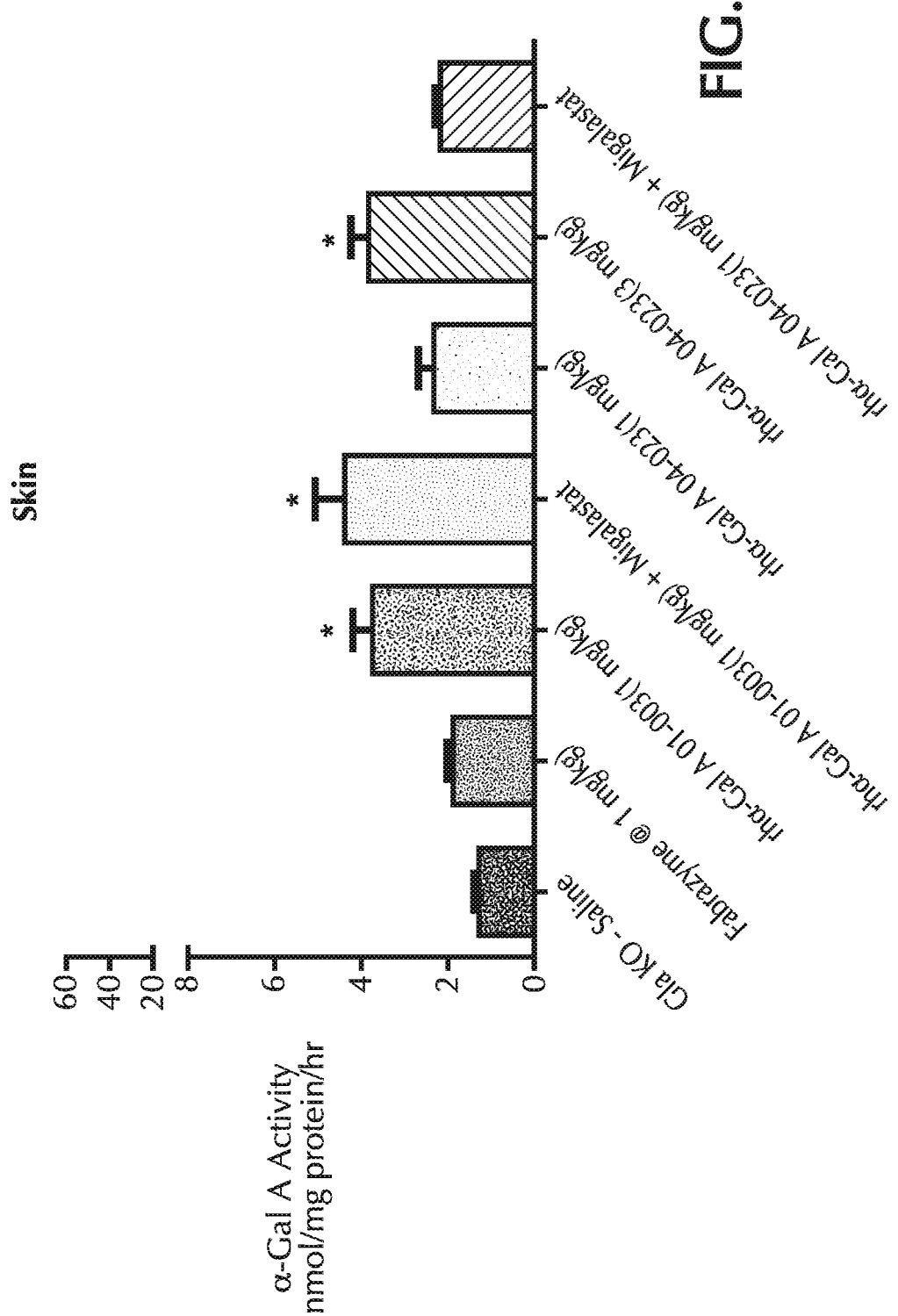
Figure 14D:
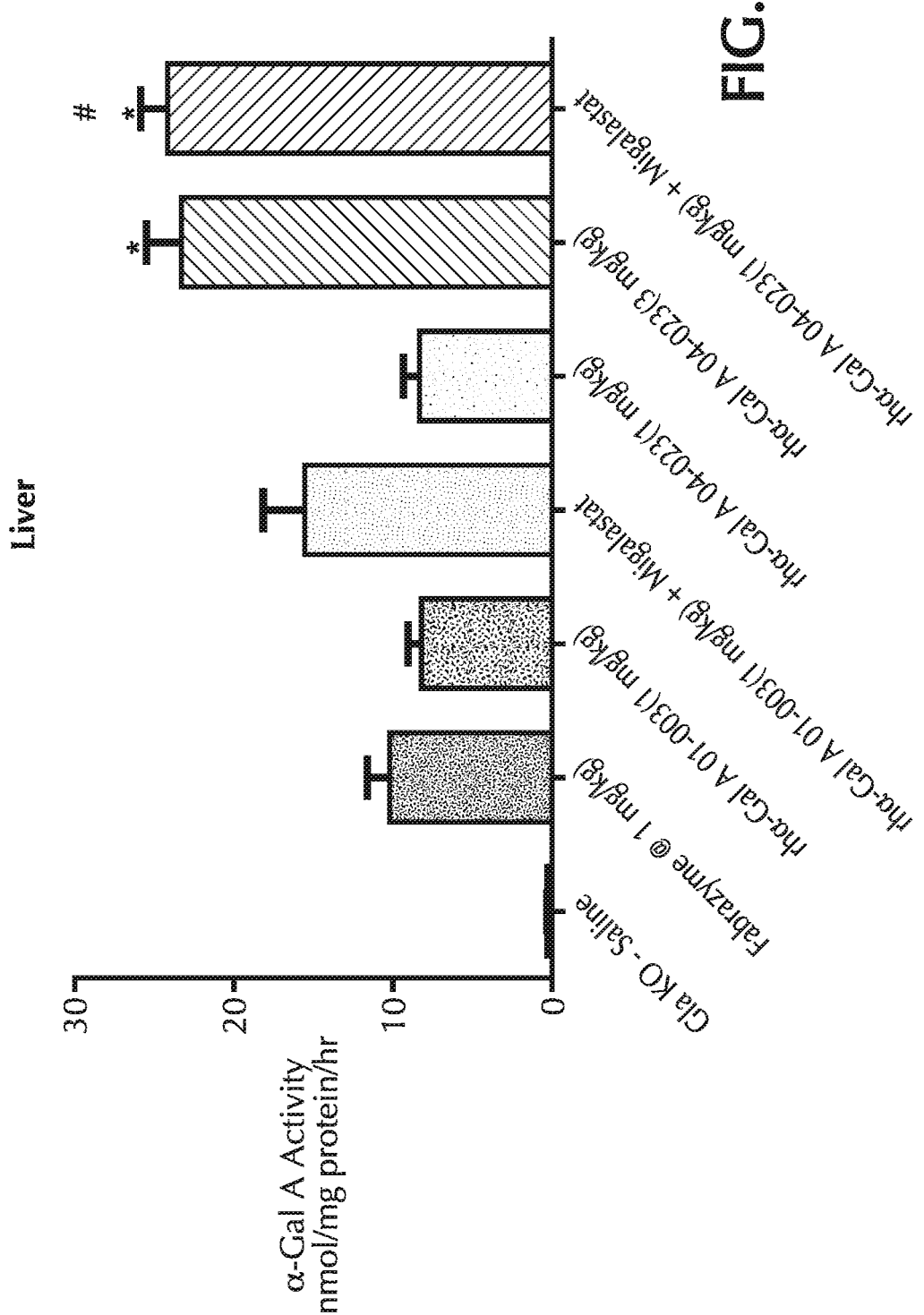
Figure 15A:
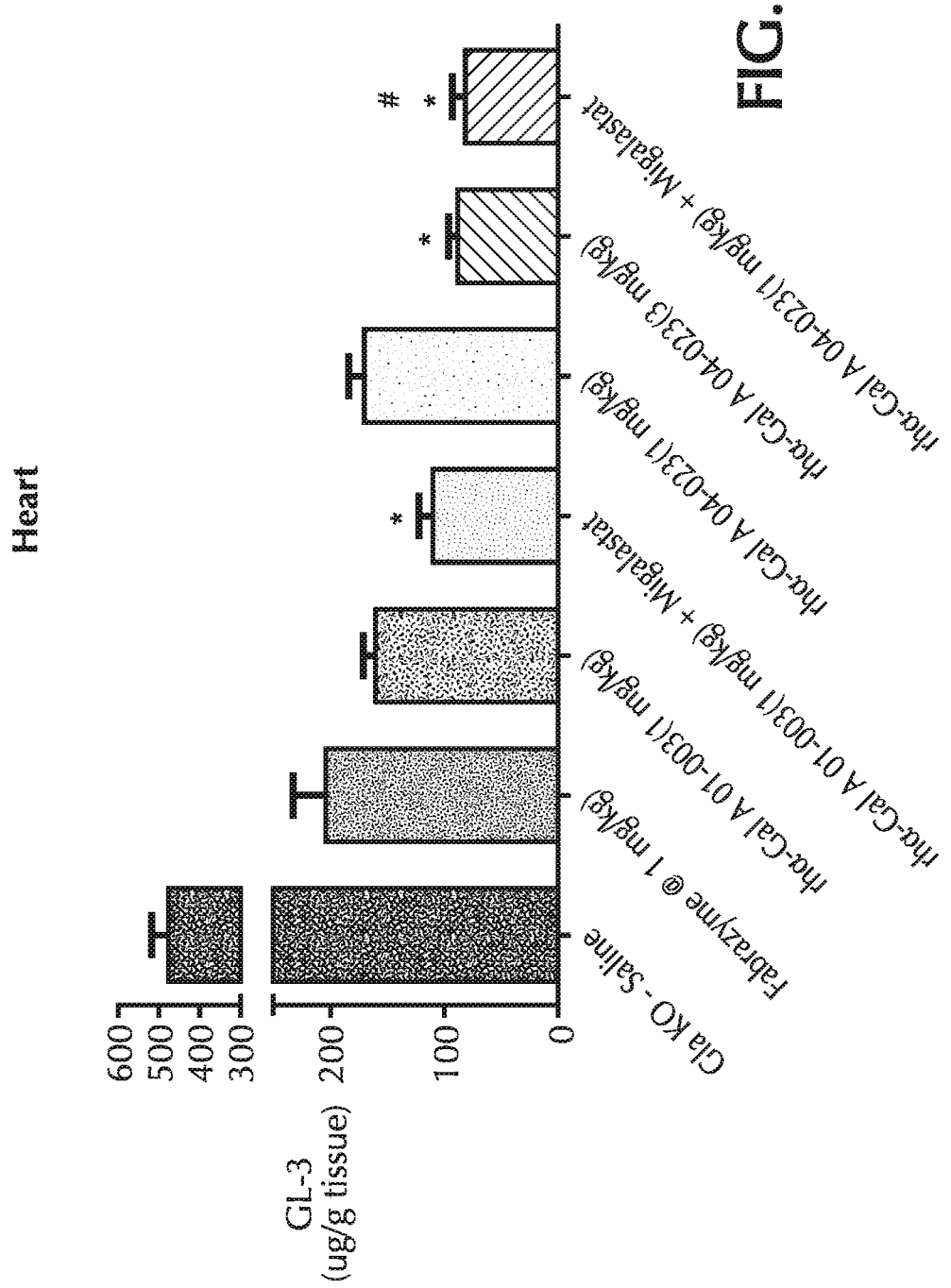
FIGS. 15A-15D show GL-3 levels in Gla KO mice heart (15A), kidney (15B), and skin (15C) and plasma lyso-Gb3 (15D) after a single administration of various ERTs with and without migalastat.
Figure 15B:
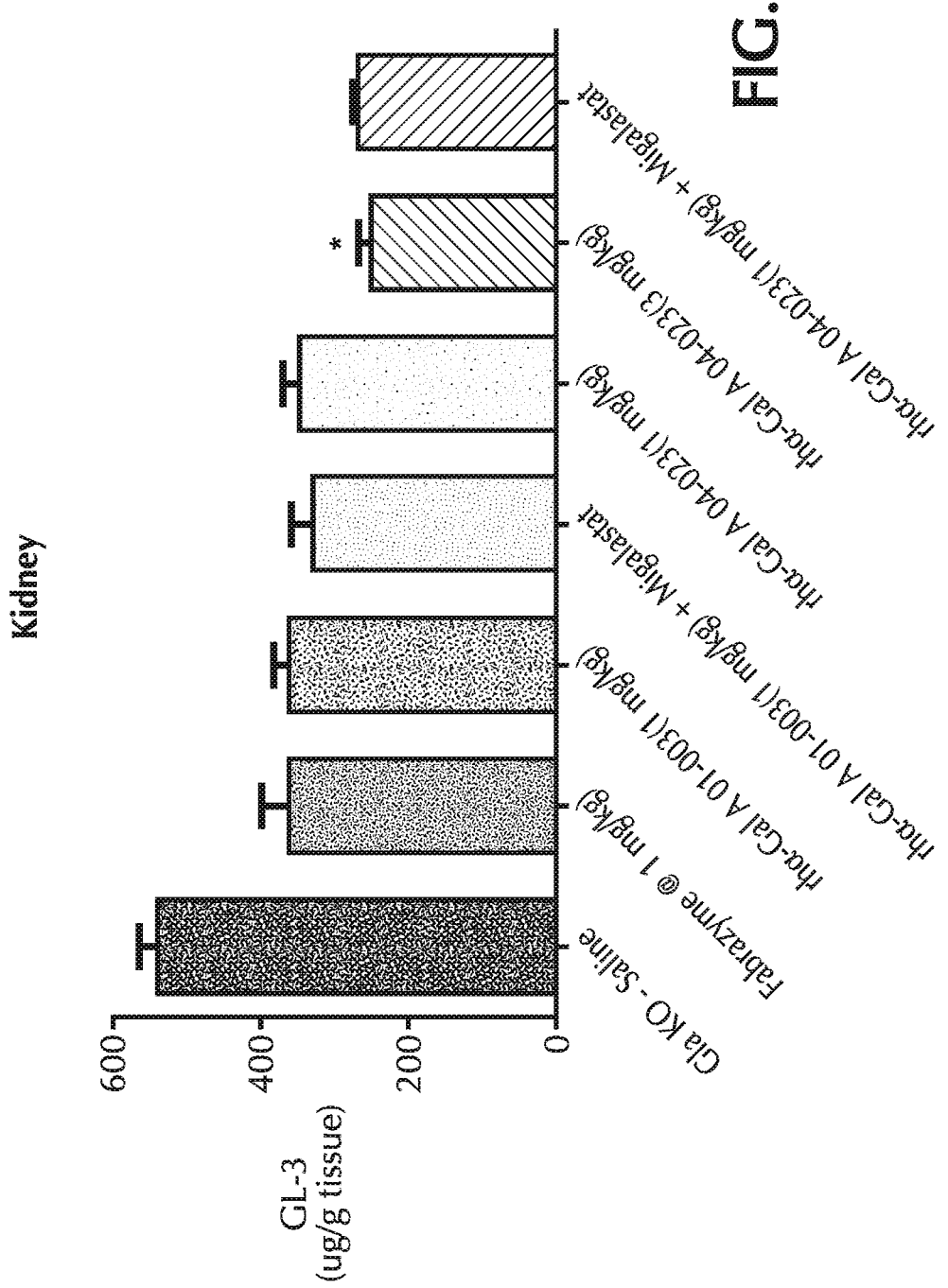
Figure 15C:
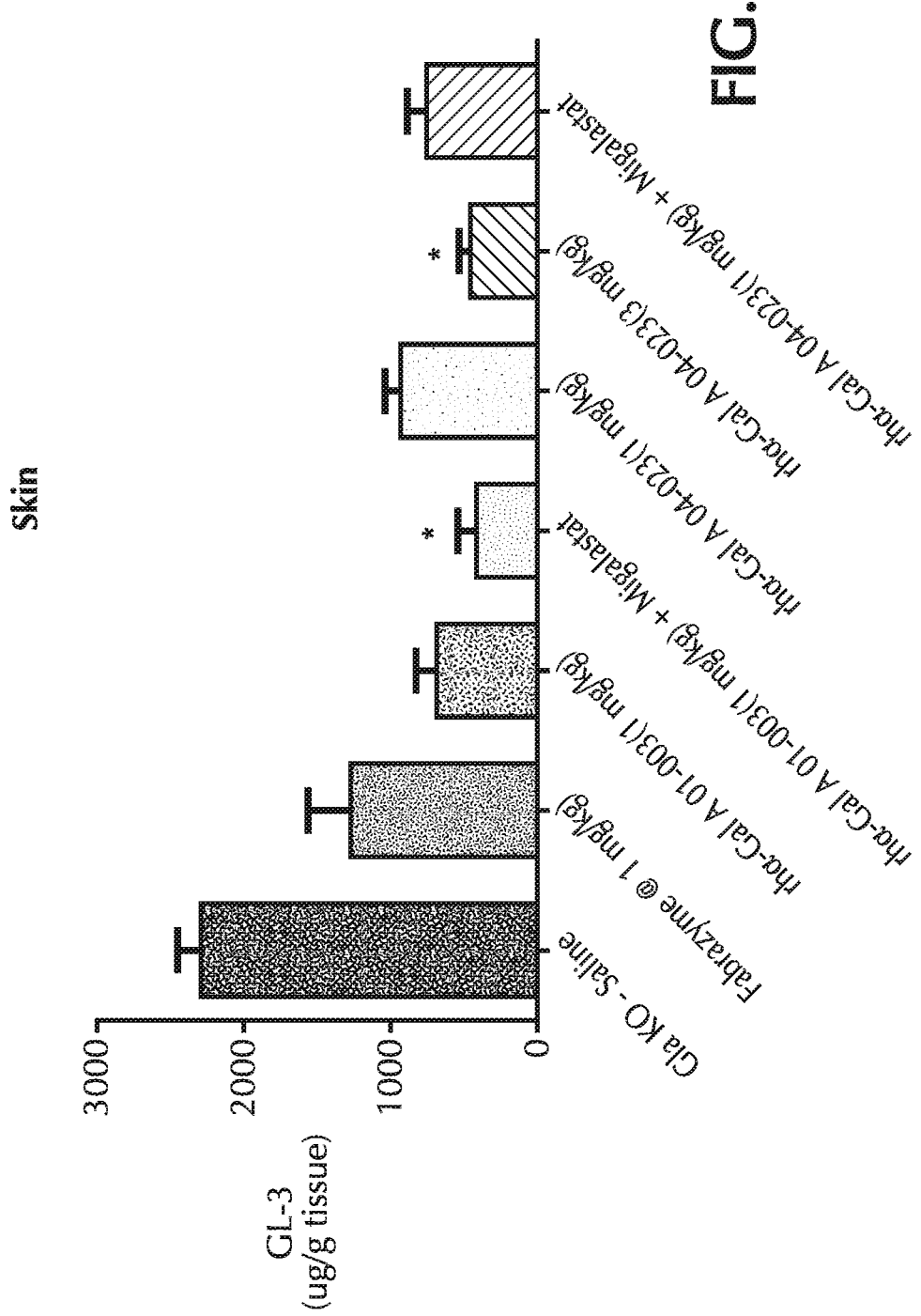
Figure 15D:
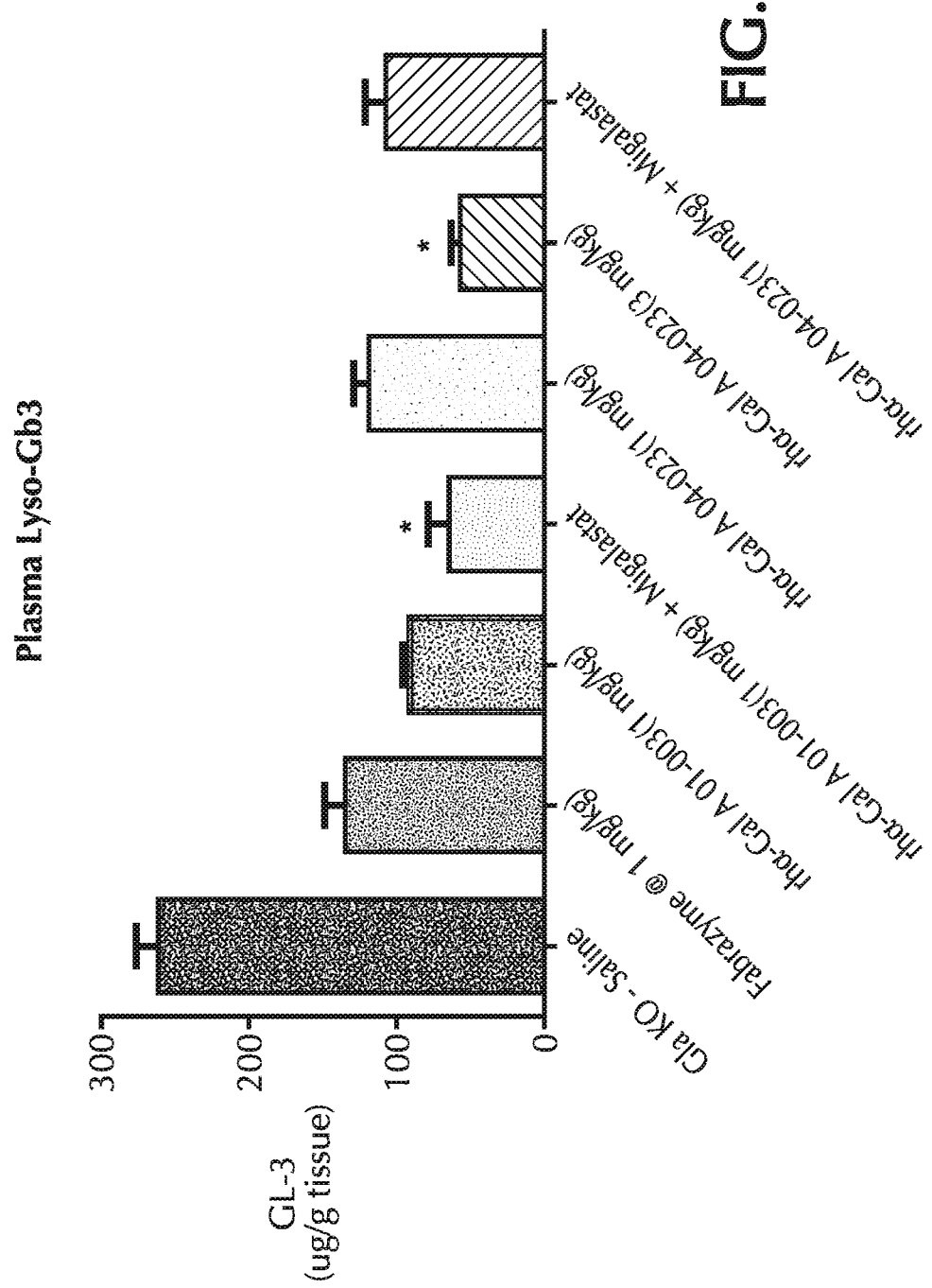

FIG. 14A shows the tissue enzyme activity in Gla KO mouse heart seven days after administration of enzyme. In heart, administration of rhα-Gal A 01-003 leads to similar enzyme activity after seven days as administration of Fabrazyme (agalsidase beta) whereas addition of migalastat to rhα-Gal A 01-003 significantly increased the enzyme activity level. All three enzymes gave similar activity in the kidney after seven days (FIG. 14B). The addition of migalastat to rhα-Gal A 01-003 significantly increased the enzyme level in kidney as did increasing the dose to 3 mg/kg (higher dose for rhα-Gal A 04-023). In skin, after seven days the enzyme activity levels were similar for rhα-Gal A 04-023 and Fabrazyme (agalsidase beta) but was higher for rhα-Gal A 01-003 with, or without, migalastat (FIG. 14C). Increasing the dose of rhα-Gal A 04-023 lead to a higher level of enzyme activity after seven days in skin (FIG. 15C). Higher enzyme levels were observed by addition of migalastat to rhα-Gal A 04-023 or by increasing the dose to 3 mg/kg (FIG. 14D).

In addition to assessment of enzyme activity in tissues, the degree of substrate reduction seven days post-administration was determined. In heart tissue, compared to 1 mg/mg of Fabrazyme (agalsidase beta), inclusion of migalastat significantly enhanced reduction of GL-3 (for rhα-Gal A 01-003 and rhα-Gal A 04-023) as did increasing the dose from 1 mg/kg to 3 mg/kg (rhα-Gal A 04-023) (FIG. 15A). In kidney (FIG. 15B), all enzyme treatments lead to a similar reduction in GL-3 except the higher dose of 3 mg/kg rhα-Gal A 04-023 which enhanced substrate reduction.

In skin (FIG. 15C), rhα-Gal A 04-023 co-formulated with migalastat leads to reduction in GL-3 that was significantly lower than Fabrazyme (agalsidase beta) alone. A dose of 3 mg/kg lead to a significantly lower level of GL-3 in skin when compared to Fabrazyme (agalsidase beta) alone (1 mg/kg). rhα-Gal A 01-003 (1 mg/kg) co-formulated with migalastat lead to a reduction in lyso-Gb3 that was significantly lower than Fabrazyme (agalsidase beta) alone (1 mg/kg). A dose of rhα-Gal A 04-023 (3 mg/kg) resulted in significantly lower levels of plasma lyso-Gb3 than Fabrazyme (agalsidase beta) alone (1 mg/kg) (FIG. 16D).

In this Example 6, the half-life of rhα-Gal A 01-003 in Gla KO mice was approximately 14 minutes compared to approx. 8 minutes for Fabrazyme (agalsidase beta), and 4 minutes for rhα-Gal A 04-023 while the addition of migalastat improved the exposure of both rhα-Gal A clones.

Based on the pharmacokinetic and efficacy data, rhα-Gal A 01-003 was selected for further development.

Example 7: Variations in Production of rhα-Gal A

Two different studies compared the pharmacokinetics of rhα-Gal A produced by different processes. Gla KO mice (n=5-7/group) were given a single IV bolus injection of 1 mg/kg of Fabrazyme (agalsidase beta) or rhα-Gal A 01-003 produced by different processes. Plasma collected from serial bleed at 5, 15, 30, 60 and 120 min and pharmacokinetics were determined as measured by α-Gal A activity. The pharmacokinetic properties of Fabrazyme (agalsidase beta) and rhα-Gal A 01-003 are provided in FIGS. 16A-16B and Tables 10 and 11. The rhα-Gal A shown in FIG. 16A and Table 10 corresponds to the preparation shown in FIG. 10C, and the rhα-Gal A shown in FIG. 16B and Table 11 corresponds to the preparation shown in FIG. 10F.

TABLE 10

|  | Fabrazyme (agalsidase beta) | rhα-Gal A 01-003 |
|---|---|---|
| $T_{1/2}{}^a$ (mins) | 7.7 | 13.5 |
| $AUC_{0-2\ hr}$ (nmol/mL/hr * hr) | 4985 | 9301 |

TABLE 11

|  | Fabrazyme (agalsidase beta) | rhα-Gal A 01-003 |
|---|---|---|
| $T_{1/2}{}^a$ (mins) | 9.0 | 9.7 |
| $AUC_{0-2\ hr}$ (nmol/mL/hr * hr) | 6417 | 8398 |

$T_{1/2}{}^a$ determined with an upper λz of 5 min. and lower λz of 30 min.

Figure 16A:
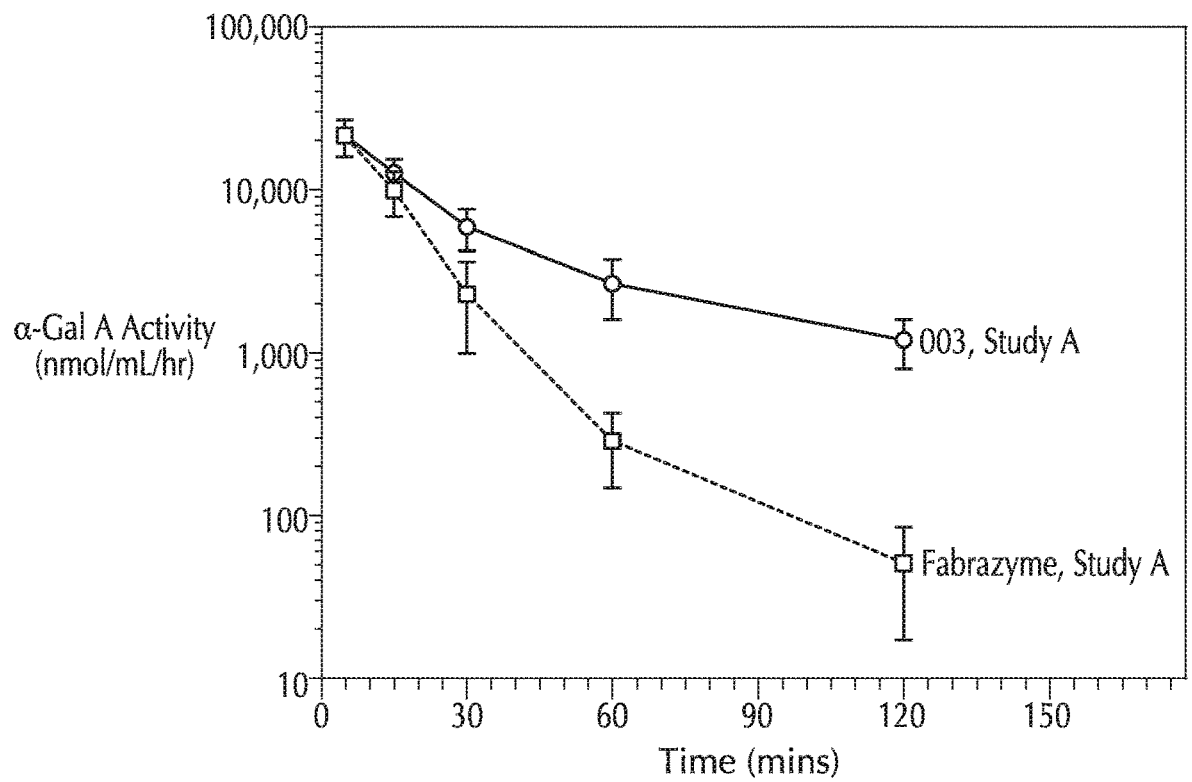
FIGS. 16A and 16B show the pharmacokinetics of Fabrazyme and rhα-Gal A produced by different processes.
Figure 16B:
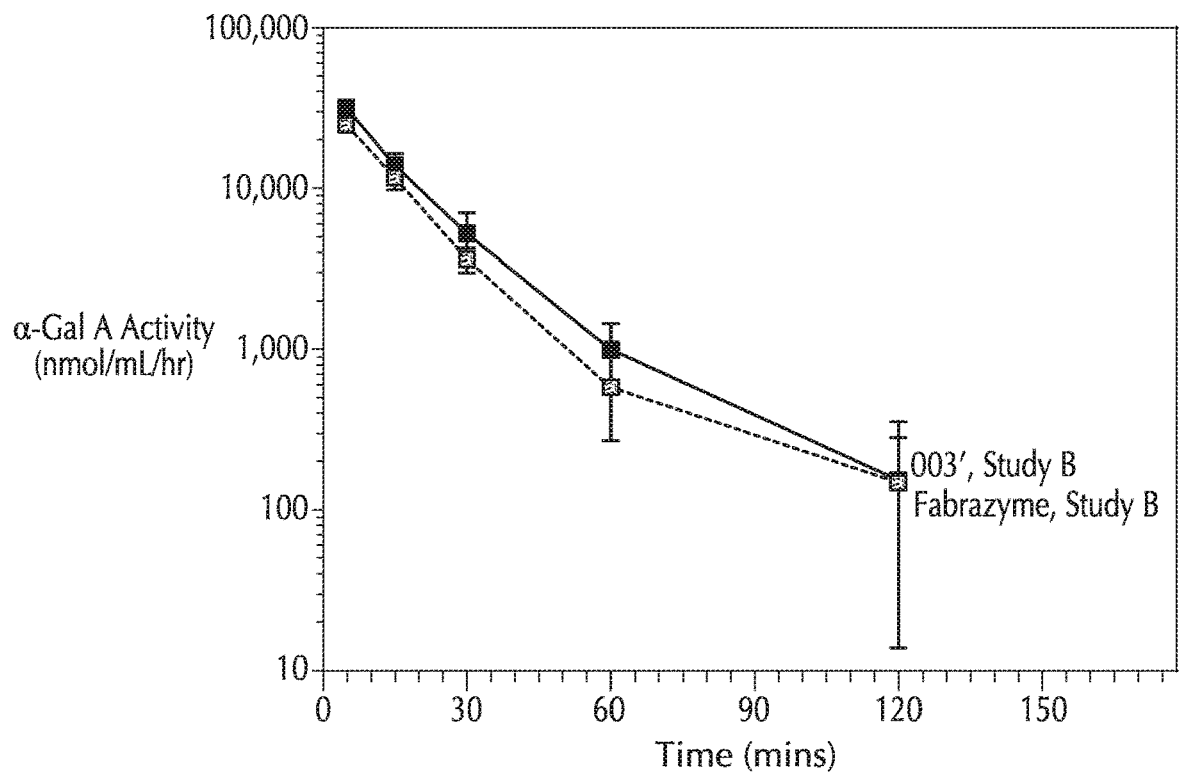

As can be seen from FIG. 16A and Table 10, rhα-Gal A 01-003 produced according to a first process had a significantly longer half-life than Fabrazyme (agalsidase beta). As can be seen from FIG. 16B and Table 11, the second process produced a version of rhα-Gal A 01-003 that has a similar apparent half-life as Fabrazyme (agalsidase beta). However, this reduction in half-life is believed to be due to increased uptake into cells due to an increased M6P content, rather than an increase in non-productive clearance. As shown in FIGS. 10C and 10F, both preparations of rhα-Gal A had a low content of neutral glycans (peaks on left of figures) and the preparation of rhα-Gal A in FIG. 10F had a higher bis-M6P content than the preparation of rhα-Gal A in FIG. 10C (peak on right of figures). Accordingly, these studies show that even similar half-lives for ERTs do not necessarily demonstrate a similar ERT product, as the ERT can be cleared due to targeting or by non-productive clearance.

Figure 17A:
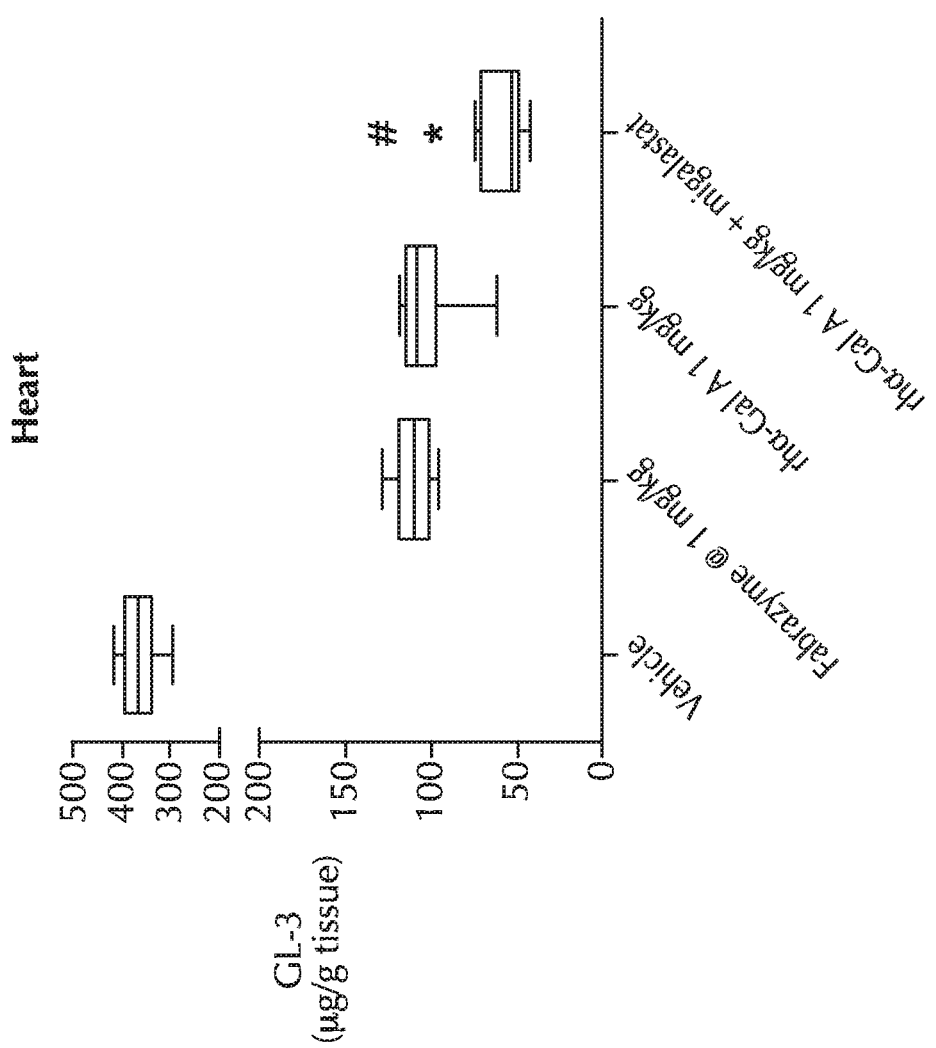
FIGS. 17A and 17B show GL-3 levels in Gla KO mice heart (17A) and kidney (17B) after a single administration of various ERTs with and without migalastat.
Figure 17B:
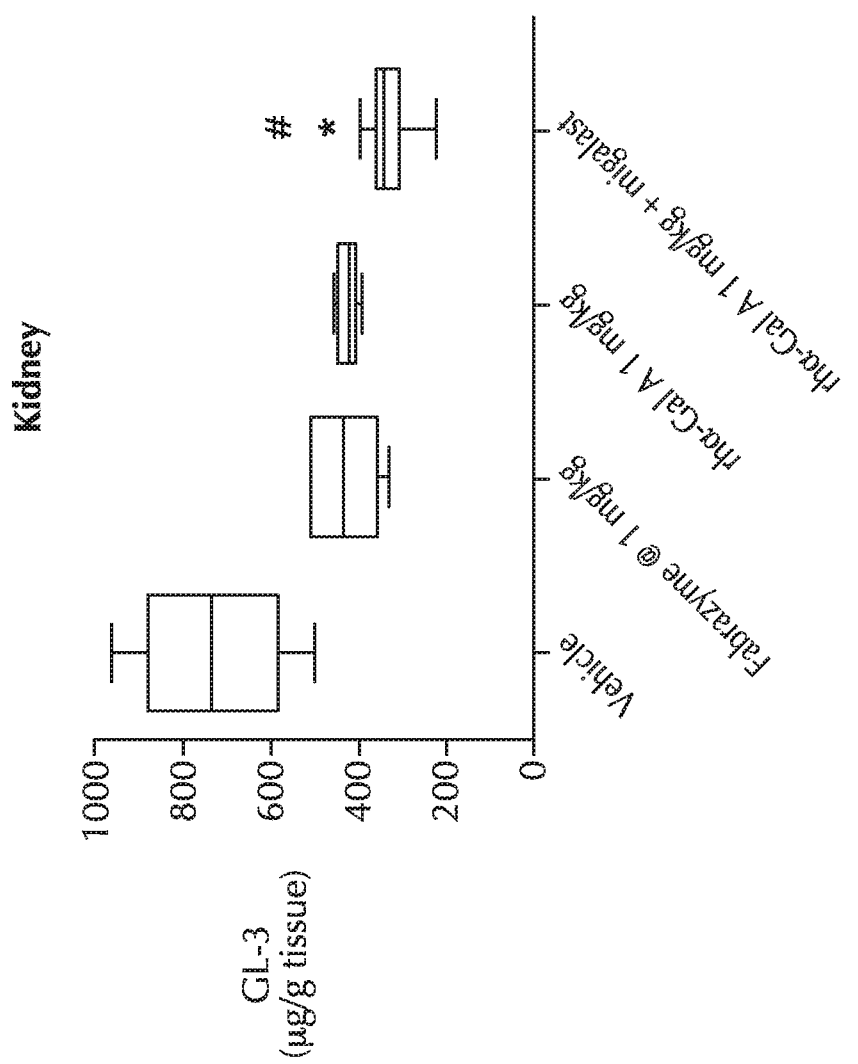

The rhα-Gal A 01-003 produced by a variation of the manufacturing process was able to reduce α-Gal A substrate in heart and kidney and was enhanced by co-formulation with migalastat (FIGS. 17A and 17B). Gla KO mice were administered 1 mg/kg of enzyme IV and GL-3 measured one week post-administration. Co-formulation with migalastat leads to greater substrate reduction than either Fabrazyme (agalsidase beta) alone or rhα-Gal A 01-003 alone.

Example 8: Pharmacokinetics of Various Doses of rhα-Gal A with and without Migalastat The pharmacokinetics of various doses of rhα-Gal A 01-003 with and without migalastat were compared to Fabrazyme (agalsidase beta). Enzyme was administered via a single bolus infusion into Gla KO mice (n=5; 40 in total; ~6 months old) with or without co-formulation with migalastat. The treatment groups are shown in Table 12.

TABLE 12

| Group | Treatment |
|---|---|
| 1 | Vehicle |
| 2 | Fabrazyme (agalsidase beta) 1 mg/kg |
| 3 | Fabrazyme (agalsidase beta) 10 mg/kg |
| 4 | rhα-Gal 01-003 A 1 mg/kg |
| 5 | rhα-Gal 01-003 A 3 mg/kg |
| 6 | rhα-Gal01-003 A 10 mg/kg |
| 7 | Co-formulation of rhα-Gal A 01-003 1 mg/kg + Migalastat 3 mg/kg |
| 8 | Co-formulation of rhα-Gal A 01-003 3 mg/kg + Migalastat 10 mg/kg |

Serial submandibular bleedings were taken for plasma at 5 min, 15 min, 30 min, 1 hr, and 2 hr. Necropsy was performed at 24 hours, and plasma and tissues were collected.

Figure 18A:
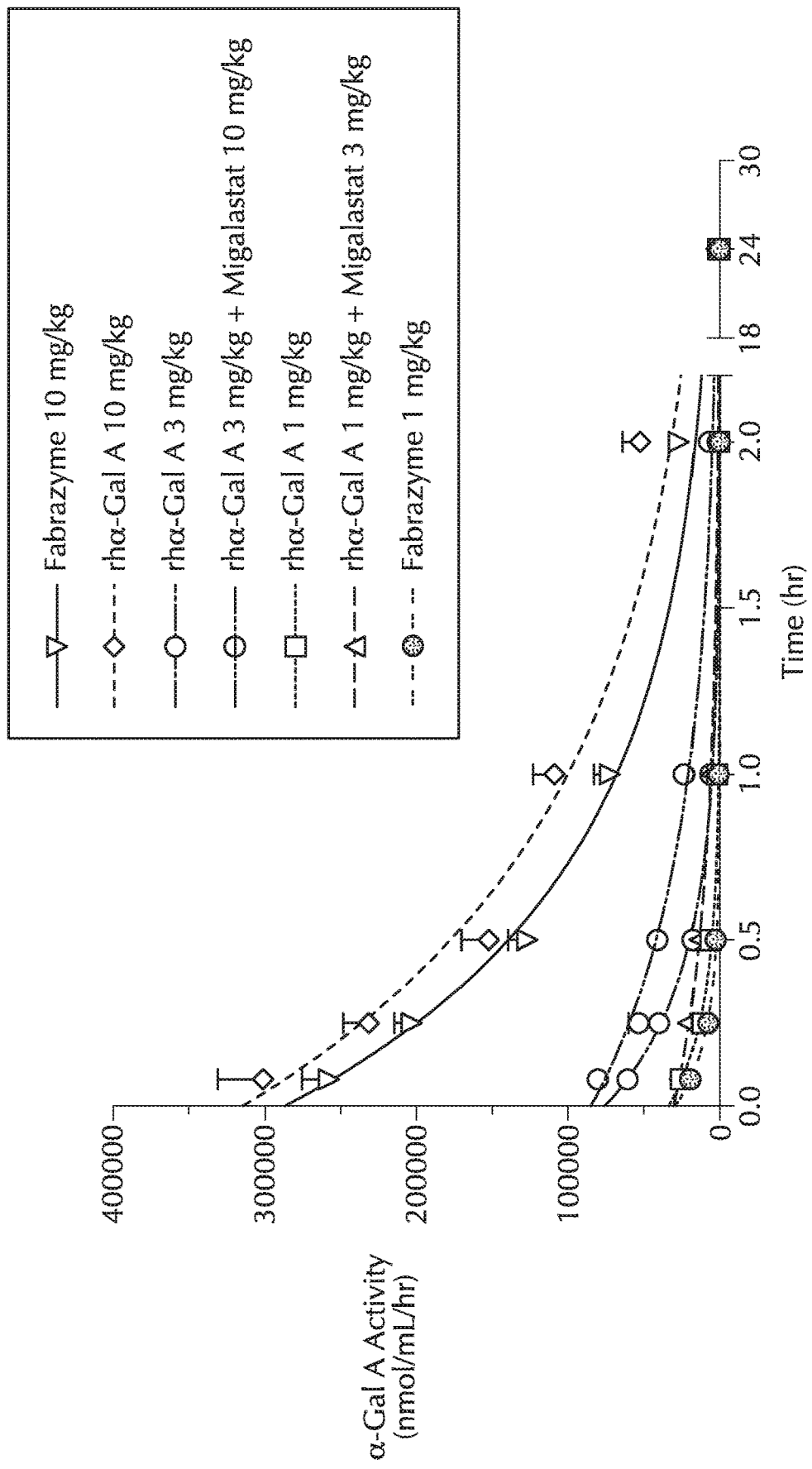
Figure 18C:
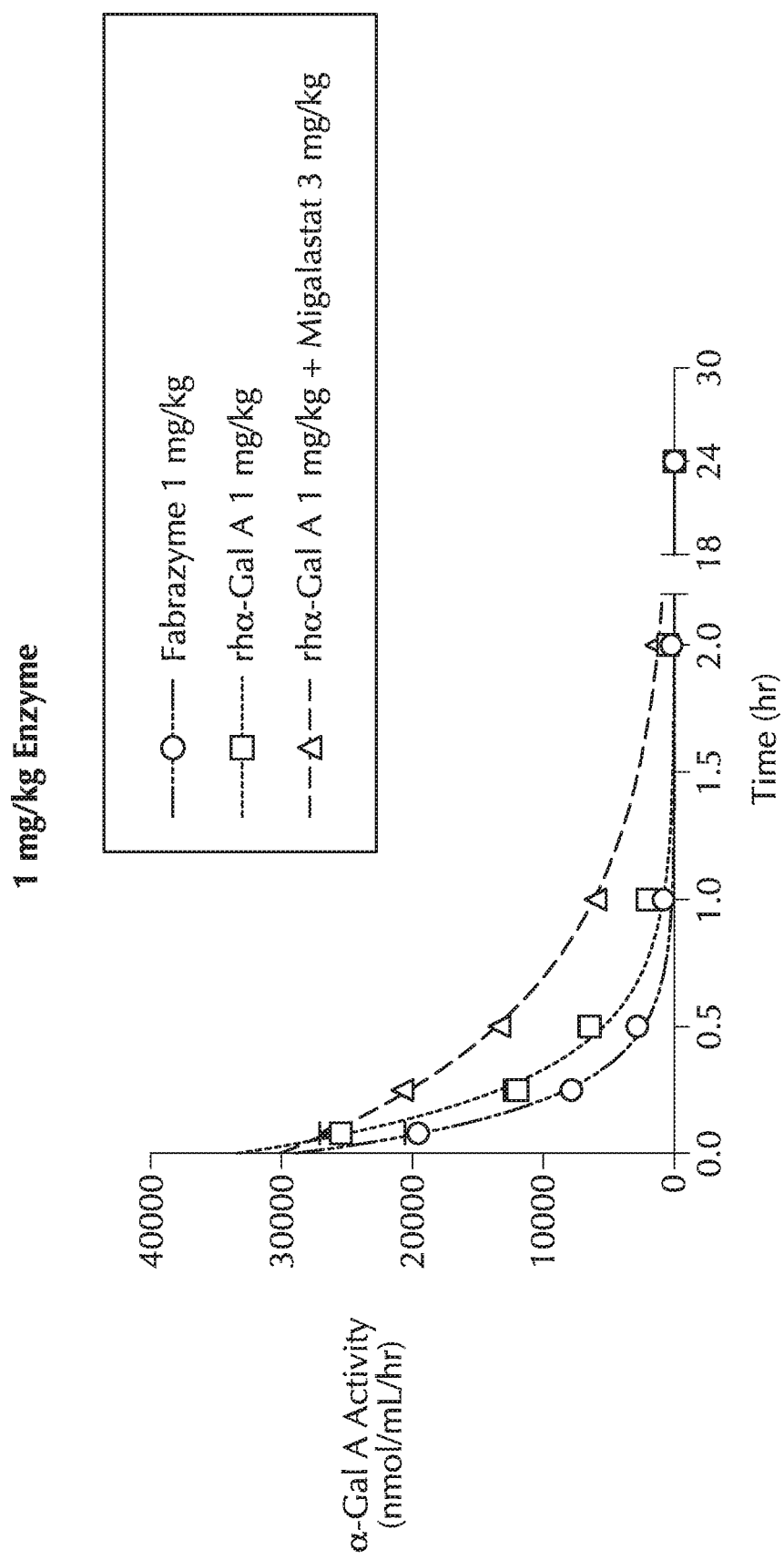
Figure 18D:
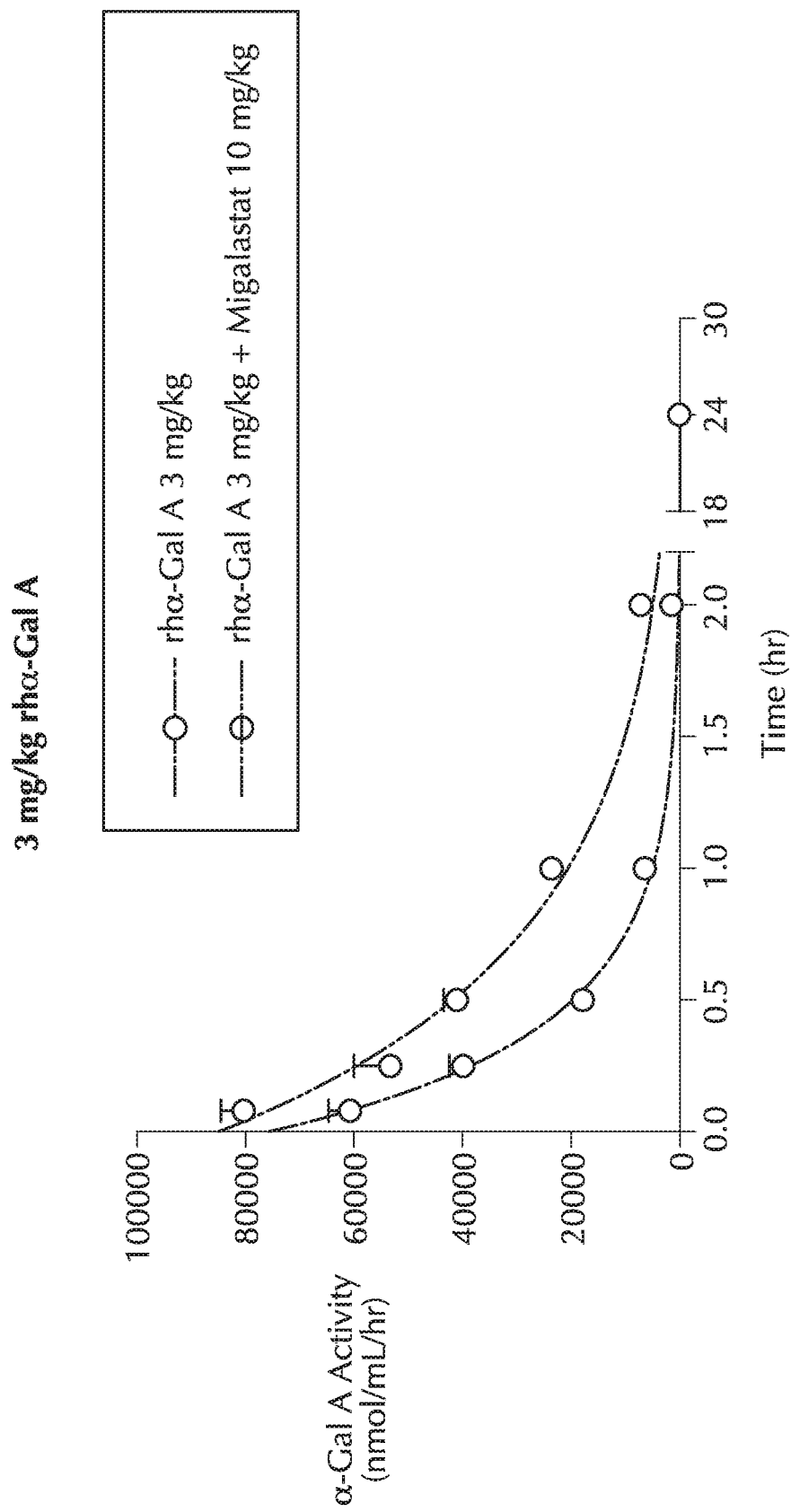
Figure 18E:
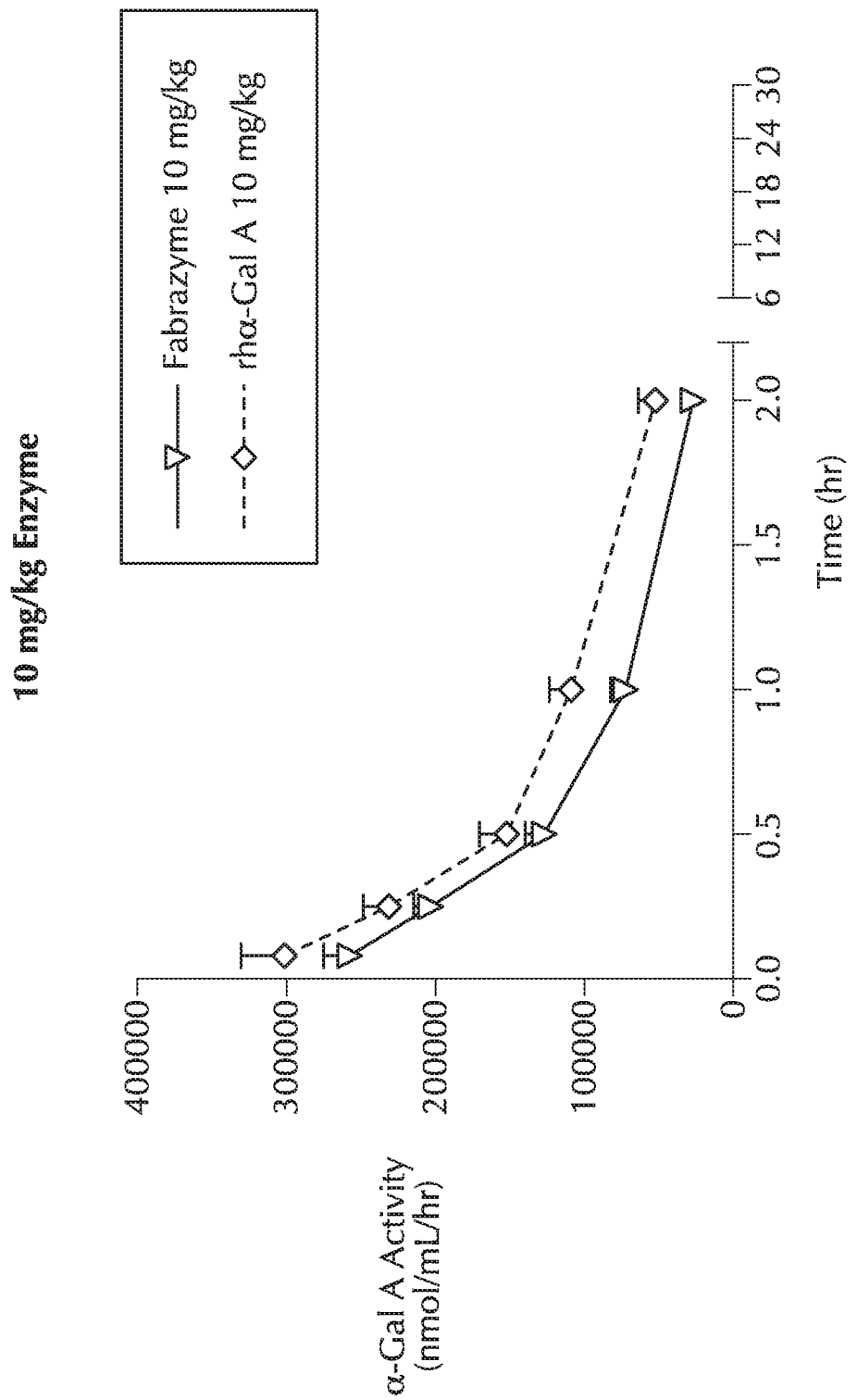
Figure 18F:
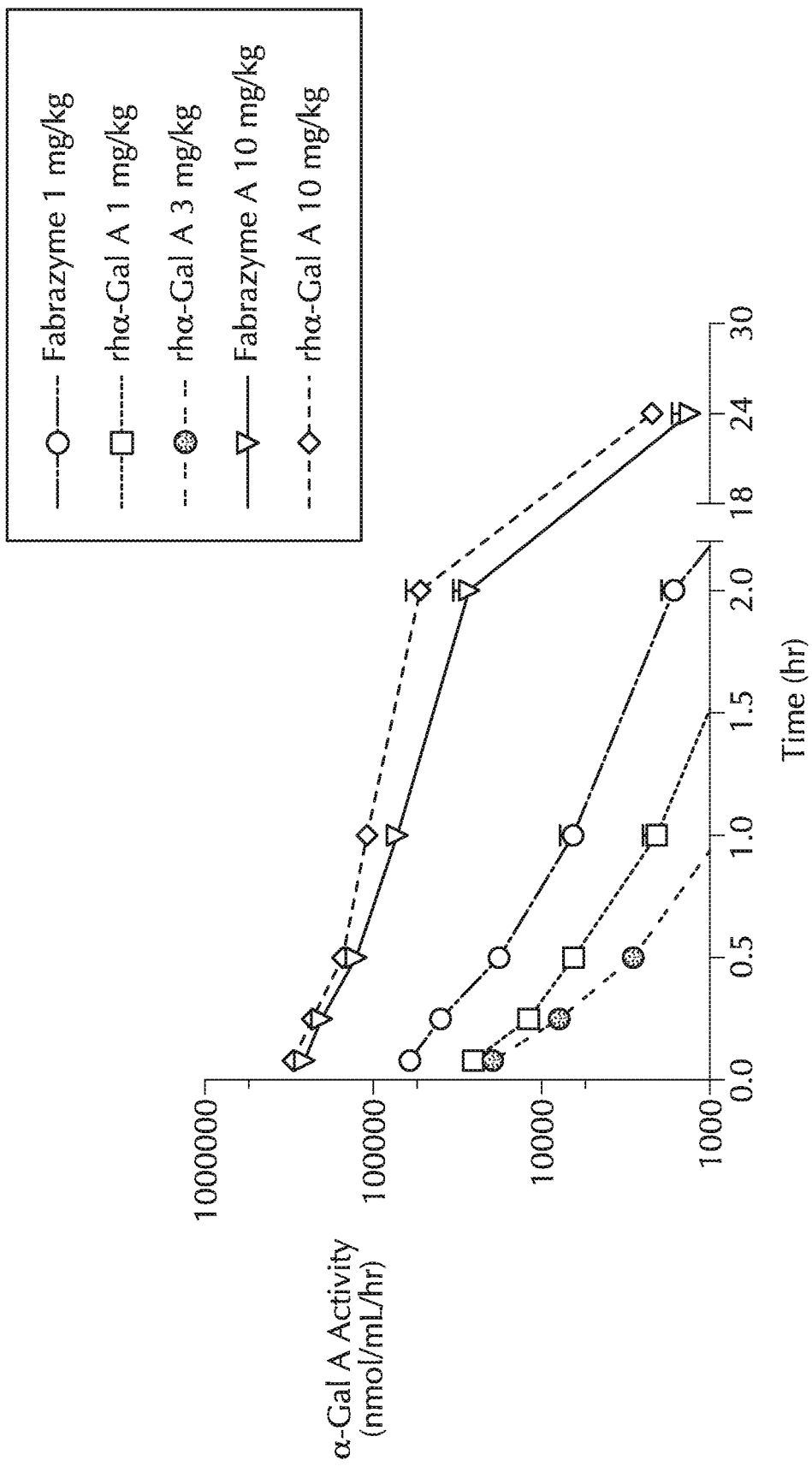

FIGS. 18A-18F show the pharmacokinetics of the various doses of rhα-Gal A with and without co-formulation with migalastat, as well as the two doses of Fabrazyme (agalsidase beta). Table 13 below shows the respective half-life for the same treatment groups. FIGS. 18A and 18B show the pharmacokinetics of all of the treatment groups. FIG. 18C focuses on the enzyme dose of 1 mg/kg for Fabrazyme (agalsidase beta), rhα-Gal A alone and rhα-Gal A with 3 mg/kg migalastat. FIG. 18D focuses on the enzyme dose of 3 mg/kg for rhα-Gal A alone and rhα-Gal A with 10 mg/kg migalastat. FIG. 18E focuses on the enzyme dose of 10 mg/kg for Fabrazyme (agalsidase beta) and rhα-Gal A. FIG. 18F focuses on the pharmacokinetics of Fabrazyme (agalsidase beta) and rhα-Gal A alone at various enzyme doses.

TABLE 13

| $t_{1/2}$ (hr) (95% CI) | Fabrazyme (agalsidase beta) | rhα-Gal A |
|---|---|---|
| 1 mg/kg | 0.14 (0.12, 0.16) | 0.19 (0.16, 0.23) |
| 1 + 3 mg/kg migalastat | | 0.44 (0.40, 0.48) |
| 3 mg/kg | | 0.26 (0.22, 0.30) |
| 3 + 10 mg/kg migalastat | | 0.49 (0.40, 0.63) |
| 10 mg/kg | 0.48 (0.40, 0.60) | 0.61 (0.47, 0.85) |

Note:
Half-life by one-phase decay in Prism GraphPad with no weighting

As can be seen from Table 13 and FIGS. 18A-18F, the half-life of each enzyme increased with increasing dose. The rhα-Gal A had dose-dependent and non-linear pharmacokinetics. At the same dose, rhα-Gal A shows a longer half-life than Fabrazyme (agalsidase beta). The co-formulation of migalastat with rhα-Gal A also substantially increased the half-life of enzyme activity in circulation, with up to a 2.3-fold increase in the circulating half-life of rhα-Gal A after co-formulation with migalastat.

Example 9: Repeat Administration Efficacy Study in Gla KO Mice

The efficacy of rhα-Gal A 01-003 with and without migalastat and Fabrazyme (agalsidase beta) were compared. Enzyme was administered via a bolus infusion into Gla KO mice with or without co-formulation with 3 mg/kg migalastat. ~16 week old male Gla KO mice (n=8; 72 in total) were given two bi-weekly IV administrations. The treatment groups are shown in Table 14 and the results are shown in FIGS. 19A-19D and 20A-20C.

TABLE 14

| Group number | Treatment |
|---|---|
| 1 | Vehicle |
| 2 | Fabrazyme (agalsidase beta) 1 mg/kg |
| 3 | Fabrazyme (agalsidase beta) 10 mg/kg |
| 4 | rhα-Gal A 1 mg/kg |
| 5 | Co-formulation of rhα-Gal A 1 mg/kg + migalastat 3 mg/kg |
| 6 | Co-formulation of rhα-Gal A 1 mg/kg + migalastat 10 mg/kg |
| 7 | rhα-Gal A 3 mg/kg |
| 8 | Co-formulation of rhα-Gal A 3 mg/kg + migalastat 3 mg/kg |
| 9 | Co-formulation of rhα-Gal A 10 mg/kg + migalastat 10 mg/kg |

Figure 19A:
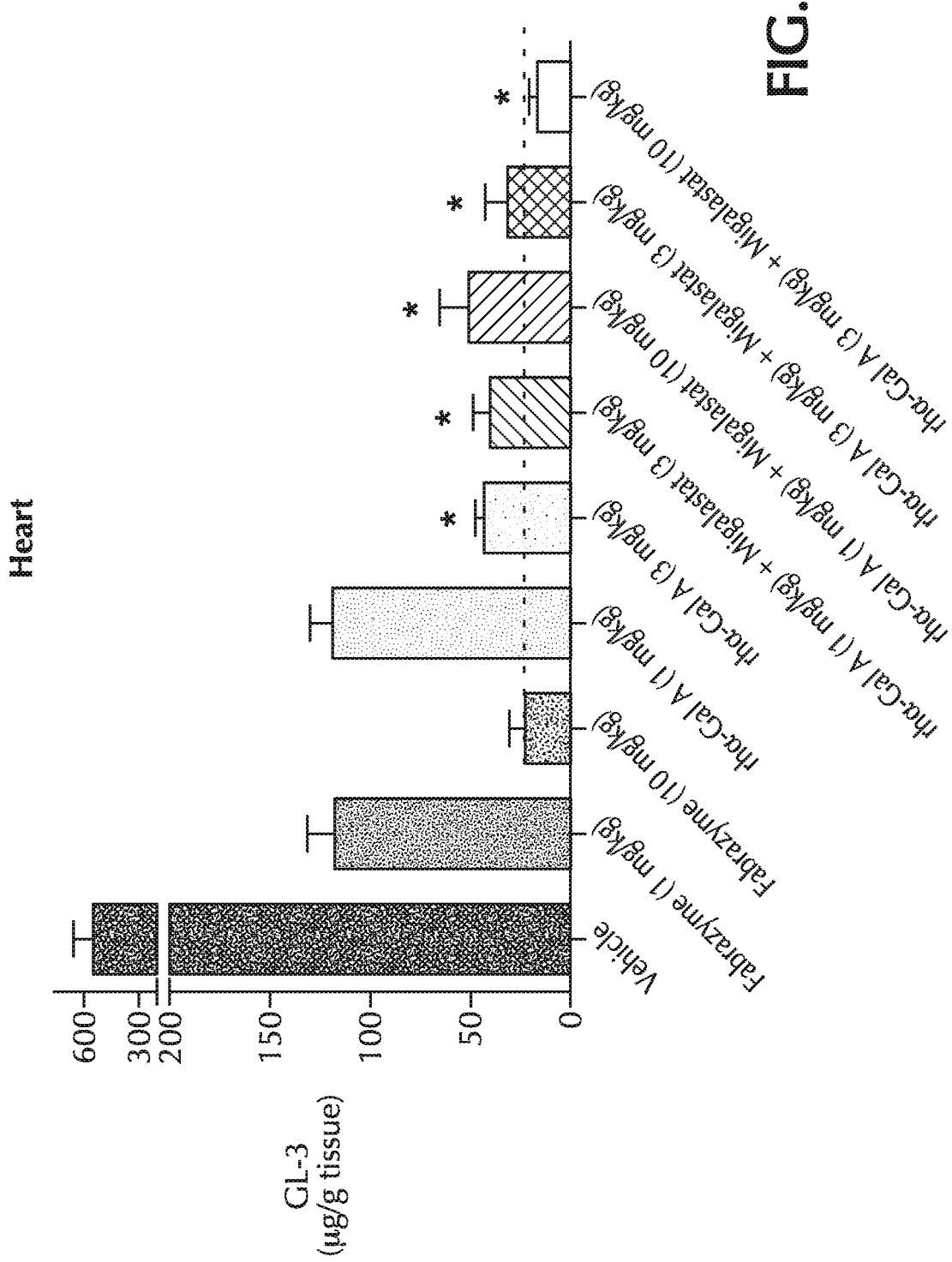
FIGS. 19A-19D show GL-3 levels in Gla KO mice heart (19A), kidney (19B), and skin (19C) and plasma lyso-Gb3 (19D) after repeat administrations of various ERTs with and without migalastat.
Figure 19B:
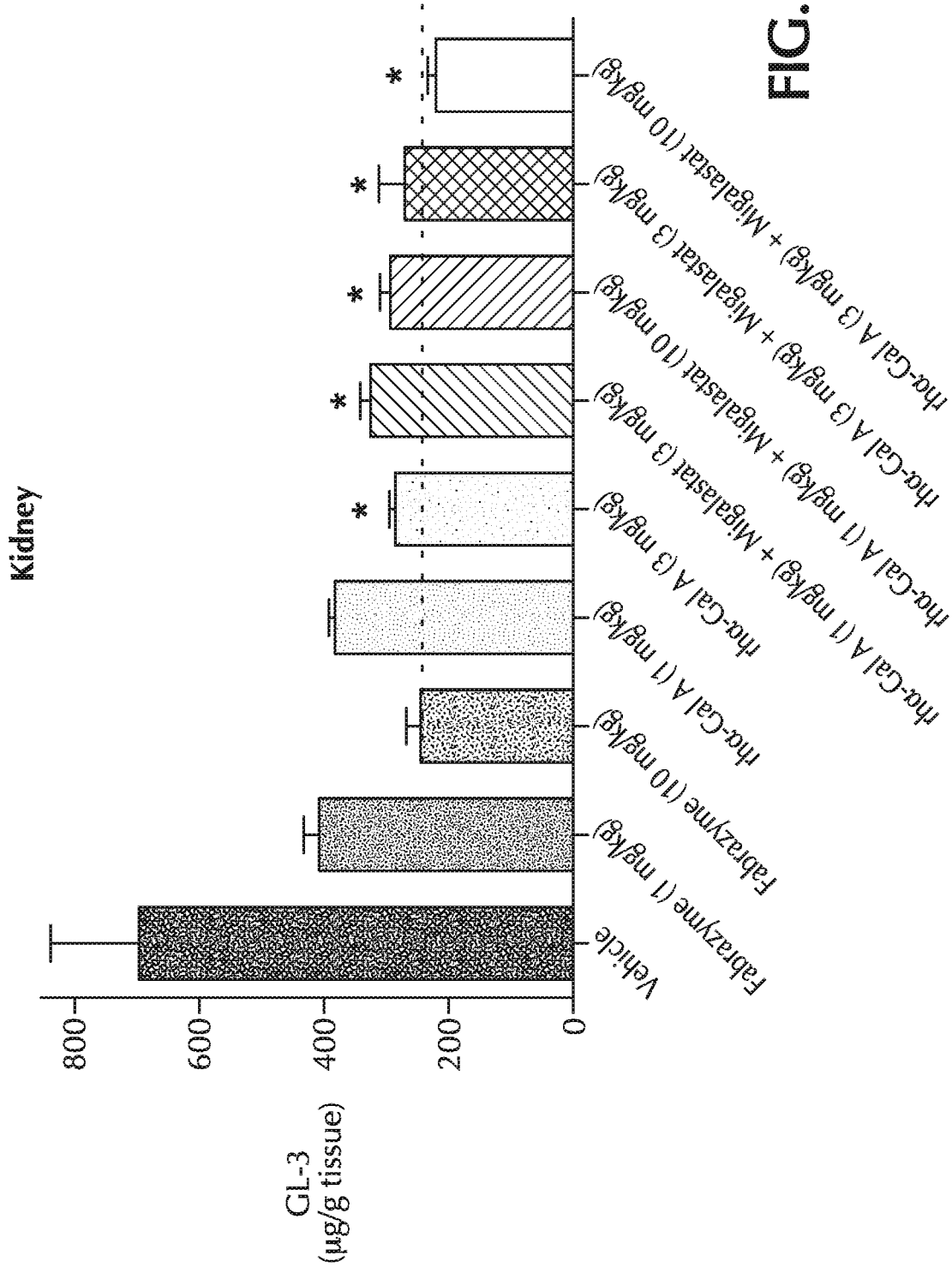

As can be seen from FIG. 19A (heart) and FIG. 19B (kidney), a good dose-response seen for rhα-Gal A and Fabrazyme (agalsidase beta) alone: 10 mg/kg Fabrazyme (agalsidase beta)>3 mg/kg rhα-Gal A>1 mg/kg rhα-Gal A=1 mg/kg Fabrazyme (agalsidase beta). Co-formulation of 1 mg/kg rhα-Gal A+3 or 10 mg/kg migalastat show significant reduction in GL-3 levels compared to 1 mg/kg Fabrazyme (agalsidase beta). 3 mg/kg rhα-Gal A co-formulated with 3 or 10 mg/kg migalastat achieved similar or even slightly better GL-3 reduction compared to 10 mg/kg Fabrazyme (agalsidase beta), with 10 mg/kg migalastat co-form appearing to deliver the best results.

Figure 19C:
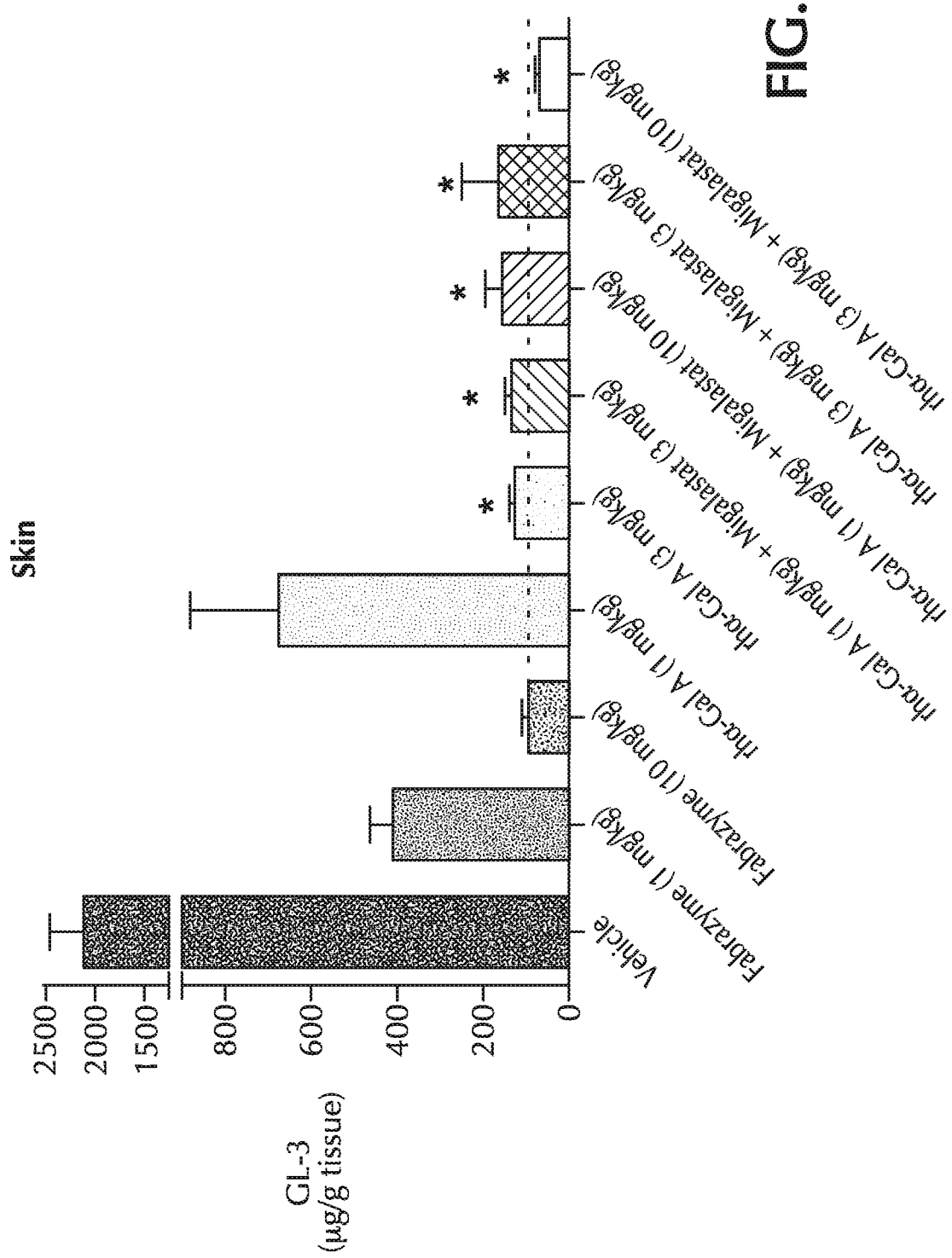
Figure 19D:
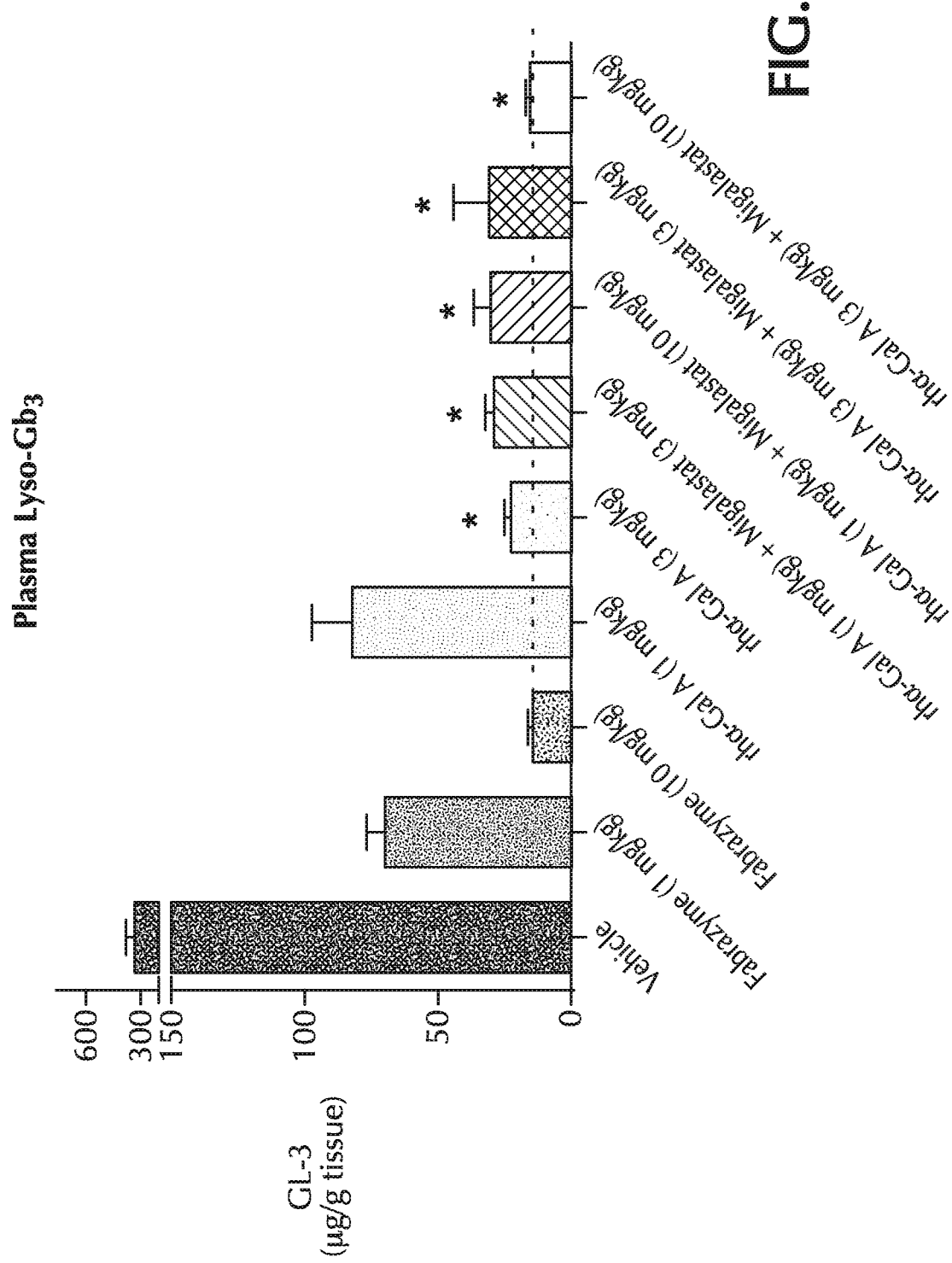
Figure 20B:
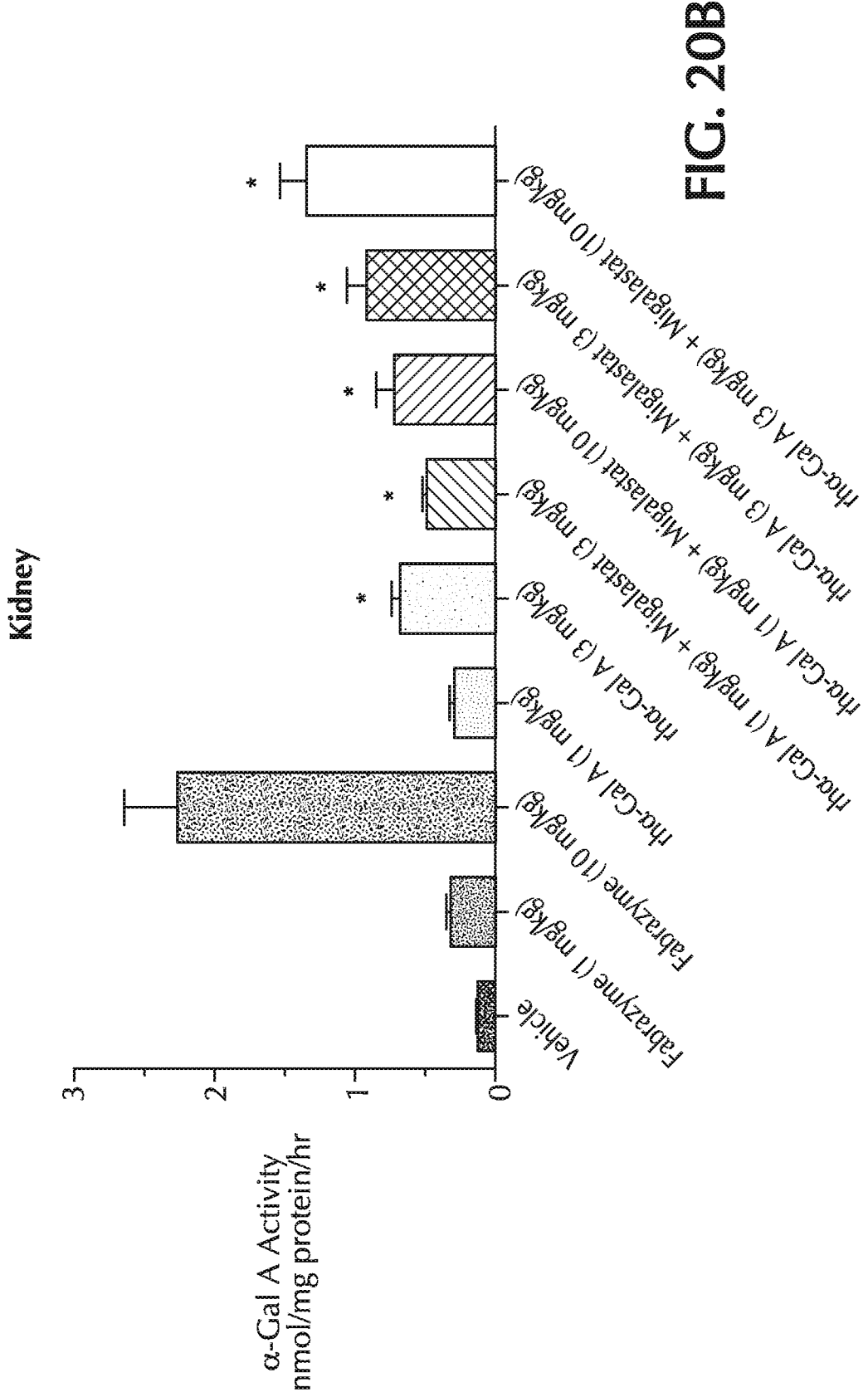
Figure 20C:
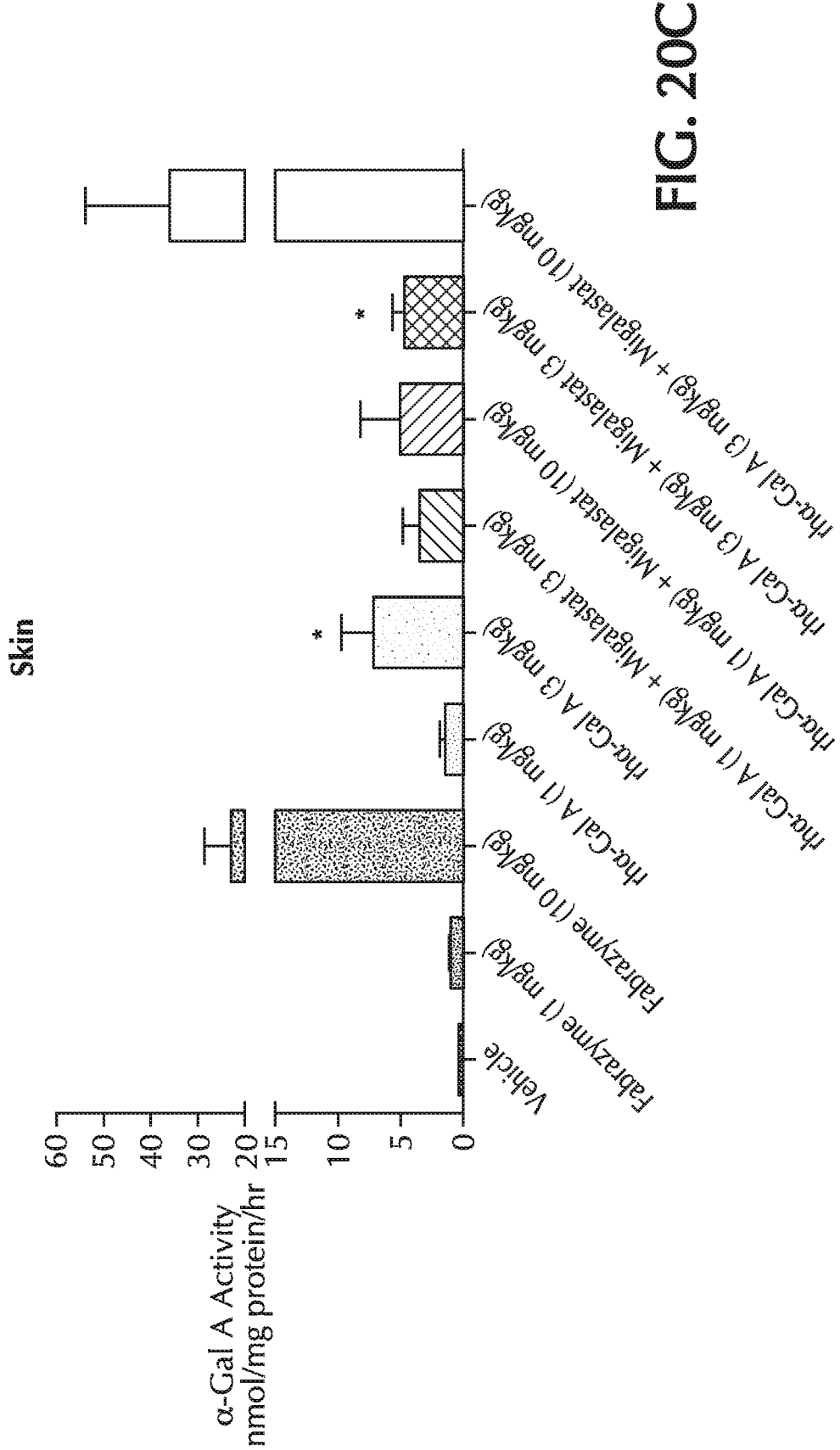
Figure 21A:
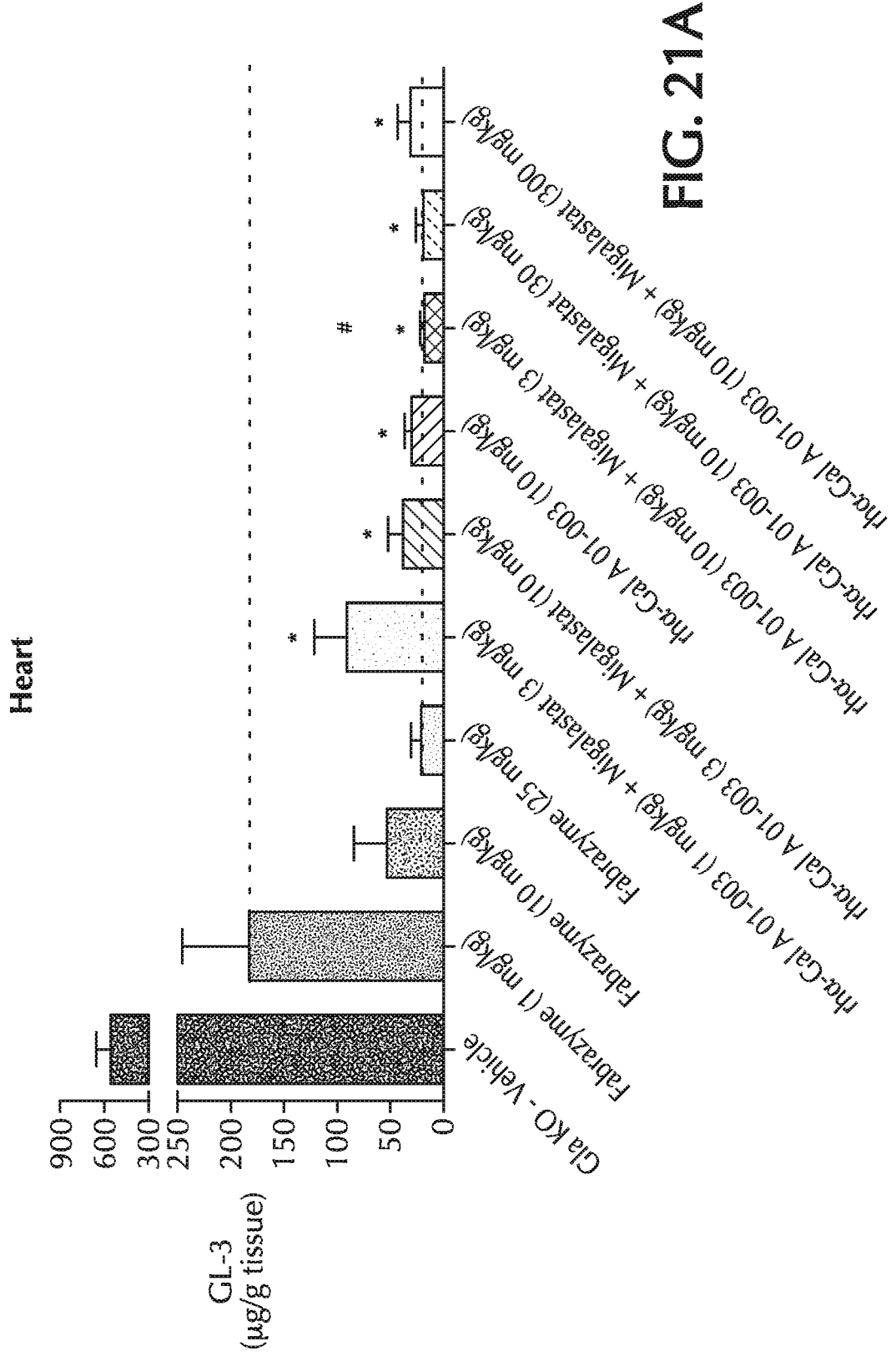
FIGS. 21A-21D shows GL-3 levels in Gla KO mice heart (21A), kidney (21B), skin (21C) and plasma lyso-Gb3 (21D) after a single administration of various ERTs with and without migalastat.
Figure 21B:
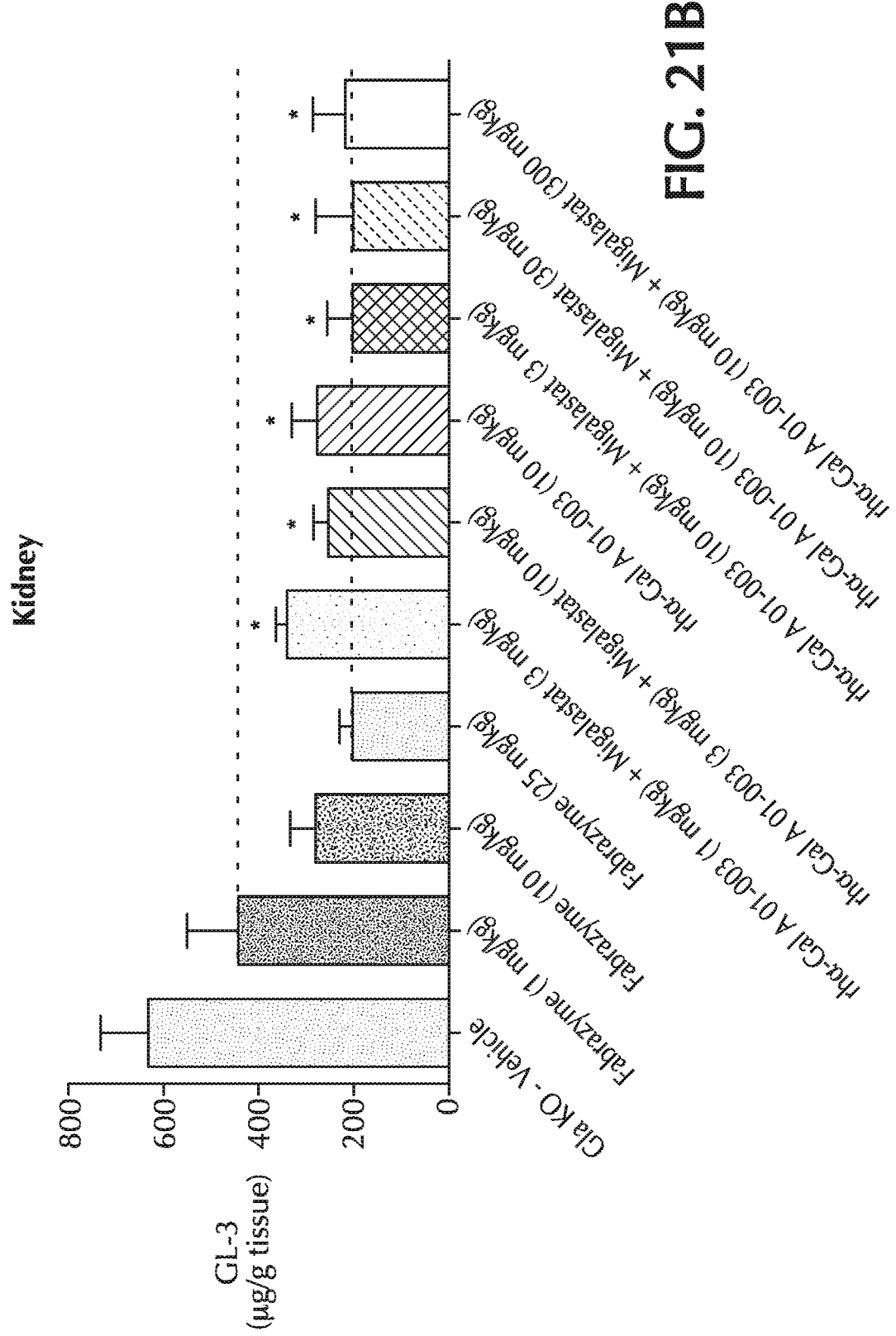
Figure 21C:
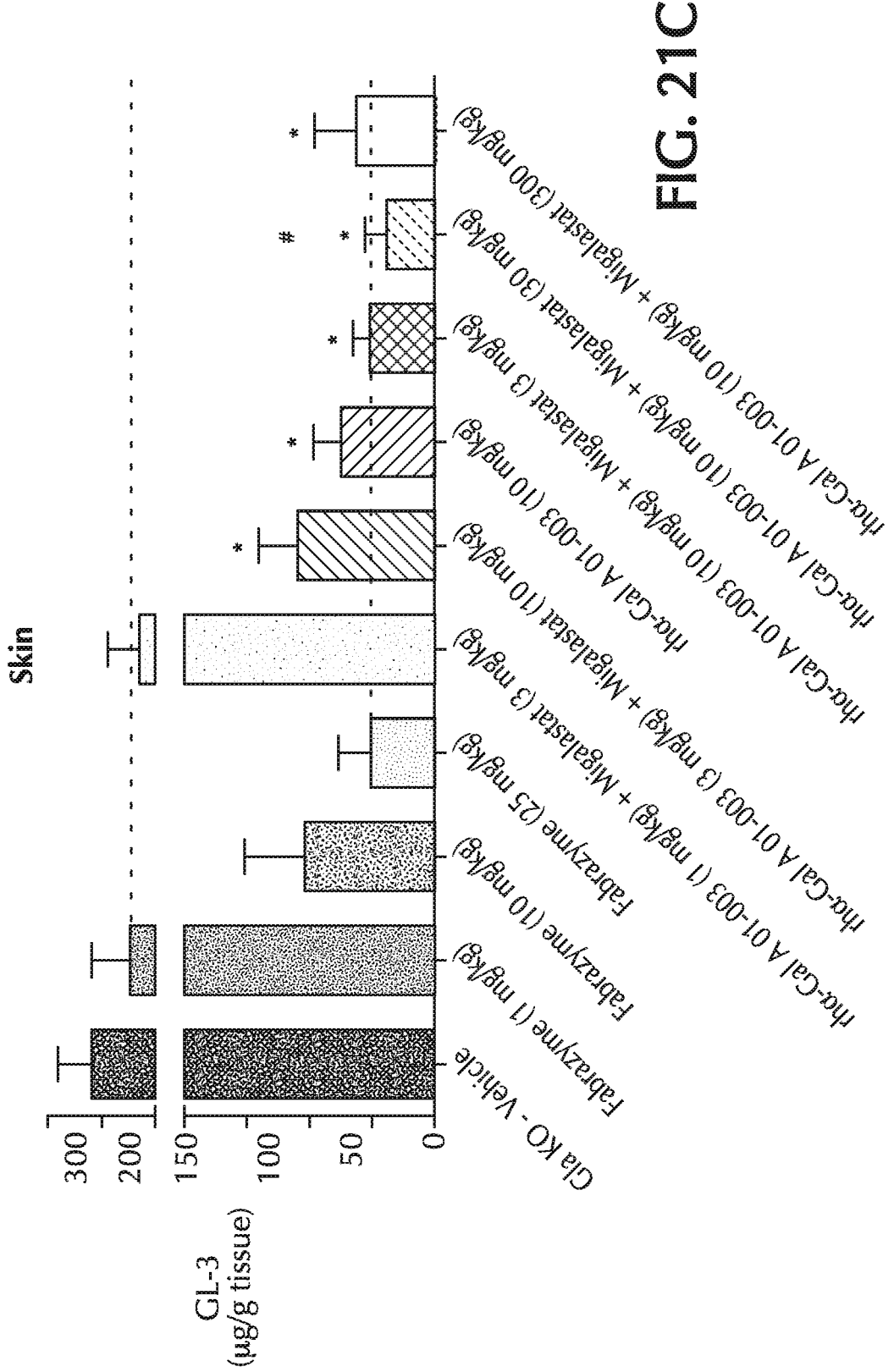
Figure 21D:
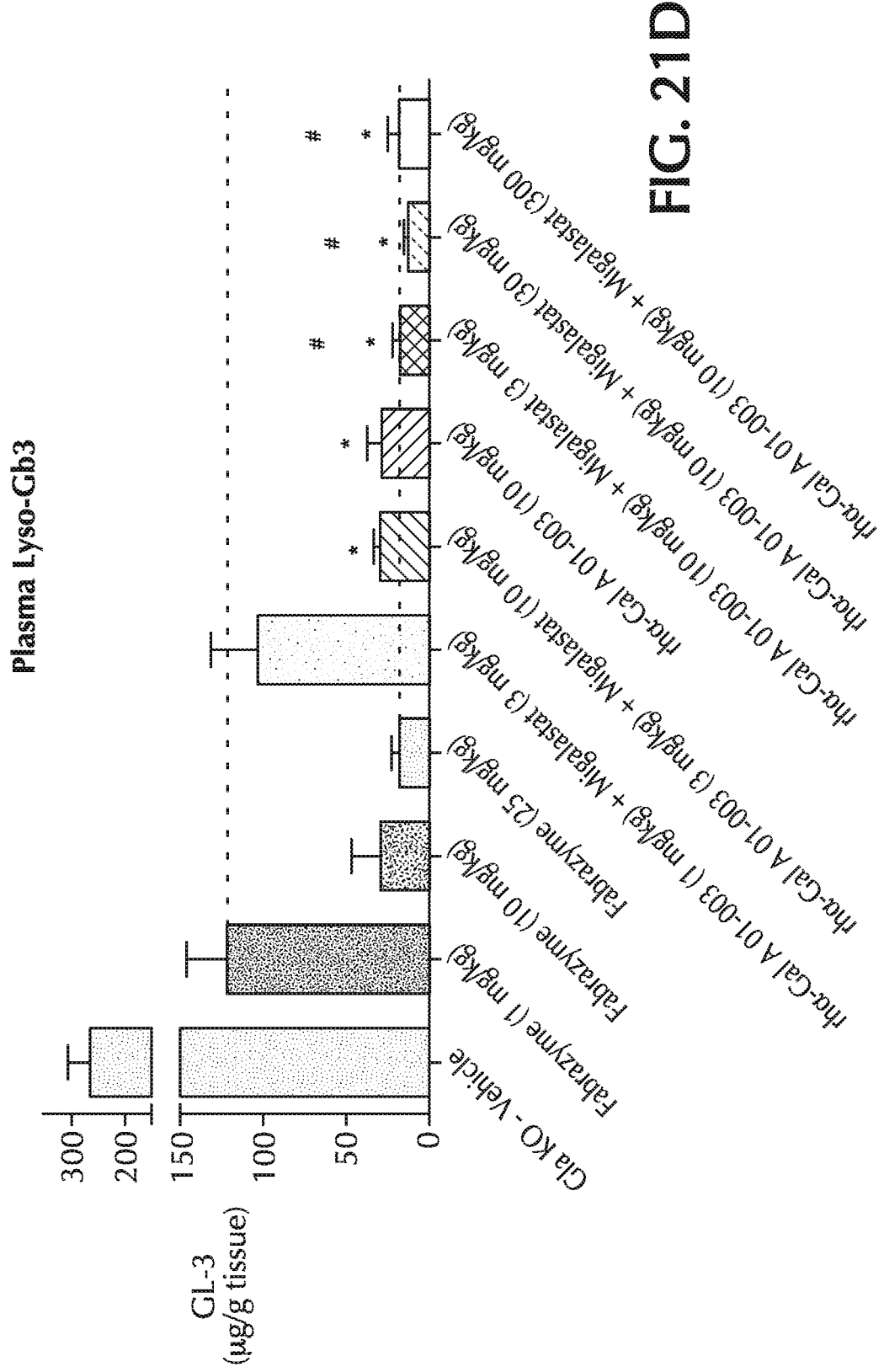

As can be seen from FIG. 19C (skin) and FIG. 19D (plasma lyso-GB3), a good dose-response seen for rhα-Gal A and Fabrazyme (agalsidase beta) alone: 10 mg/kg Fabrazyme (agalsidase beta)>3 mg/kg rhα-Gal A>1 mg/kg rhα-Gal A ≈1 mg/kg Fabrazyme (agalsidase beta). In 1 mg/kg rhα-Gal A group there was high variability (with one likely outlier). Overall, a similar observation to heart and kidney. Co-formulation of 1 mg/kg rhα-Gal A+3 or 10 mg/kg migalastat shows significant lower GL-3 levels than 1 mg/kg Fabrazyme (agalsidase beta). 3 mg/kg rhα-Gal A co-formulated with 3 or 10 mg/kg migalastat achieved similar or even slightly better GL-3 reduction compared to 10 mg/kg Fabrazyme (agalsidase beta), with 10 mg/kg migalastat co-form appearing to deliver the best results.

Example 10: Single Administration Efficacy Comparison of Various Doses of rhα-Gal A The efficacy of rhα-Gal A 01-003 with and without migalastat and Fabrazyme (agalsidase beta) were compared. Enzyme was administered via a single bolus infusion into Gla KO mice with or without co-formulation with migalastat. ~18 week old male Gla KO mice (7 per group) were given a single bolus IV administration and necropsies were performed 7 days after dose. The treatment groups are shown in Table 15 and the results are shown in FIGS. 21A-21D and Tables 16-19.

TABLE 15

| Group number | Treatment |
|---|---|
| 1 | Vehicle |
| 2 | Fabrazyme (agalsidase beta) 1 mg/kg |
| 3 | Fabrazyme (agalsidase beta) 10 mg/kg |
| 4 | Fabrazyme (agalsidase beta) 25 mg/kg |
| 5 | Co-formulation of rhα-Gal A 1 mg/kg + migalastat 3 mg/kg |
| 6 | Co-formulation of rhα-Gal A 3 mg/kg + migalastat 10 mg/kg |
| 7 | rhα-Gal A 10 mg/kg |
| 8 | Co-formulation of rhα-Gal A 10 mg/kg + migalastat 3 mg/kg |
| 9 | Co-formulation of rhα-Gal A 10 mg/kg + migalastat 30 mg/kg |
| 10 | Co-formulation of rhα-Gal A 10 mg/kg + migalastat 300 mg/kg |

TABLE 16

| GL-3 levels | | Heart (µg/g tissue) | % reduction compared to Fabrazyme (1 mg/kg) | Kidney (µg/g tissue) | % reduction compared to Fabrazyme (1 mg/kg) | Skin (µg/g tissue) | % reduction compared to Fabrazyme (1 mg/kg) |
|---|---|---|---|---|---|---|---|
| Fabrazyme 1 mg/kg | — | 183.23 | | 443 | | 1465 | |
| — | rhα-Gal A 1 mg/kg + migalastat 3 mg/kg | 91.40 | 50.12 | 340 | 23.25 | 1300 | 11.26 |
| — | rhα-Gal A 3 mg/kg + migalastat 10 mg/kg | 38.10 | 79.21 | 254 | 42.66 | 219 | 85.05 |

TABLE 17

| GL-3 levels | | Heart (µg/g tissue) | % reduction compared to Fabrazyme (10 mg/kg) | Kidney (µg/g tissue) | % reduction compared to Fabrazyme (10 mg/kg) | Skin (µg/g tissue) | % reduction compared to Fabrazyme (10 mg/kg) |
|---|---|---|---|---|---|---|---|
| Fabrazyme 10 mg/kg | — | 53.20 | | 281 | | 207 | |
| rhα-Gal A 10 mg/kg | — | 30.30 | 43.05 | 277 | 1.42 | 149 | 28.02 |
| — | rhα-Gal A 10 mg/kg + migalastat 3 mg/kg | 18.10 | 65.98 | 203 | 27.76 | 104 | 49.76 |
| — | rhα-Gal A 10 mg/kg + migalastat 30 mg/kg | 19.30 | 63.72 | 202 | 28.11 | 76.80 | 62.90 |
| — | rhα-Gal A 10 mg/kg + migalastat 300 mg/kg | 31.10 | 41.54 | 219 | 22.06 | 124 | 40.10 |
| Fabrazyme 25 mg/kg | — | 21.10 | | 203 | | 102 | |

TABLE 18

| Plasma lyso-Gb$_3$ levels | | Plasma (ng/mL) | % reduction compared to Fabrazyme (1 mg/kg) |
|---|---|---|---|
| Fabrazyme 1 mg/kg | — | 122 | |
| — | rhα-Gal A 1 mg/kg + migalastat 3 mg/kg | 103 | 15.57 |
| — | rhα-Gal A 3 mg/kg + migalastat 10 mg/kg | 29 | 75.66 |

TABLE 19

| Plasma lyso-Gb$_3$ levels | | Plasma (ng/mL) | % reduction compared to Fabrazyme (10 mg/kg) |
|---|---|---|---|
| Fabrazyme 10 mg/kg | — | 29.5 | |
| rhα-Gal A 10 mg/kg | — | 28.7 | 2.71 |
| — | rhα-Gal A 10 mg/kg + migalastat 3 mg/kg | 17.6 | 40.34 |
| — | rhα-Gal A 10 mg/kg + migalastat 30 mg/kg | 12.6 | 57.29 |
| — | rhα-Gal A 10 mg/kg + migalastat 300 mg/kg | 18.3 | 37.97 |
| Fabrazyme 25 mg/kg | — | 18.1 | |

As can be seen from FIGS. 21A-21D and Tables 16-19, the co-formulation of rhα-Gal A 1 mg/kg+migalastat 3 mg/kg had a greater reduction in substrate (GL-3 and lyso-Gb3) than a Fabrazyme (agalsidase beta) at a dose of 1 mg/kg, and the co-formulation of rhα-Gal A 3 mg/kg+migalastat 10 mg/kg was comparable to the higher dose of Fabrazyme (agalsidase beta) of 10 mg/kg. The co-formulation of rhα-Gal A 10 mg/kg with migalastat achieved similar efficacy as the higher dose of Fabrazyme (agalsidase beta) of 25 mg/kg, with the co-formulation of rhα-Gal A 10 mg/kg+ migalastat 30 mg/kg providing the greatest overall substrate reduction. The rhα-Gal A dose of 10 mg/kg provided greater substrate reduction than an equivalent dose of Fabrazyme (agalsidase beta) of 10 mg/kg, and the co-formulation with migalastat further enhanced the substrate reduction.

Example 11: Intravenously Administered Migalastat Dose Escalation to Evaluate Safety, Tolerability and Pharmacokinetics Healthy volunteers received migalastat HCl via the IV route of administration to evaluate safety, tolerability, and pharmacokinetics. Another study was performed to determine the absolute bioavailability of migalastat after an oral capsule dose as compared to an IV administered dose of migalastat HCl in healthy volunteers. Characterizing the PK behavior of migalastat alone after IV administration was expected to allow for a more precise prediction of migalastat HCl proposed doses in co-formulation with rhα-Gal A. The absolute bioavailability arm was added to determine the exposure ratio of a 150 mg oral dose relative to a 150 mg dose administered as an IV infusion. This was investigated to determine if oral to IV bridging was possible and to provide an accurate dose determination of IV migalastat HCl for co-administration and/or co-formulation with rhα-Gal A. A list of the primary and secondary objectives and endpoints is provided in Table 20.

In all cohorts, the duration of the IV infusion with migalastat HCl (or placebo, if applicable) was 2 hours (±10 min) at a constant rate of 125 mL/h.

Figure 22:
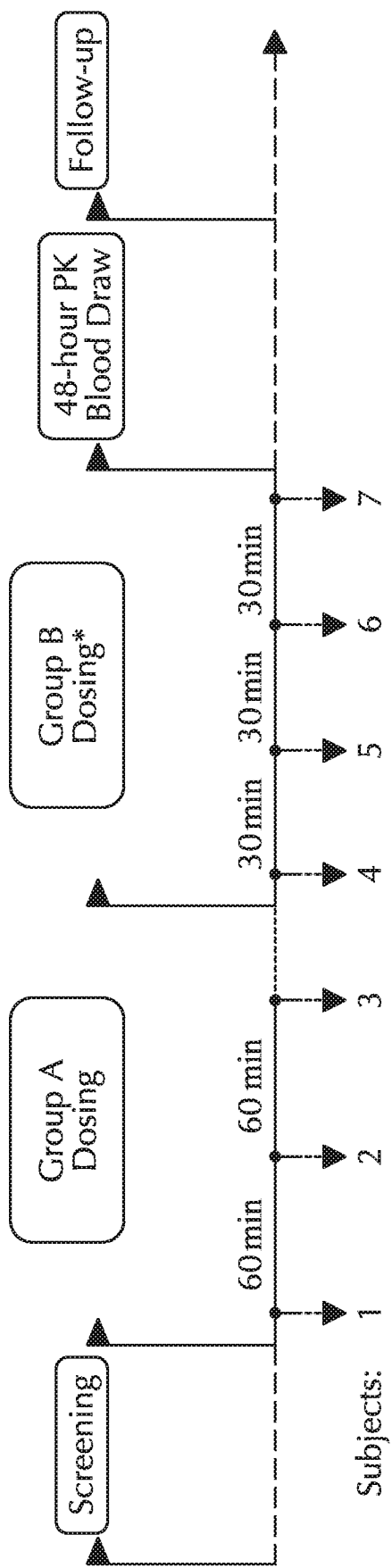
FIG. 22 shows a single dose cohort design for a study of migalastat intravenous dosing in human subjects.

Cohorts 1, 2, 3: Subjects in Cohorts 1, 2, and 3 received IV administered single ascending doses of migalastat HCl. Seven subjects were enrolled into each cohort (5 subjects randomized to migalastat HCl and 2 subjects randomized to placebo). Dosing of Cohorts 1, 2, and 3 was staggered to allow for safety and tolerability review before proceeding with the next group. Therefore, Cohorts 1, 2, and 3 were each divided into 2 sub-groups: Group A (2 subjects randomized to migalastat HCl and 1 subject randomized to placebo) and Group B (3 subjects randomized to migalastat HCl and 1 subject randomized to placebo). Subjects in Group B were dosed the day following completion of Group A dosing. Except for Cohort 3B, which was dosed 31 days after Cohort 3A because an interim PK review was performed on emerged data from Cohort 3A. Additionally, initiation of infusion was staggered by 60 minutes for Group A subjects, and by 30 minutes for Group B subjects (see FIG. 22).

*In all cohorts, dosing of subjects in Group B started the day after dosing in Group A. Except for Cohort 3B which was dosed 31 days after Cohort 3A, because an interim PK review of Cohort 3A was performed.

Cohort 4: An open-label crossover arm (Cohort 4) was added to assess the absolute bioavailability of orally administered 150 mg migalastat HCl capsule relative to 2-hour IV infusion of 150 mg migalastat HCl. Cohort 4 consisted of 2

TABLE 20

| Objectives | Endpoints |
|---|---|
| PRIMARY | |
| Determine the pharmacokinetics of migalastat HCL following a single 2-hour infusion in healthy subjects | Plasma PK: $AUC_{0-\infty}$, $AUC_{0-t}$, $C_{max}$, $t_{max}$, $CL_T$, $V_z$, and $t^{1/2}$ for migalastat |
| Determine the safety and tolerability of a single migalastat HCl 2-hour infusion in healthy subjects | Safety: adverse events (AEs) including infusion site reactions and allergic reactions, clinically significant changes in safety laboratory tests (hematology, chemistry, and urinalysis), vital signs (blood pressure, heart rate, respiratory rate, temperature), physical examinations, and 12-lead electrocardiograms (ECGs) |
| Secondary | |
| Determine dose proportionality of migalastat following a single 2-hour IV infusion in healthy subjects (at doses of 0.3, 1.0, and 10.0 mg/kg) | Plasma PK: $AUC_{0-\infty}$, $AUC_{0-t}$, and $C_{max}$ |
| Determine the urinary excretion of the unchanged migalastat following a single 2-hour IV infusion in healthy subjects | Urinary PK: $Ae_{0-24\,h}$, Fe, $CL_r$ of migalastat |
| Determine the absolute bioavailability of plasma migalastat | Plasma PK: $F_{abs}$, the point estimate for $AUC_{0-\infty}$, $AUC0$-t, ratios and 90% confidence intervals (CIs) |

Figure 23:
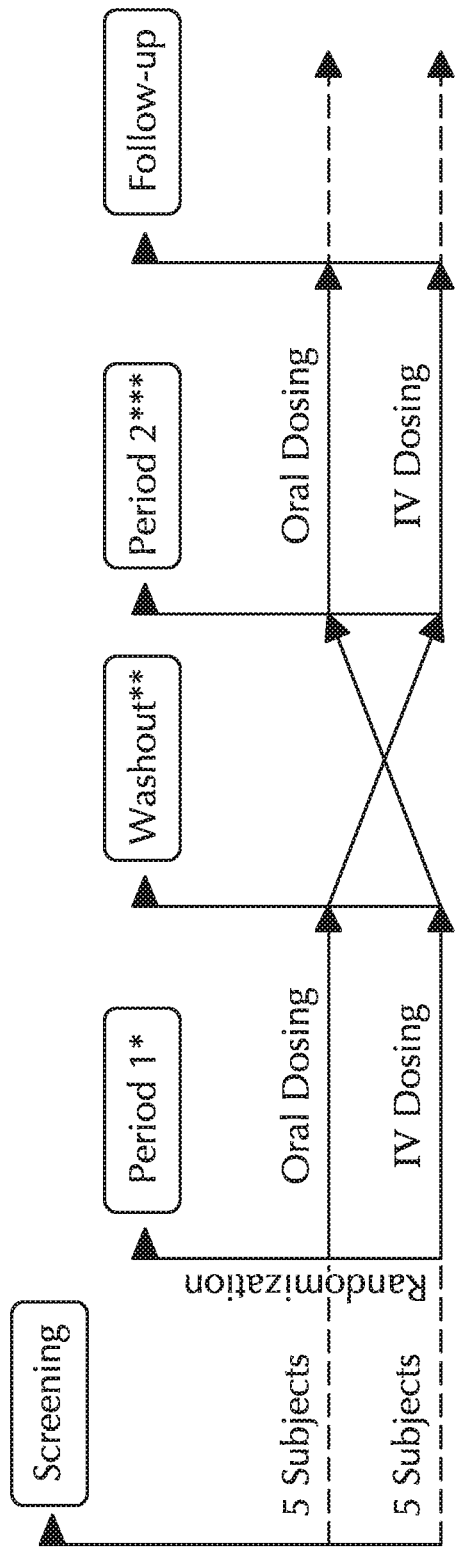
FIG. 23 shows cohort crossover design for a study of migalastat intravenous and oral administration in human subjects.

Type of Study: This Phase 1 study was a single-center study consisting of 2 designs. Cohorts 1, 2, and 3 were performed according to a randomized, double-blind, placebo-controlled, single ascending dose (SAD) IV study design to evaluate the safety, tolerability, and PK of IV administered migalastat HCl or IV administered placebo in healthy subjects. Cohort 4 was an open-label, randomized two-way crossover arm designed to assess the absolute bioavailability of orally administered migalastat HCl relative to IV administered migalastat HCl in healthy subjects.

sequential treatment periods with a washout period of 7 days between study drug administrations (FIG. 23). Cohort 4 enrolled 10 subjects all of whom received active drug (no placebo was administered). Cohort 4 was randomized such that 5 subjects received the oral formulation and 5 subjects received the IV formulation during Period 1, followed by the alternate formulation during Period 2.

*During Period 1, all Day −1 through Day 3 assessments were performed.  The washout period was 7 days. * During Period 2, subjects repeated all Day −1 through Day 3 assessments.

Dose Escalation: This escalating design was chosen to allow careful increase of the dose, after assessment of safety and tolerability of each preceding dose. The IV administered single ascending doses of migalastat HCl include a starting dose of 0.3 mg/kg (Cohort 1), a mid-range dose of 1.0 mg/kg (Cohort 2), and a highest dose of permitted at any time during a cohort based on emergent safety, tolerability, and PK data, up to a maximum allowed dose of 13.0 mg/kg. As per CSP Amendment 3.1 (see Appendix 16.1.1 and Section 9.8.1), the top dose of this study (Cohort 3) was estimated to not exceed the following limit: The maximum exposure (AUC) following oral administration of 1250 mg migalastat HCl of 116 h*μg/mL (115,931 h*ng/mL).

Treatments Administered: In all cohorts, the duration of the IV infusion with migalastat HCl (or placebo, if applicable) was 2 hours (±10 min) at a constant rate of 125 mL/h. Subjects enrolled in Cohorts 1, 2, and 3 were randomized to receive one of the following doses of migalastat HCl (n=5) or placebo (n=2):

Cohort 1 (0.3 mg/kg IV):migalastat HCl (n=5) or placebo (n=2)

Cohort 2 (1.0 mg/kg IV):migalastat HCl (n=5) or placebo (n=2)

Cohort 3 (10.0 mg/kg IV):migalastat HCl (n=5) or placebo (n=2).

Cohort 4: Period 1: 150 mg migalastat HCl capsule (n=5) or 150 mg migalastat HCl via IV infusion (n=5). Period 2: 150 mg migalastat HCl capsule (n=5) or 150 mg migalastat HCl via IV infusion (n=5)

The migalastat HCl used for infusion was 50 mg/ml and the placebo was 0.9% sodium chloride. The oral migalastat HCl was administered as a 150 mg gelatin tablet.

Selection of Doses in the Study: The current single dose levels were selected on the basis of predicted human PK following IV dosing, non-clinical safety margins, and target therapeutic migalastat exposures for efficacy. A starting single IV infusion of 0.3 mg/kg migalastat HCl in humans was selected based on large safety margins (Table 21). Likewise, the migalastat HCl 10 mg/kg dose in humans was supported by previous oral human migalastat exposures and preclinical safety margins (Table 22). Based on a mass-balance study, the recovery of migalastat was high, indicating that migalastat is well absorbed, however, approximately 20% to 25% may represent unabsorbed drug. As such, the predicted exposures were expected to be as much as 1.25-fold greater following IV dosing to account for possible unabsorbed drug following oral dosing.

TABLE 21

Predicted Human Migalastat AUC and $C_{max}$ Following Single IV Dose Administration and Exposure Margins to General Toxicology NOAELs

| Migalastat HCl Dose (mg/kg) | Predicted Median AUC (h.μg/mL) | Fold Cover to NOAEL AUC Rat[1] | Fold Cover to NOAEL AUC Monkey[2] | Predicted Median $C_{max}$ (μg/mL) | Fold Cover to NOAEL $C_{max}$ Rat[1] | Fold Cover to NOAEL $C_{max}$ Monkey[2] |
|---|---|---|---|---|---|---|
| 0.3 | 1.86 | 134 | 165 | 0.36 | 65 | 68 |
| 10.0 | 61.5 | 4.05 | 4.98 | 12.1 | 1.93 | 2.02 |

Abbreviations: AUC = area under the concentration-time curve; $C_{max}$ = maximum observed concentration; HCl = hydrochloride; NOAEL = no observed adverse effect level.
[1]Rat NOAEL (1500 μg/kg/day): AUC = 249 μg.h/mL, $C_{max}$ = 23.4 μg/mL.
[2]Monkey NOAEL (500 mg/kg/day): AUC = 306 μg.h/mL, $C_{max}$ = 24.5 μg/mL.

TABLE 22

Predicted Human Migalastat AUC and $C_{max}$ Following Single IV Dose Administration and Exposure Margins to Human Observed Oral Migalastat Exposures Following a Single Oral Dose of 1250 mg

| Migalastat HCl Dose (mg/kg) | Predicted Median AUC (h.μg/mL) | Fold Cover to AUC from human oral 1250 mg Min[1] | Fold Cover to AUC from human oral 1250 mg Median[2] | Fold Cover to AUC from human oral 1250 mg Max[3] | Predicted Median $C_{max}$ (μg/mL) | Fold Cover to $C_{max}$ from human oral 1250 mg Min[1] | Fold Cover to $C_{max}$ from human oral 1250 mg Median[2] | Fold Cover to $C_{max}$ from human oral 1250 mg Max[3] |
|---|---|---|---|---|---|---|---|---|
| 0.3 | 1.86 | 15.5 | 39 | 62 | 0.36 | 2.6 | 36 | 61 |
| 10.0 | 61.5 | 0.47 | 1.19 | 1.89 | 12.1 | 0.08 | 1.07 | 1.81 |

Abbreviations: AUC = area under the concentration-time curve; $C_{max}$ = maximum observed concentration; HCl = hydrochloride; Max = maximum; Min = minimum.
[1]Minimum observed individual PK exposures: AUC = 28.9 h.μg/mL, $C_{max}$ = 4.78 μg/mL.
[2]Median observed individual PK exposures: AUC = 73.2 h.μg/mL, $C_{max}$ = 13.0 μg/mL.
[3]Maximum observed individual PK exposures: AUC = 115.9 h.μg/mL, $C_{max}$ = 21.9 μg/mL.

Oral administration of the 150 mg migalastat HCl capsule was well tolerated in previous clinical studies conducted in healthy volunteers and Fabry patients. Additionally, single dose administrations up to 2000 mg migalastat HCl to healthy volunteers in Phase 1 studies have been well tolerated. Oral administrations have demonstrated linear exposures to 1250 mg migalastat HCl. A phase 2a study conducted in 23 Fabry patients demonstrated improved tissue uptake of active α-Gal A into skin following co-administration of a single oral administration of 150 mg migalastat HCl with 0.2, 0.5, and 1.0 mg/kg agalsidase. Additionally, oral 150 mg migalastat HCl has been safely administered every other day to Fabry patients with amenable mutations in Phase 2 and 3 studies in the monotherapy program.

Figure 24A:
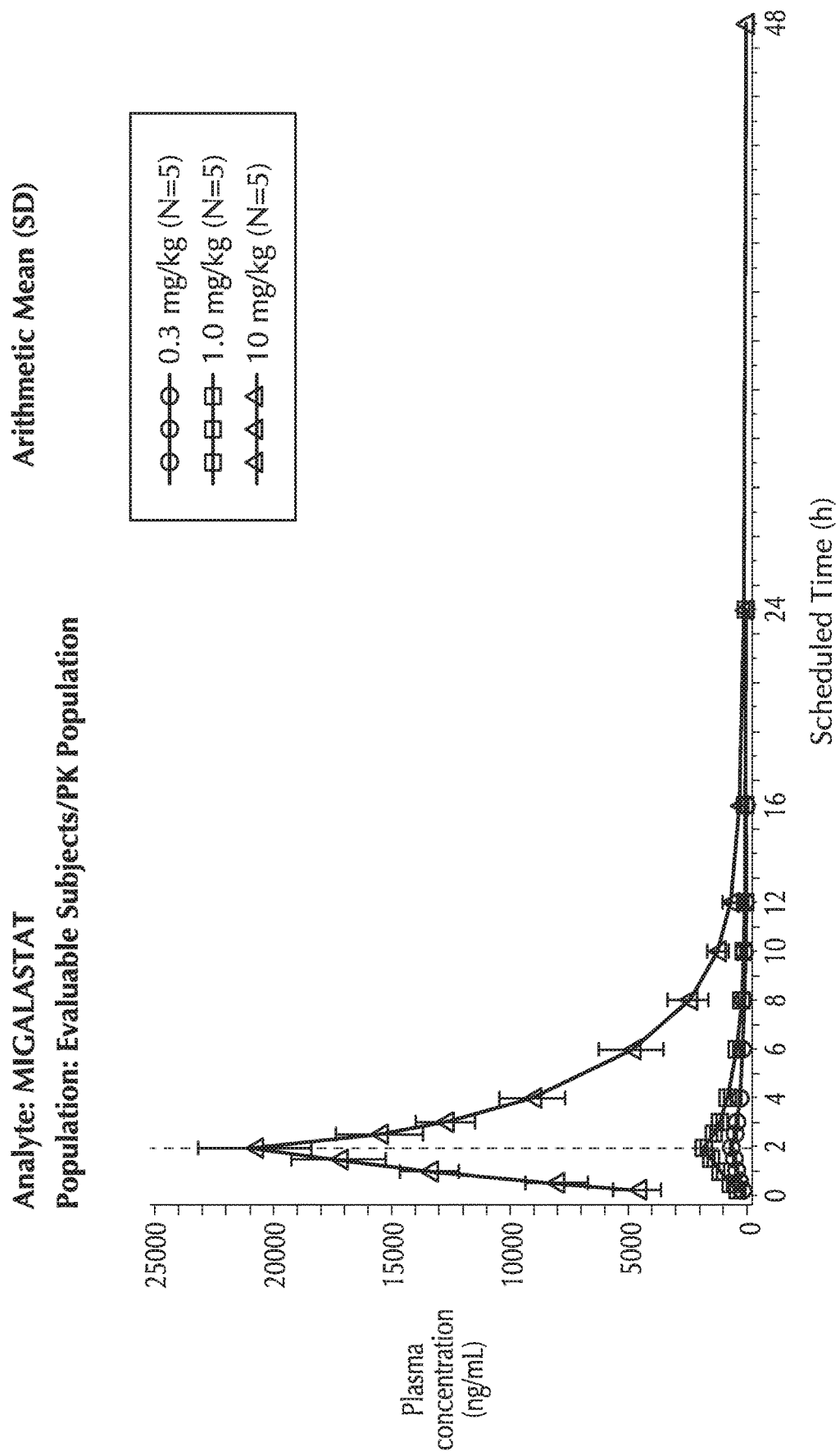
FIGS. 24A and 24B show the pharmacokinetic profile of migalastat intravenous dosing in human subjects.
Figure 24B:
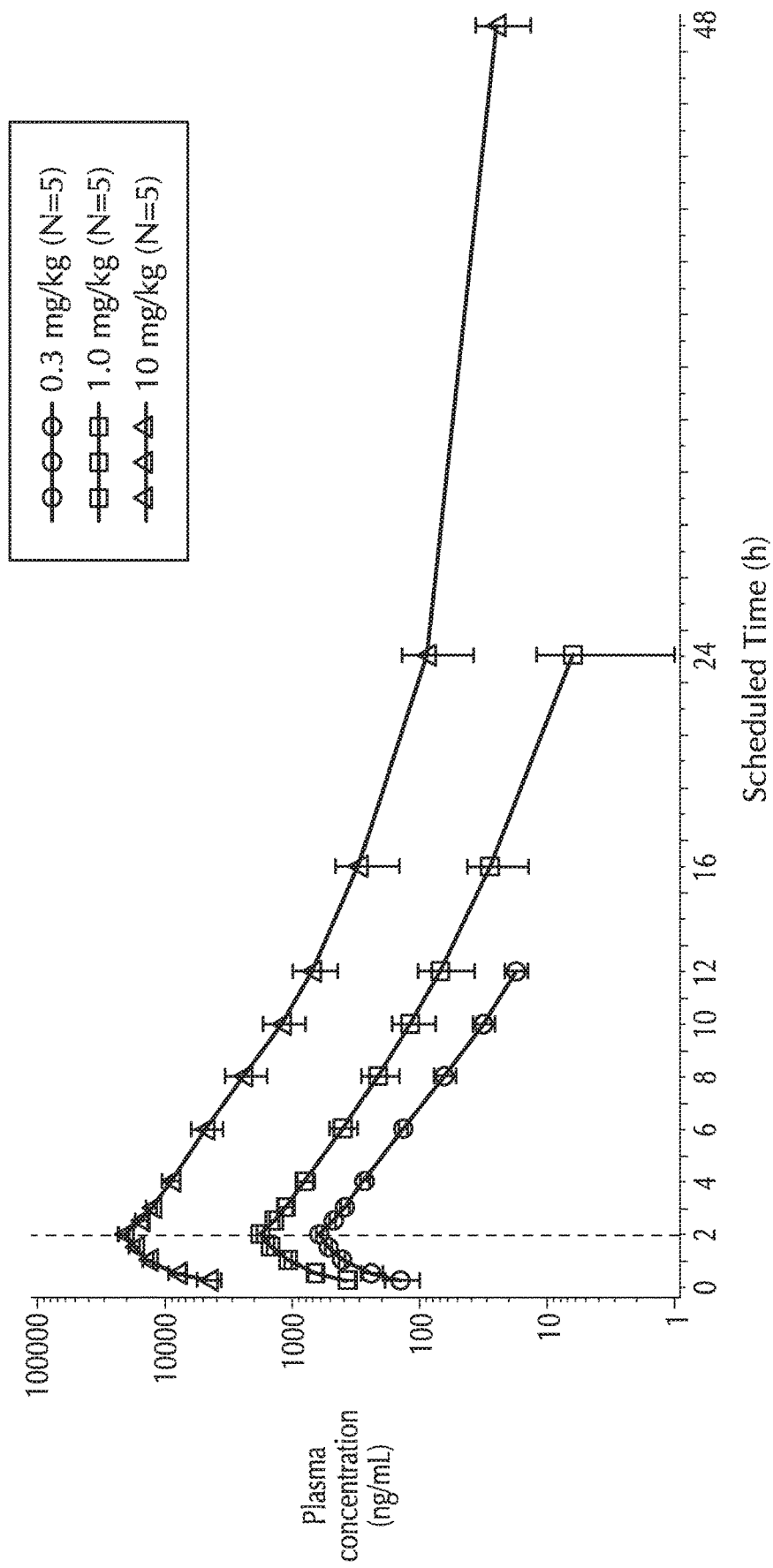

Cohorts 1, 2, and 3 (SAD): After a single 2-hour IV infusion of migalastat HCl at doses in the range of 0.3 to 10 mg/kg, maximum arithmetic mean plasma concentrations of migalastat were typically reached at the end of infusion, corresponding to 2 h after start of infusion. The mean migalastat plasma concentration-time profiles displayed a clear dose-dependent increase in plasma concentrations following increasing IV doses of migalastat HCl. After reaching a maximum, the migalastat concentrations decreased rapidly until 12 h post-dose. At the higher dose levels (0.3 mg/kg and 10 mg/kg), the initial rapid decline of migalastat concentrations was followed by a more gradual decline in an apparently biphasic manner (FIGS. 24A and 24B show pharmacokinetics with a linear and logarithmic scale, respectively). Combined individual migalastat plasma concentration-time profiles showed minimal inter-individual differences in individual PK profiles across tested IV doses.

Figure 25A:
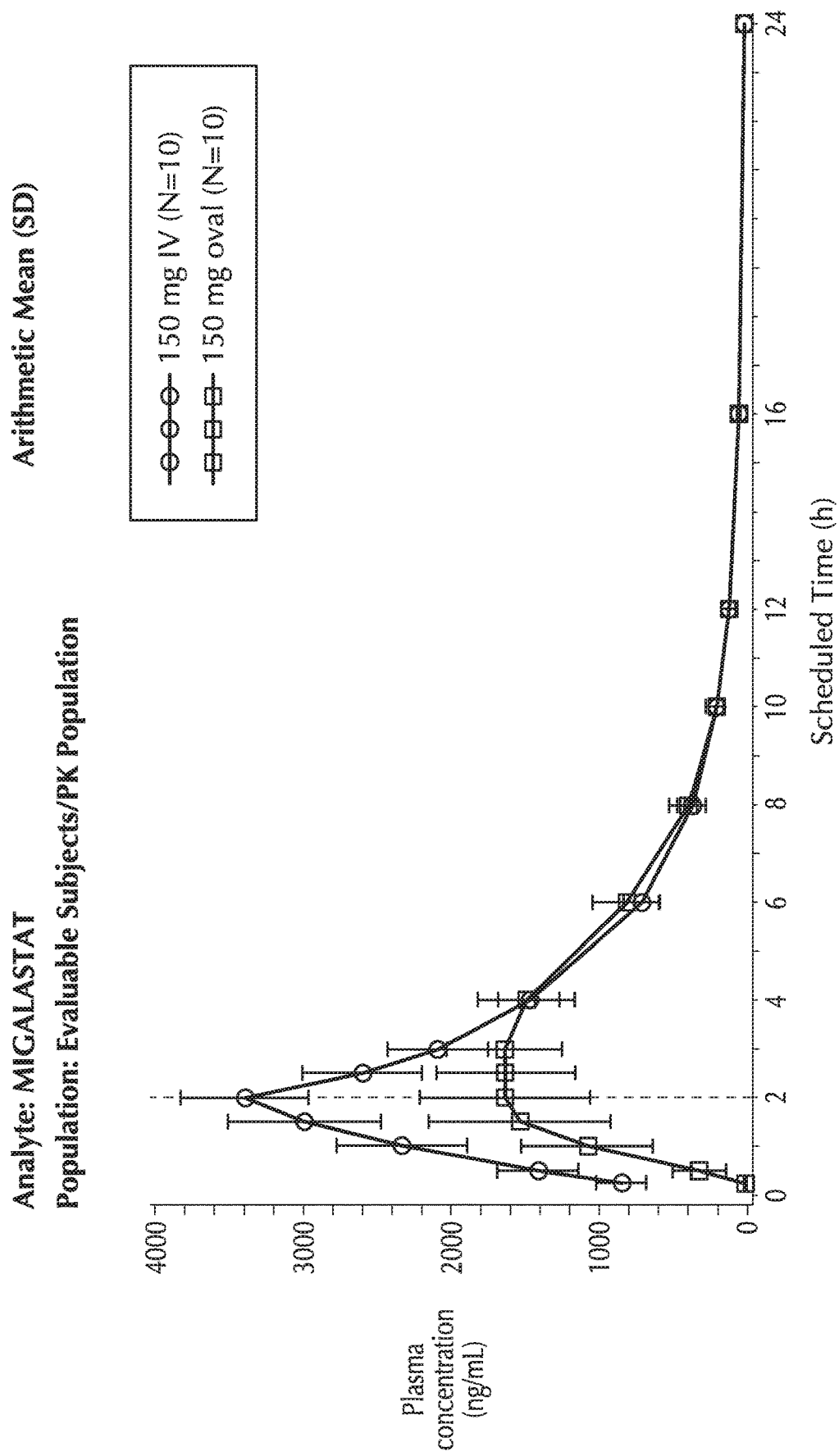
FIGS. 25A and 25B show a comparison of the pharmacokinetic profiles of intravenous and oral administration of migalastat.
Figure 25B:
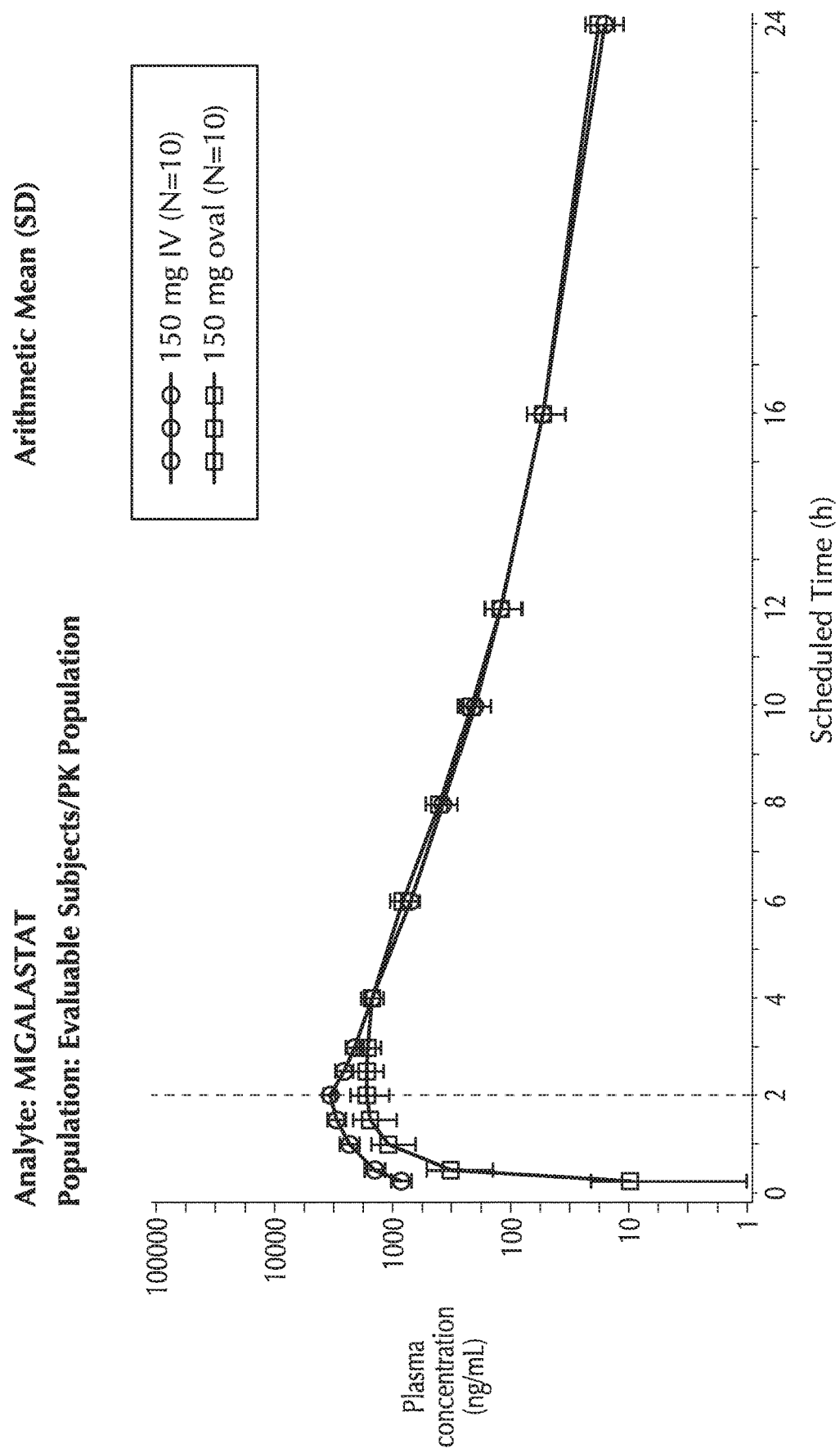

Cohort 4: After oral administration of 150 mg migalastat HCl, migalastat appeared in plasma within 0.25 h to 0.5 h post-dose (0.25 h was the first post-dose sampling time point). Maximum arithmetic mean plasma concentrations of migalastat were typically reached between 2 h and 4 h post oral dose. For most subjects a single peak plasma concentration was observed, except that for Subject 022 an initial peak concentration at 1.5 h was followed by a second and higher peak concentration at 4 h post oral dose. For Subject 030 a similar plateau phase was observed between 1 h and 1.5 h post oral dose, followed by a peak concentration at 3 h post-dose. After IV administration of 150 mg migalastat HCl the maximum arithmetic mean plasma concentrations of migalastat were reached at the end of infusion (corresponding to 2 h after start of infusion), similar to the SAD data. The maximum arithmetic mean plasma concentrations were approximately 2-fold higher after IV dosing than after oral dosing of migalastat HCl. After reaching a maximum, for both oral and IV administration of migalastat HCl the migalastat concentrations decreased rapidly followed by a more gradual decline in an apparently biphasic manner (FIGS. 25A and 25B show pharmacokinetics with a linear and logarithmic scale, respectively).

Combined individual migalastat plasma concentration-time profiles showed more inter-individual differences in individual PK profiles after oral administration of 150 mg migalastat HCl than after IV administration of 150 mg migalastat HCl. Also the inter-individual differences in PK profiles appeared to be more pronounced after the 150 mg IV dose than after the 0.3 to 10 mg/kg IV dose range, probably related to inter-individual differences in the rate and extent of absorption and clearance after the 150 mg oral dose, or because the 150 mg IV dose was not corrected for the individual subjects' weight.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A human recombinant α-galactosidase A (rhα-Gal A), comprising a protein with an amino acid sequence having at least 98% sequence identity to SEQ ID NO: 1 or SEQ ID NO: 2, wherein the protein has less than 10% of total N-linked oligosaccharides that are neutral as measured by normal-phase liquid chromatography on an amino column and the protein has 3.5 to 6 moles of mannose-6-phosphate (M6P) residues per mole of rhα-Gal A homodimer as measured by normal-phase liquid chromatography on an amino column.

2. The rhα-Gal A of claim 1, wherein the rhα-Gal A has one or more of:
   at least 17% of total N-linked oligosaccharides that contain a single sialic acid residue as measured by normal-phase liquid chromatography on an amino column;
   at least 20% of total N-linked oligosaccharides that contain two sialic acid residues as measured by normal-phase liquid chromatography on an amino column;
   at least 40% of total N-linked oligosaccharides that contain one or two sialic acid residues as measured by normal-phase liquid chromatography on an amino column; or
   at least 4 moles of sialic acid residues per mole of rhα-Gal A homodimer as measured by normal-phase liquid chromatography on an amino column.

3. The rhα-Gal A of claim 1, wherein the rhα-Gal A has at least 50% of total N-linked oligosaccharides that contain sialic acid as measured by normal-phase liquid chromatography on an amino column.

4. The rhα-Gal A of claim 1, wherein the rhα-Gal A has at least 25% of total N-linked oligosaccharides that are mono-mannose-6-phosphate and at least 6% of total N-linked oligosaccharides that are bis-mannose-6-phosphate as measured by normal-phase liquid chromatography on an amino column.

5. The rhα-Gal A of claim 1, wherein the rhα-Gal A has at least 7 moles of sialic acid residues per mole of rhα-Gal A homodimer as measured by normal-phase liquid chromatography on an amino column.

6. The rhα-Gal A of claim 1, wherein the rhα-Gal A has at least 22% of total N-linked oligosaccharides that contain two sialic acid residues as measured by normal-phase liquid chromatography on an amino column.

7. The rhα-Gal A of claim 1, wherein the rhα-Gal A has at least 14% of total N-linked oligosaccharides that are bis-mannose-6-phosphate as measured by normal-phase liquid chromatography on an amino column.

8. A pharmaceutical composition comprising a pharmaceutically acceptable carrier and the rhα-Gal A of claim 1.

9. The pharmaceutical composition of claim 8, further comprising a pharmacological chaperone for rhα-Gal A.

10. The pharmaceutical composition of claim 9, wherein the pharmacological chaperone is migalastat or salt thereof.

11. The pharmaceutical composition of claim 10, wherein the pharmacological chaperone is migalastat hydrochloride.

12. The pharmaceutical composition of claim 10, wherein the pharmaceutical composition comprises:
   0.5 to 20 µM of the rhα-Gal A; and
   50 to 20,000 µM migalastat or salt thereof.

13. The pharmaceutical composition of claim 12, wherein the pharmacological chaperone is migalastat hydrochloride.

14. The pharmaceutical composition of claim 10, wherein the pharmaceutical composition comprises:
   1 to 10 µM of the rhα-Gal A; and
   100 to 10,000 µM migalastat or salt thereof.

15. The pharmaceutical composition of claim 14, wherein the pharmacological chaperone is migalastat hydrochloride.

16. The pharmaceutical composition of claim 12, wherein the migalastat or a salt thereof and the rhα-Gal A are present in a molar ratio of the migalastat or a salt thereof to the rhα-Gal A of between 13,000:1 and 50:1.

17. The pharmaceutical composition of claim 16, wherein the pharmacological chaperone is migalastat hydrochloride.

18. The pharmaceutical composition of claim 8, wherein the composition is formulated for intravenous, intraarterial, intramuscular, intradermal, subcutaneous, or intraperitoneal administration.

19. A method for treating Fabry disease in a patient, the method comprising administering the pharmaceutical composition of claim 8 to a patient in need thereof.

20. The rhα-Gal A of claim 1, wherein the rhα-Gal A has 3.5 to 6 moles of mannose-6-phosphate (M6P) residues per mole of rhα-Gal A homodimer and at least 4 moles of sialic acid residues per mole of rhα-Gal A homodimer as measured by normal-phase liquid chromatography on an amino column.

21. The rhα-Gal A of claim 1, wherein the rhα-Gal A has 4 to 6 moles of mannose-6-phosphate (M6P) residues per mole of rhα-Gal A homodimer and at least 5 moles of sialic acid residues per mole of rhα-Gal A homodimer as measured by normal-phase liquid chromatography on an amino column.

22. The method of claim 19, further comprising administering migalastat or a salt thereof before, after or simultaneously with the administration of the pharmaceutical composition.

23. The rhα-Gal A of claim 1, wherein the rhα-Gal A has 1.5% to 5% of total N-linked oligosaccharides that are neutral as measured by normal-phase liquid chromatography on an amino column.

24. The rhα-Gal A of claim 1, wherein the rhα-Gal A has 3.5 to 4.5 moles of mannose-6-phosphate (M6P) residues per mole of rhα-Gal homodimer as measured by normal-phase liquid chromatography on an amino column.

* * * * *

SEQUENCE LISTING

<160> NUMBER OF SEQ ID NOS: 3

<210> SEQ ID NO 1
<211> LENGTH: 429
<212> TYPE: PRT
<213> ORGANISM: Homo sapiens

<400> SEQUENCE: 1

```
Met Gln Leu Arg Asn Pro Glu Leu His Leu Gly Cys Ala Leu Ala Leu
1               5                   10                  15

Arg Phe Leu Ala Leu Val Ser Trp Asp Ile Pro Gly Ala Arg Ala Leu
            20                  25                  30

Asp Asn Gly Leu Ala Arg Thr Pro Thr Met Gly Trp Leu His Trp Glu
        35                  40                  45

Arg Phe Met Cys Asn Leu Asp Cys Gln Glu Glu Pro Asp Ser Cys Ile
    50                  55                  60

Ser Glu Lys Leu Phe Met Glu Met Ala Glu Leu Met Val Ser Glu Gly
65                  70                  75                  80

Trp Lys Asp Ala Gly Tyr Glu Tyr Leu Cys Ile Asp Asp Cys Trp Met
                85                  90                  95
```

```
Ala Pro Gln Arg Asp Ser Glu Gly Arg Leu Gln Ala Asp Pro Gln Arg
            100                 105                 110

Phe Pro His Gly Ile Arg Gln Leu Ala Asn Tyr Val His Ser Lys Gly
        115                 120                 125

Leu Lys Leu Gly Ile Tyr Ala Asp Val Gly Asn Lys Thr Cys Ala Gly
    130                 135                 140

Phe Pro Gly Ser Phe Gly Tyr Tyr Asp Ile Asp Ala Gln Thr Phe Ala
145                 150                 155                 160

Asp Trp Gly Val Asp Leu Leu Lys Phe Asp Gly Cys Tyr Cys Asp Ser
                165                 170                 175

Leu Glu Asn Leu Ala Asp Gly Tyr Lys His Met Ser Leu Ala Leu Asn
            180                 185                 190

Arg Thr Gly Arg Ser Ile Val Tyr Ser Cys Glu Trp Pro Leu Tyr Met
        195                 200                 205

Trp Pro Phe Gln Lys Pro Asn Tyr Thr Glu Ile Arg Gln Tyr Cys Asn
    210                 215                 220

His Trp Arg Asn Phe Ala Asp Ile Asp Asp Ser Trp Lys Ser Ile Lys
225                 230                 235                 240

Ser Ile Leu Asp Trp Thr Ser Phe Asn Gln Glu Arg Ile Val Asp Val
                245                 250                 255

Ala Gly Pro Gly Gly Trp Asn Asp Pro Asp Met Leu Val Ile Gly Asn
            260                 265                 270

Phe Gly Leu Ser Trp Asn Gln Val Thr Gln Met Ala Leu Trp Ala
        275                 280                 285

Ile Met Ala Ala Pro Leu Phe Met Ser Asn Asp Leu Arg His Ile Ser
    290                 295                 300

Pro Gln Ala Lys Ala Leu Leu Gln Asp Lys Asp Val Ile Ala Ile Asn
305                 310                 315                 320

Gln Asp Pro Leu Gly Lys Gln Gly Tyr Gln Leu Arg Gln Gly Asp Asn
                325                 330                 335

Phe Glu Val Trp Glu Arg Pro Leu Ser Gly Leu Ala Trp Ala Val Ala
            340                 345                 350

Met Ile Asn Arg Gln Glu Ile Gly Gly Pro Arg Ser Tyr Thr Ile Ala
        355                 360                 365

Val Ala Ser Leu Gly Lys Gly Val Ala Cys Asn Pro Ala Cys Phe Ile
    370                 375                 380

Thr Gln Leu Leu Pro Val Lys Arg Lys Leu Gly Phe Tyr Glu Trp Thr
385                 390                 395                 400

Ser Arg Leu Arg Ser His Ile Asn Pro Thr Gly Thr Val Leu Leu Gln
                405                 410                 415

Leu Glu Asn Thr Met Gln Met Ser Leu Lys Asp Leu Leu
            420                 425

<210> SEQ ID NO 2
<211> LENGTH: 398
<212> TYPE: PRT
<213> ORGANISM: Homo sapiens

<400> SEQUENCE: 2

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
            20                  25                  30

Ile Ser Glu Lys Leu Phe Met Glu Met Ala Glu Leu Met Val Ser Glu
        35                  40                  45
```

Gly Trp Lys Asp Ala Gly Tyr Glu Tyr Leu Cys Ile Asp Asp Cys Trp
 50                  55                  60

Met Ala Pro Gln Arg Asp Ser Glu Gly Arg Leu Gln Ala Asp Pro Gln
 65                  70                  75                  80

Arg Phe Pro His Gly Ile Arg Gln Leu Ala Asn Tyr Val His Ser Lys
                 85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
            115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
            195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
            260                 265                 270

Ser Pro Gln Ala Lys Ala Leu Leu Gln Asp Lys Asp Val Ile Ala Ile
            275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
            340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
370                 375                 380

Gln Leu Glu Asn Thr Met Gln Met Ser Leu Lys Asp Leu Leu
385                 390                 395

<210> SEQ ID NO 3
<211> LENGTH: 1290
<212> TYPE: DNA
<213> ORGANISM: Homo sapiens

<400> SEQUENCE: 3
atgcagctga ggaatcccga gctccacctg ggctgtgctc tggctctgcg gttcctggcc    60
ctcgtgtcct gggacatccc tggcgctagg gccctcgata acggactggc ccggacccccc  120

```
acaatgggat ggctccactg ggaaaggttc atgtgcaatc tggactgtca ggaggaaccc      180
gactcctgca tcagcgaaaa gctcttcatg gagatggccg agctgatggt gagcgagggc      240
tggaaggacg ccggctacga gtatctgtgc atcgatgact gctggatggc ccctcaaagg      300
gactccgaag gcaggctgca ggctgatccc caaaggtttc cccacggaat ccggcagctc      360
gccaactacg tgcattccaa gggcctcaag ctcggcatct acgccgacgt gggcaacaaa      420
acatgcgccg gattccccgg cagcttcggc tactacgaca tcgacgccca gacattcgct      480
gattggggag tggacctgct gaagttcgac ggctgttact gcgattccct ggaaaacctg      540
gccgacggct acaaacacat gtccctcgcc ctgaaccgga caggcaggtc catcgtgtac      600
agctgcgagt ggcccctgta catgtggcct ttccagaagc ccaactacac agagatcagg      660
cagtactgca accactggag gaacttcgct gacatcgacg actcctggaa gagcatcaag      720
agcatcctgg actggaccag cttcaaccag gagaggatcg tggacgtggc tggacccgga      780
ggctggaacg accccgatat gctggtgatt ggcaacttcg gactgagctg gaaccagcag      840
gtgacccaga tggccctgtg ggccattatg gccgctcccc tgttcatgtc caacgacctg      900
aggcacatca gcccccaggc caaggctctg ctgcaggaca aggatgtgat cgccatcaac      960
caggaccccc tgggcaagca gggctaccag ctgaggcaag gagataactt cgaggtgtgg      1020
gagaggcccc tgtccggact ggcttgggcc gtggccatga tcaatcggca ggagatcggc      1080
ggaccccggt cctacaccat tgctgtggcc agcctgggaa aaggagtcgc ctgcaacccc      1140
gcctgcttca ttacccagct gctccccgtg aagcggaagc tgggcttcta tgagtggacc      1200
agcaggctga ggtcccatat caatcctacc ggcaccgtcc tcctccagct cgagaatacc      1260
atgcagatga gcctcaagga tctgctgtga                                     1290
```